US008968884B2

(12) United States Patent
Hong et al.

(10) Patent No.: US 8,968,884 B2
(45) Date of Patent: Mar. 3, 2015

(54) COMPOUND AND ORGANIC LIGHT EMITTING DEVICE USING THE SAME

(75) Inventors: Sung-Kil Hong, Daejeon (KR); Wook-Dong Cho, Daejeon (KR); Jae-Soon Bae, Daejeon (KR); Ji-Eun Kim, Daejeon (KR); Hyun Nam, Daejeon (KR); Jun-Gi Jang, Daejeon (KR); Byung-Sun Jeon, Seoul (KR); Mun-Kyu Joo, Busan (KR); Hye-Young Jang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 104 days.

(21) Appl. No.: 12/741,996

(22) PCT Filed: Nov. 7, 2008

(86) PCT No.: PCT/KR2008/006588

§ 371 (c)(1), (2), (4) Date: May 7, 2010

(87) PCT Pub. No.: WO2009/061156

PCT Pub. Date: May 14, 2009

(65) Prior Publication Data

US 2011/0127495 A1 Jun. 2, 2011

(30) Foreign Application Priority Data

Nov. 8, 2007 (KR) ........................ 10-2007-0113852

(51) Int. Cl.

| | |
|---|---|
| ***H01L 51/54*** | (2006.01) |
| ***C07D 409/10*** | (2006.01) |
| ***C09K 11/06*** | (2006.01) |
| ***C07D 409/14*** | (2006.01) |
| ***H01L 51/00*** | (2006.01) |
| *H01L 51/50* | (2006.01) |

(52) U.S. Cl.
CPC .............. *C09K 11/06* (2013.01); *C07D 409/10* (2013.01); *C07D 409/14* (2013.01); *H01L 51/0061* (2013.01); *H01L 51/0072* (2013.01); *C09K 2211/1007* (2013.01); *C09K 2211/1011* (2013.01); *C09K 2211/1014* (2013.01); *C09K 2211/1029* (2013.01); *C09K 2211/1092* (2013.01); *H01L 51/0068* (2013.01); *H01L 51/5012* (2013.01); *H01L 51/5048* (2013.01); *H01L 51/5088* (2013.01)
USPC .............................. 428/690; 585/27; 548/444

(58) Field of Classification Search
None
See application file for complete search history.

(56) References Cited

U.S. PATENT DOCUMENTS

| | | | | |
|---|---|---|---|---|
| 6,660,410 | B2 * | 12/2003 | Hosokawa | 428/690 |
| 7,737,627 | B2 | 6/2010 | Hwang et al. | |
| 2002/0045061 | A1 | 4/2002 | Hosokawa | |
| 2003/0170423 | A1 | 9/2003 | Katsumoto et al. | |

(Continued)

FOREIGN PATENT DOCUMENTS

| | | |
|---|---|---|
| CN | 1365381 | 8/2002 |
| CN | 1701111 | 11/2005 |

(Continued)

*Primary Examiner* — J. L. Yang
(74) *Attorney, Agent, or Firm* — McKenna Long & Aldridge LLP

(57) ABSTRACT

The present invention provides a novel compound that is capable of largely improving life span, efficiency, electrochemical stability and thermal stability of the organic light emitting device, and an organic light emitting device in which said compound is included in an organic compound layer.

15 Claims, 1 Drawing Sheet

(56) References Cited

U.S. PATENT DOCUMENTS

| | | | | |
|---|---|---|---|---|
| 2004/0086745 | A1* | 5/2004 | Iwakuma et al. | 428/690 |
| 2005/0221124 | A1 | 10/2005 | Hwang et al. | |
| 2006/0020136 | A1 | 1/2006 | Hwang et al. | |
| 2007/0020483 | A1* | 1/2007 | Park et al. | 428/690 |
| 2007/0049760 | A1 | 3/2007 | Kawakami et al. | |
| 2007/0231503 | A1 | 10/2007 | Hwang et al. | |
| 2008/0124572 | A1 | 5/2008 | Mizuki et al. | |

FOREIGN PATENT DOCUMENTS

| | | | | |
|---|---|---|---|---|
| EP | 1 205 527 | A1 | 5/2002 | |
| EP | 1205527 | A1 * | 5/2002 | C09K 11/06 |
| EP | 2 085 382 | A1 | 8/2009 | |
| JP | 09-310066 | A | 12/1997 | |
| JP | 9-310066 | A | 12/1997 | |
| JP | 2003-133075 | A | 5/2003 | |
| JP | 2004-515506 | | 5/2004 | |
| JP | 2005-048004 | A | 2/2005 | |
| JP | 2005-290000 | A | 10/2005 | |
| JP | 2006-028176 | A | 2/2006 | |
| JP | 2007-110097 | | 4/2007 | |
| JP | 2007-110097 | A | 4/2007 | |
| JP | 2008-078362 | A | 4/2008 | |
| KR | 0573137 | | 4/2006 | |
| TW | 200304937 | | 10/2003 | |
| TW | 200600565 | | 1/2006 | |
| WO | WO 01/72927 | A1 | 10/2001 | |
| WO | WO 03/080760 | A1 | 10/2003 | |
| WO | WO 2005-090512 | A1 | 9/2005 | |
| WO | WO-2005/090512 | A1 * | 9/2005 | C09K 11/06 |
| WO | WO 2006-043647 | A1 | 4/2006 | |
| WO | WO 2008-029729 | A1 | 3/2008 | |
| WO | WO 2008/062636 | A1 | 5/2008 | |

* cited by examiner

COMPOUND AND ORGANIC LIGHT EMITTING DEVICE USING THE SAME

This application is a 35 U.S.C. §371 National Stage entry of International Application No. PCT/KR2008/006588, filed on Nov. 7, 2008, and claims priority to Korean Application No. 10-2007-0113852, filed on Nov. 8, 2007, which are all hereby incorporated by reference in their entireties.

TECHNICAL FIELD

The present invention relates to an organic light emitting device in which a novel compound that is capable of largely improving a life span, efficiency, electrochemical stability and thermal stability of the organic light emitting device is included in an organic compound layer. This application claims priority from Korean Patent Application No. 10-2007-0113852 filed on Nov. 18, 2007, in the KIPO, the disclosure of which is incorporated herein by reference in its entirety.

BACKGROUND ART

An organic light emission phenomenon is an example of a conversion of current into visible rays through an internal process of a specific organic molecule. The organic light emission phenomenon is based on the following mechanism. When organic material layers are interposed between an anode and a cathode, if voltage is applied between the two electrodes, electrons and holes are injected from the cathode and the anode into the organic material layer. The electrons and the holes which are injected into the organic material layer are recombined to form an exciton, and the exciton is reduced to a bottom state to emit light. An organic light emitting device which is based on the above mechanism typiccollectivelyy comprises a cathode, an anode, and organic material layer(s), for example, organic material layers including a hole injection layer, a hole transport layer, a light emitting layer, and an electron transport layer, interposed therebetween.

The materials used in the organic light emitting device are mostly pure organic materials or complexes of organic material and metal. The material used in the organic light emitting device may be classified as a hole injection material, a hole transport material, a light emitting material, an electron transport material, or an electron injection material, according to its use. In connection with this, an organic material having a p-type property, which is easily oxidized and is electrochemiccollectivelyy stable when it is oxidized, is mostly used as the hole injection material or the hole transport material. Meanwhile, an organic material having an n-type property, which is easily reduced and is electrochemiccollectivelyy stable when it is reduced, is used as the electron injection material or the electron transport material. As the light emitting layer material, an organic material having both p-type and n-type properties is preferable, which is stable when it is oxidized and when it is reduced. Also a material having high light emission efficiency for conversion of the exciton into light when the exciton is formed is preferable.

In addition, it is preferable that the material used in the organic light emitting device further have the following properties.

First, it is preferable that the material used in the organic light emitting device have excellent thermal stability. The reason is that joule heat is generated by movement of electric charges in the organic light emitting device. NPB, which has recently been used as the hole transport layer material, has a glass transition temperature of 100° C. or lower, thus it is difficult to apply to an organic light emitting device requiring a high current.

Second, in order to produce an organic light emitting device that is capable of being actuated at low voltage and has high efficiency, holes and electrons which are injected into the organic light emitting device must be smoothly transported to a light emitting layer, and must not be released out of the light emitting layer. To achieve this, a material used in the organic light emitting device must have a proper band gap and a proper HOMO or LUMO energy levels. A LUMO energy level of PEDOT:PSS, which is currently used as a hole transport material of an organic light emitting device produced using a solution coating method, is lower than that of an organic material used as a light emitting layer material, thus it is difficult to produce an organic light emitting device having high efficiency and a long lifespan.

Moreover, the material used in the organic light emitting device must have excellent chemical stability, electric charge mobility, and interfacial characteristic with an electrode or an adjacent layer. That is to say, the material used in the organic light emitting device must be little deformed by moisture or oxygen. Furthermore, proper hole or electron mobility must be assured so as to balance densities of the holes and of the electrons in the light emitting layer of the organic light emitting device to maximize the formation of excitons. Additionally, it has to be able to have a good interface with an electrode including metal or metal oxides so as to assure stability of the device.

Accordingly, there is a need to develop an organic material having the above-mentioned requirements in the art.

DISCLOSURE

Technical Problem

Therefore, the present inventors aim to provide an organic light emitting device that includes a hetero compound derivative which is capable of satisfying conditions required of a material which may be used for an organic light emitting device, for example, a proper energy level, electrochemical stability, and thermal stability, and which has a chemical structure capable of playing various roles required for the organic light emitting device, depending on a substituent group.

Technical Solution

The present invention provides a compound of the following Formula 1.

In addition, the present invention provides an organic light emitting device which comprises a first electrode, organic material layer(s) having one or more layers and comprising a light emitting layer, and a second electrode, wherein the first electrode, the organic material layer(s), and the second electrode form a layered structure and at least one layer of the organic material layer(s) includes a compound of the following Formula 1 or a compound of Formula 1 into which a thermosetting or photo-crosslinkable functional group is introduced.

[Formula 1]

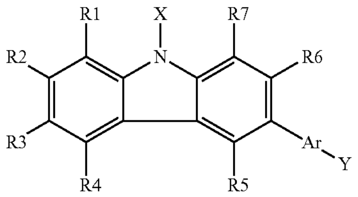

wherein X is $-(A)_m-(B)_n$,

Y is $-(B)_p$,

Ar is an arylene group having 6 to 40 carbon atoms, which is substituted or unsubstituted with one or more substituent groups selected from the group consisting of nitro, nitrile, halogen, an alkyl group, an alkoxy group and an amino group; or a divalent hetero ring group, which is substituted or unsubstituted with one or more substituent groups selected from the group consisting of nitro, nitrile, halogen, an alkyl group, an alkoxy group and an amino group;

A is an aryl group, which is substituted or unsubstituted with one or more substituent groups selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted hetero ring group, a nitrile group and an acetylene group, B is an arylamine group, which is substituted or unsubstituted with one or more substituent groups selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted hetero ring group, a nitrile group and an acetylene group; or a hetero ring group including O, N or S as a heteroatom, which is substituted or unsubstituted with one or more substituent groups selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted hetero ring group, a nitrile group and an acetylene group, m and n are an integer in the range of 1 to 10 and an integer in the range of 0 to 10, respectively, p is an integer in the range of 1 to 10, and R1 to R7 are each independently selected from the group consisting of hydrogen; an alkyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a nitrile group and an acetylene group; an alkoxy group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a nitrile group and an acetylene group; an aryl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a nitrile group and an acetylene group; an amino group, which is substituted with one or more substituent groups selected from the group consisting of an alkyl group, an alkenyl group, a substituted or unsubstituted aryl group, a substituted or unsubstituted arylalkyl group, and a substituted or unsubstituted arylalkenyl group; a nitro group; and a halogen group, and said R1 to R7 may form an aliphatic or hetero condensation ring in conjunction with adjacent groups.

Advantageous Effects

A compound according to the present invention may be used as an organic material layer material, particularly, a hole injection material and/or a hole transport material in an organic light emitting device, and in the case of when it is used in the organic light emitting device, a driving voltage of the device may be reduced, light efficiency may be improved, and a life span property of the device may be improved because of thermal stability of the compound.

BEST MODE

Figure 1:
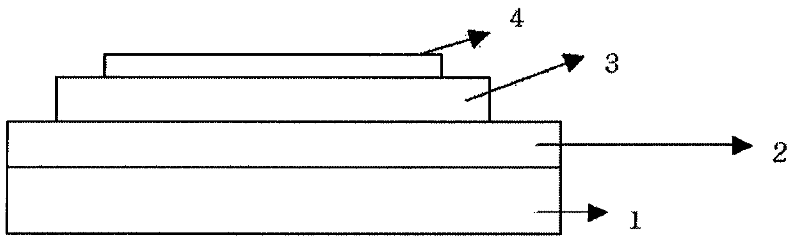
FIG. 1 illustrates an organic light emitting device comprising a substrate 1, an anode 2, a light emitting layer 3, and a cathode 4.
Figure 2:
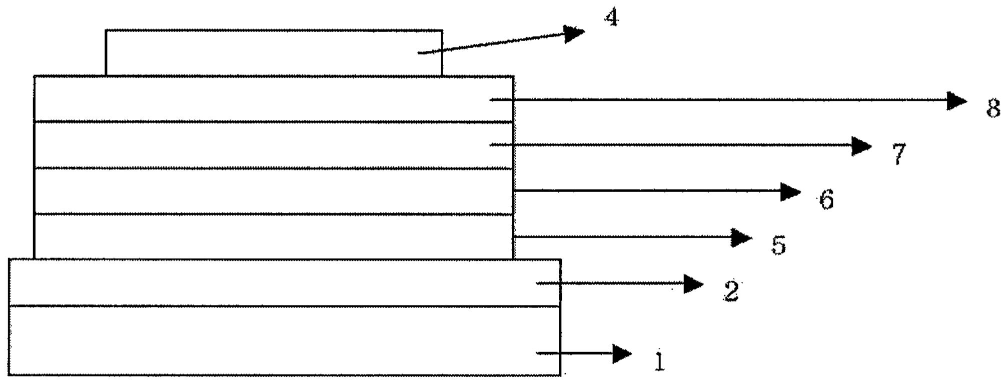
FIG. 2 illustrates an organic light emitting device comprising a substrate 1, an anode 2, a hole injection layer 5, a hole transport layer 6, a light emitting layer 7, an electron transport layer 8, and a cathode 4.

A substituent group of Formula 1 will be described in detail below.

In R1 to R7 of Formula 1, the number of carbon atoms of the alkyl group, the alkoxy group, and the alkenyl group is not particularly limited, but it is preferable that it is in the range of 1 to 20.

The length of the alkyl group that is included in the compound does not affect the conjugation length of the compound, but may auxiliarily affect an application method of the compound to the organic light emitting device, for example, the application of a vacuum deposition method or a solution coating method.

Illustrative, but non-limiting, examples of the aryl group of R1 to R7 of Formula 1 include monocyclic aromatic rings, such as a phenyl group, a biphenyl group, a terphenyl group, and a stilbene group, and multicyclic aromatic rings, such as a naphthyl group, an anthracenyl group, a phenanthrene group, a pyrenyl group, and a perylenyl group.

Illustrative, but non-limiting, examples of the hetero ring group of R1 to R7 of Formula 1 include a thiophenyl group, a furan group, a pyrrolyl group, an imidazolyl group, a thiazolyl group, an oxazolyl group, an oxadiazolyl group, a triazolyl group, a pyridyl group, a pyradazine group, a quinolinyl group, an isoquinoline group, and an acridyl group.

A of Formula 1 is an aryl group, and preferably, illustrative, but non-limiting, examples thereof include monocyclic aromatic rings, such as a phenyl group, a biphenyl group, a terphenyl group, and a stilbene group, and multicyclic aromatic rings, such as a naphthyl group, an anthracenyl group, a phenanthrene group, a pyrenyl group, and a perylenyl group.

In the case of when B of Formula 1 is a hetero ring, preferably, illustrative, but non-limiting, examples thereof include a thiophenyl group, a furan group, a pyrrolyl group, an imidazolyl group, a thiazolyl group, an oxazolyl group, an oxadiazolyl group, a triazolyl group, a pyridyl group, a pyradazine group, a quinolinyl group, an isoquinoline group, and an acridyl group.

The compound that is represented by Formula 1 may be preferably a compound that is represented by any one of the following Formula 2 and Formula 3.

[Formula 2]

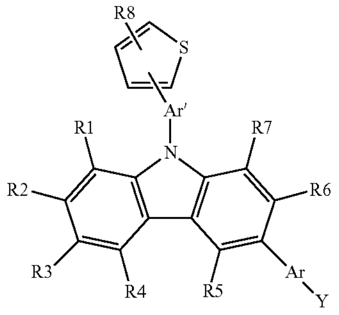

[Formula 3]

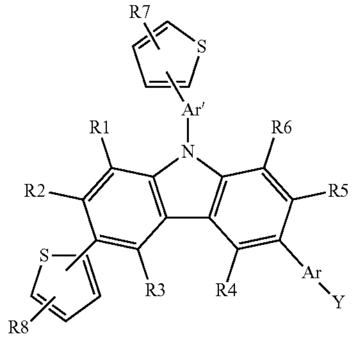

In Formula 2 and Formula 3, Ar's are each independently selected from the group consisting of a phenyl group, a biphenyl group, a terphenyl group, a stilbene group, a naphthyl group, an anthracenyl group, a phenanthrene group, a pyrenyl group, a perylenyl group, and Ar, Y and R1 to R8 are the same as definitions in respects to Ar, Y and R1 to R7 of Formula 1.

In addition, the compound that is represented by Formula 1 may be preferably a compound that is represented by any one of the following Formula 2-1 and Formula 3-1.

[Formula 2-1]

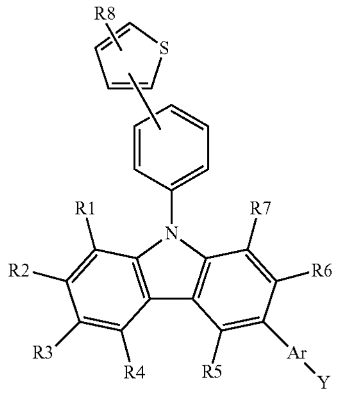

[Formula 3-1]

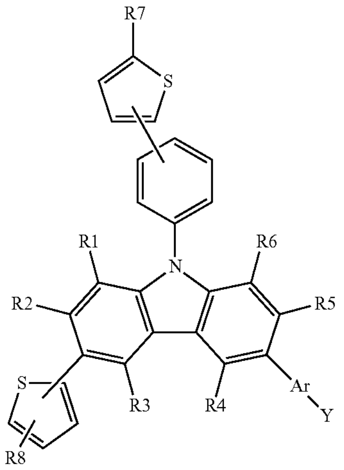

In Formula 2-1 and Formula 3-1, Ar, Y and R1 to R8 are the same as definitions in respects to Ar, Y and R1 to R7 of Formula 1.

In addition, the compound that is represented by Formula 1 may be preferably a compound that is represented by any one of the following Formula 2-2 and Formula 3-2.

[Formula 2-2]

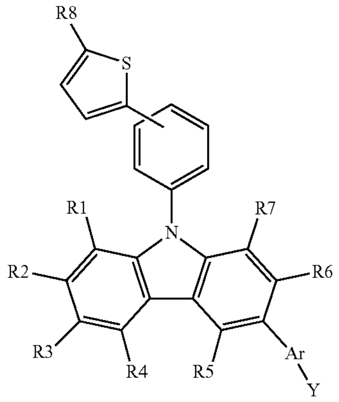

-continued
[Formula 3-2]
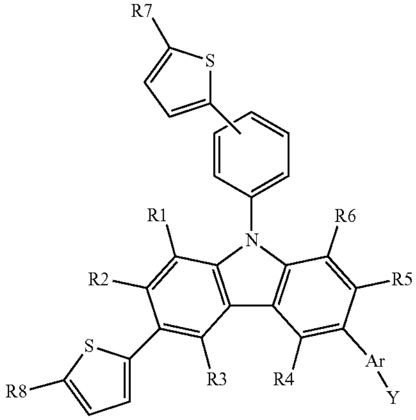
In Formula 2-2 and Formula 3-2, Ar, Y and R1 to R8 are the same as definitions in respects to Ar, Y and R1 to R7 of Formula 1.
In addition, in the case of arylamine, illustrative, but non-limiting examples thereof may preferably include the following groups.
1
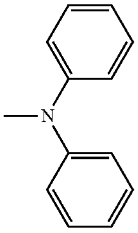
2
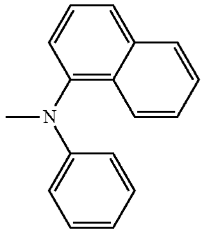
3
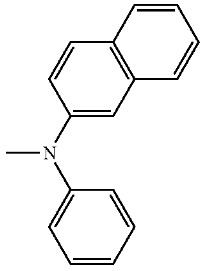
-continued
4
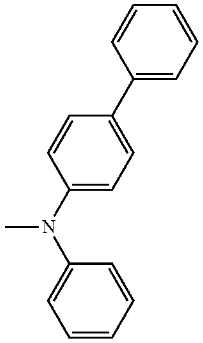
5
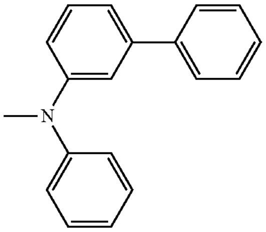
6
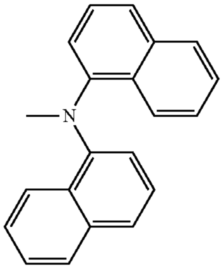
7
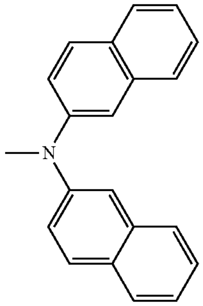
8
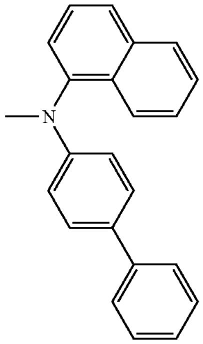

-continued
9
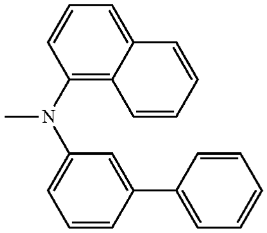
10
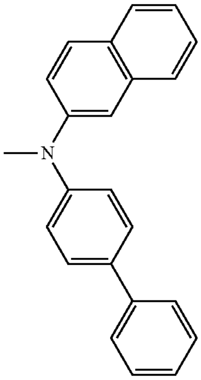
11
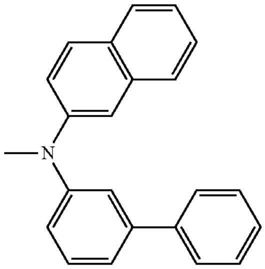
12
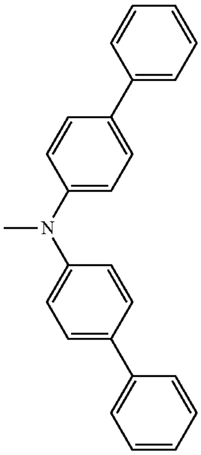
-continued
13
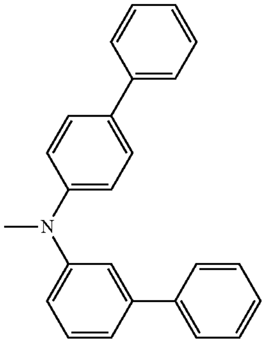
14
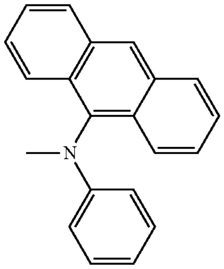
15
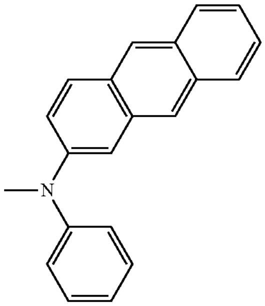
16
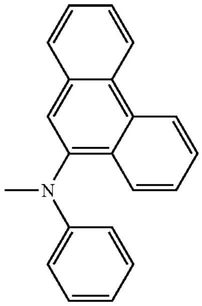
17
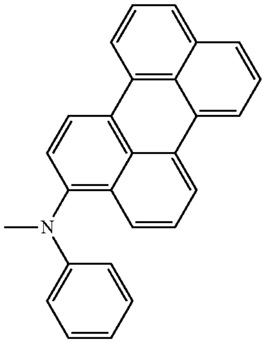

-continued
18
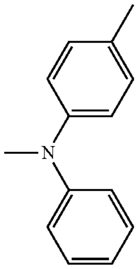
19
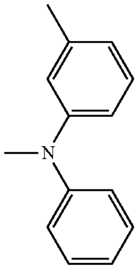
20
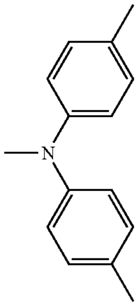
21
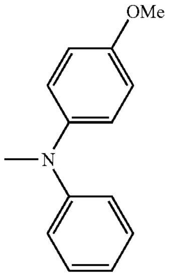
22
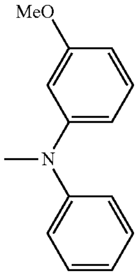
-continued
23
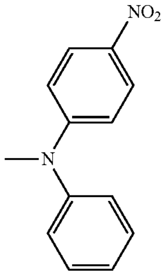
24
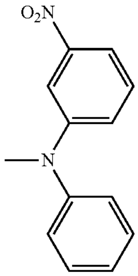
25
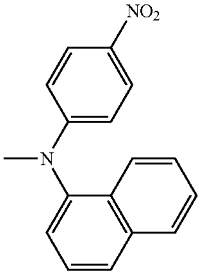
26
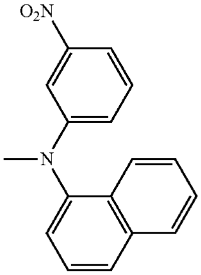
27
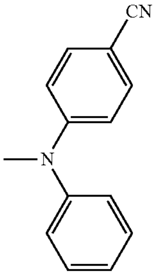

-continued
28
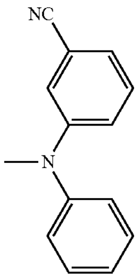
29
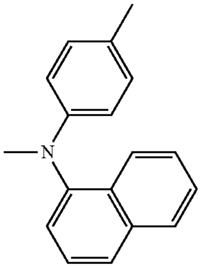
30
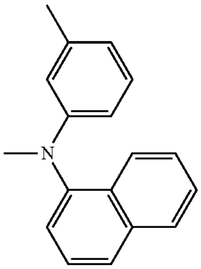
31
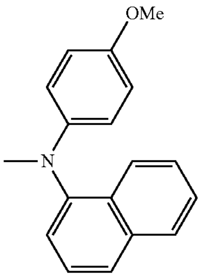
32
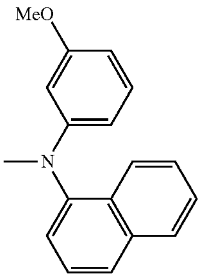
-continued
33
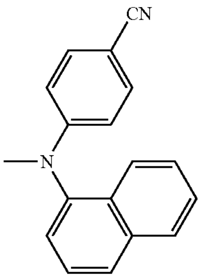
34
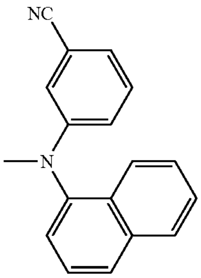
35
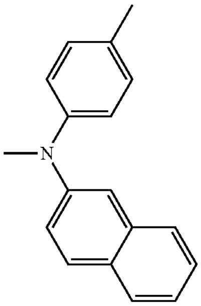
36
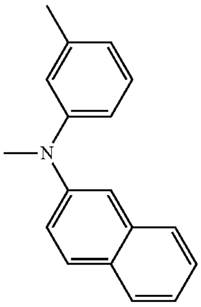
37
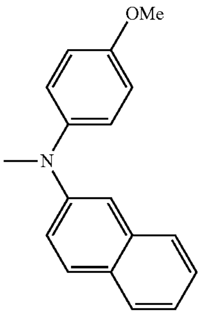

-continued
38
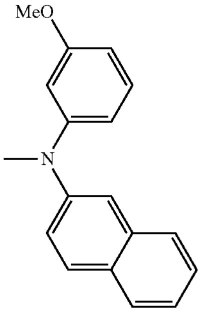
39
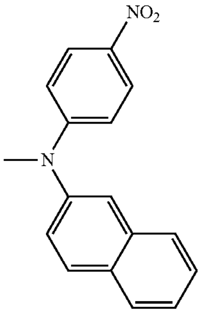
40
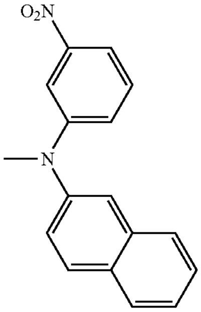
41
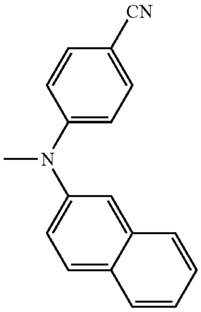
42
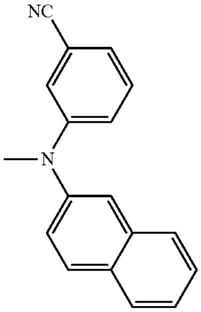
-continued
43
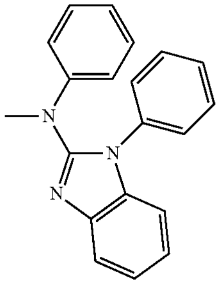
44
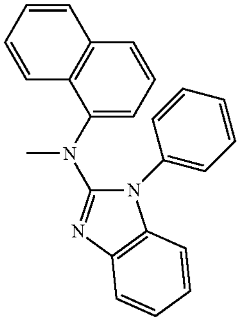
45
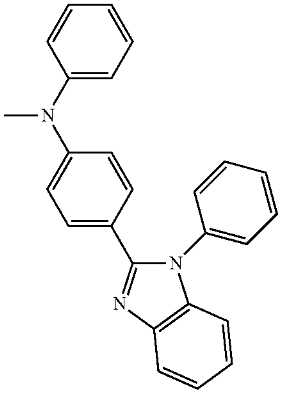
46
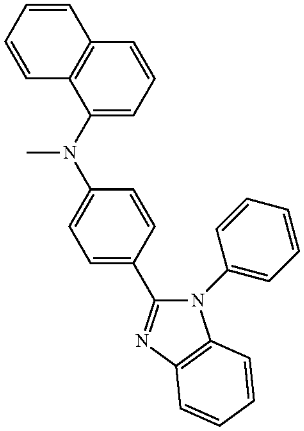

-continued
47
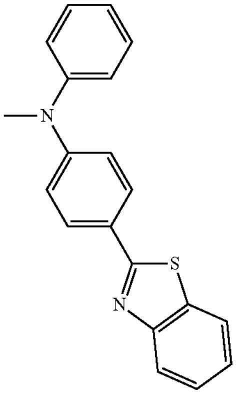
48
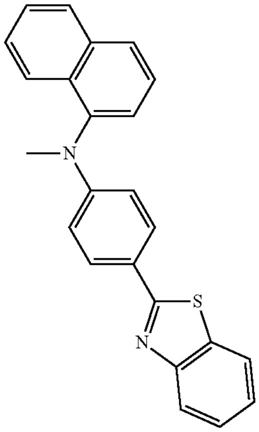
49
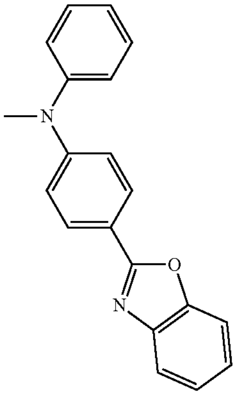
-continued
50
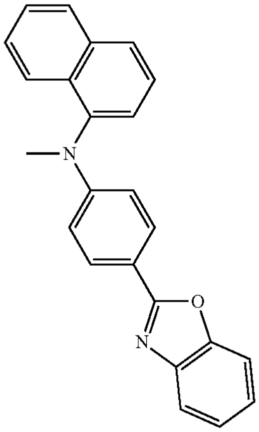
51
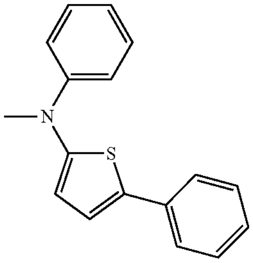
52
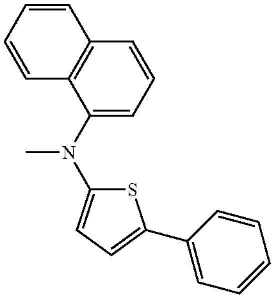
53
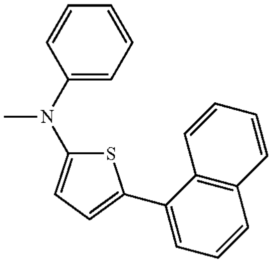
54
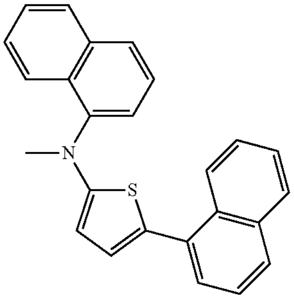

-continued
55
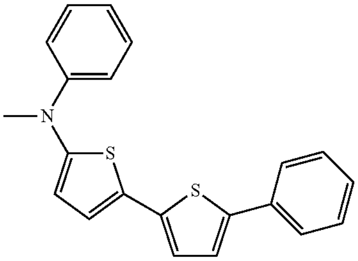
56
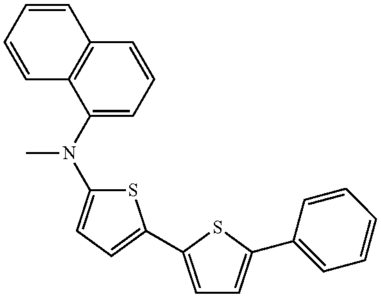
57
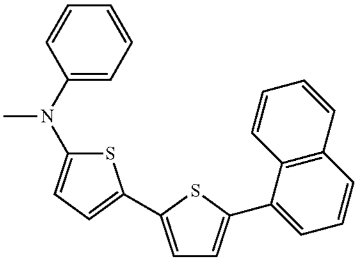
58
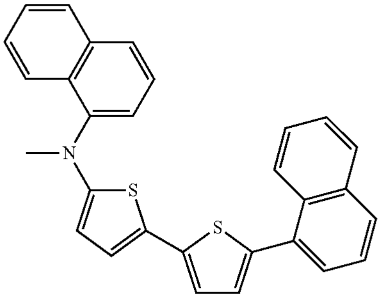
59
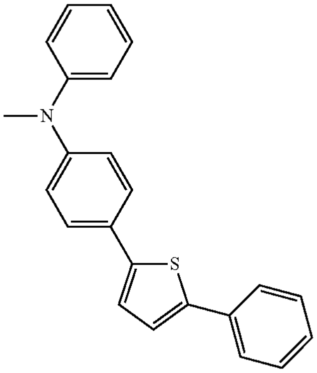
-continued
60
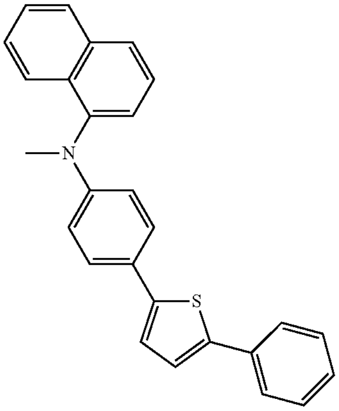
61
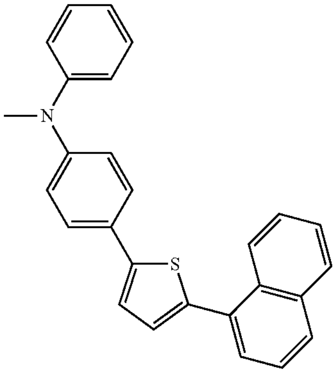
62
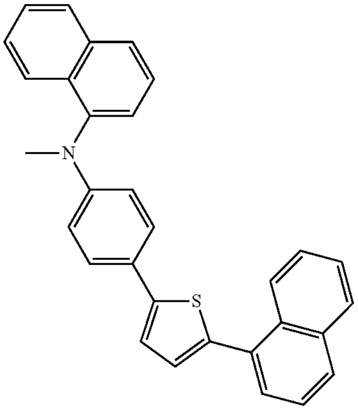
63
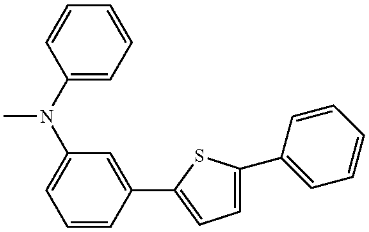

-continued
64
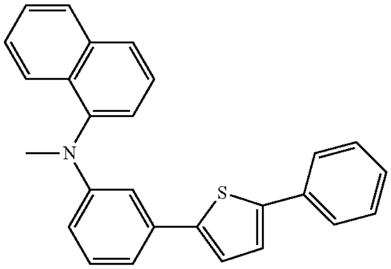
65
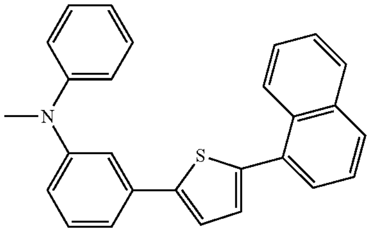
66
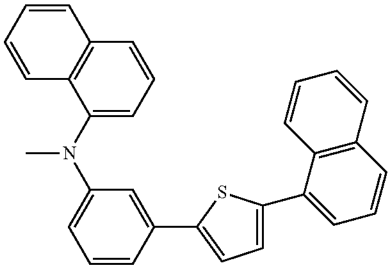
67
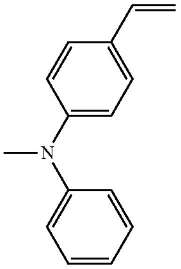
68
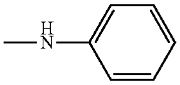
69
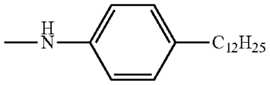
-continued
70
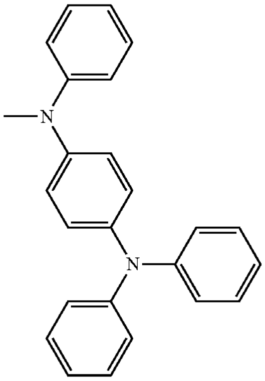
71
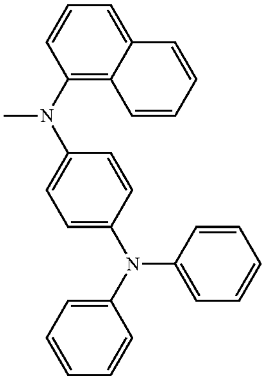
72
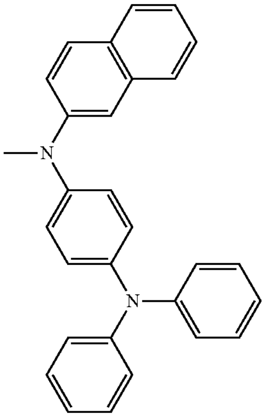

-continued
73
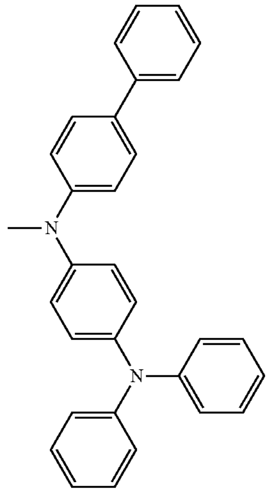
74
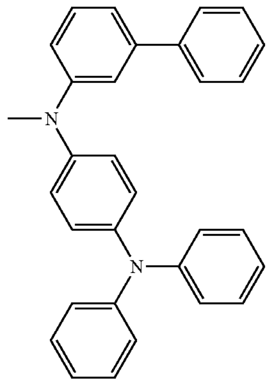
75
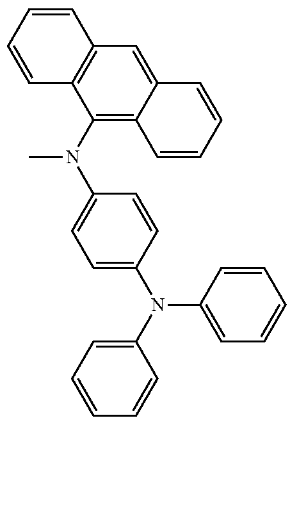
-continued
76
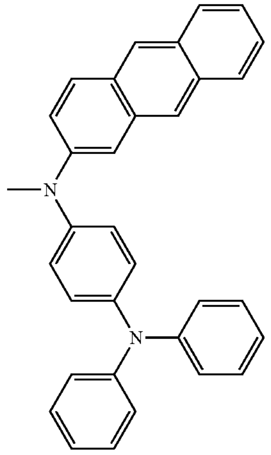
77
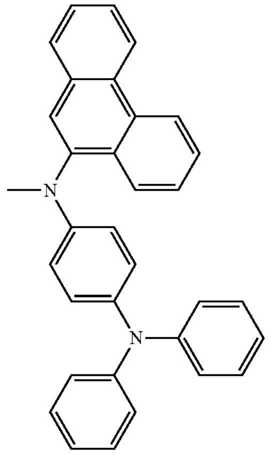
78
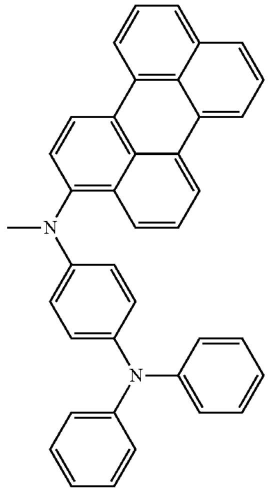

-continued
79
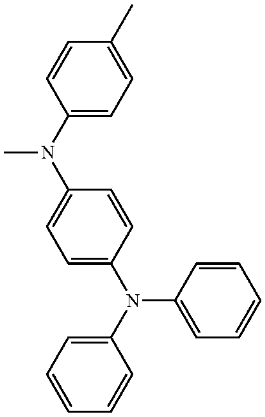
80
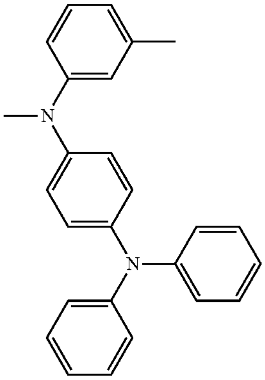
81
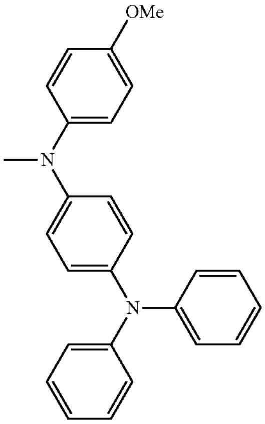
82
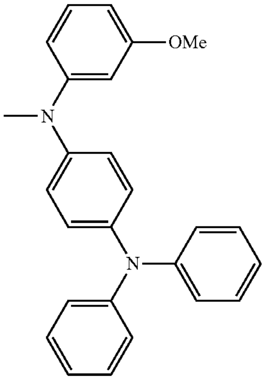
-continued
83
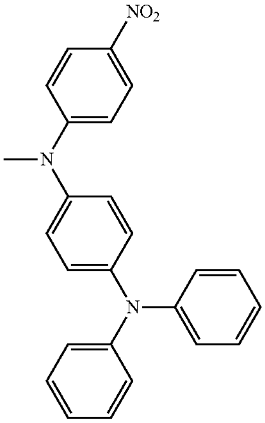
84
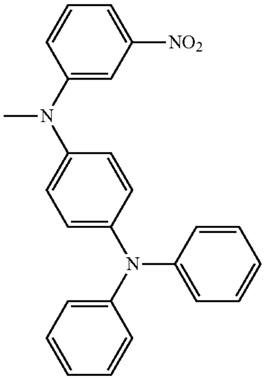
85
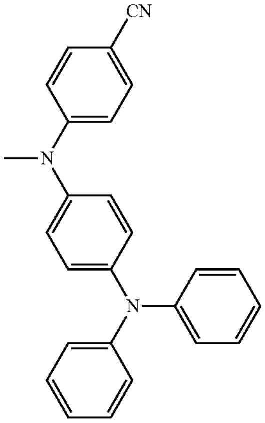
86
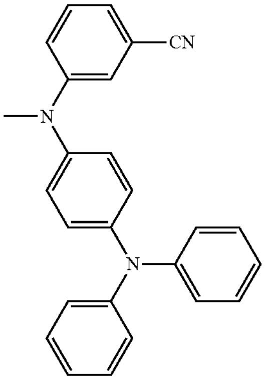

-continued
87
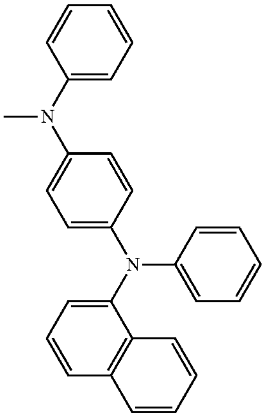
88
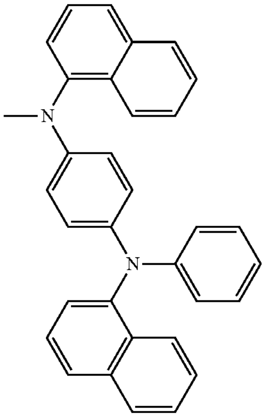
89
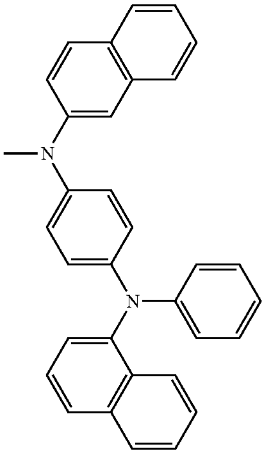
-continued
90
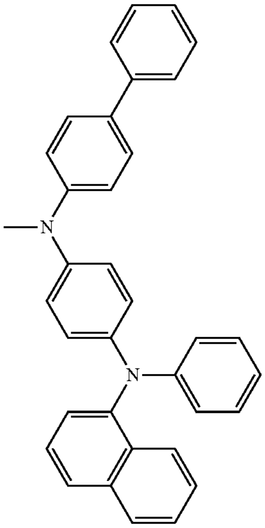
91
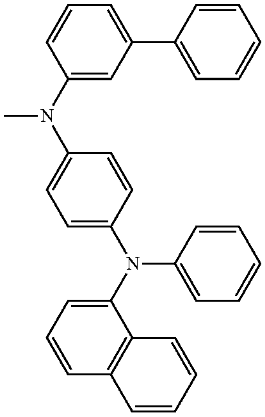
92
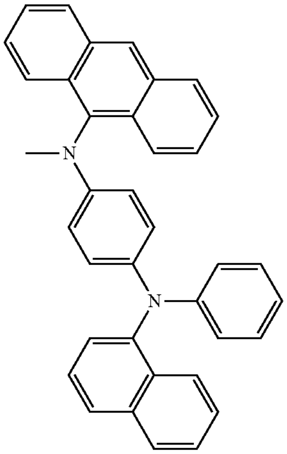

-continued
93
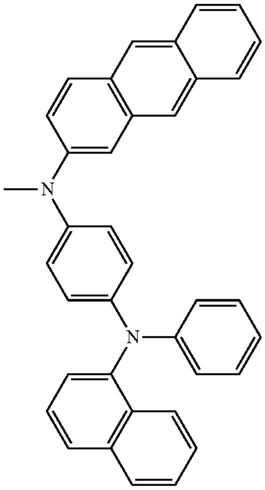
94
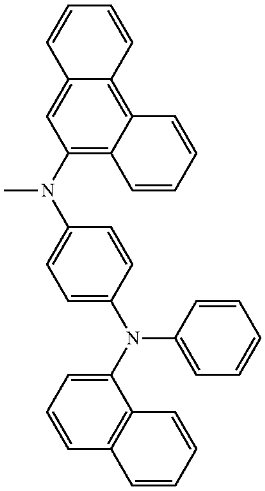
95
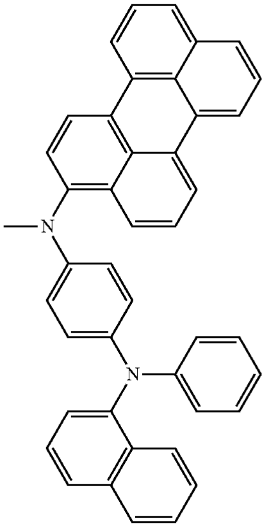
-continued
96
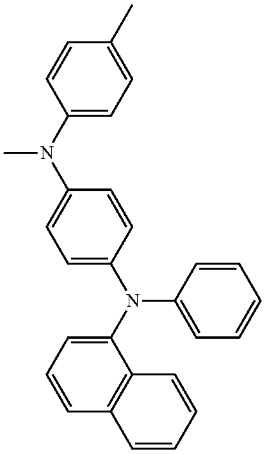
97
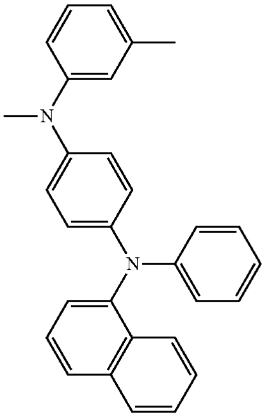
98
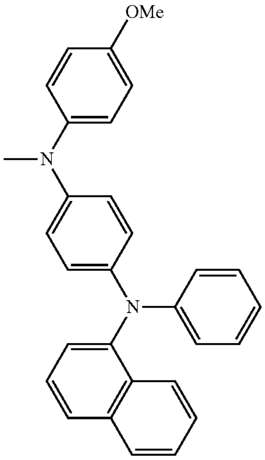

-continued
99
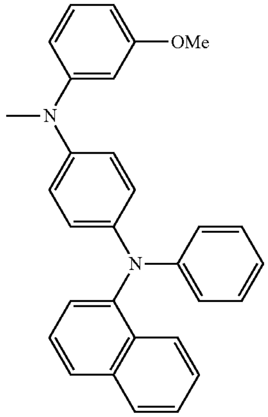
100
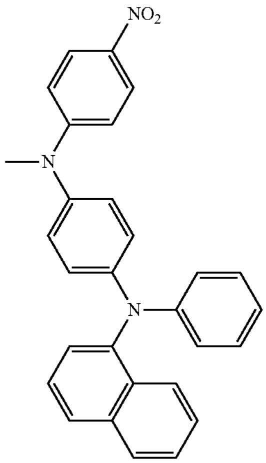
101
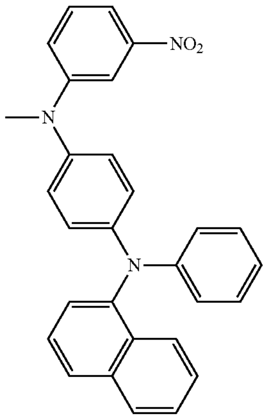
-continued
102
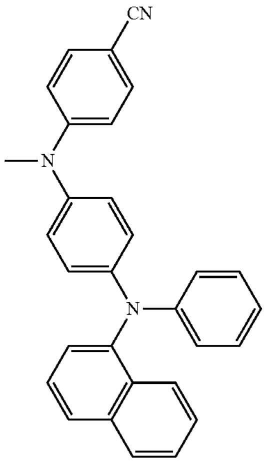
103
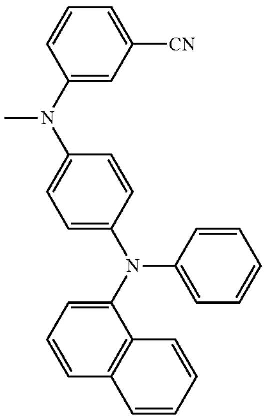
104
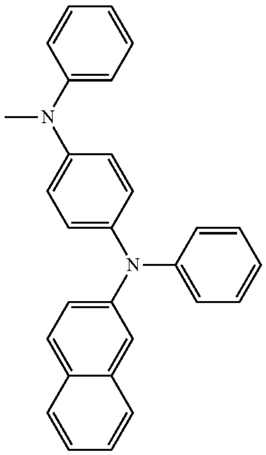

-continued
105
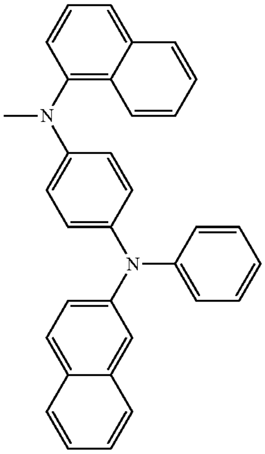
106
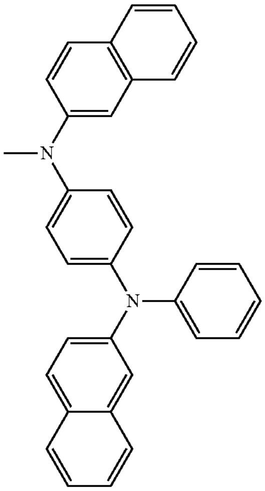
107
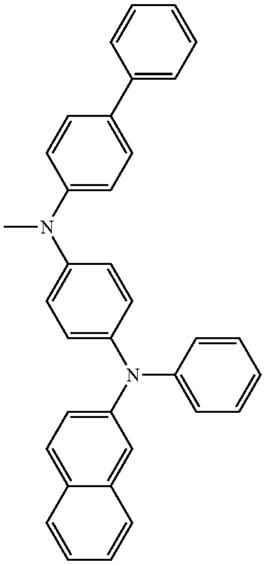
-continued
108
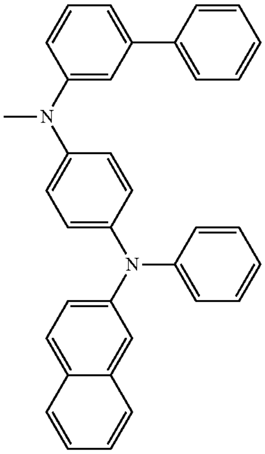
109
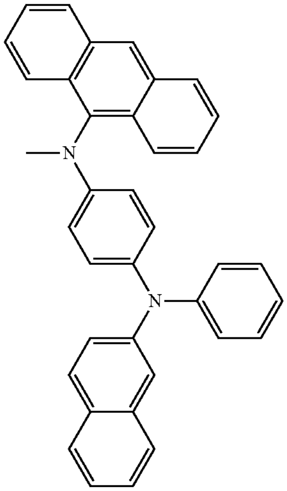
110
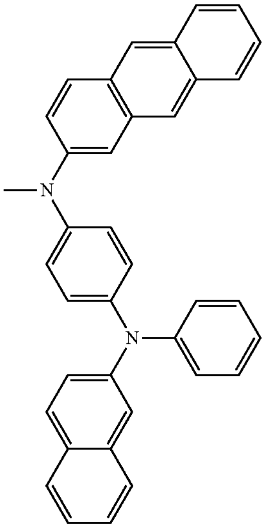

-continued
111
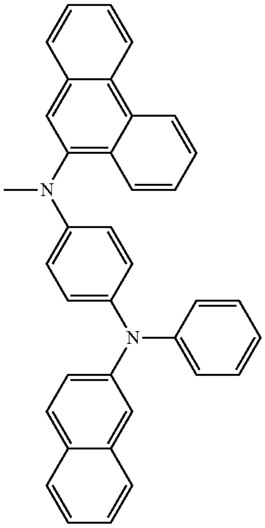
112
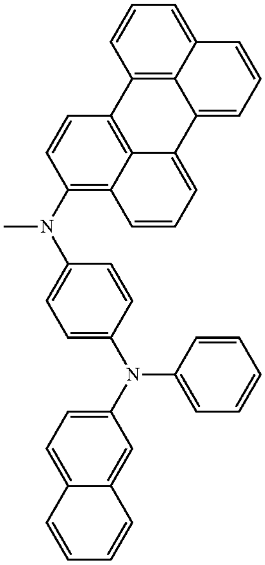
113
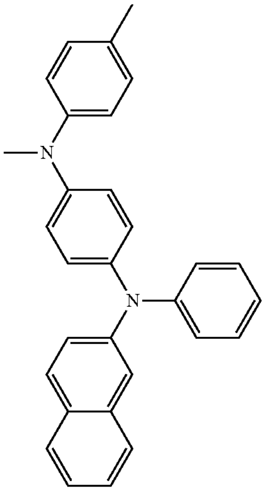
-continued
114
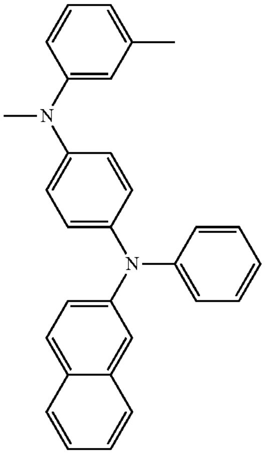
115
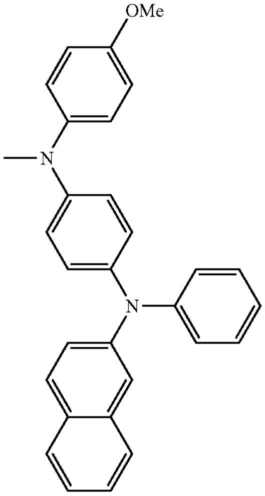
116
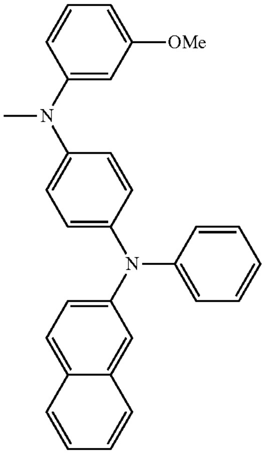

-continued
117
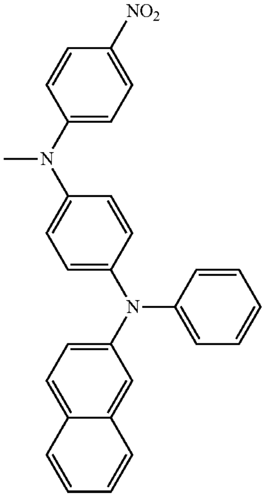
118
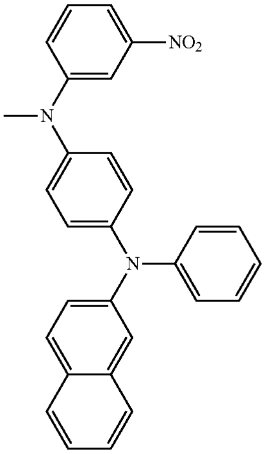
119
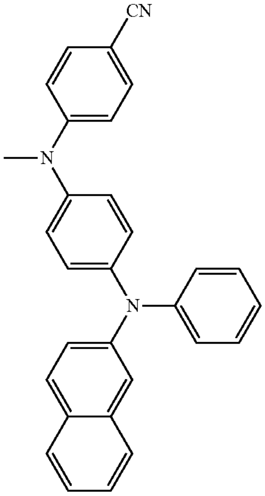
-continued
120
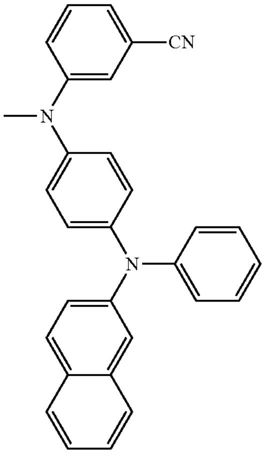
121
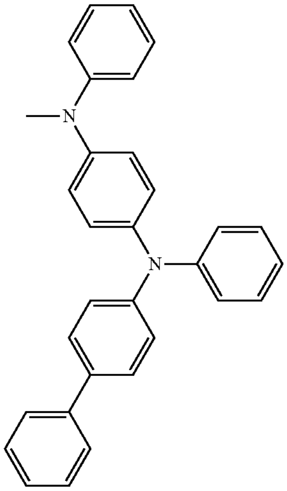
122
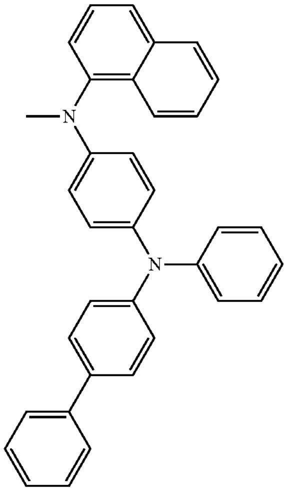

-continued
123
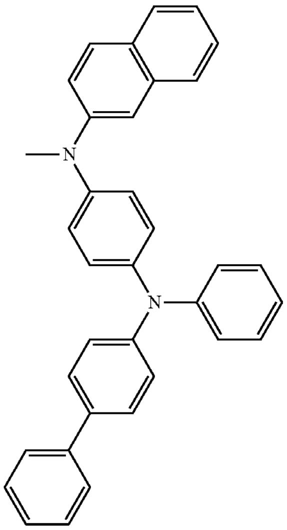
124
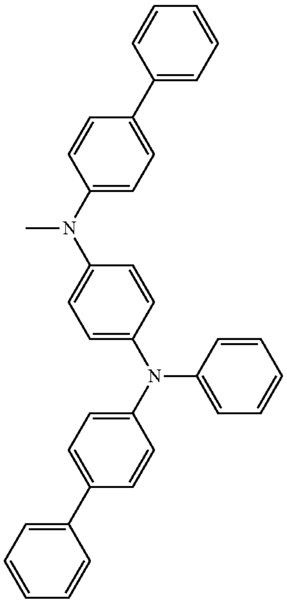
125
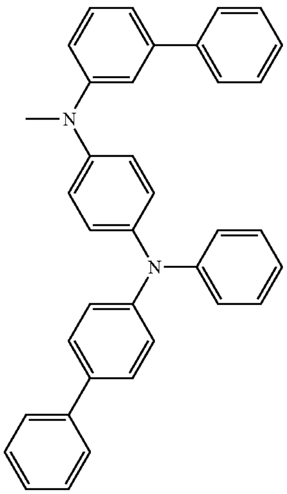
-continued
126
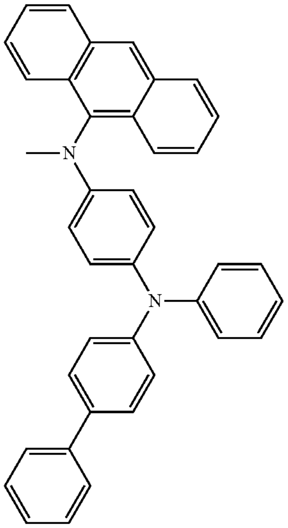
127
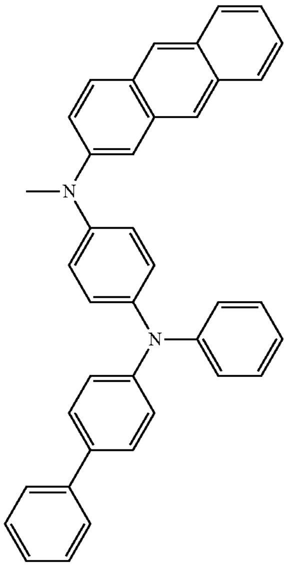
128
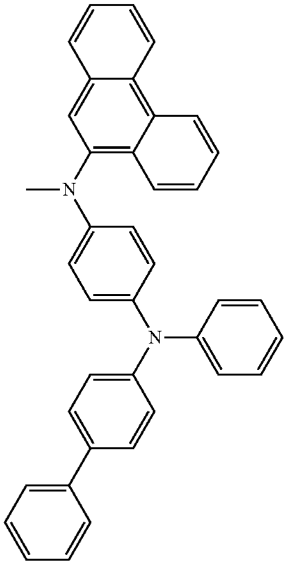

-continued
129
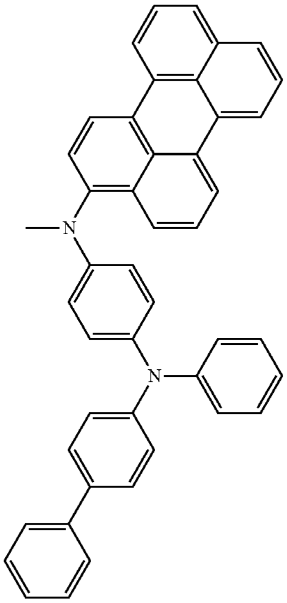
130
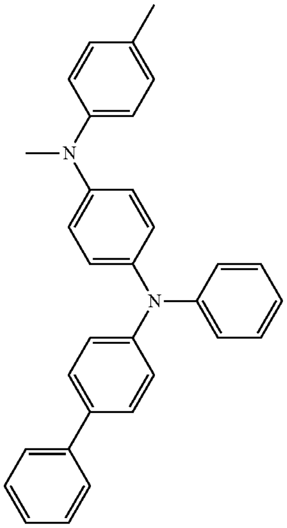
131
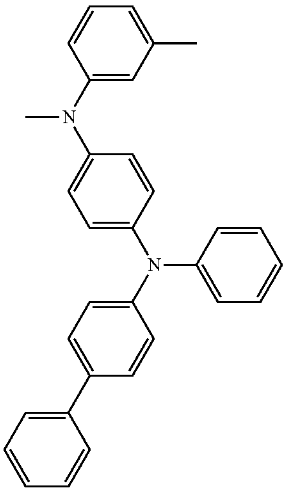
-continued
132
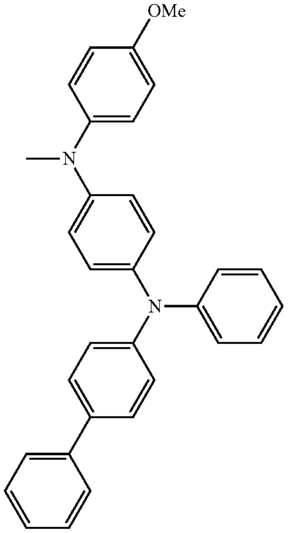
133
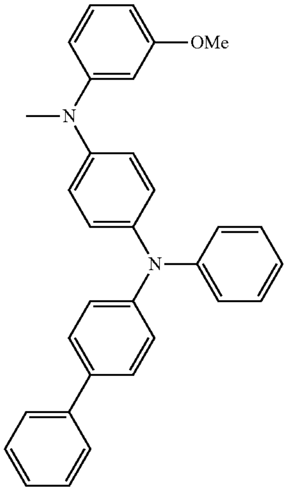
134
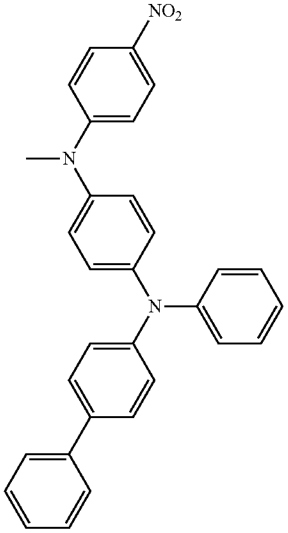

-continued
135
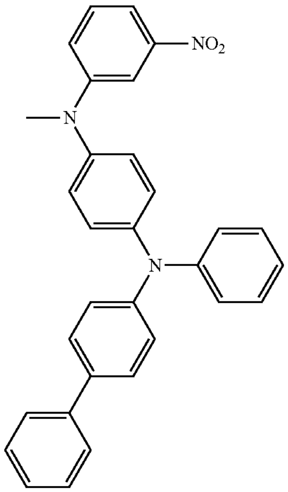
136
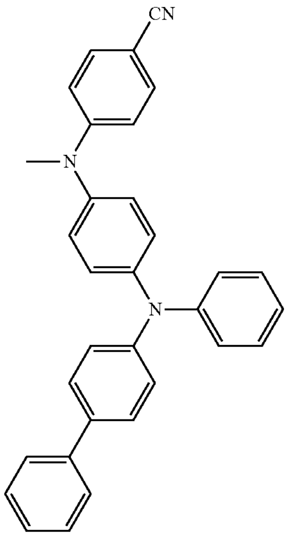
137
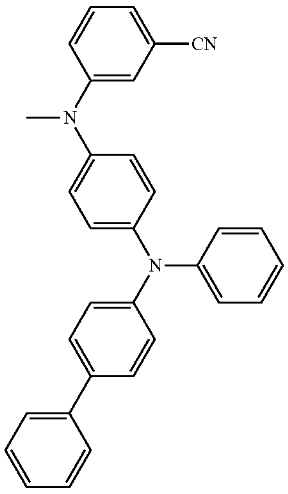
-continued
138
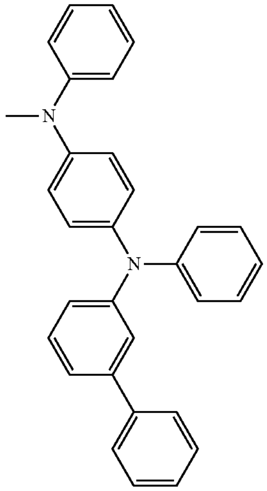
139
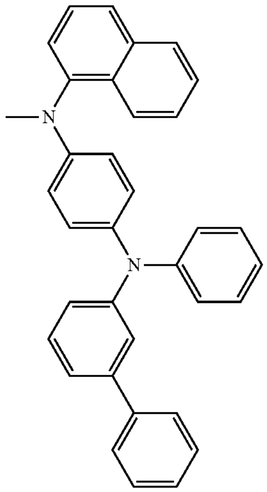
140
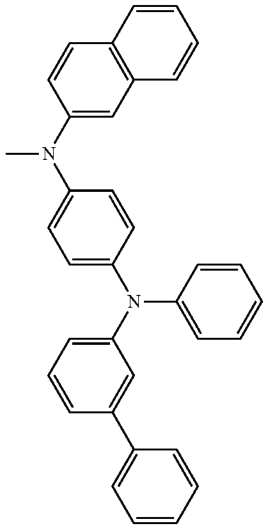

-continued
141
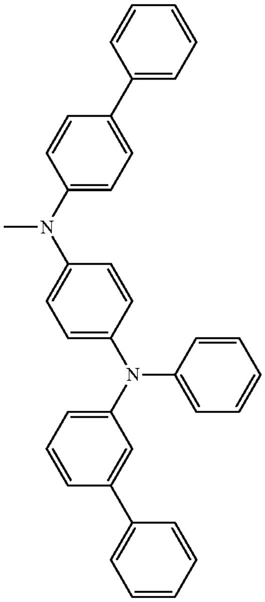
142
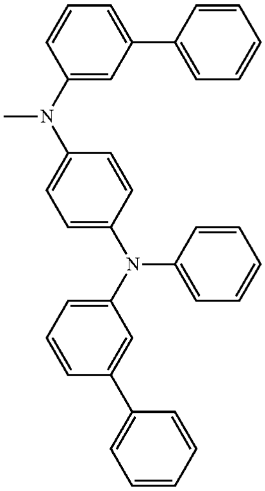
143
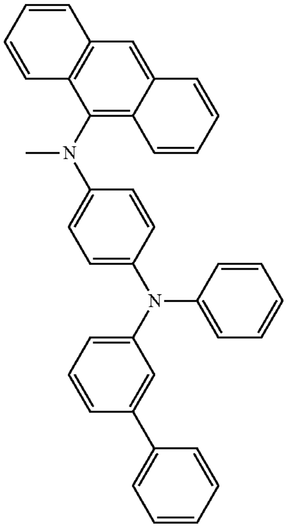
-continued
144
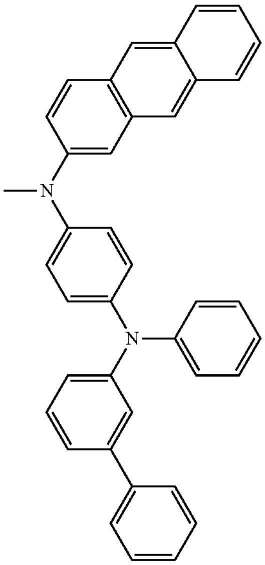
145
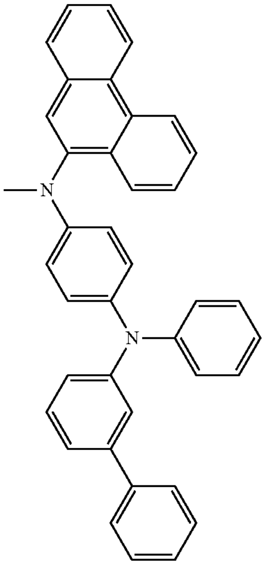

-continued
146
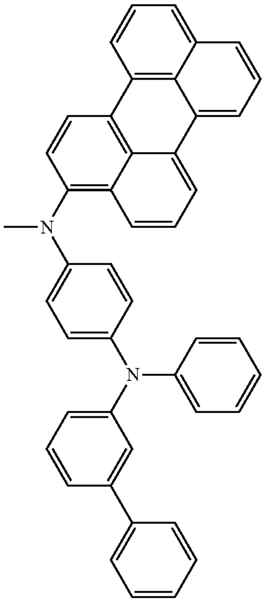
147
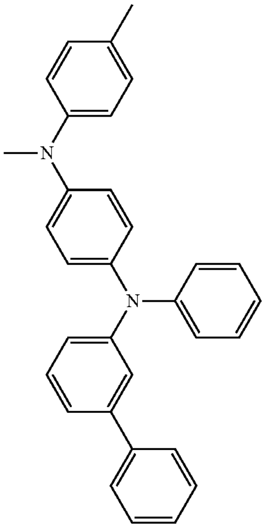
148
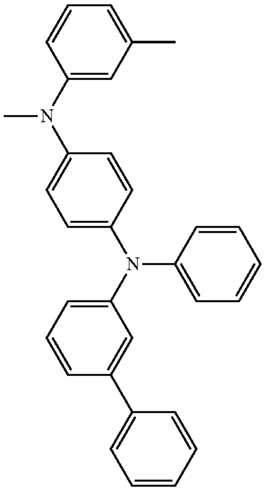
-continued
149
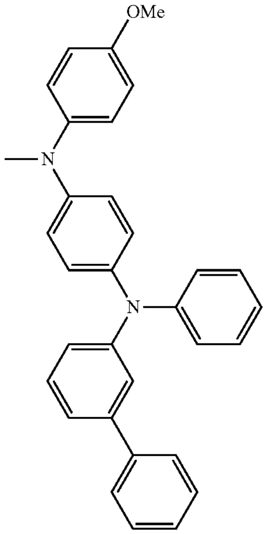
150
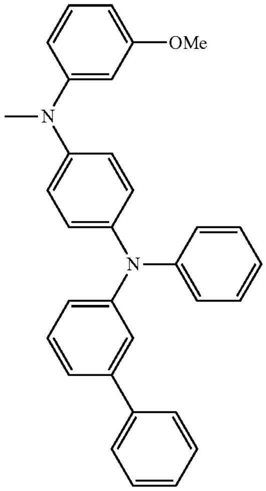
151
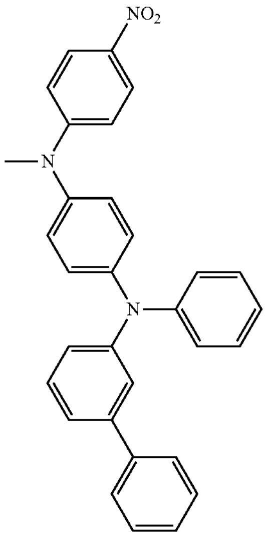

-continued
152
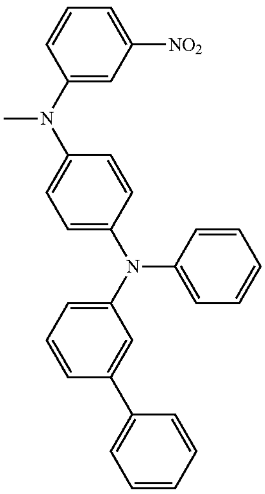
153
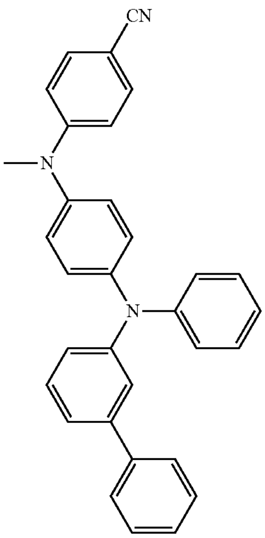
154
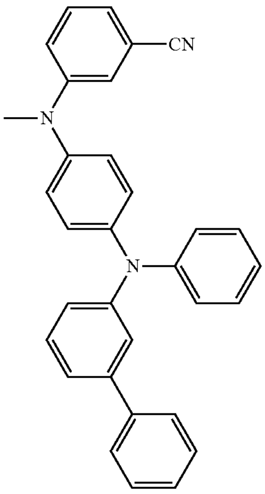
-continued
155
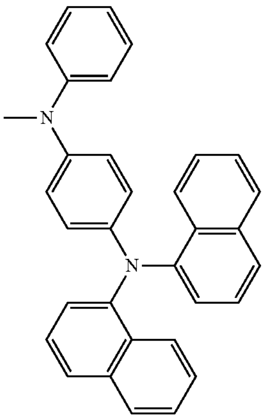
156
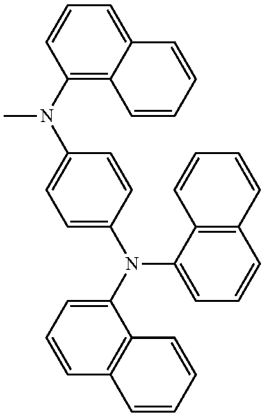
157
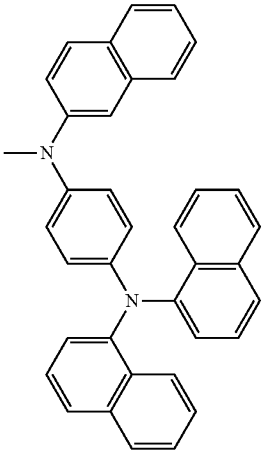

-continued
158
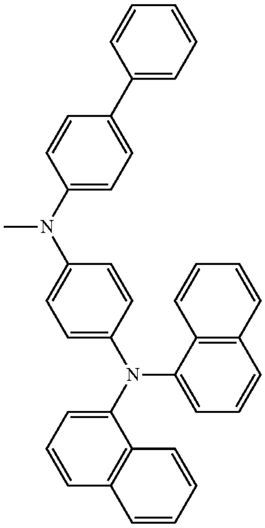
159
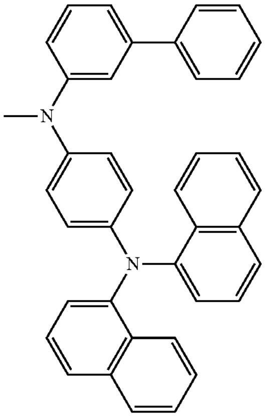
160
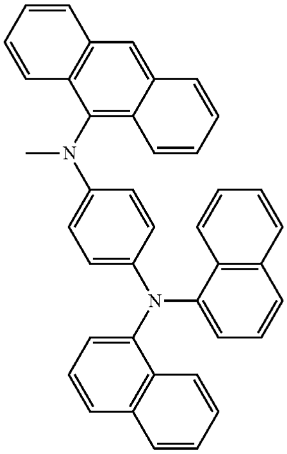
-continued
161
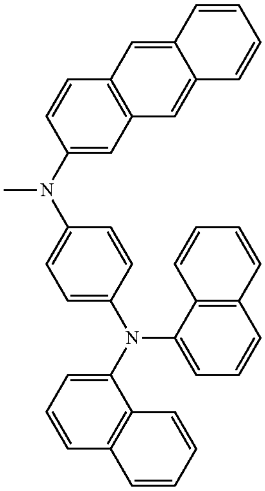
162
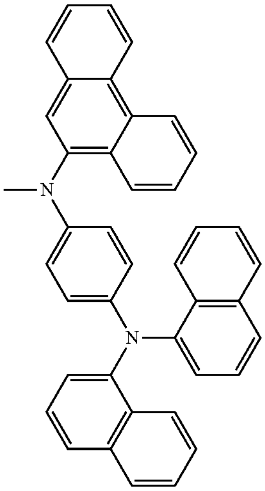
163
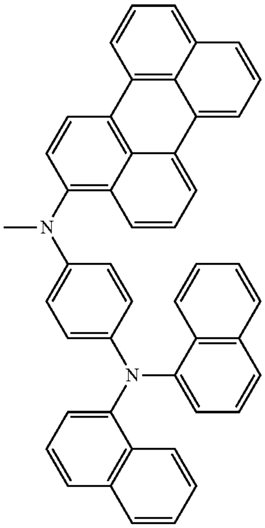

-continued
164
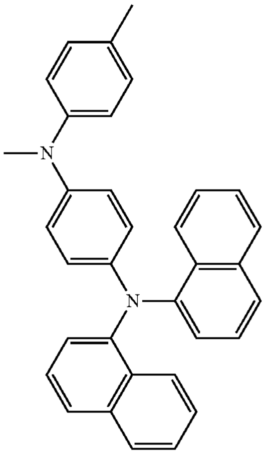
165
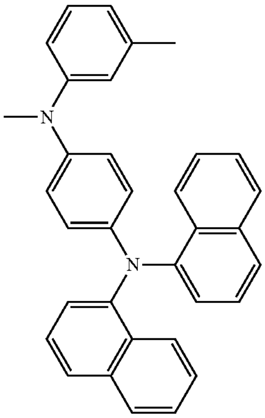
166
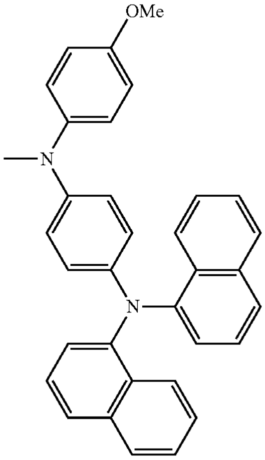
-continued
167
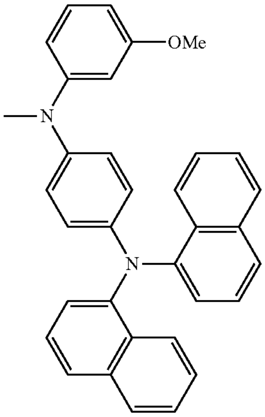
168
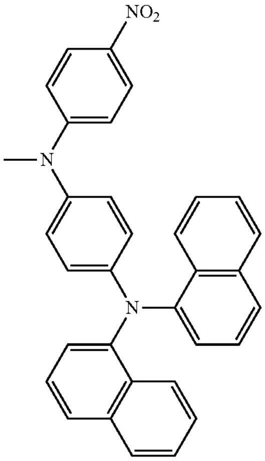
169
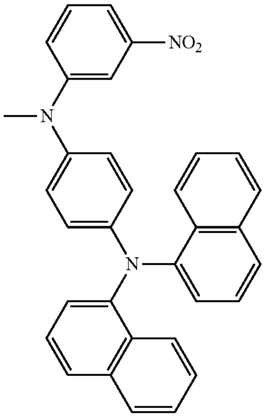

-continued
170
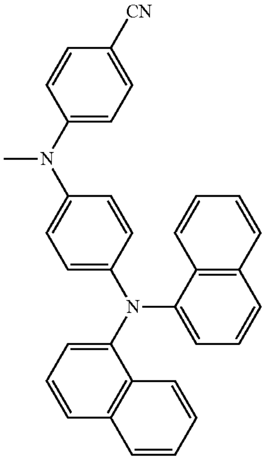
171
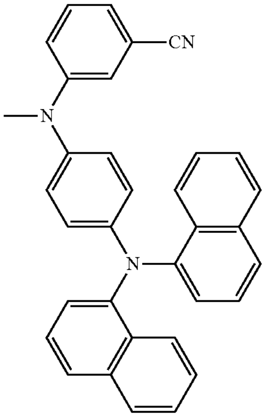
172
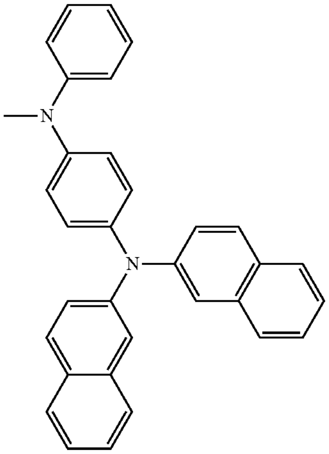
-continued
173
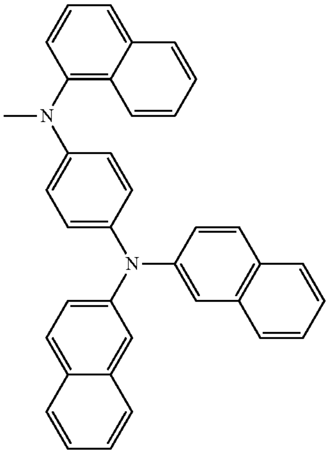
174
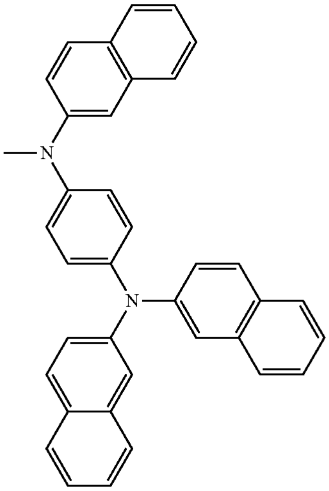
175
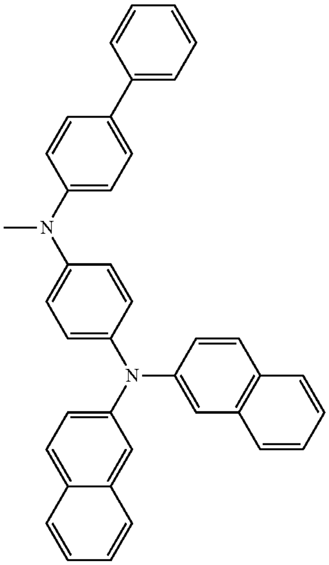

-continued
176
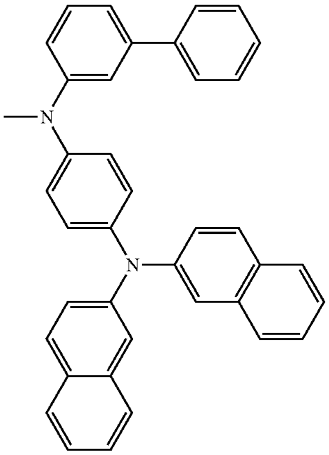
177
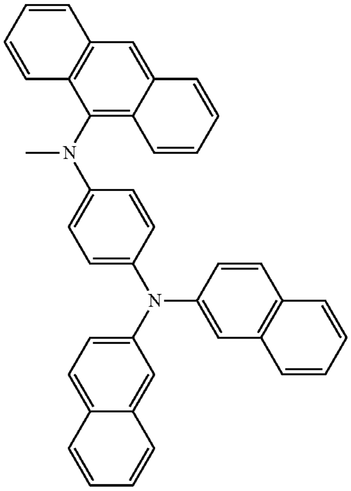
178
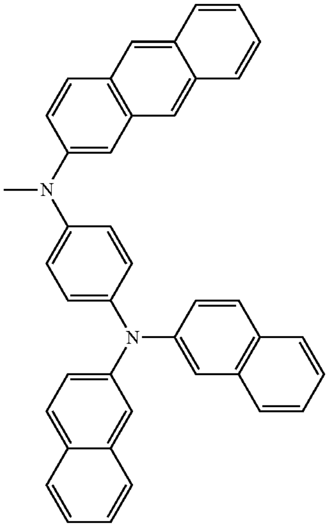
-continued
179
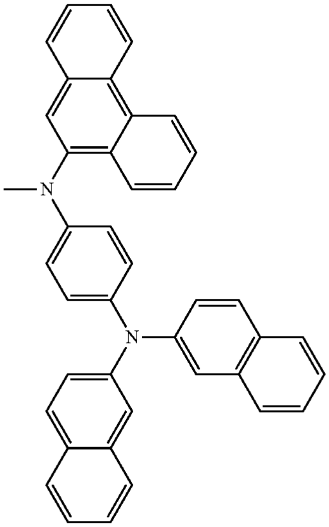
180
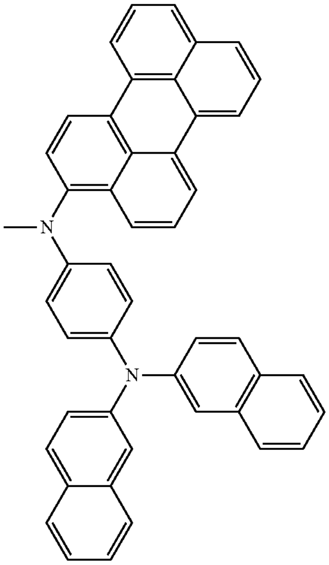
181
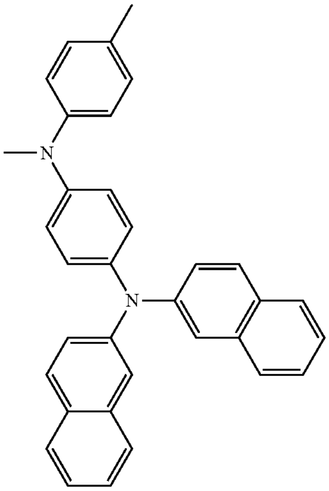

-continued
182
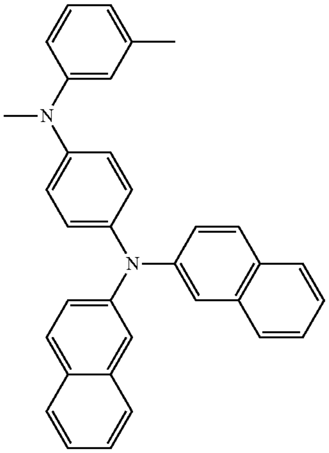
183
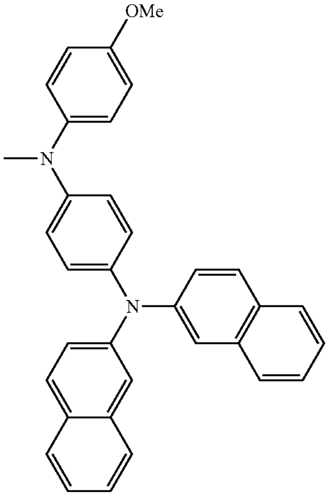
184
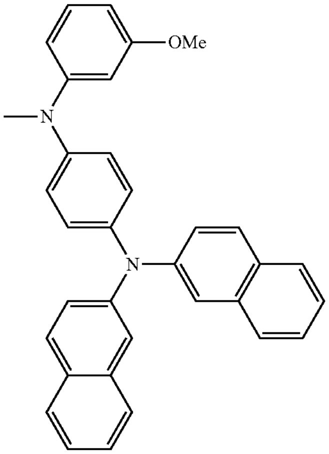
-continued
185
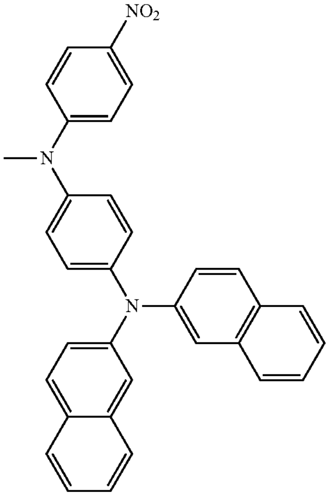
186
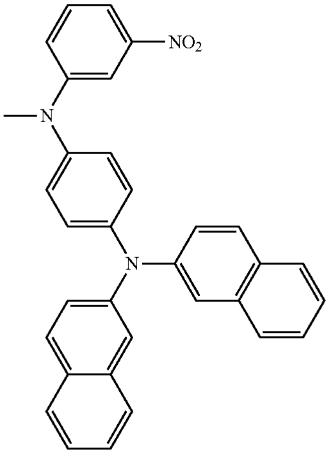
187
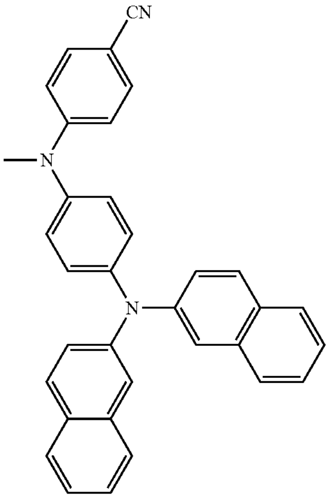

-continued
188
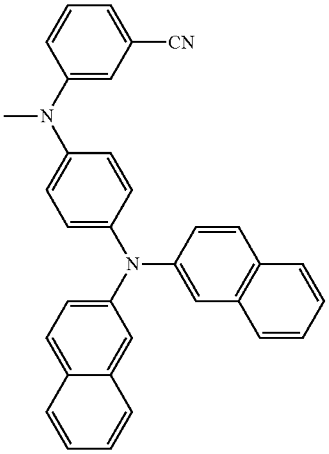
189
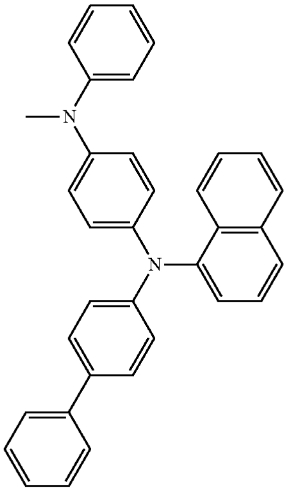
190
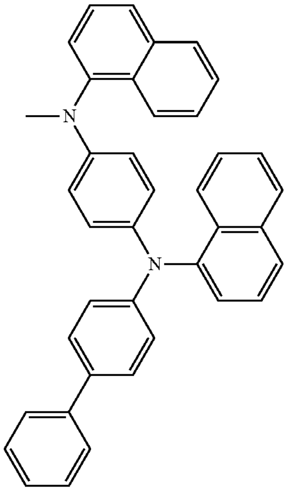
-continued
191
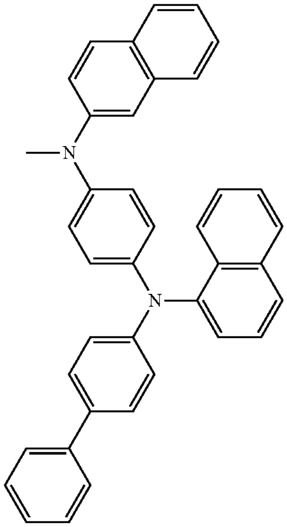
192
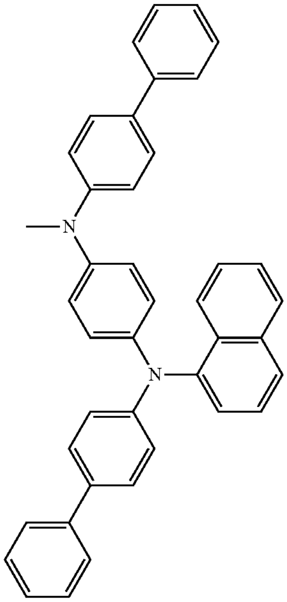
193
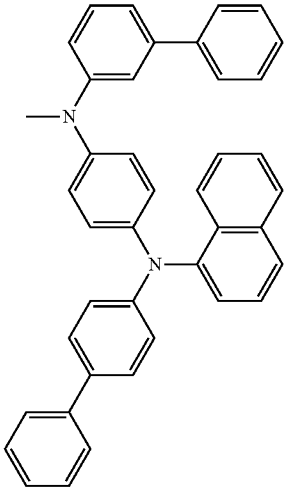

-continued
194
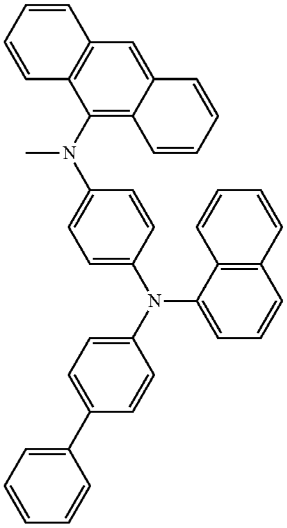
195
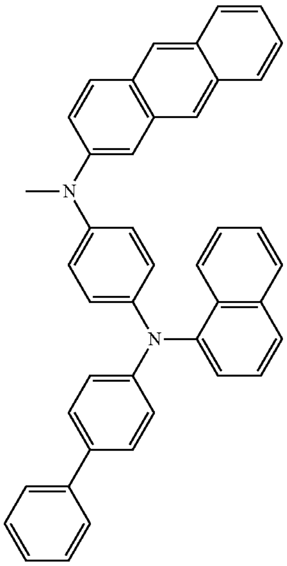
196
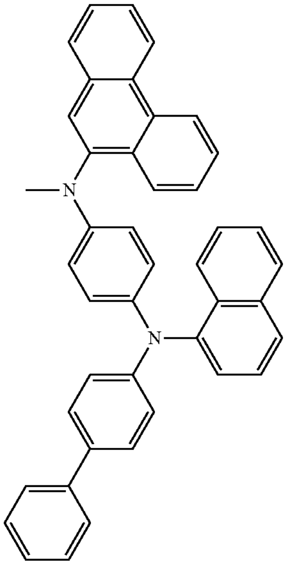
-continued
197
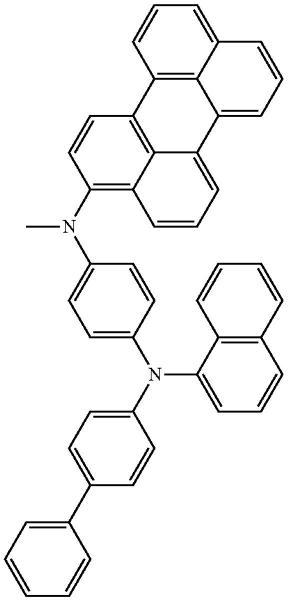
198
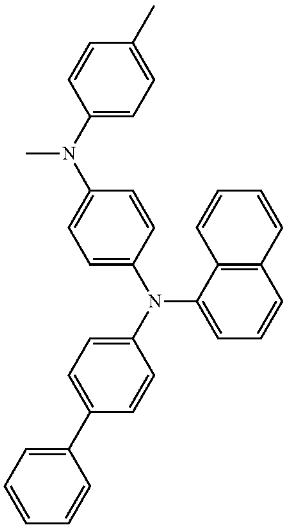
199
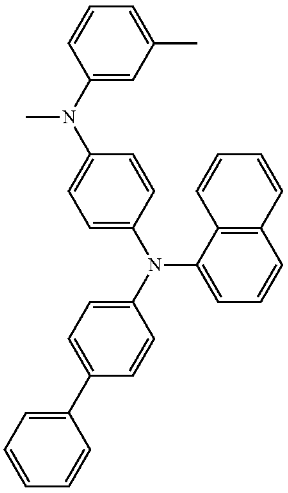

-continued
200
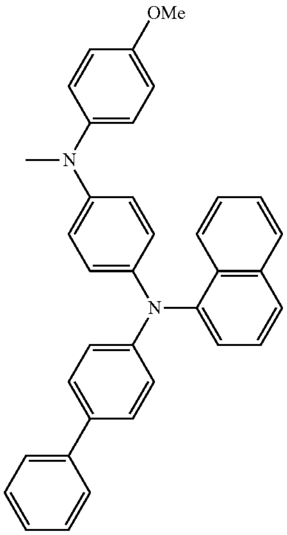
201
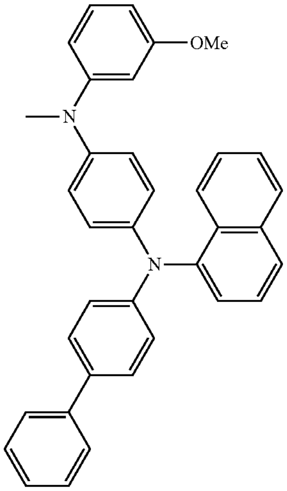
202
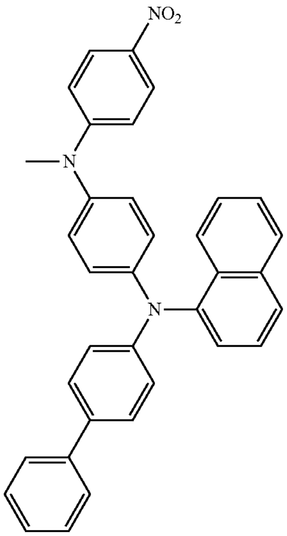
-continued
203
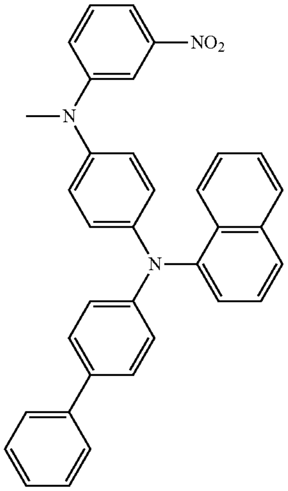
204
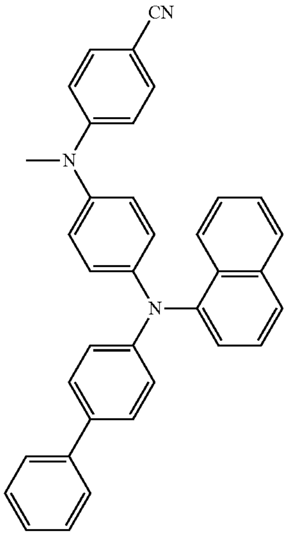
205
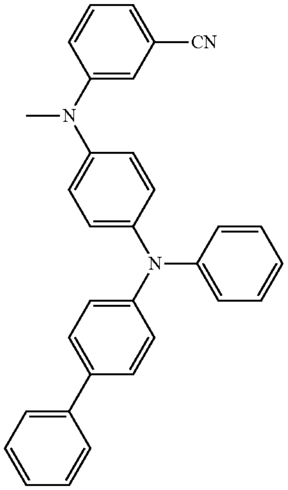

-continued
206
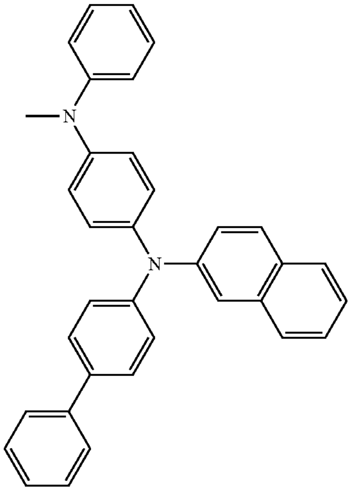
207
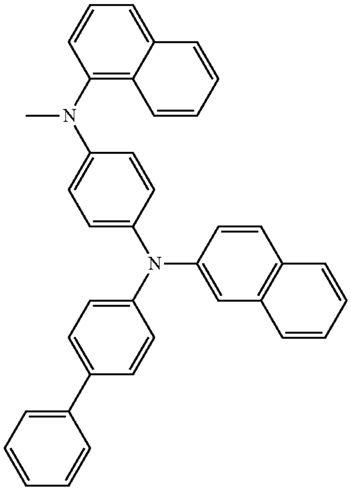
208
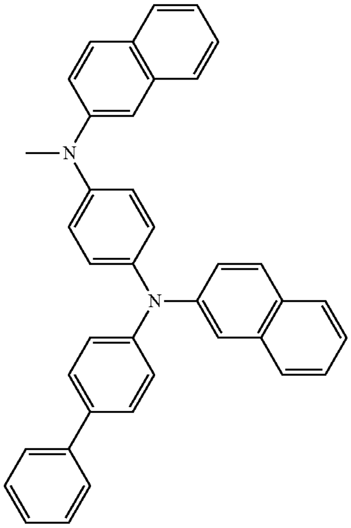
-continued
209
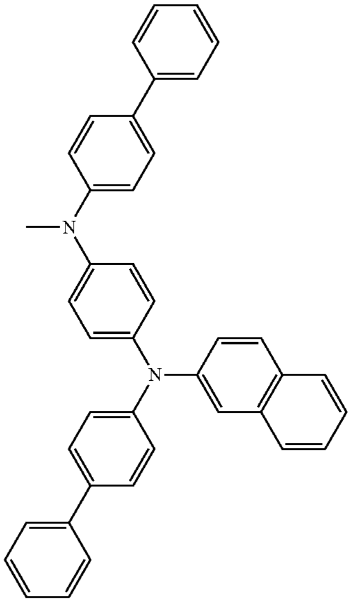
210
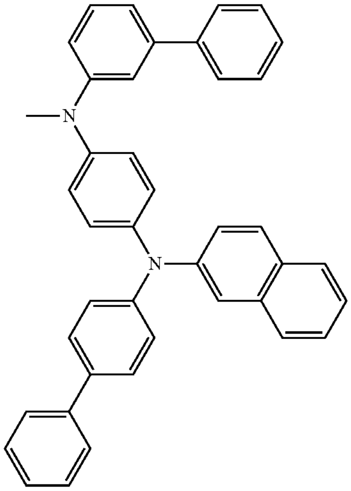
211
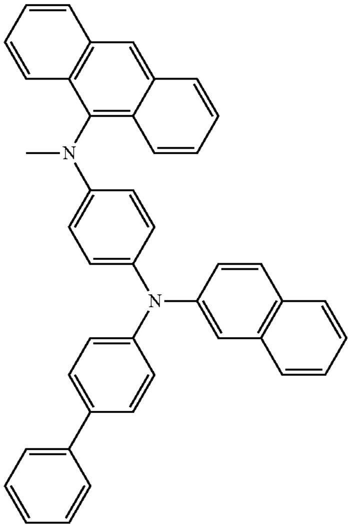

-continued
212
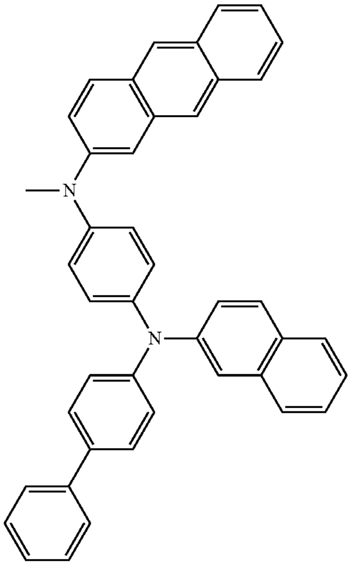
213
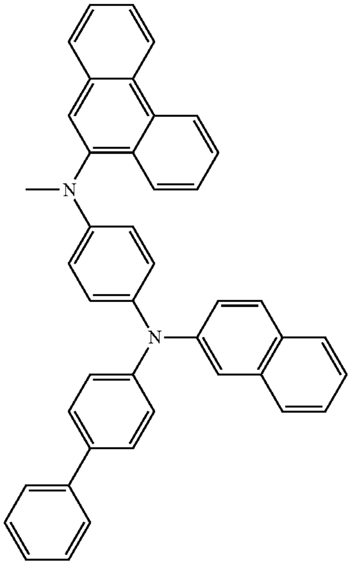
-continued
214
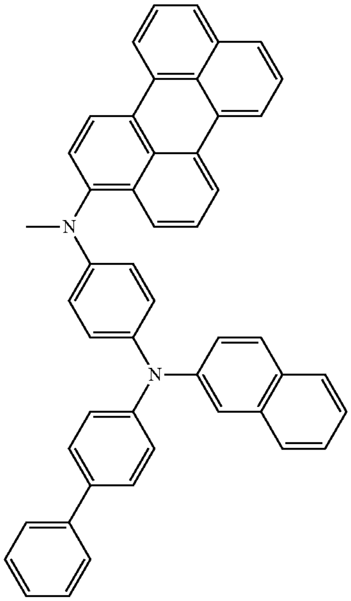
215
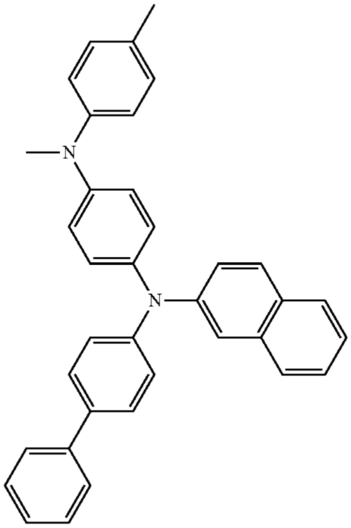
216
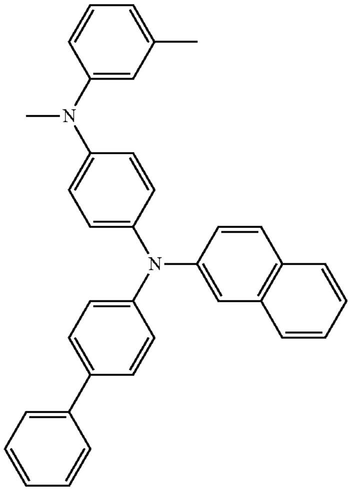

-continued
217
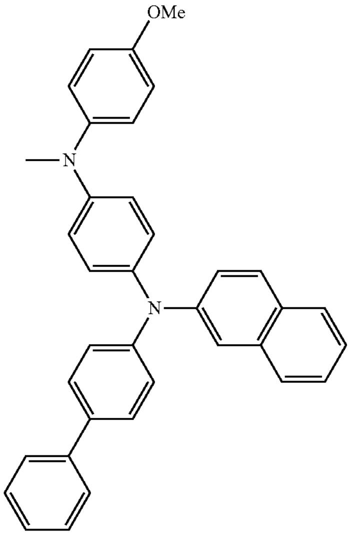
218
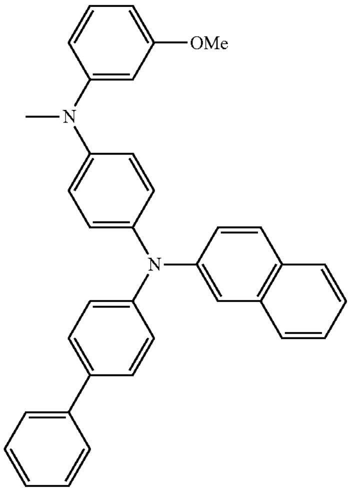
219
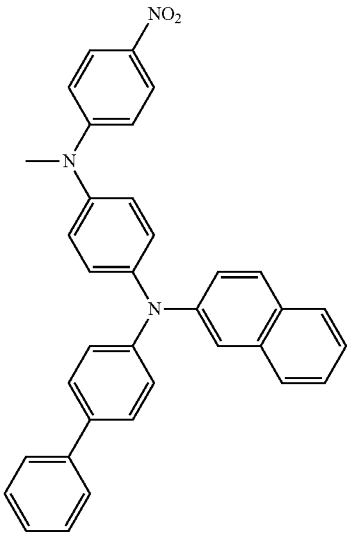
-continued
220
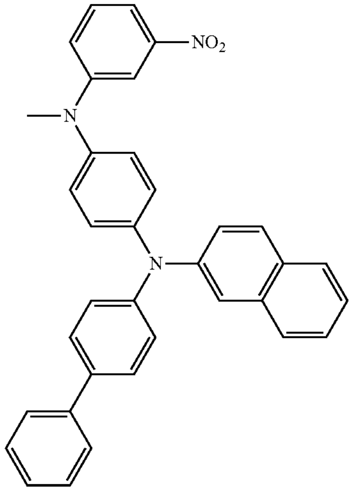
221
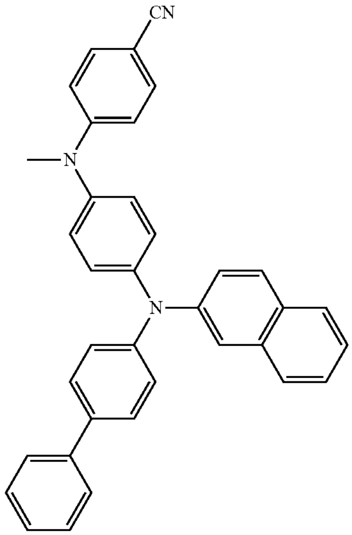
222
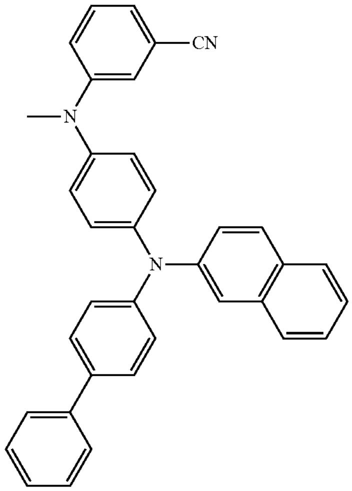

223
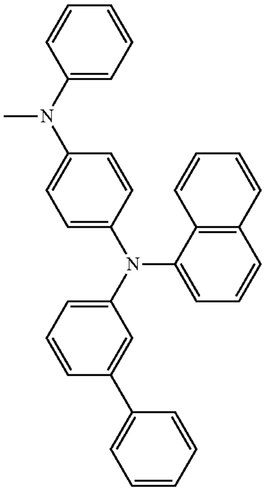
224
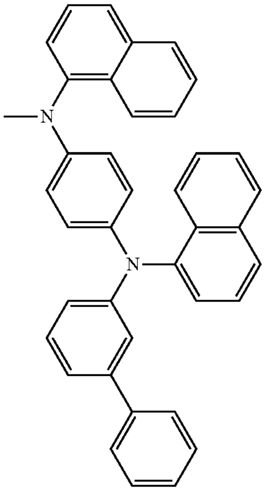
225
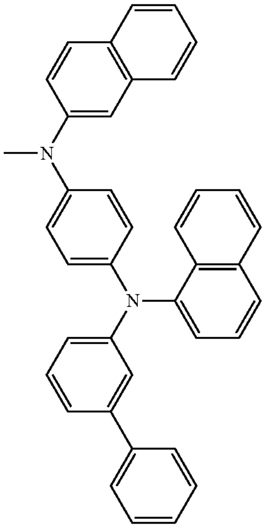
226
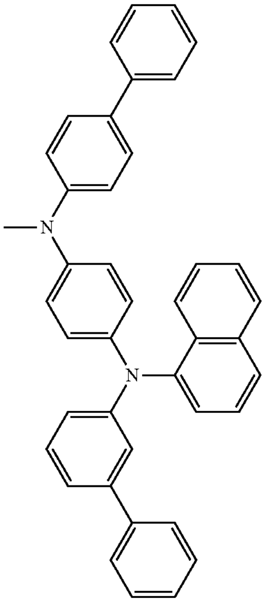
227
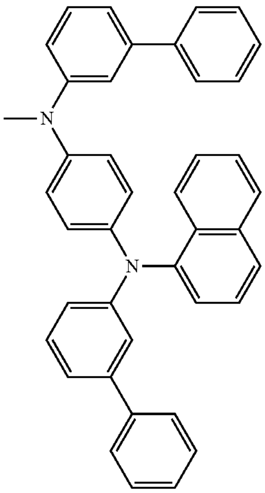
228
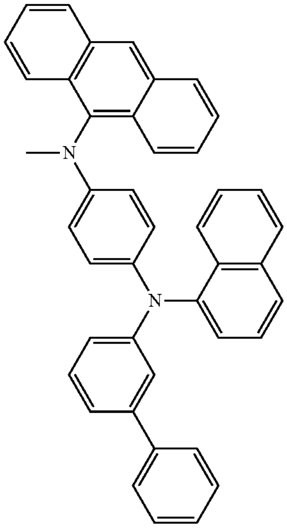

-continued
229
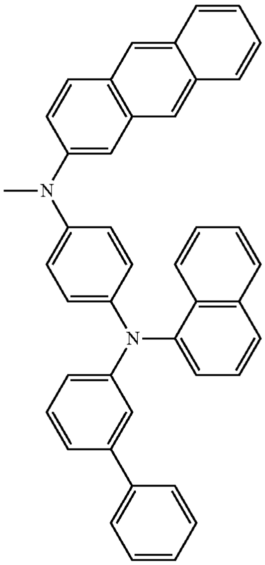
230
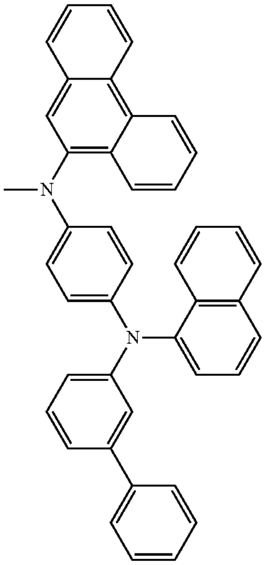
-continued
231
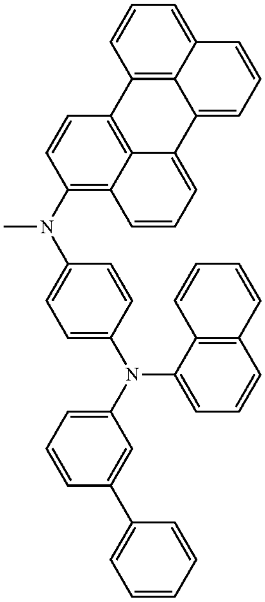
232
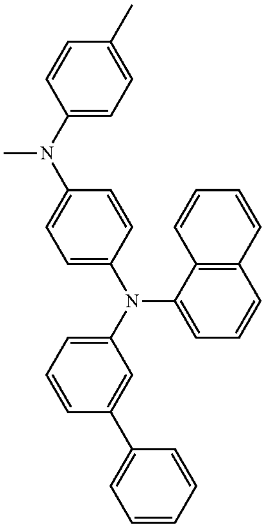
233
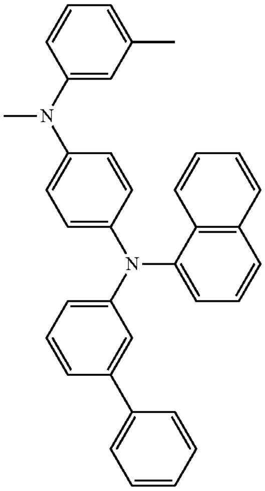

-continued
234
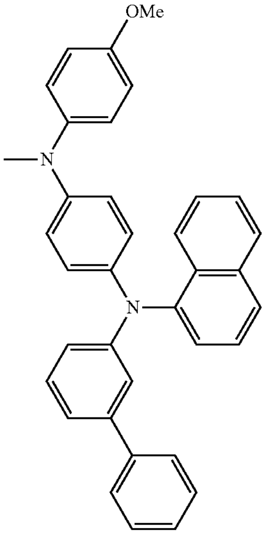
235
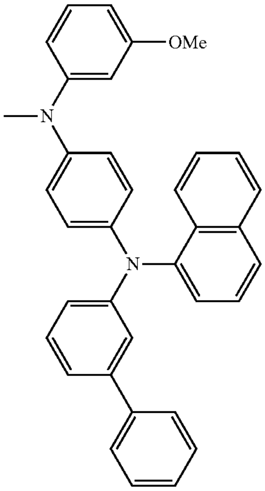
236
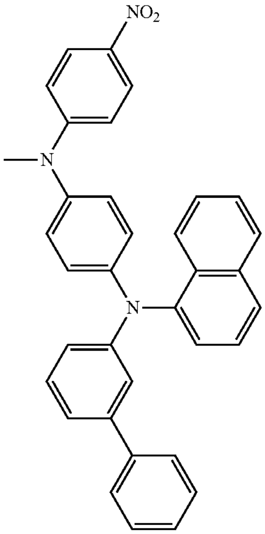
-continued
237
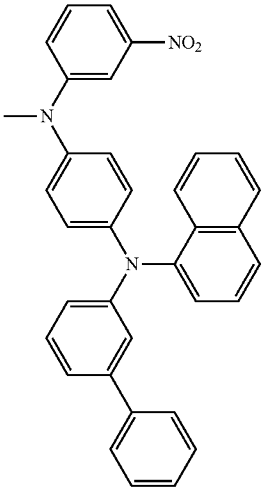
238
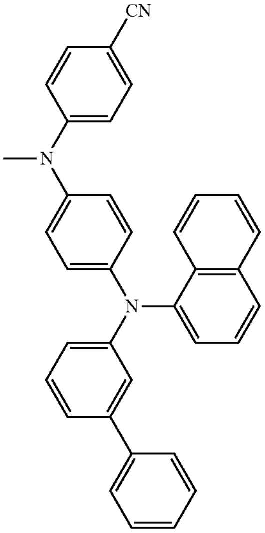
239
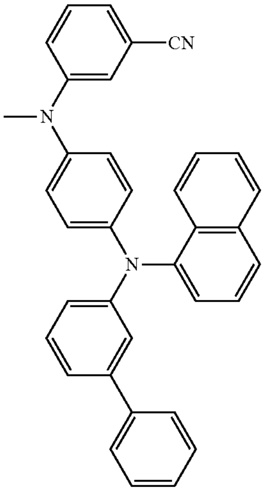

-continued
240
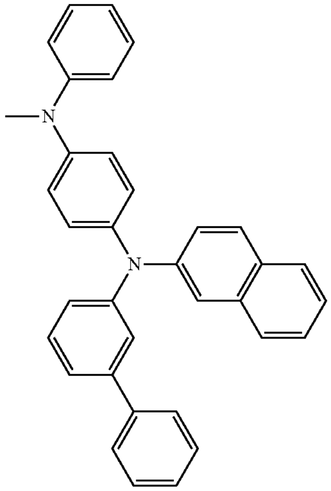
241
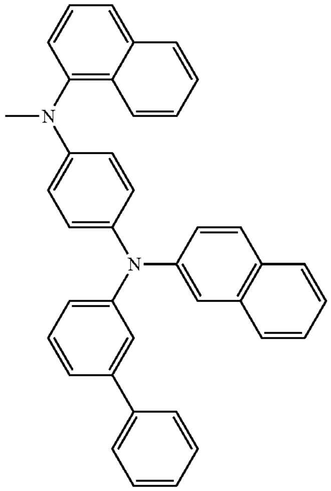
242
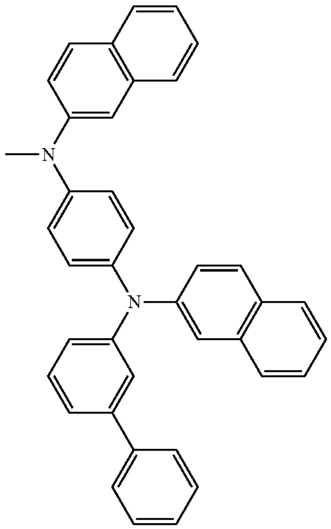
-continued
243
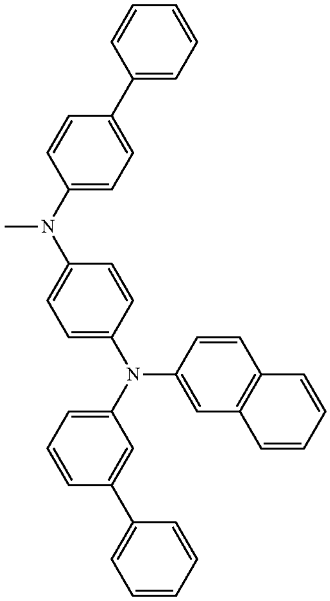
244
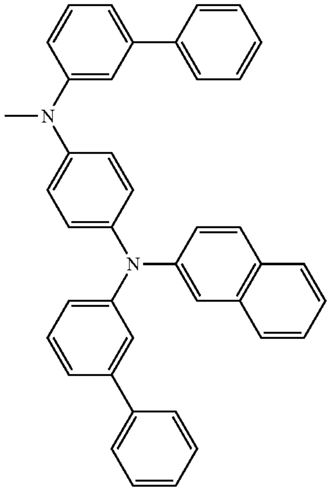
245
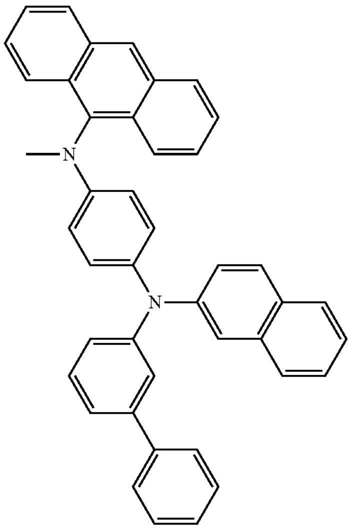

-continued
246
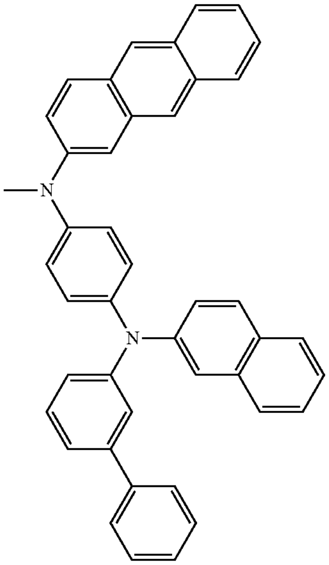
247
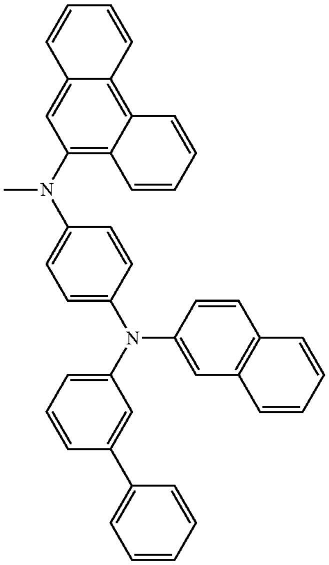
-continued
248
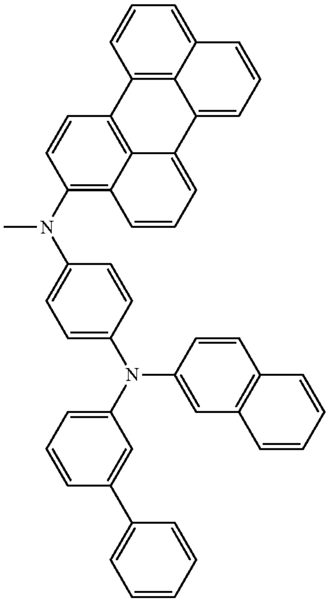
249
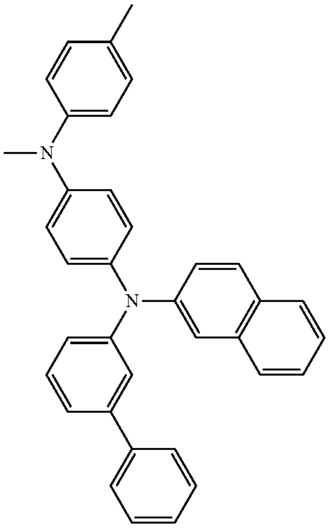
250
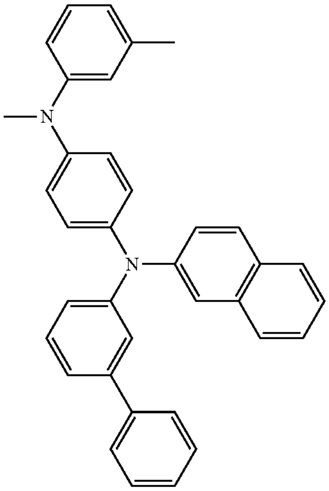

-continued
251
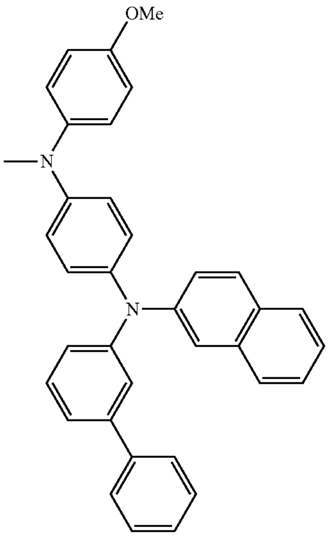
252
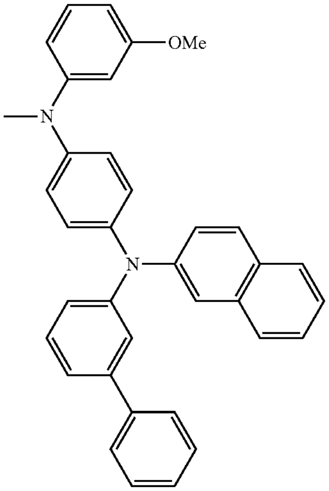
253
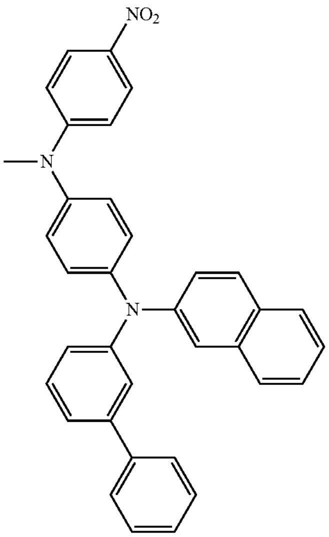
-continued
254
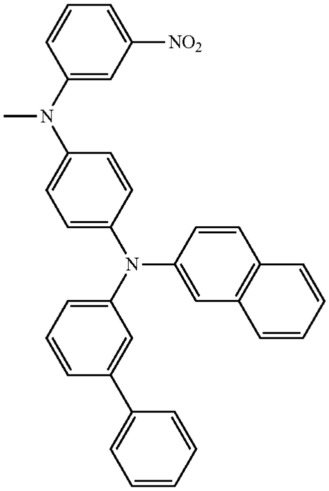
255
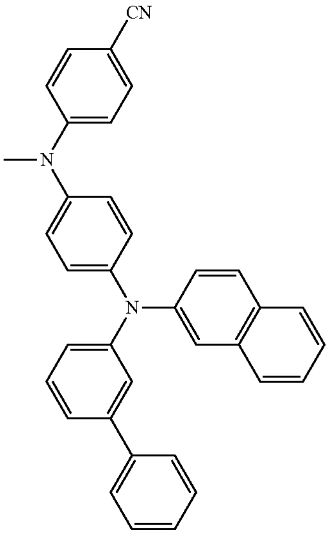
256
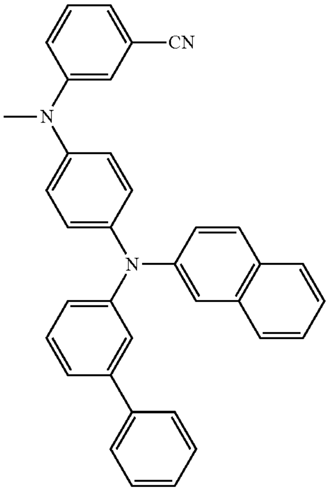

-continued
257
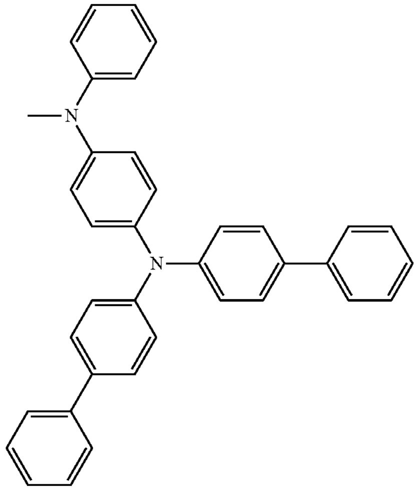
258
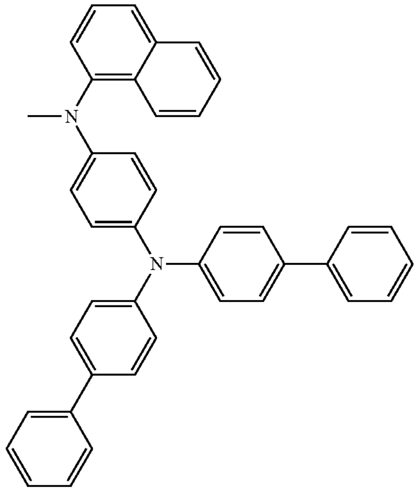
259
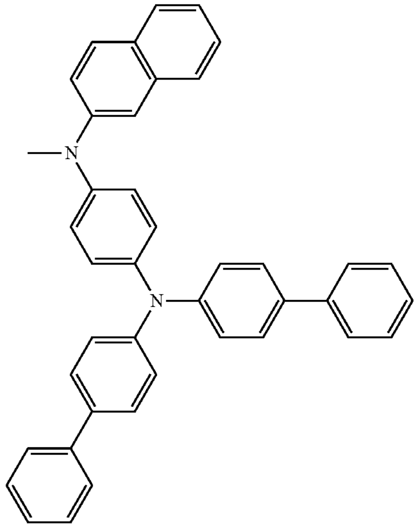
-continued
260
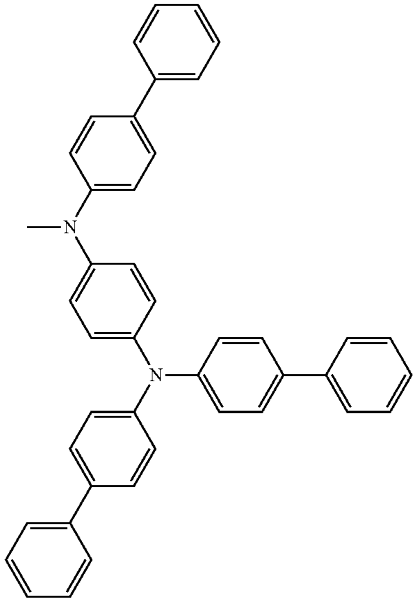
261
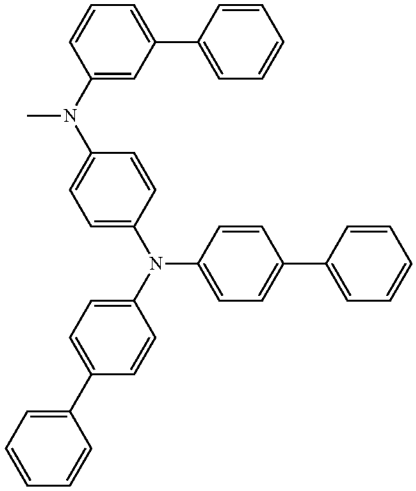
262
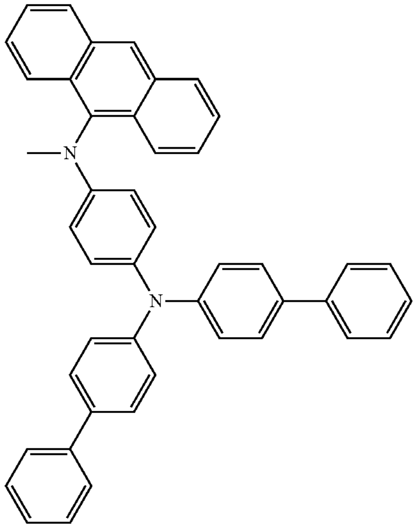

263
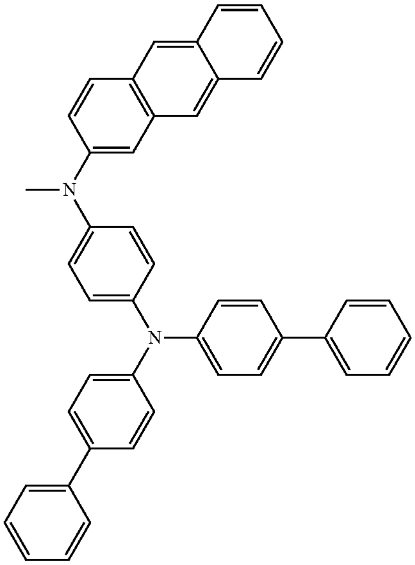
264
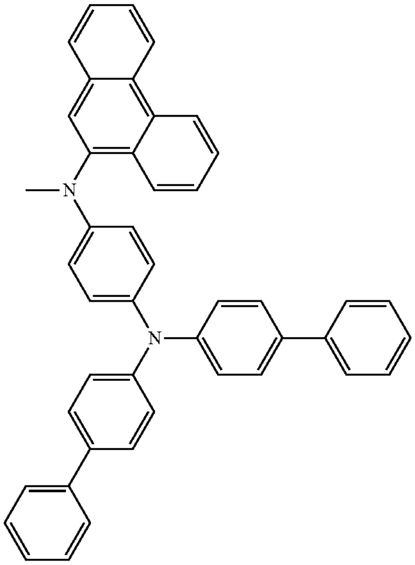
265
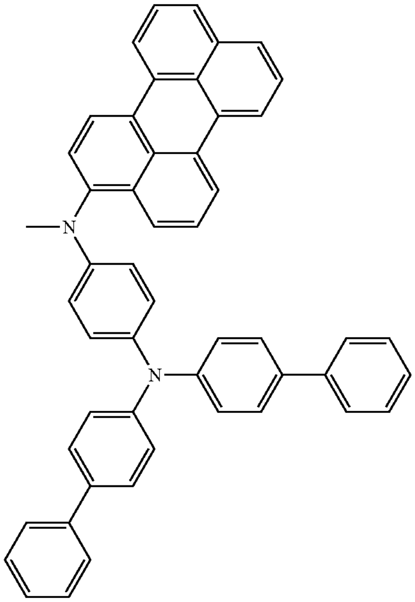
266
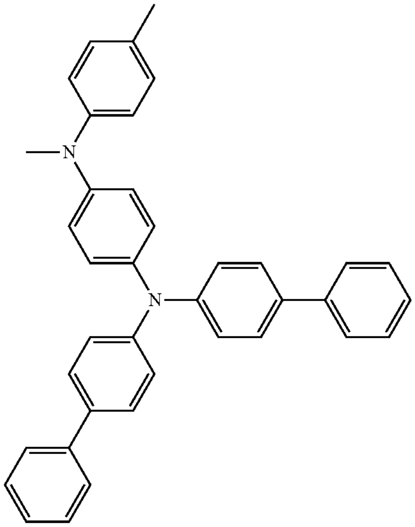
267
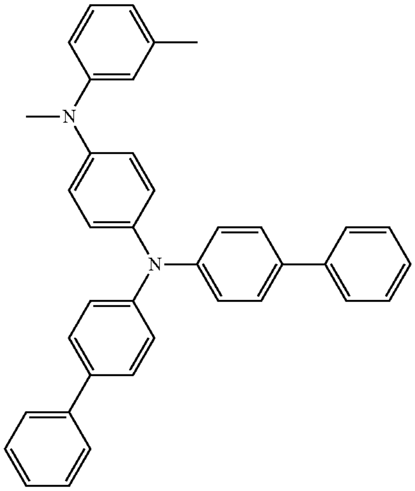

-continued
268
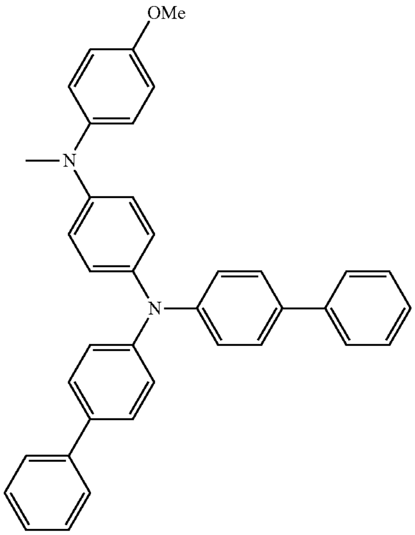
269
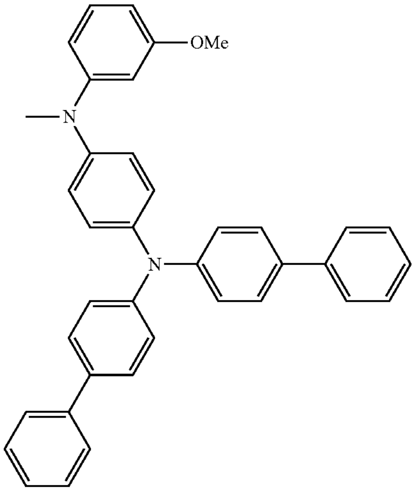
270
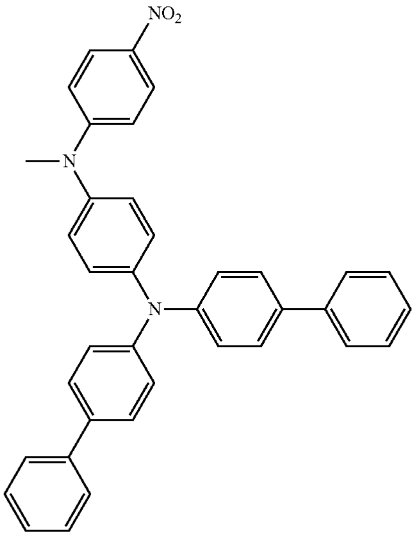
-continued
271
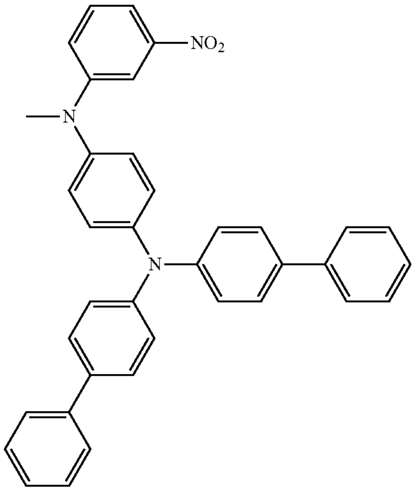
272
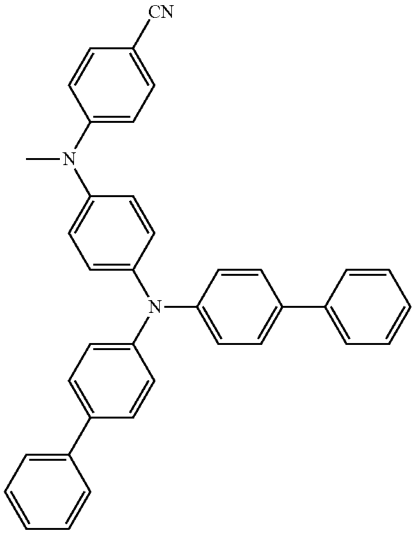
273
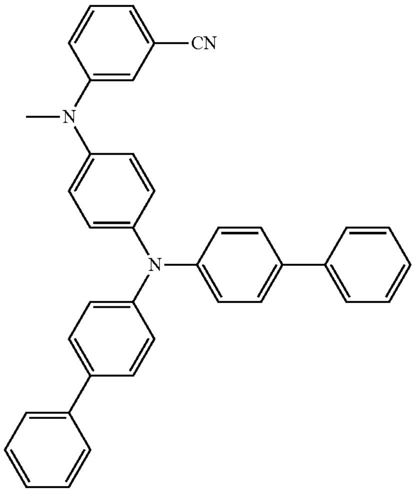

274
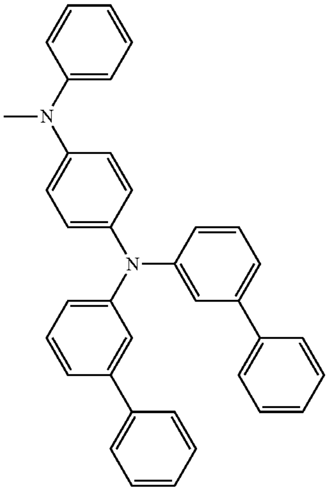
275
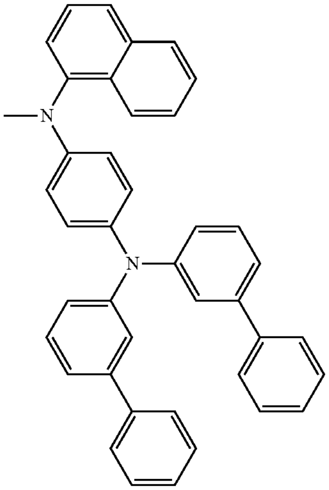
276
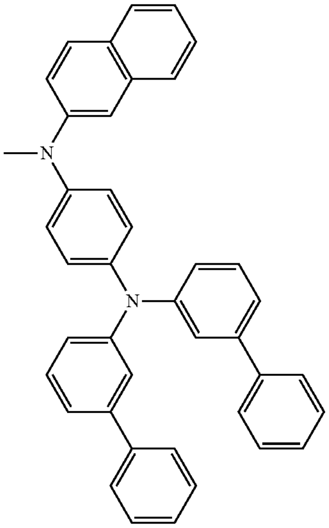
277
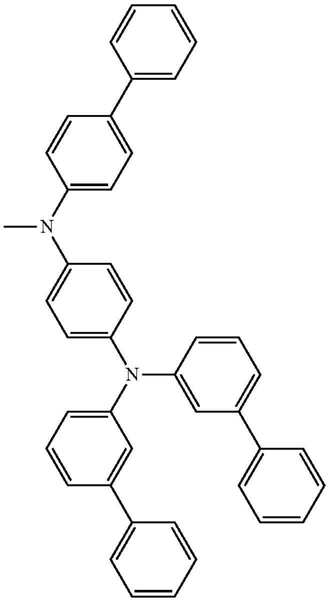
278
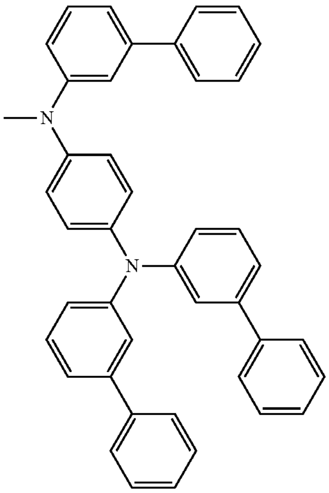
279
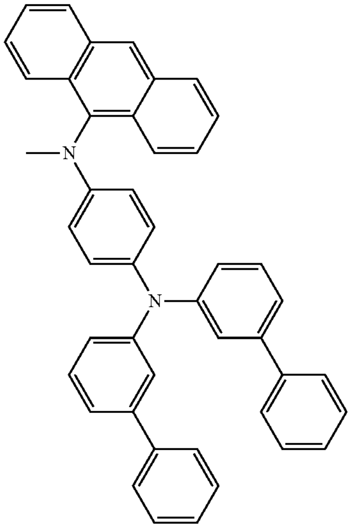

-continued
280
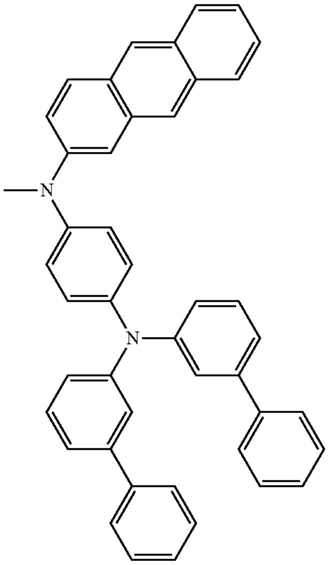
281
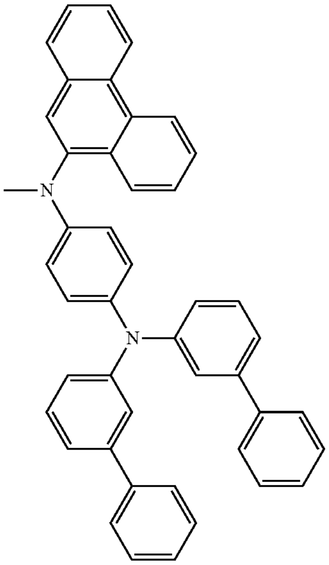
-continued
282
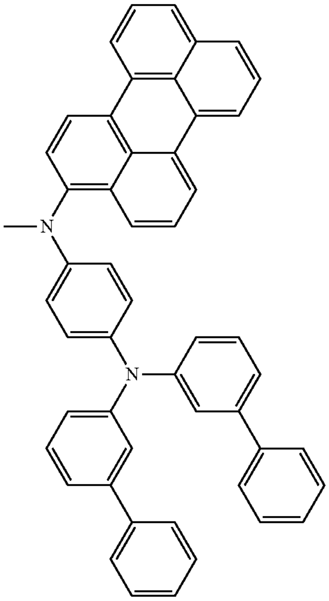
283
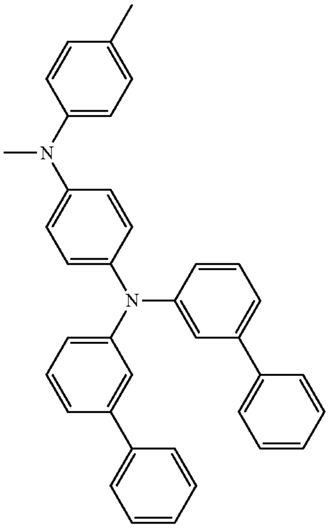
284
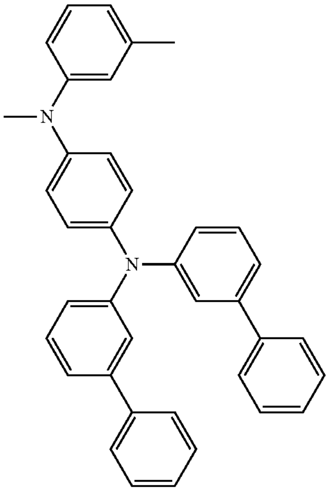

-continued
285
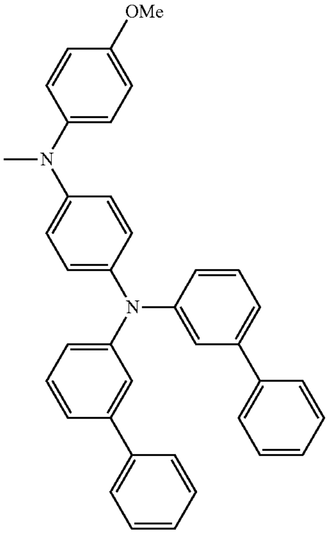
286
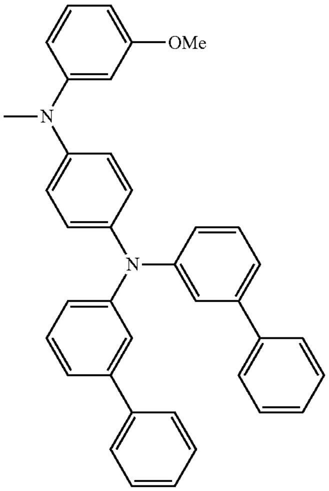
287
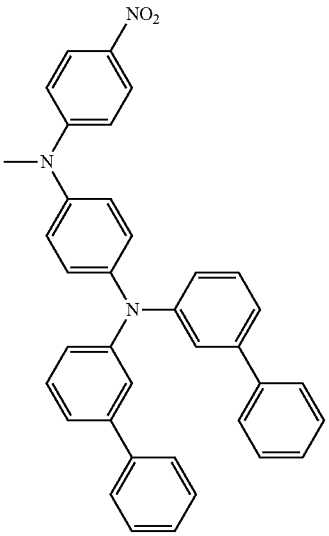
-continued
288
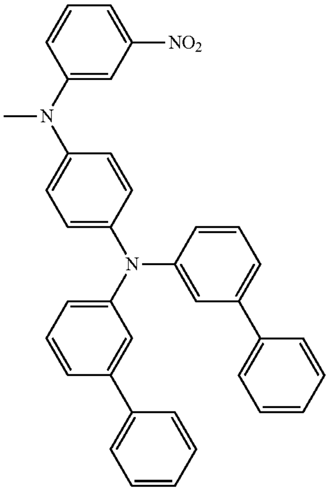
289
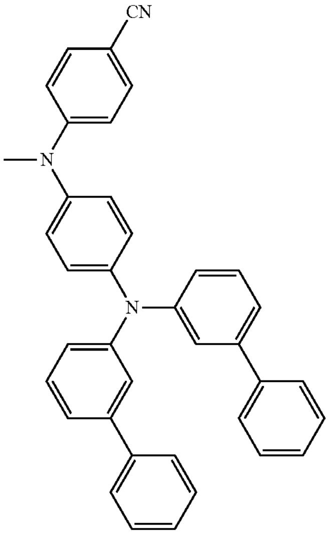
290
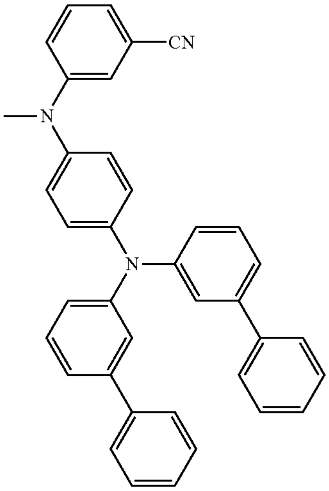

-continued
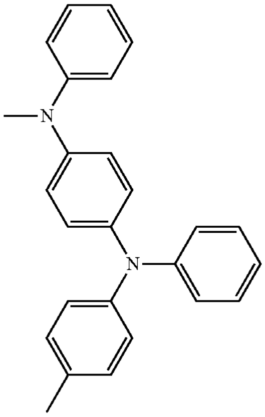
291
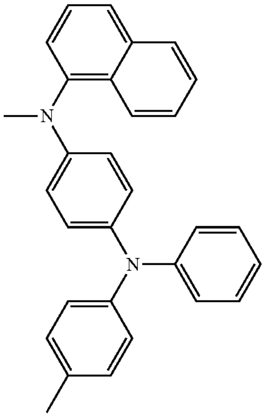
292
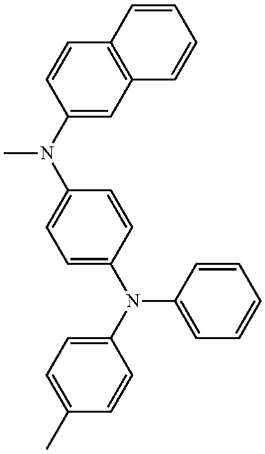
293
-continued
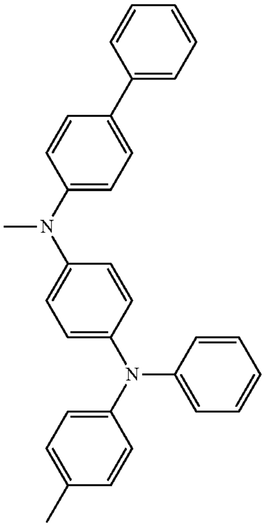
294
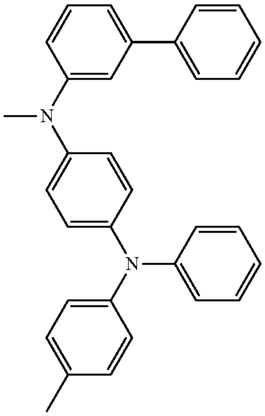
295
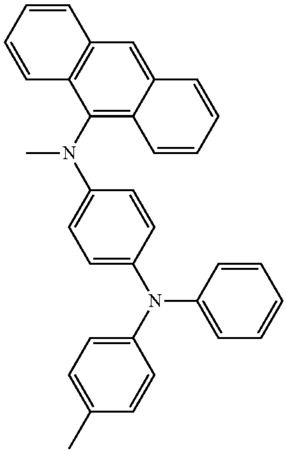
296

-continued
297
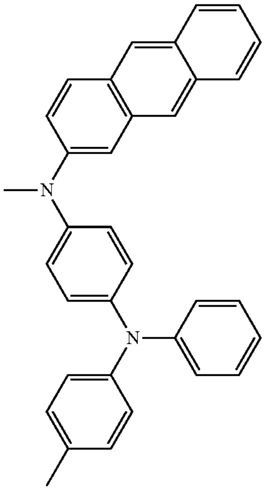
298
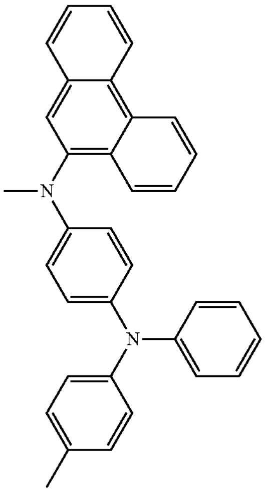
299
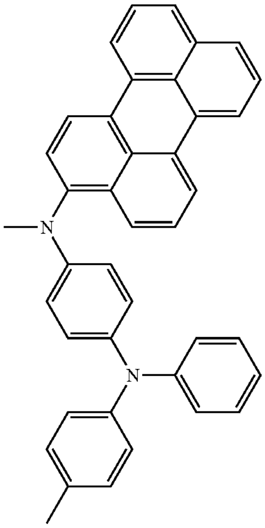
-continued
300
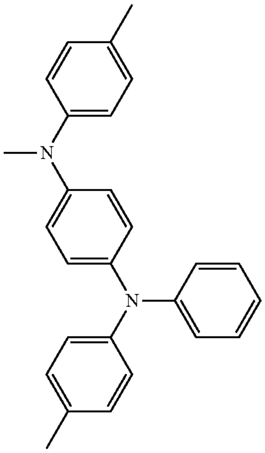
301
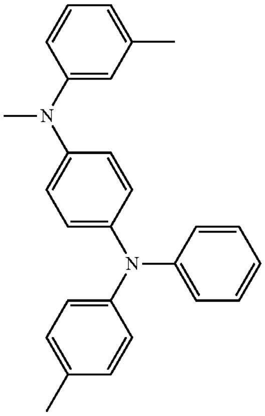
302
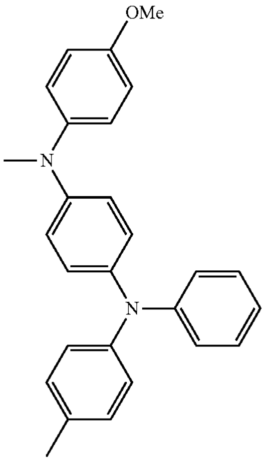

-continued
303
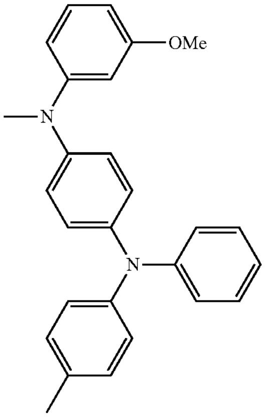
304
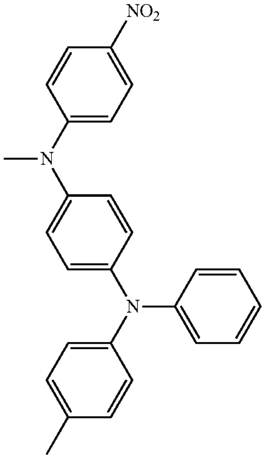
305
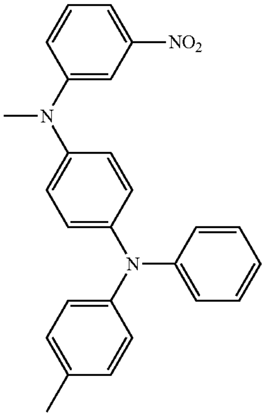
-continued
306
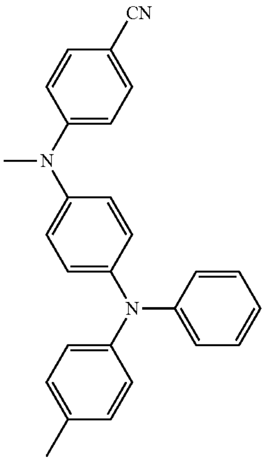
307
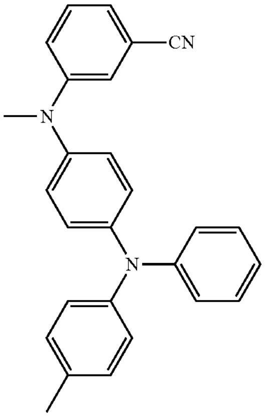
308
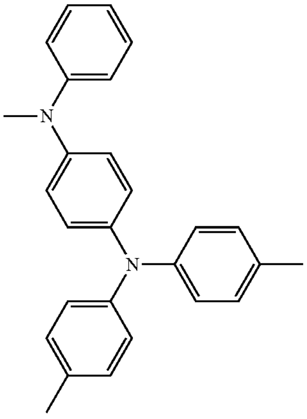

-continued
309
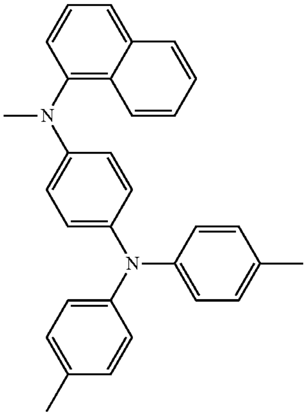
310
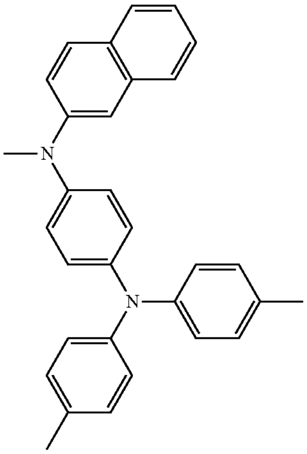
311
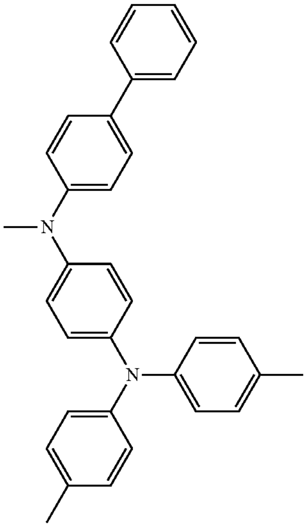
-continued
312
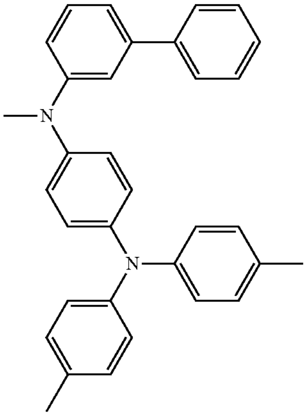
313
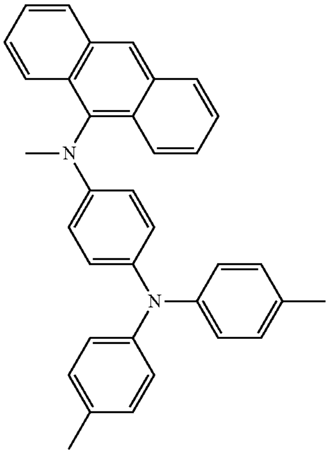
314
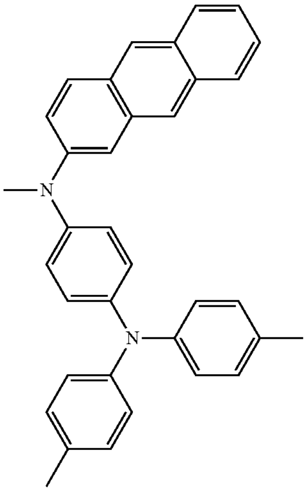

315
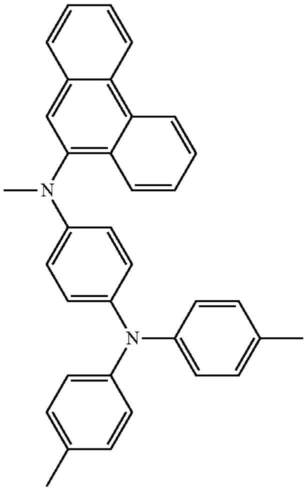
316
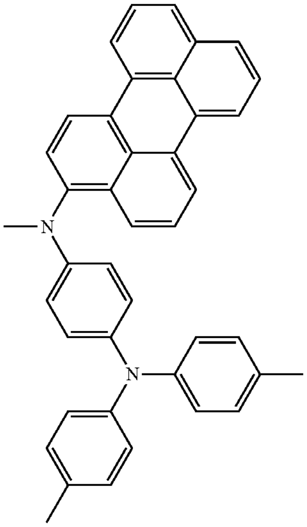
317
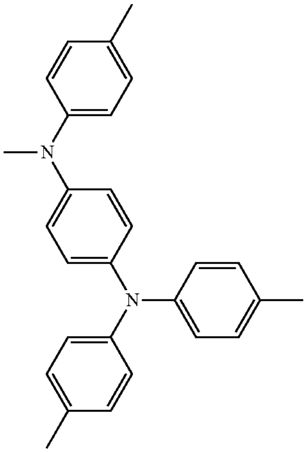
318
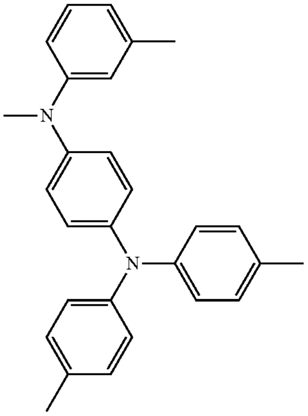
319
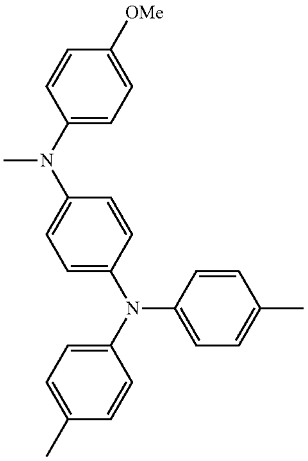
320
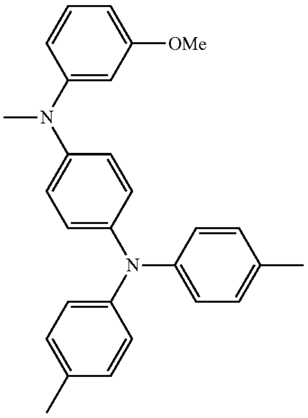

-continued
321
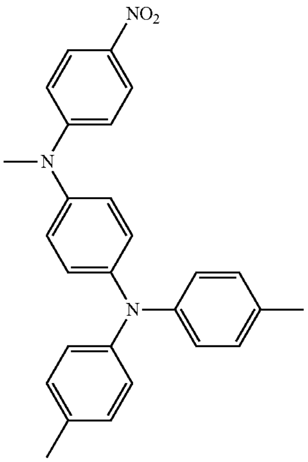
322
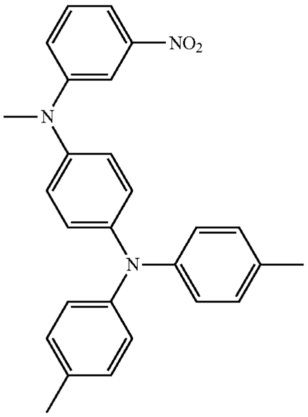
323
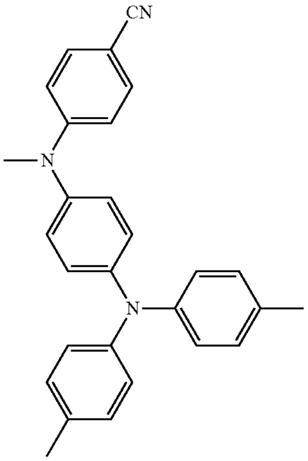
-continued
324
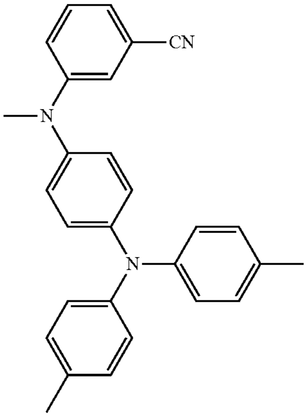
325
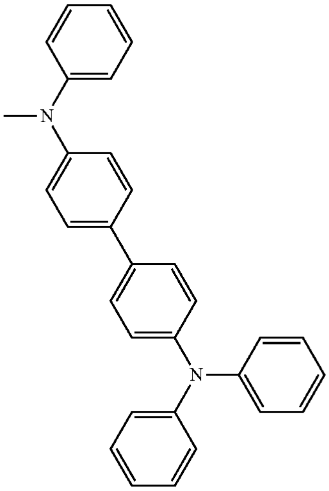
326
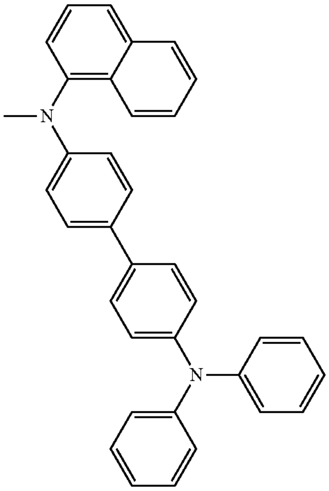

-continued
327
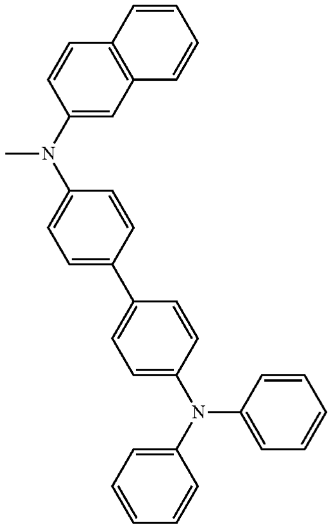
328
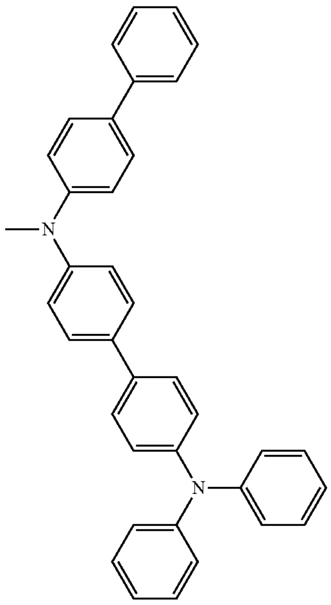
329
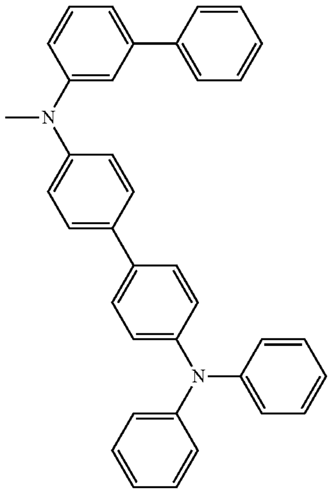
-continued
330
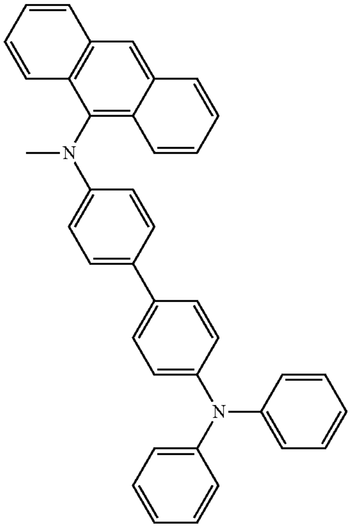
331
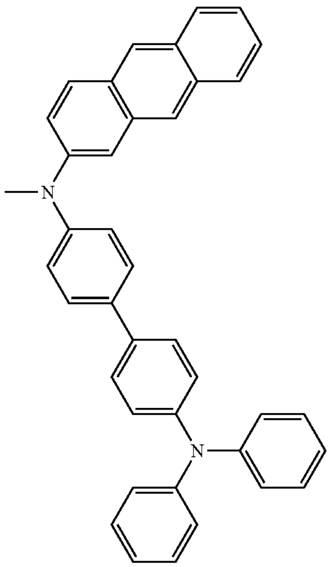
332
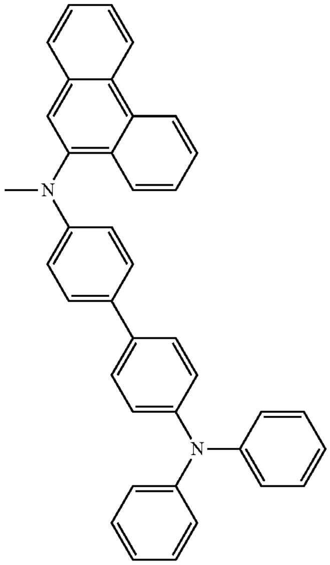

-continued
333
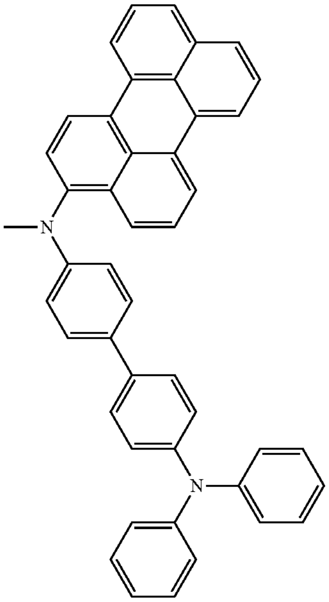
334
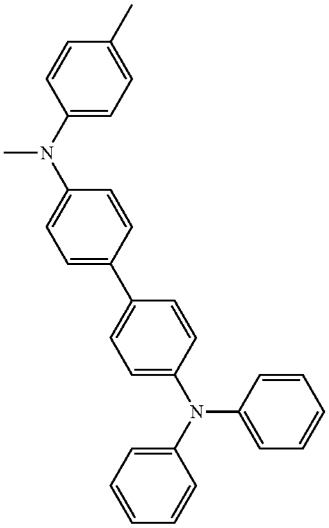
335
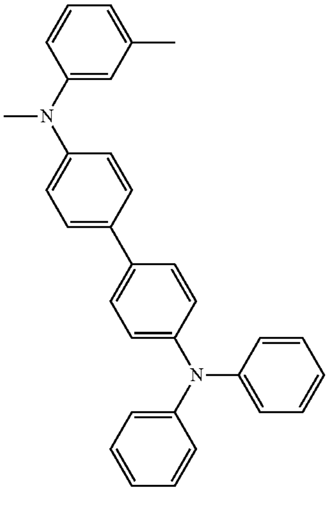
-continued
336
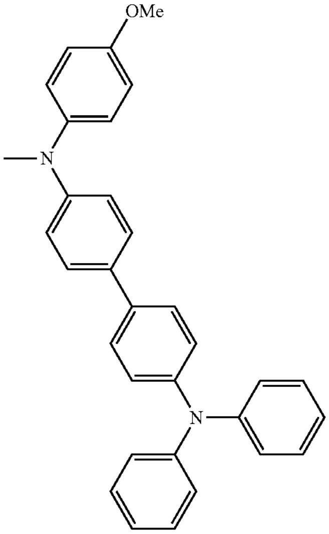
337
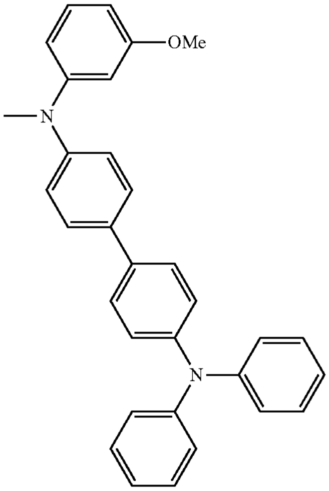
338
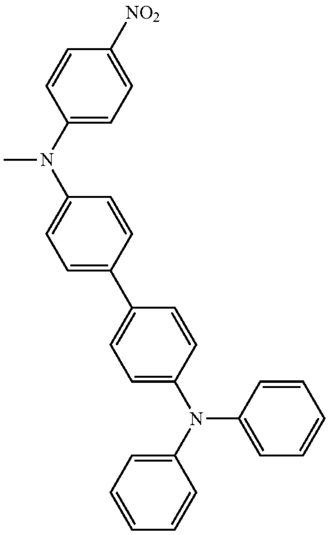

-continued
339
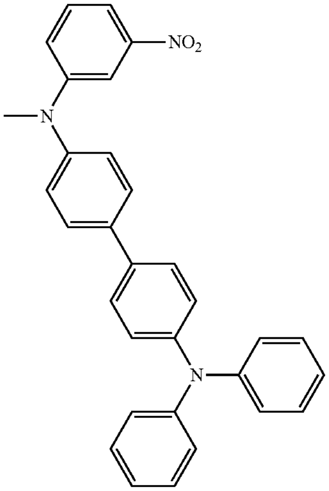
340
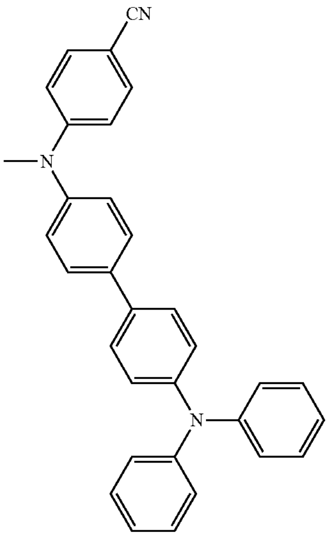
341
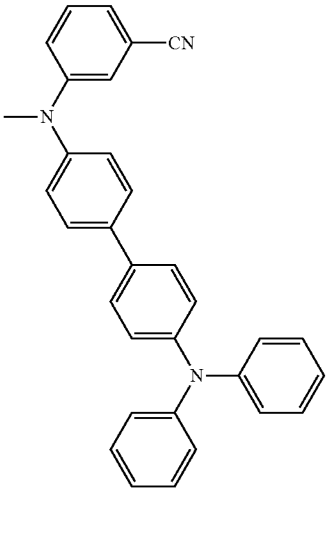
-continued
342
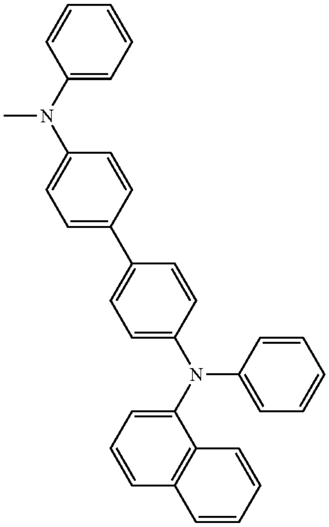
343
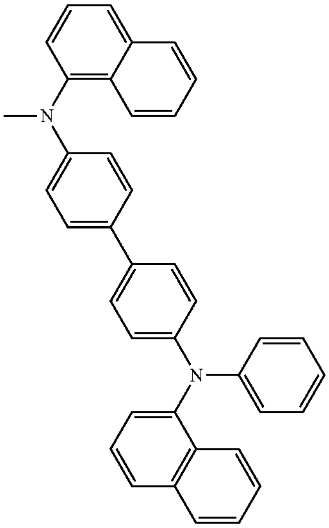
344
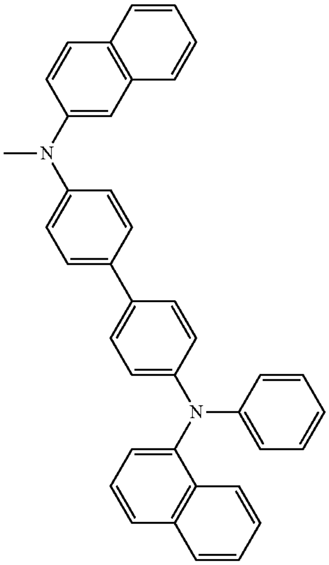

-continued
345
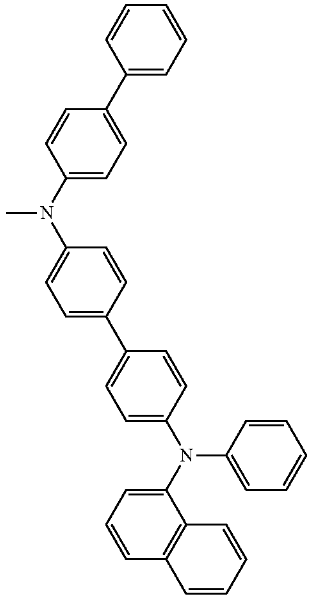
-continued
347
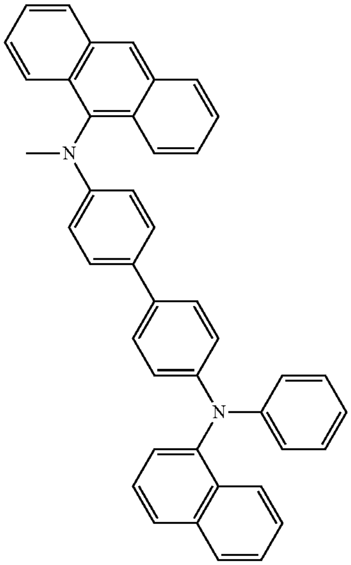
346
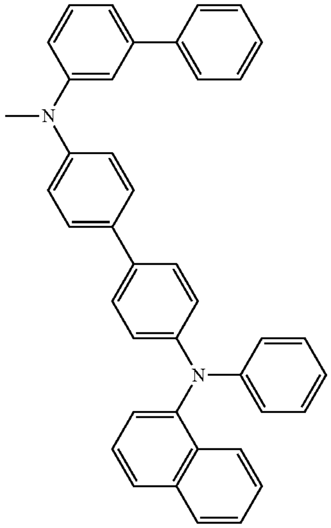
348
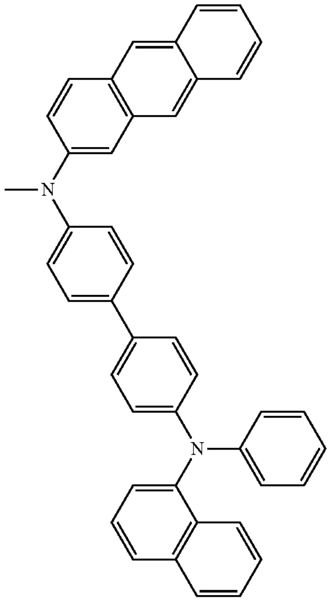

-continued
349
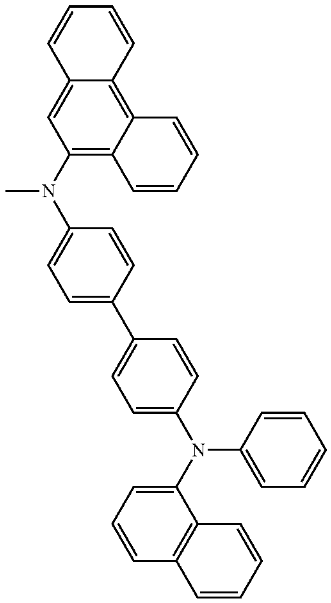
350
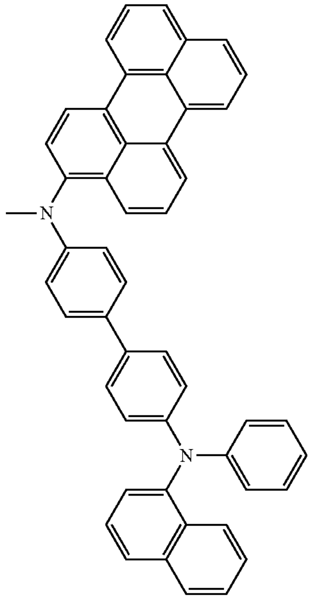
-continued
351
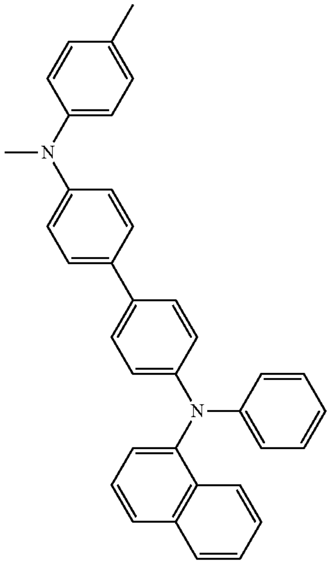
352
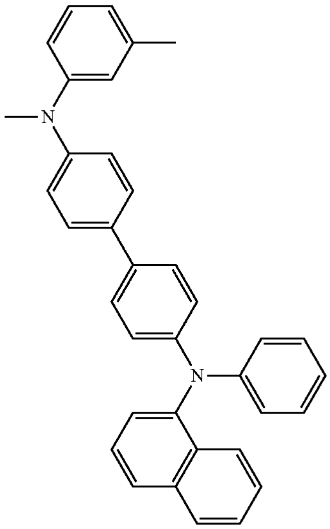
353
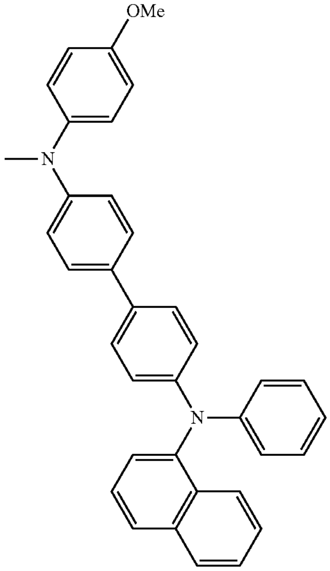

-continued
354
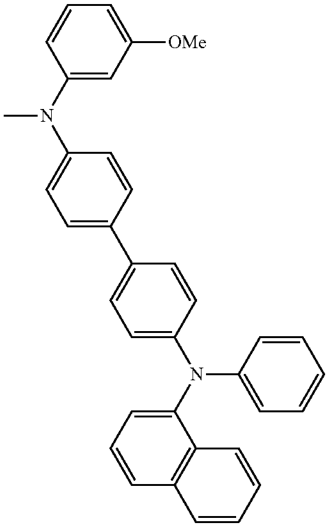
355
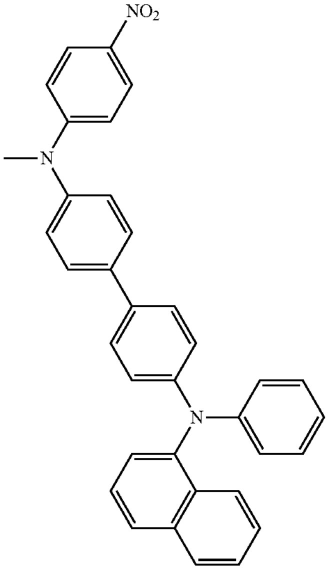
356
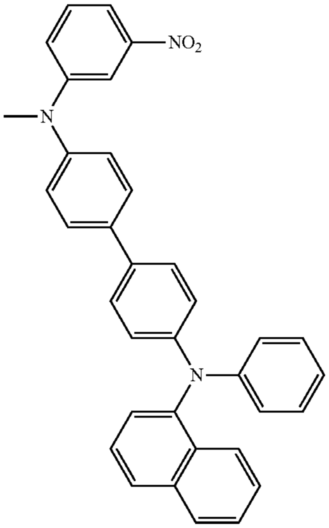
-continued
357
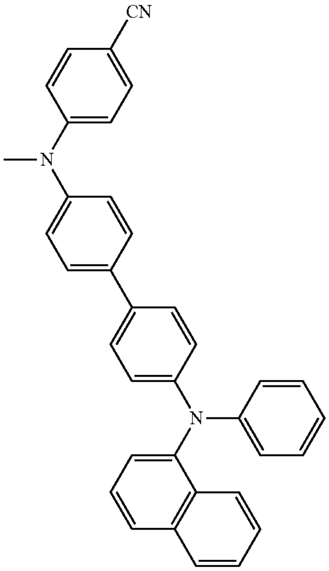
358
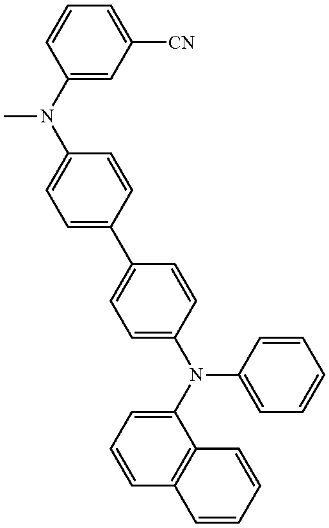
359
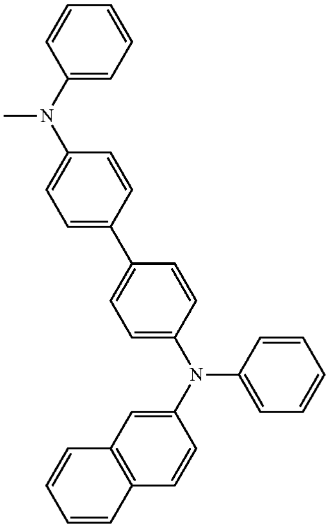

-continued
360
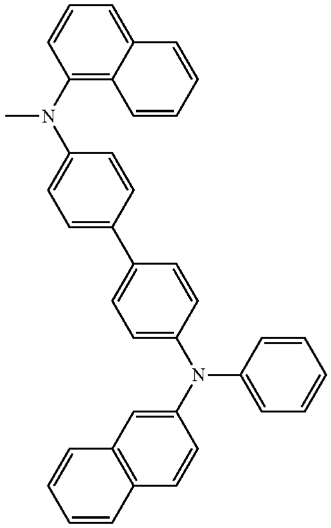
361
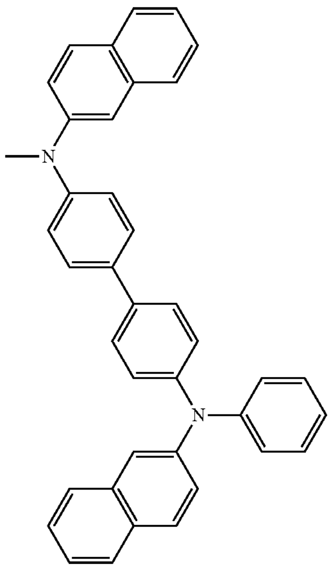
-continued
362
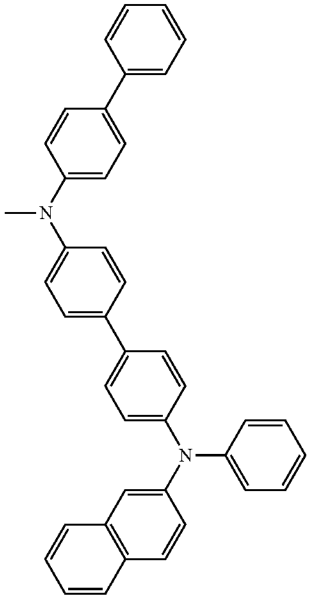
363
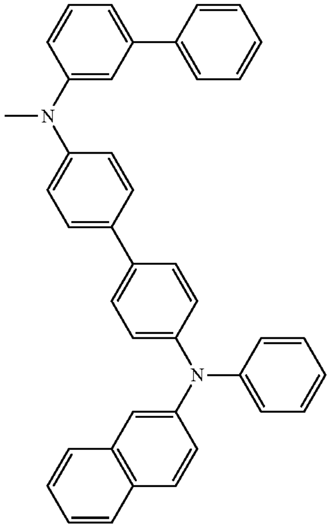

-continued
364
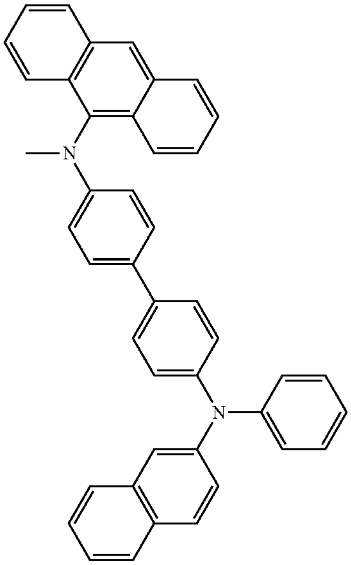
365
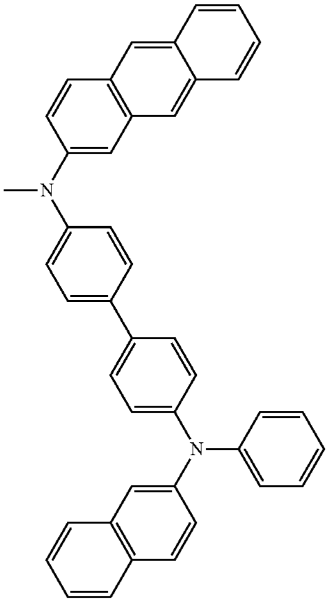
-continued
366
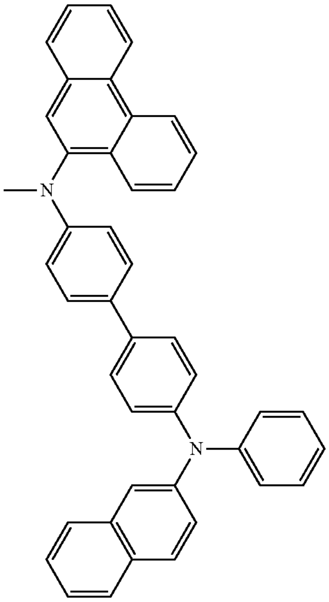
367
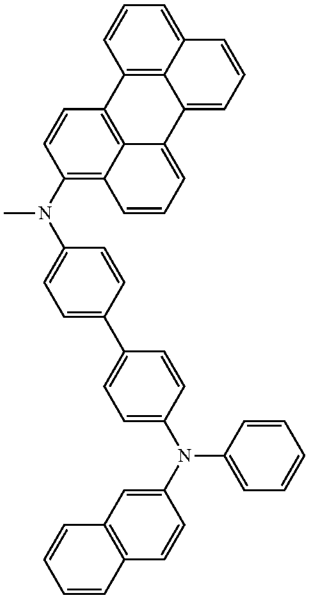

-continued
368
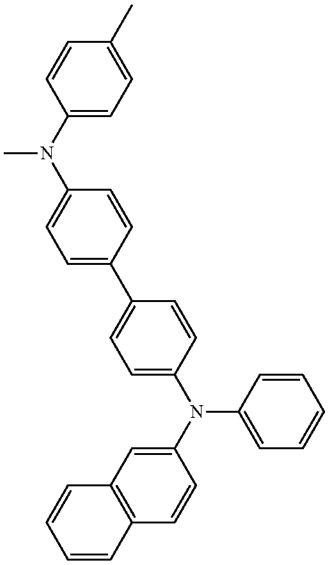
369
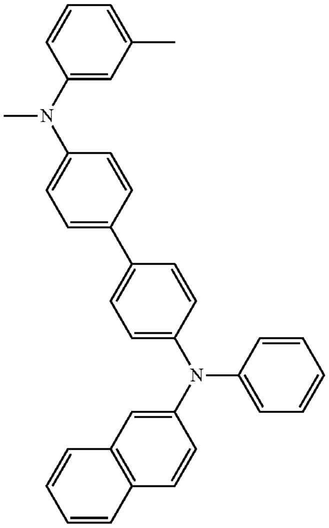
370
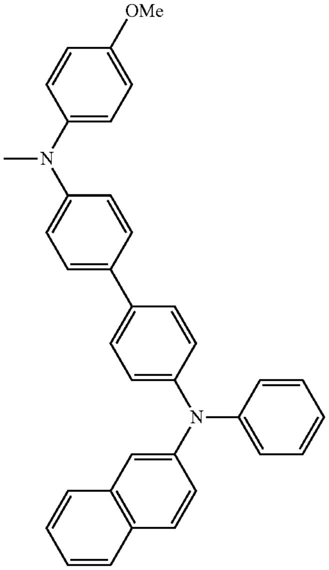
-continued
371
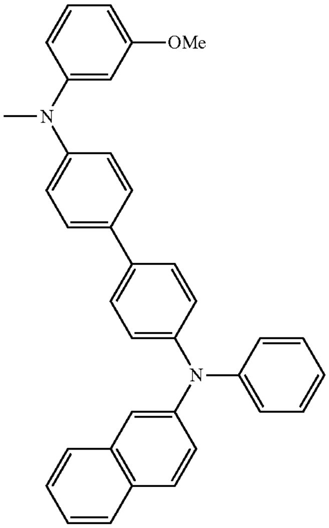
372
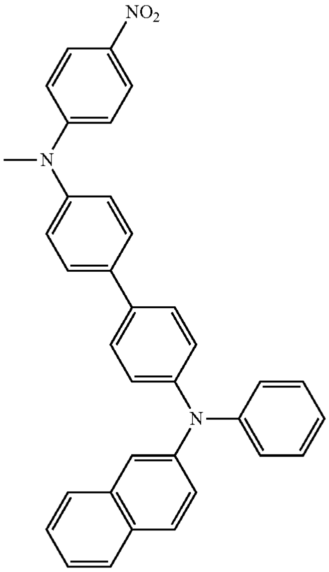
373
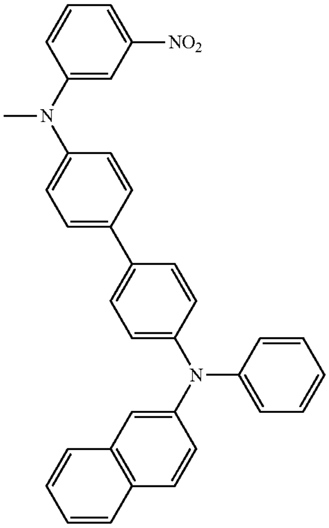

374
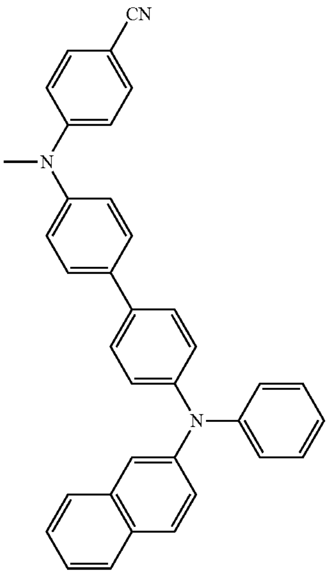
375
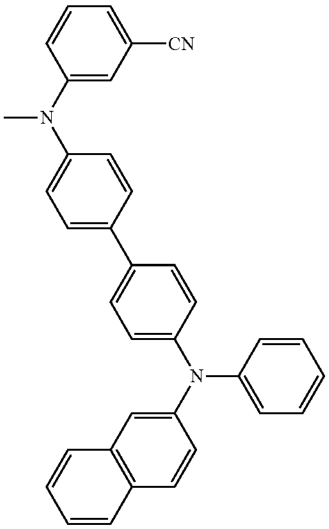
376
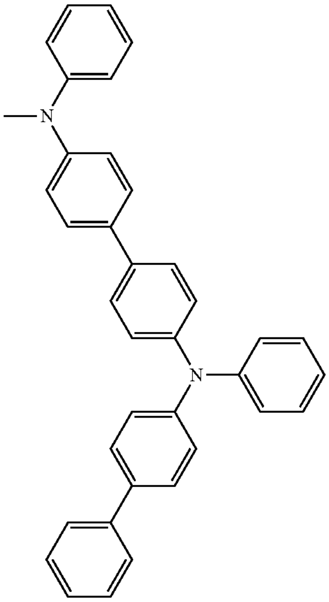
377
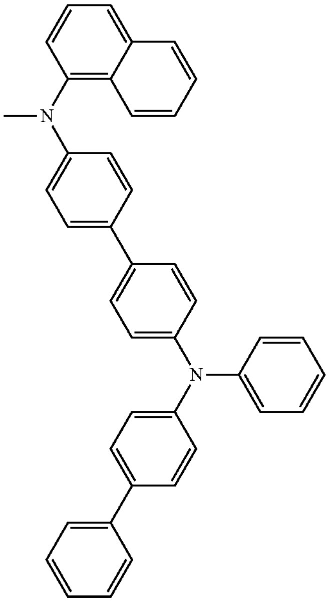

-continued
378
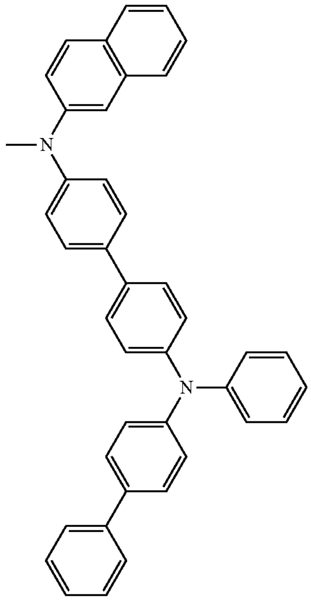
380
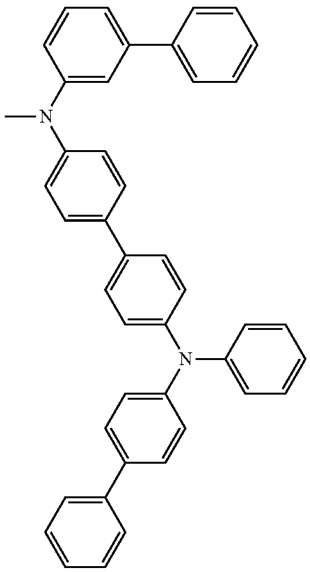
379
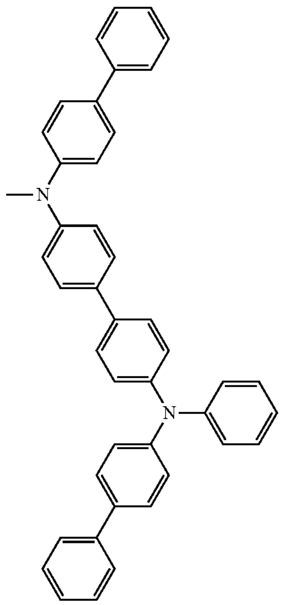
381
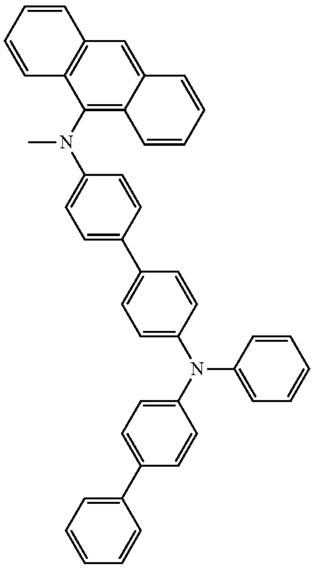

-continued
382
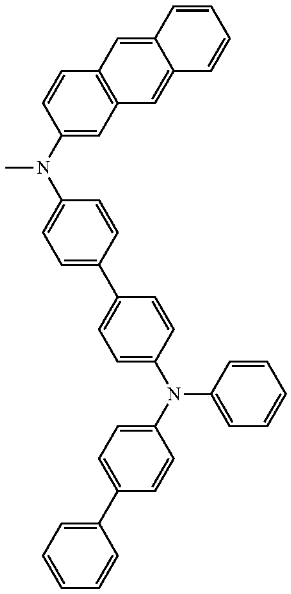
383
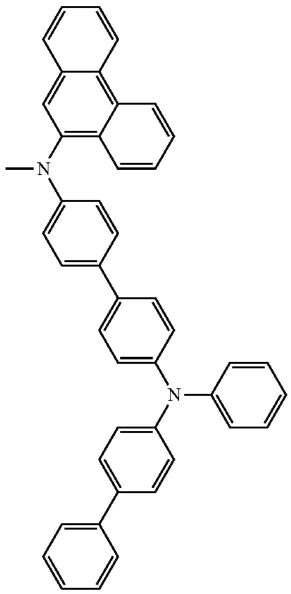
-continued
384
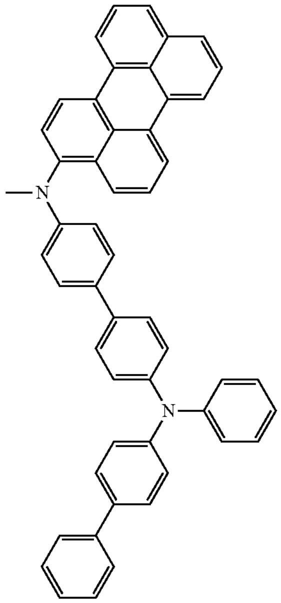
385
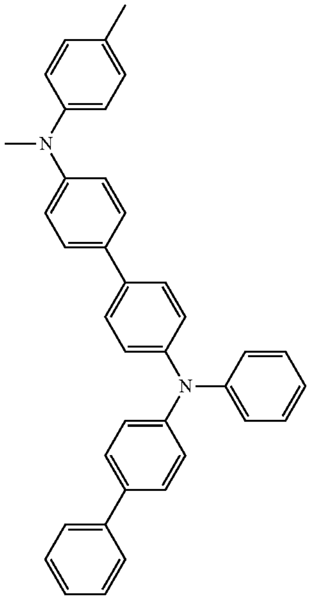

-continued
386
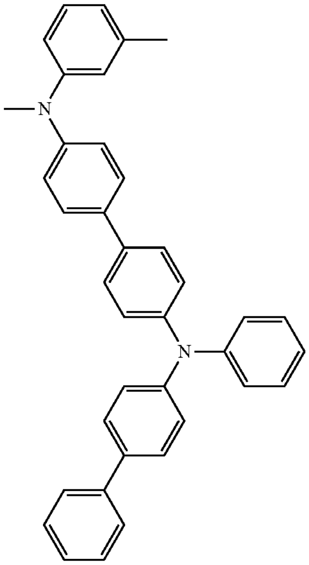
287
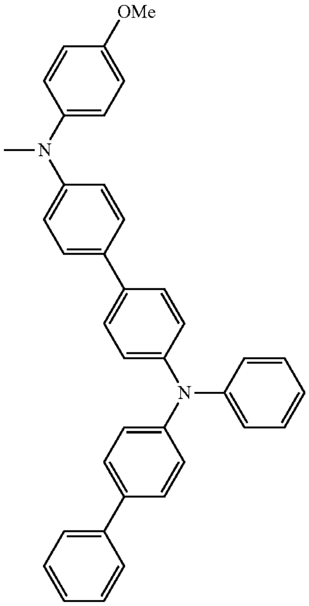
-continued
288
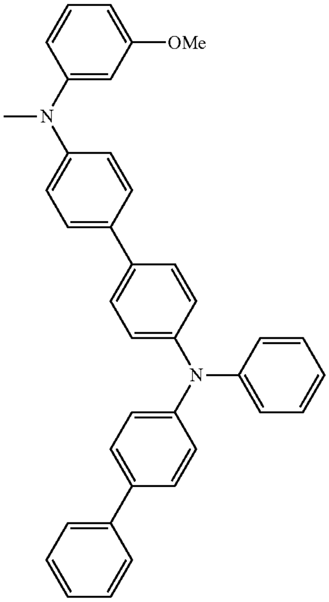
289
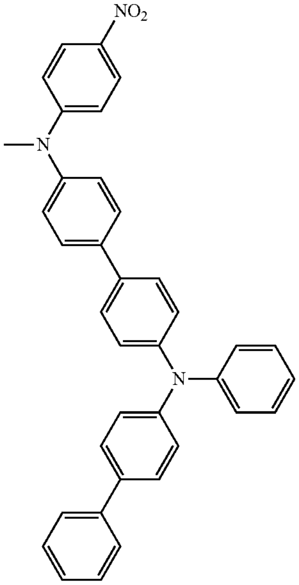

-continued
390
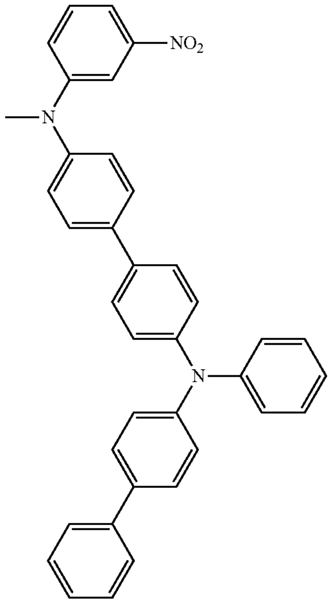
391
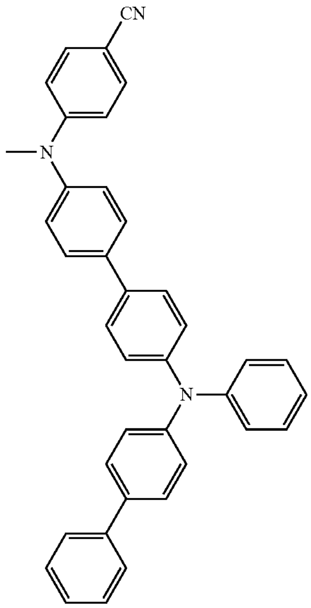
-continued
392
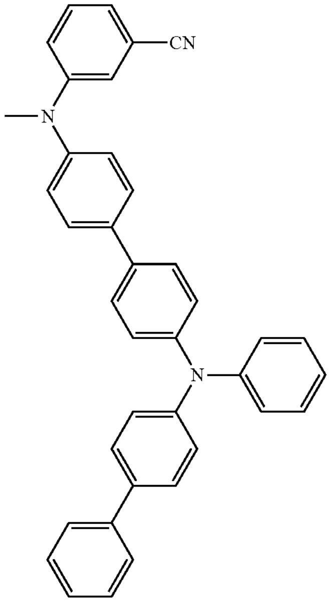
393
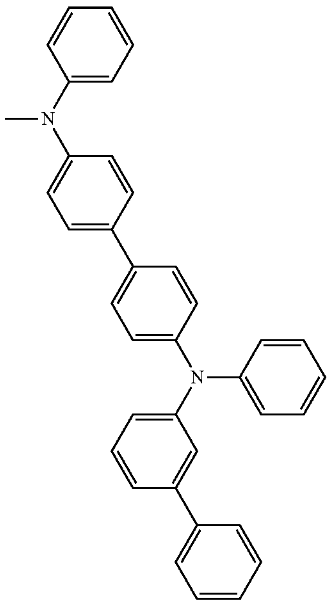

394
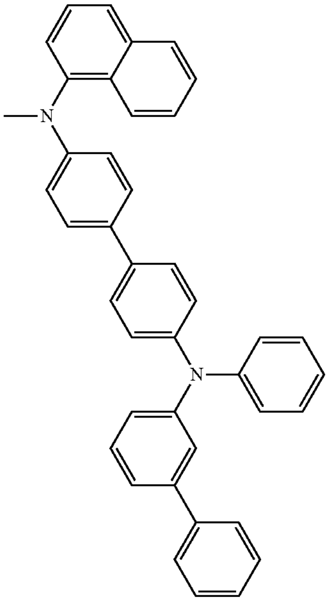
395
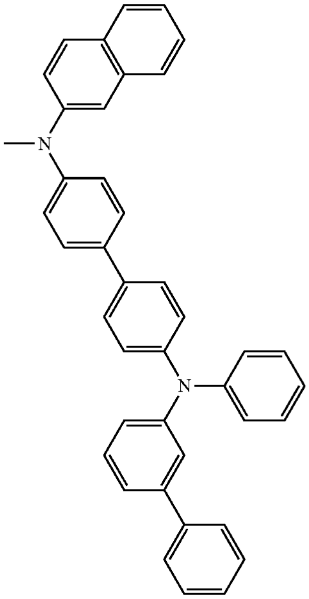
396
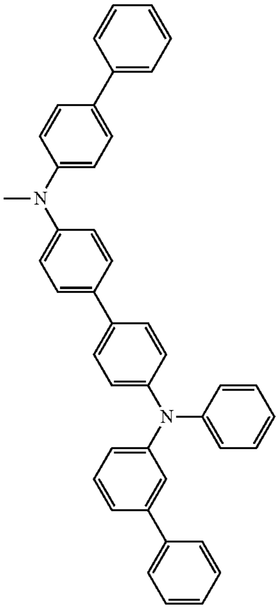
397
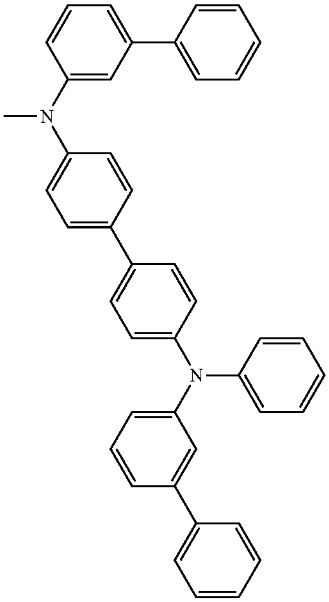

-continued
398
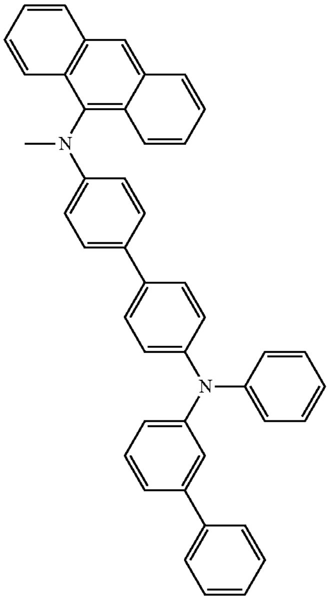
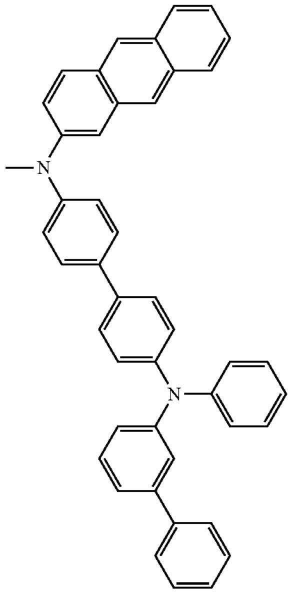
399
-continued
400
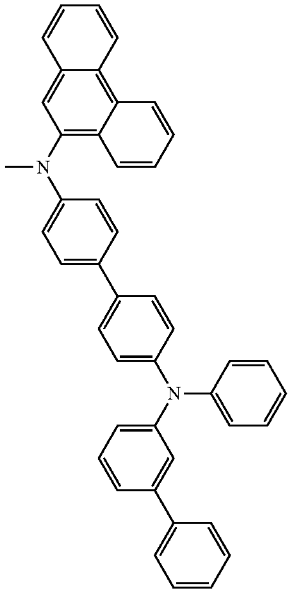
401
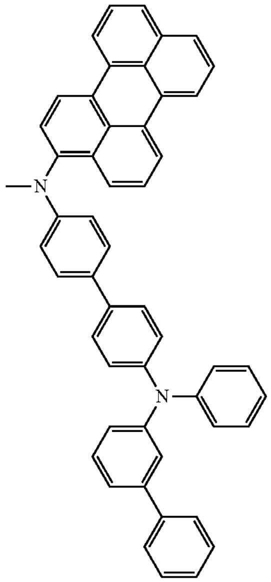

402
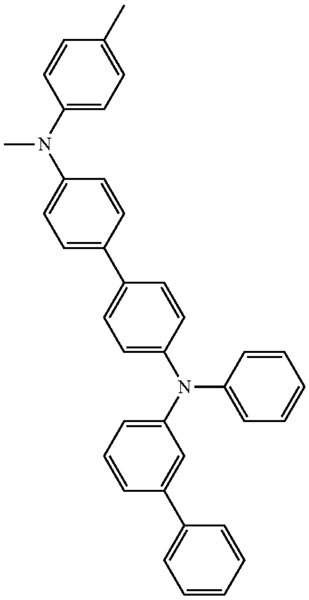
403
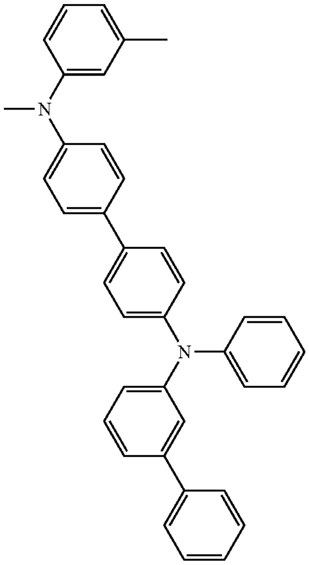
404
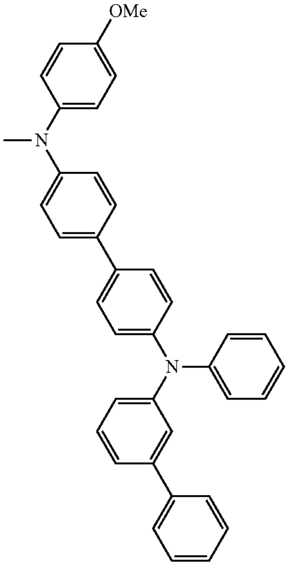
405
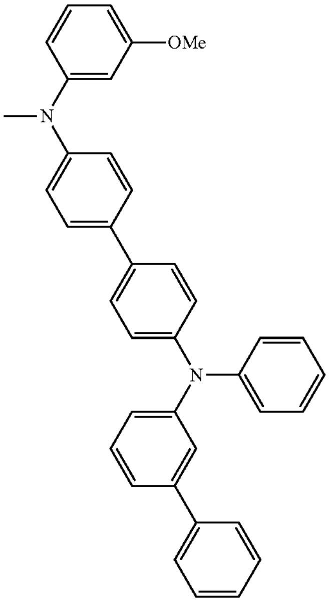

-continued
406
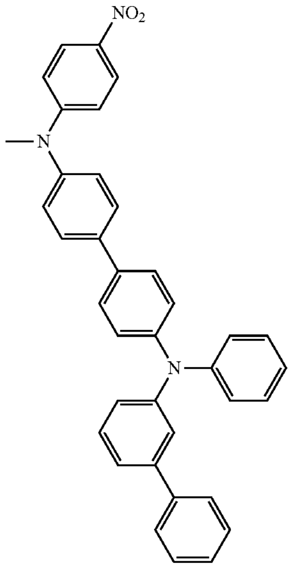
407
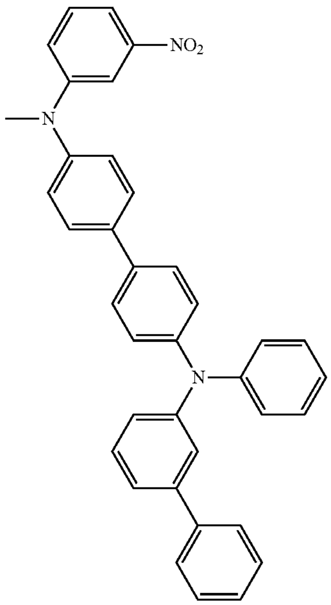
-continued
408
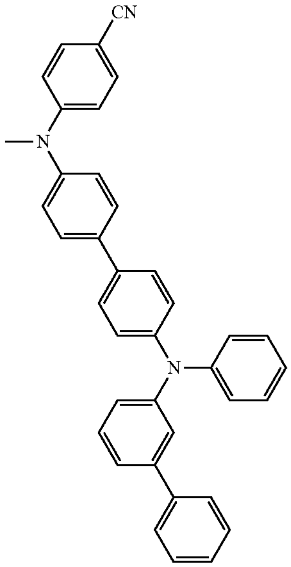
409
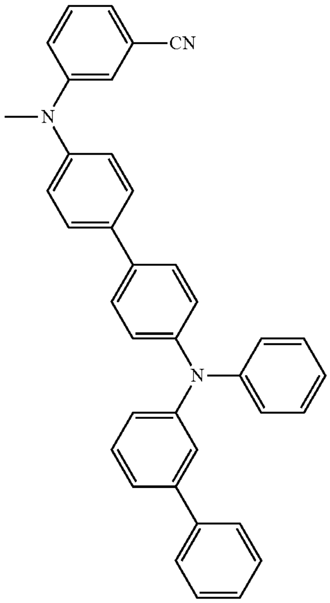

-continued
410
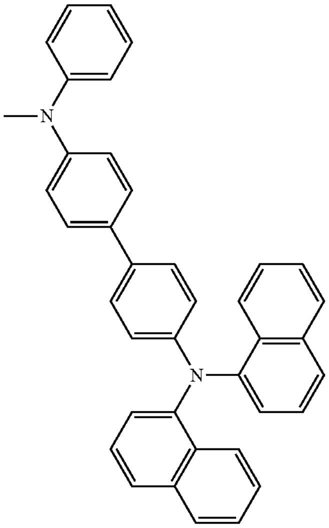
411
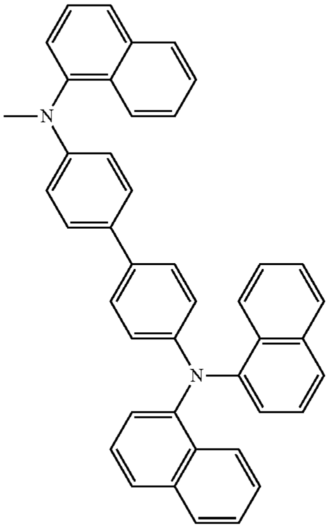
412
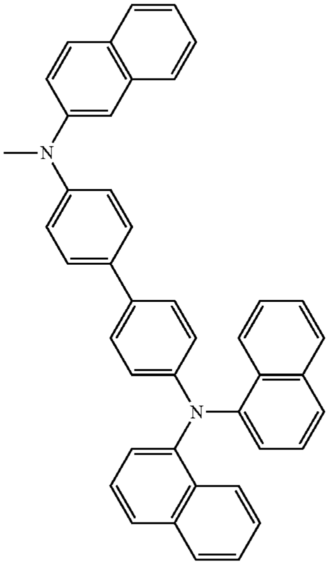
-continued
413
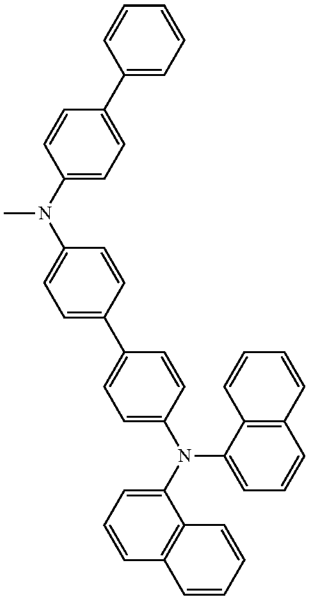
414
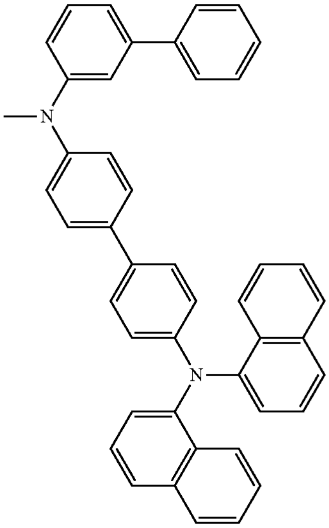

-continued
415
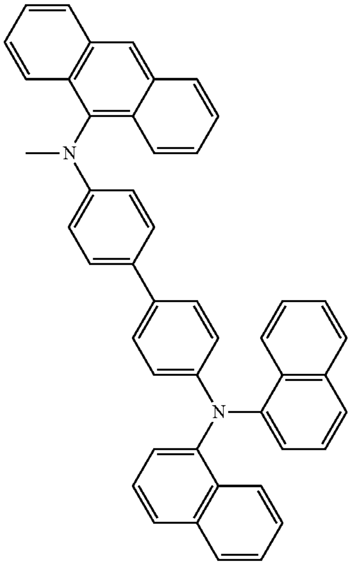
416
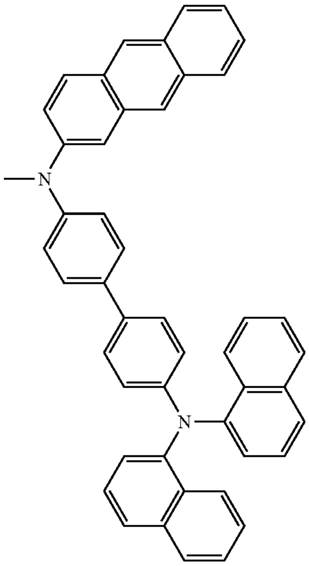
-continued
417
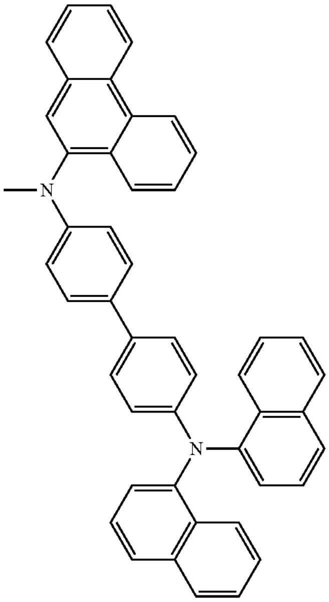
418
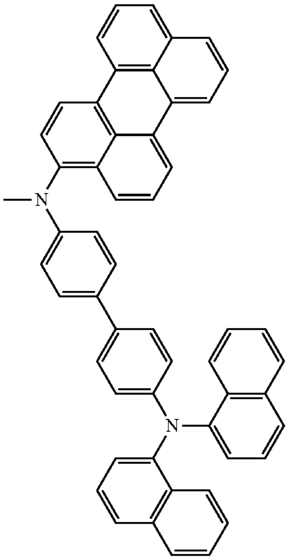

-continued
419
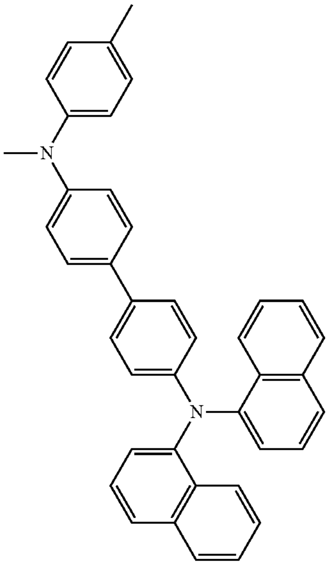
420
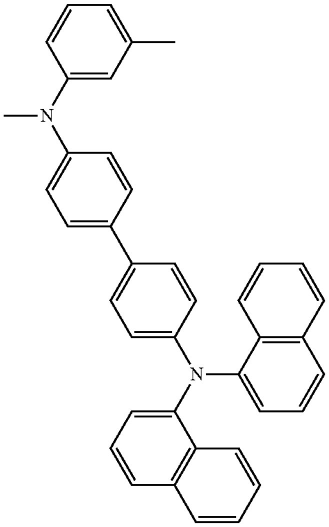
421
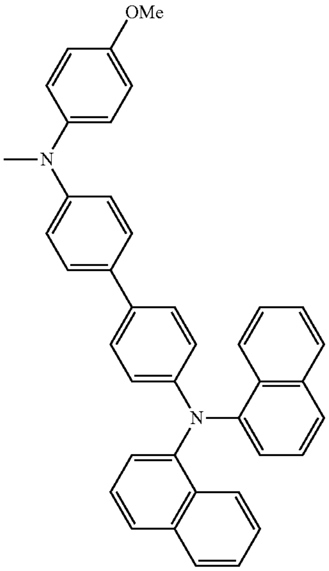
-continued
422
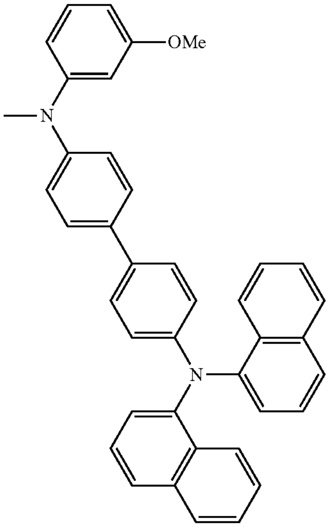
423
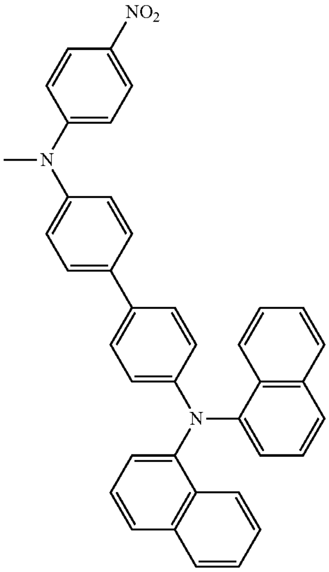
424
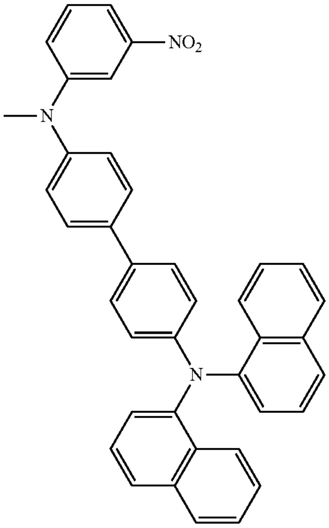

-continued
425
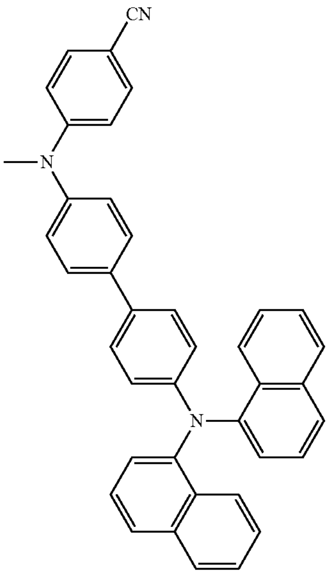
426
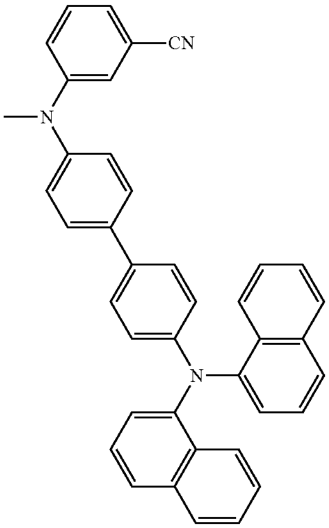
427
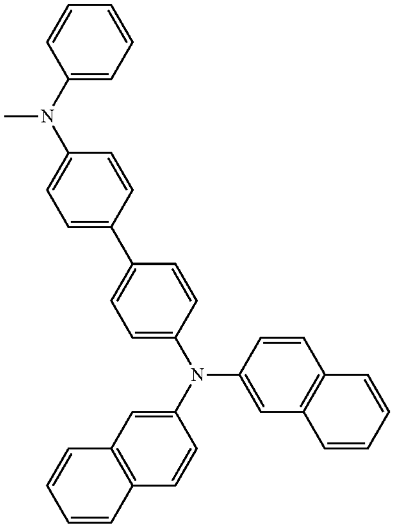
-continued
428
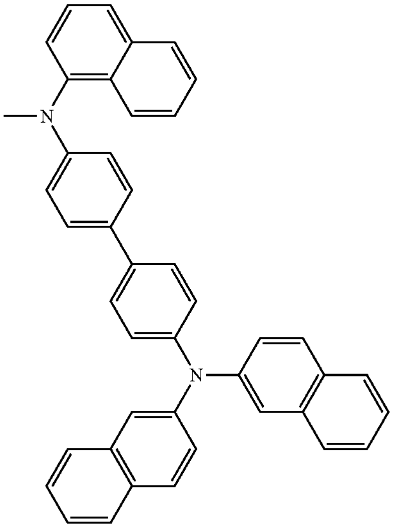
429
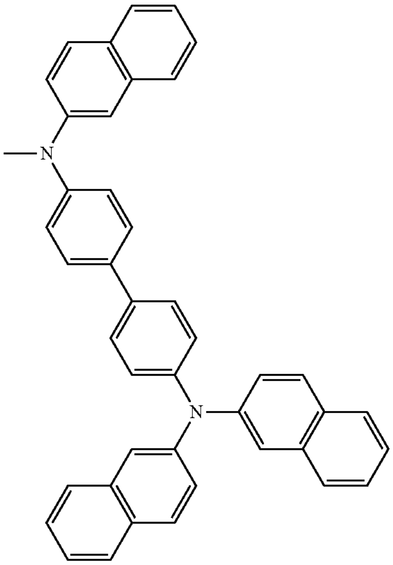
430
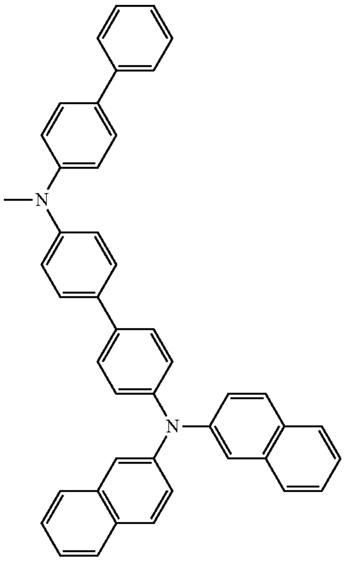

-continued
431
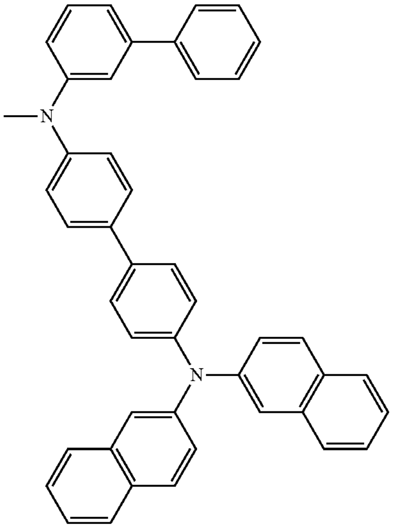
432
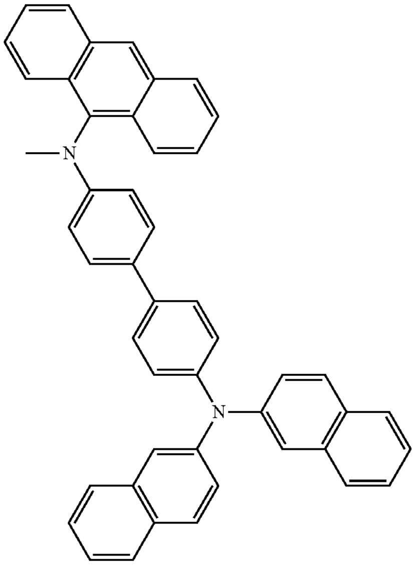
-continued
433
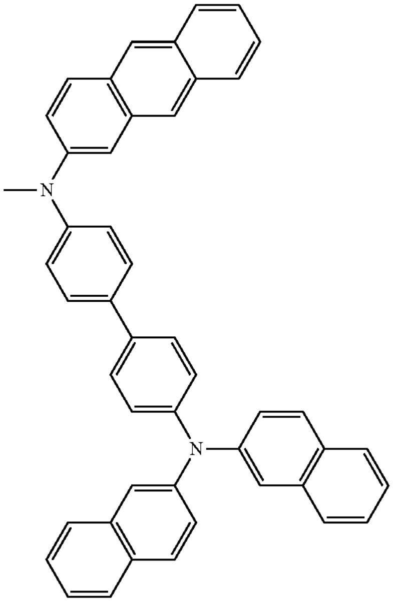
434
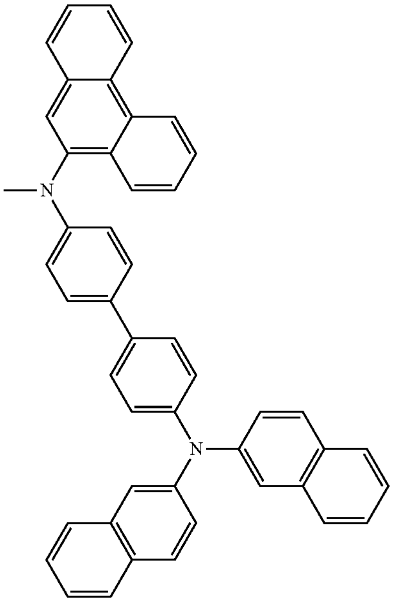

-continued
435
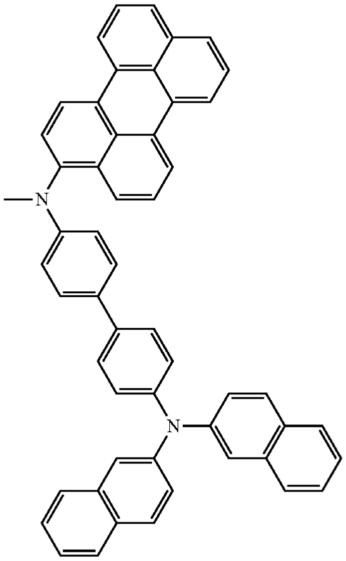
436
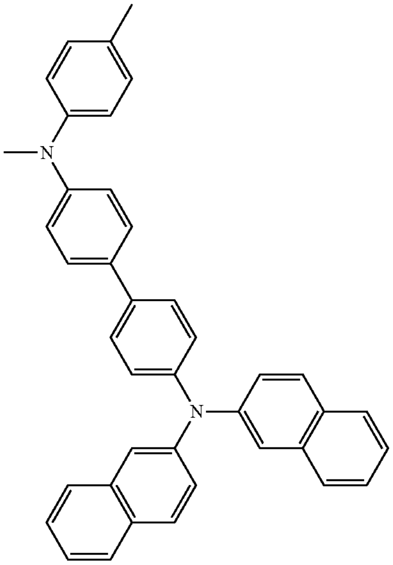
437
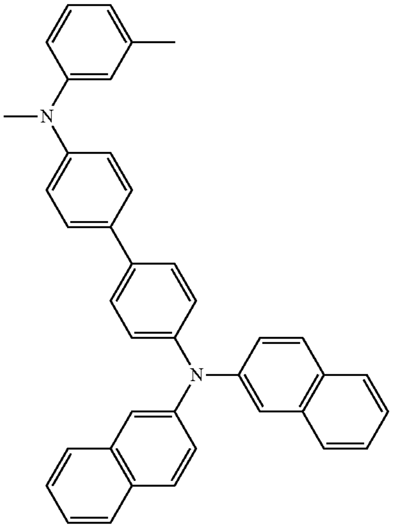
-continued
438
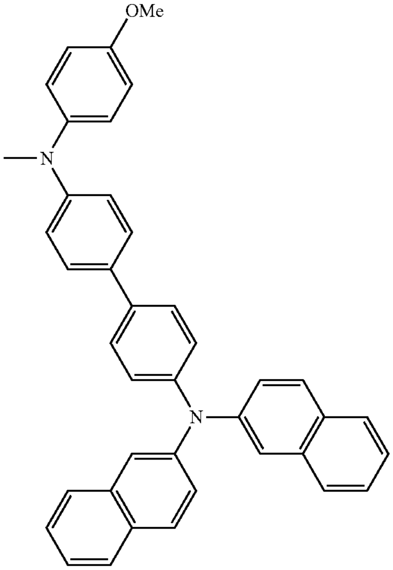
439
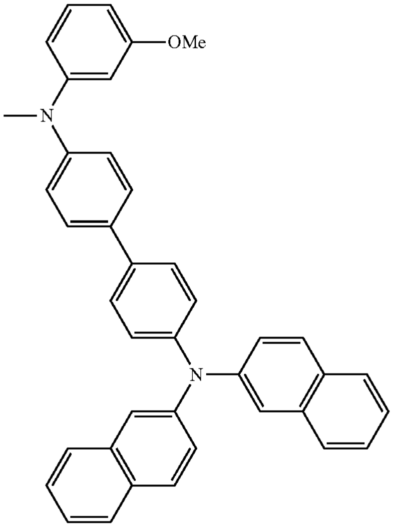
440
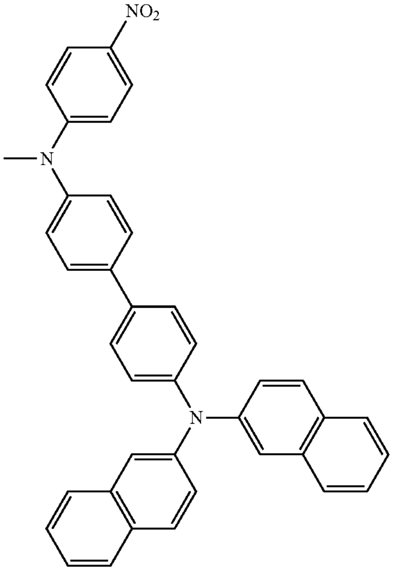

-continued
441
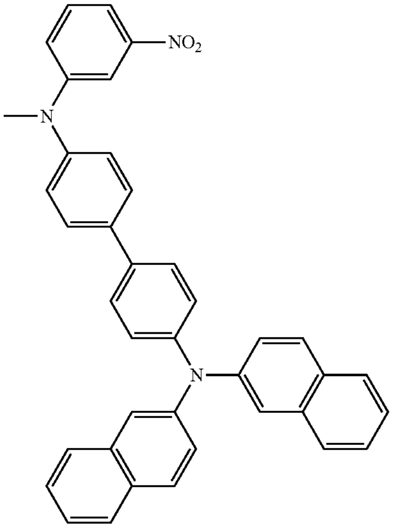
442
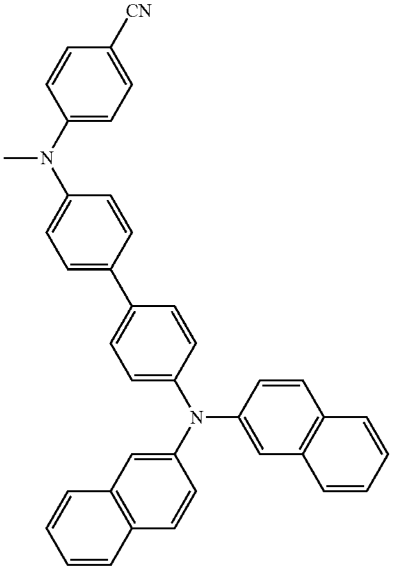
443
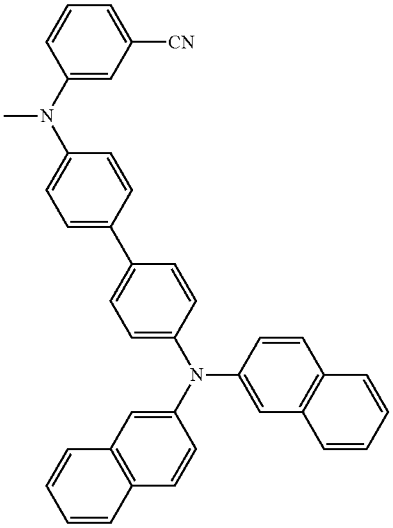
-continued
444
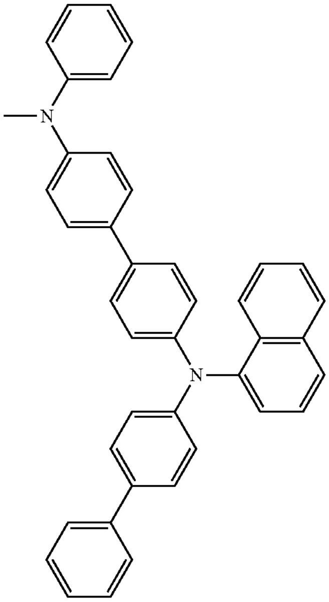
445
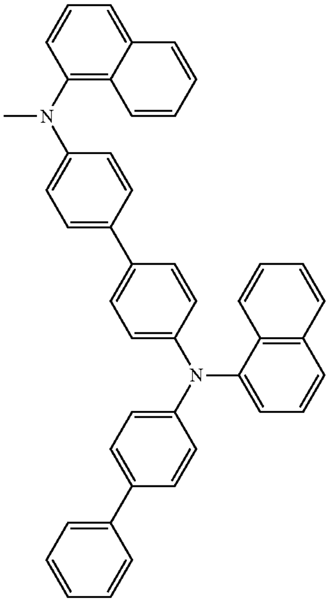

-continued
446
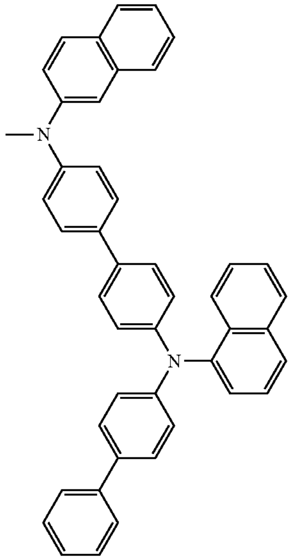
447
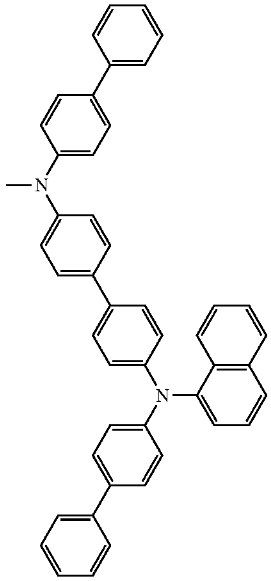
-continued
448
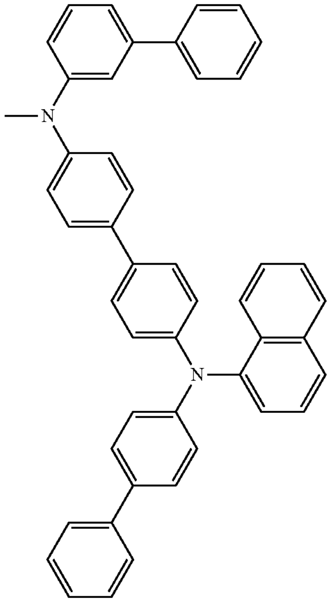
449
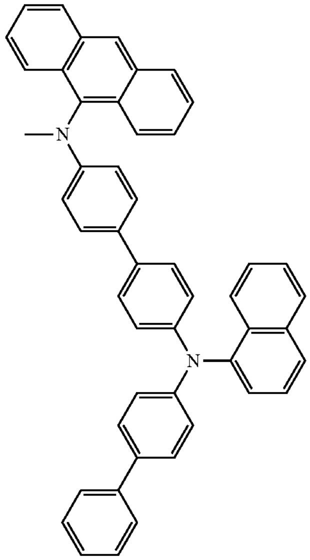

450
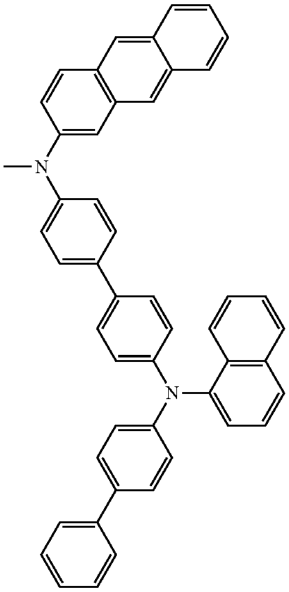
451
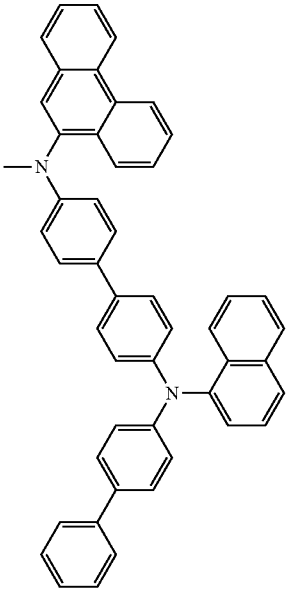
452
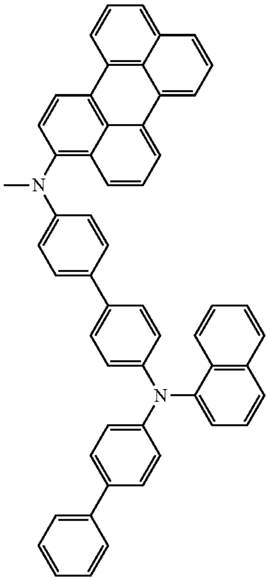
453
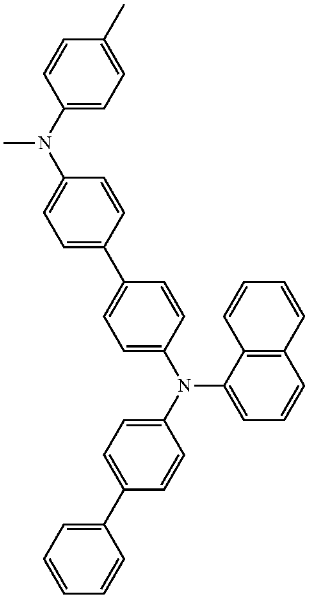

-continued
454
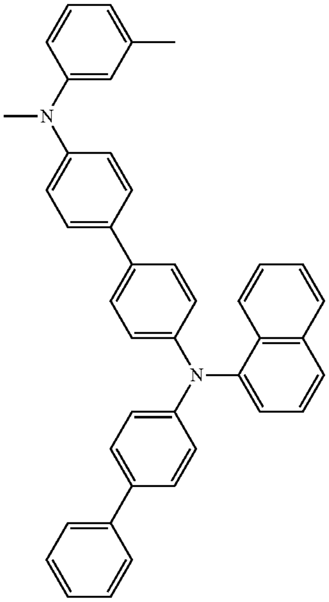
-continued
456
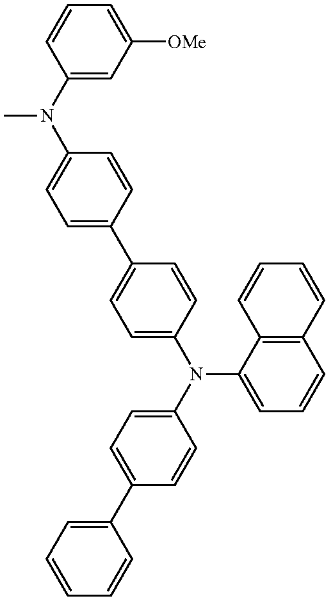
455
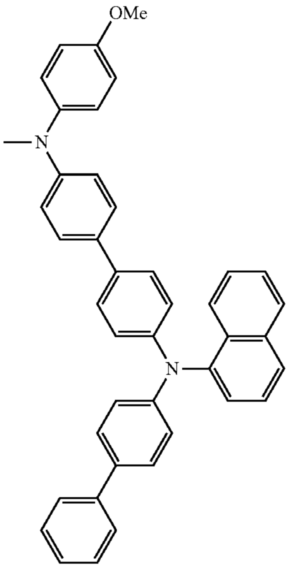
457
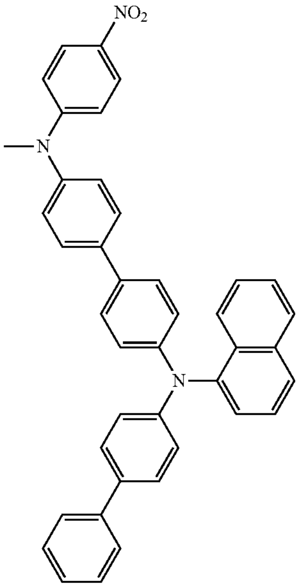

-continued
458
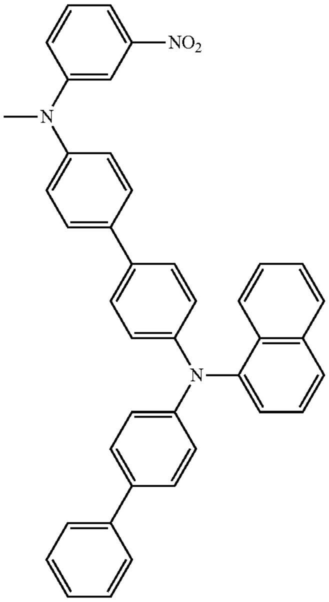
459
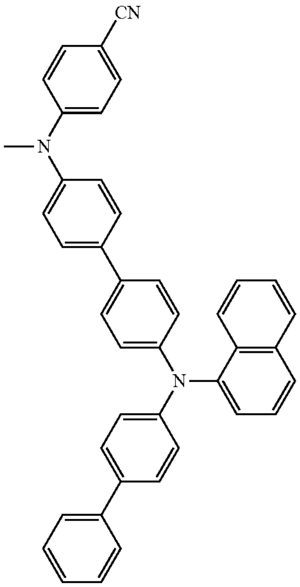
-continued
460
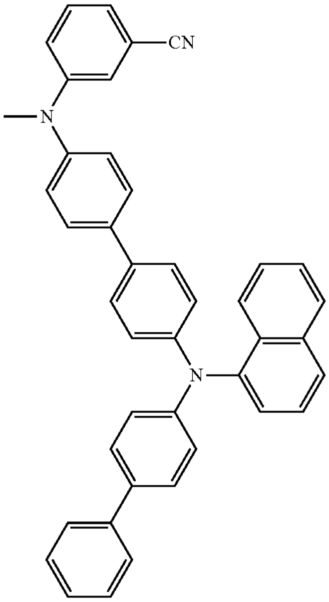
461
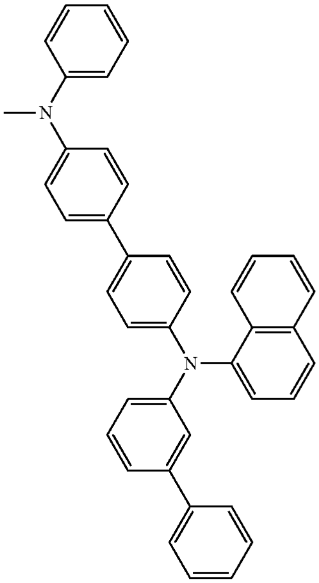

-continued
462
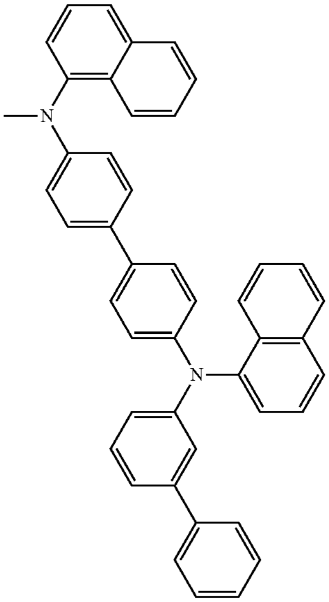
463
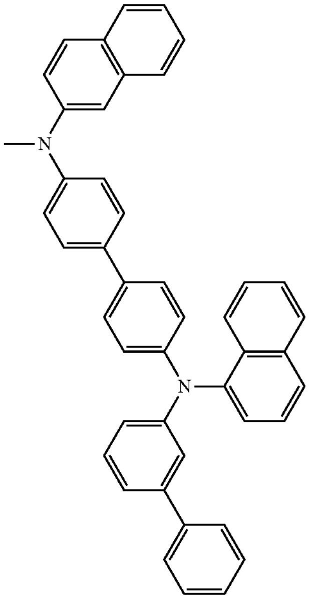
-continued
464
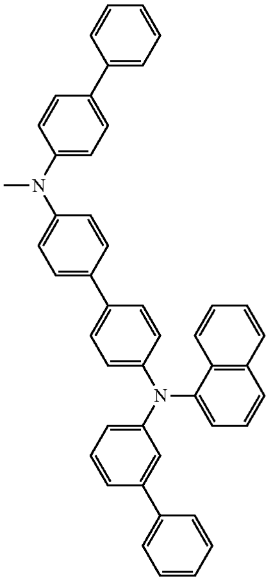
465
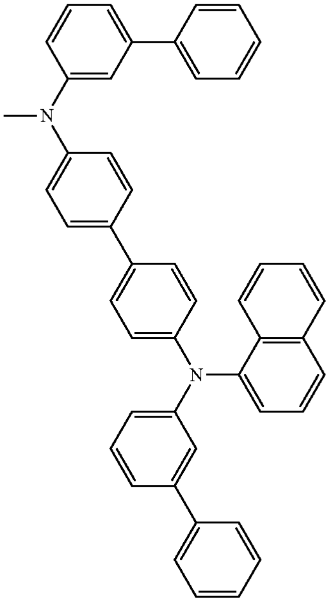

466
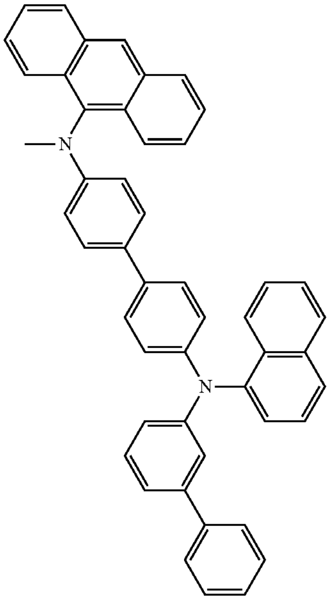
467
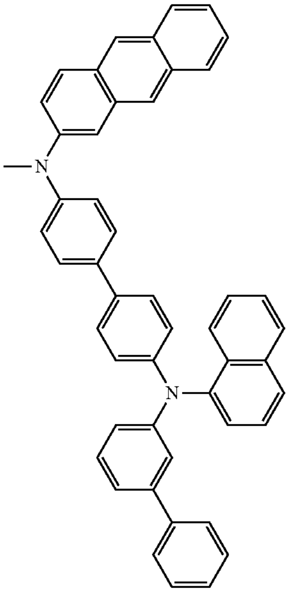
468
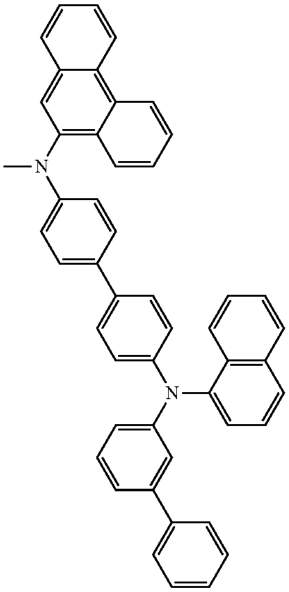
469
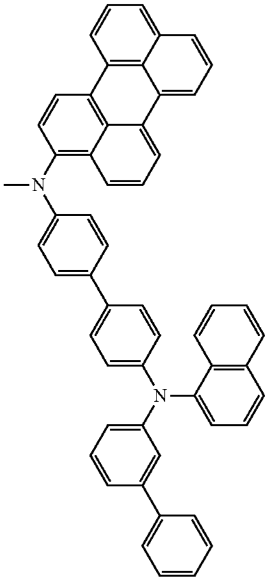

-continued
470
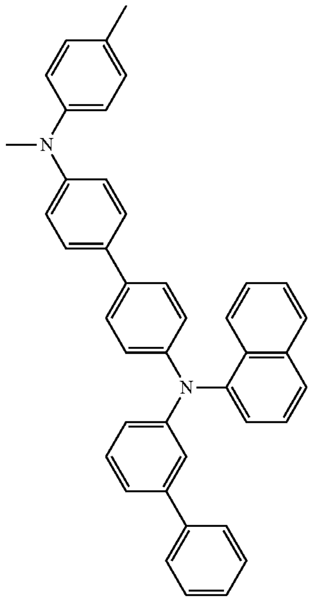
472
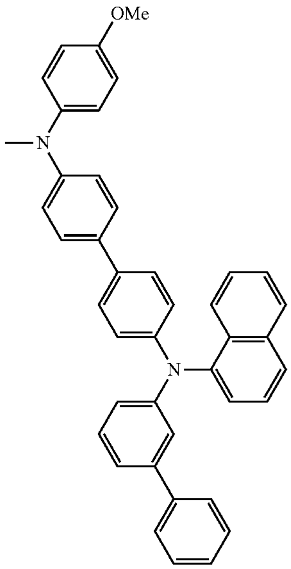
471
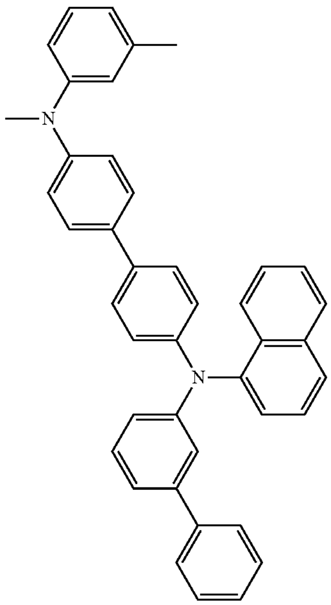
473
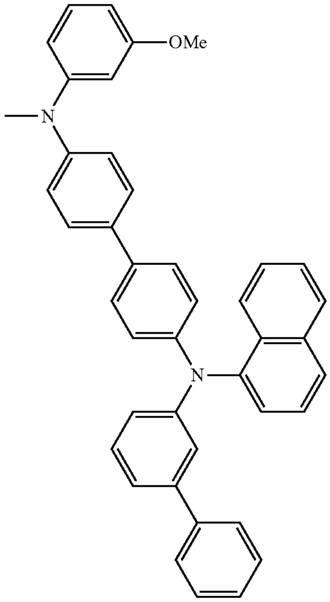

-continued
474
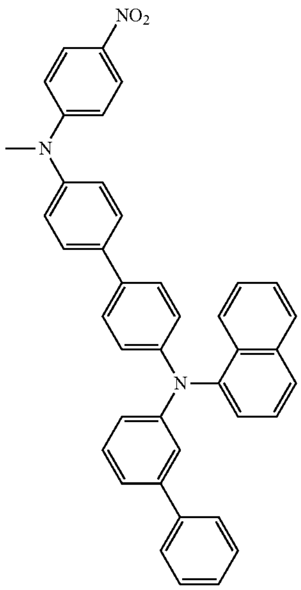
475
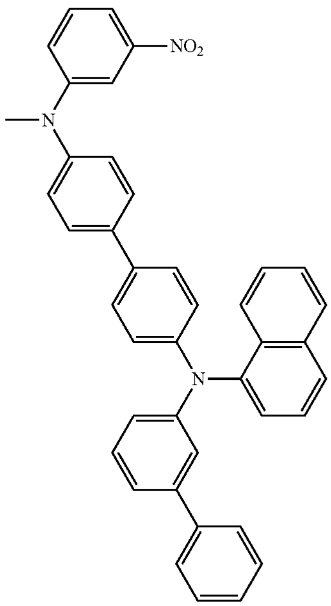
-continued
476
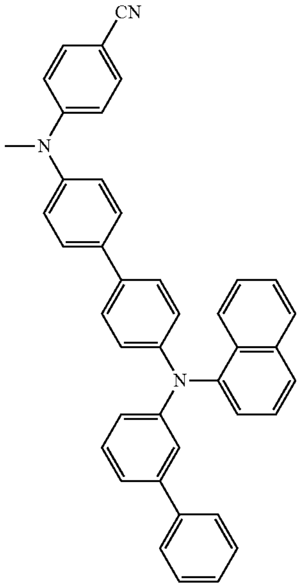
477
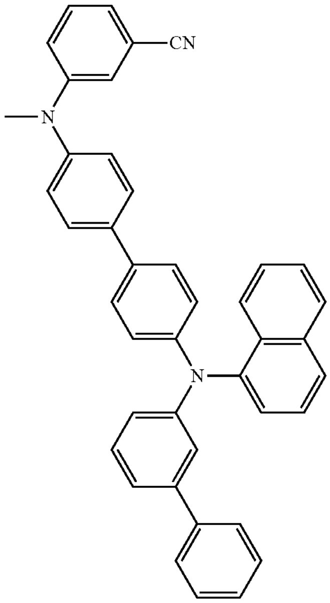

-continued
478
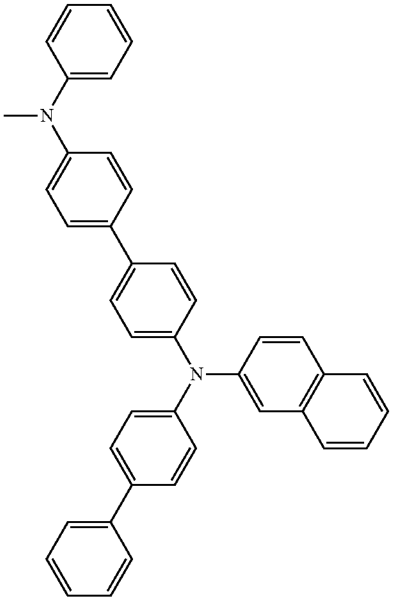
479
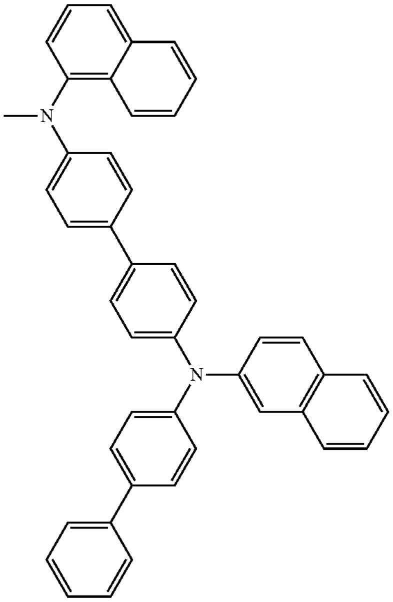
-continued
480
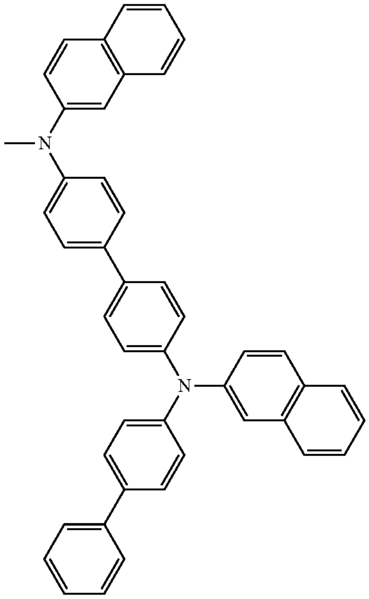
481
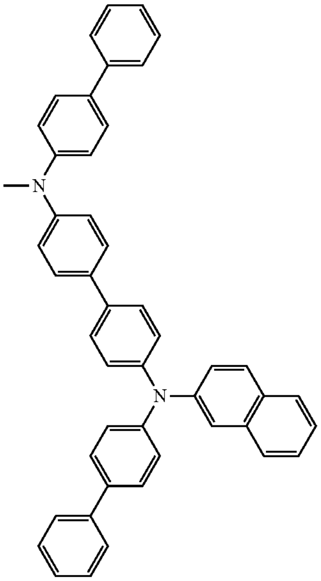

-continued
482
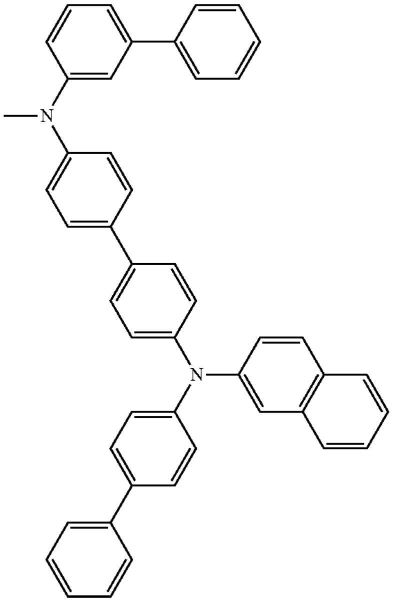
483
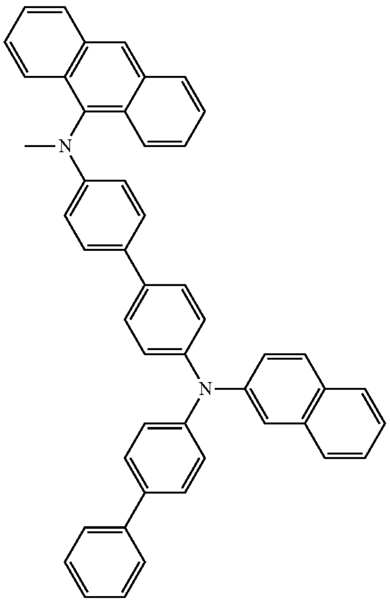
-continued
484
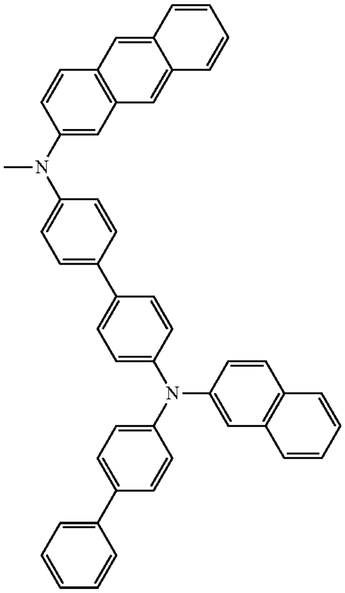
485
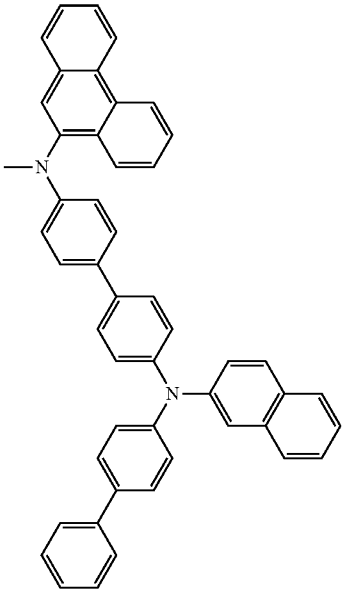

-continued
486
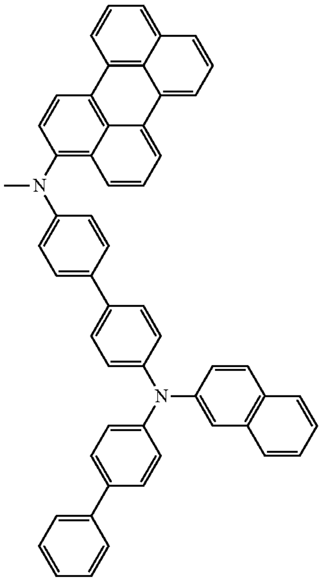
487
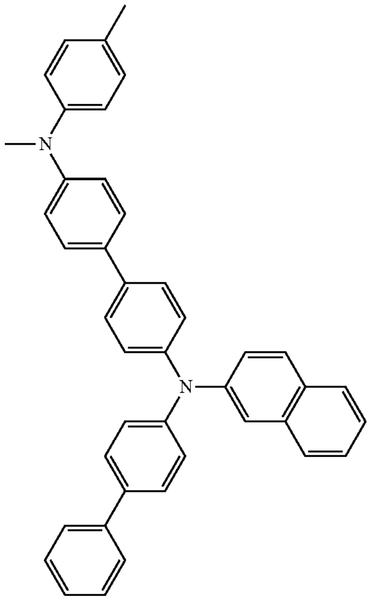
-continued
488
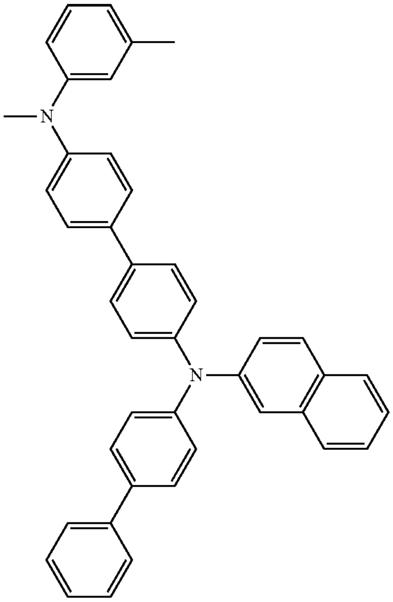
489
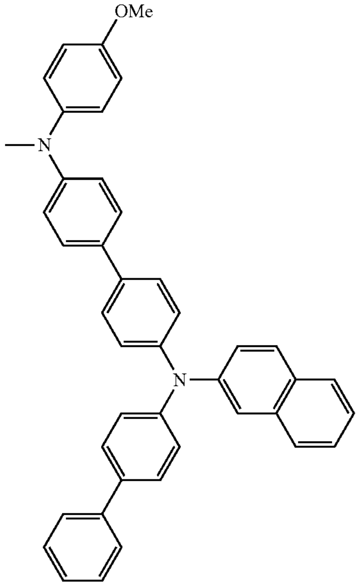

-continued
490
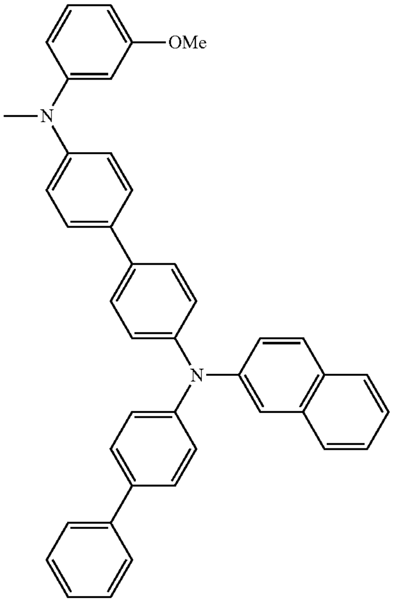
491
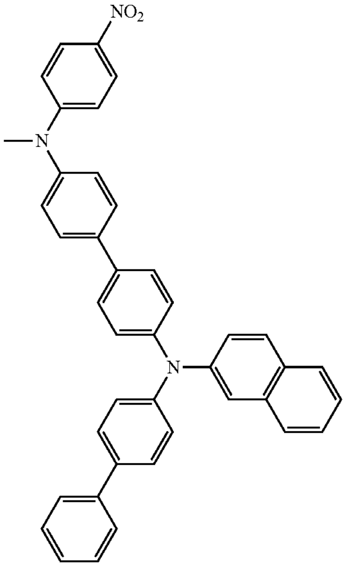
-continued
492
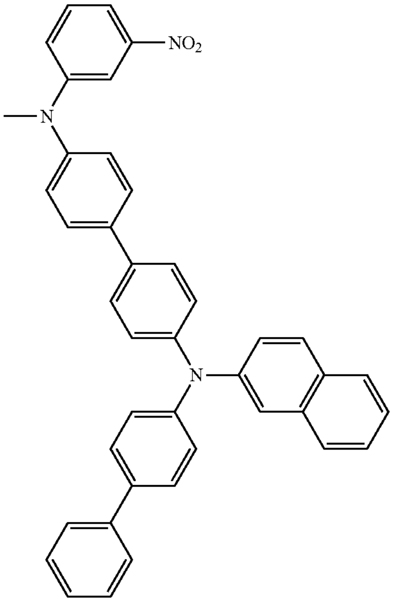
493
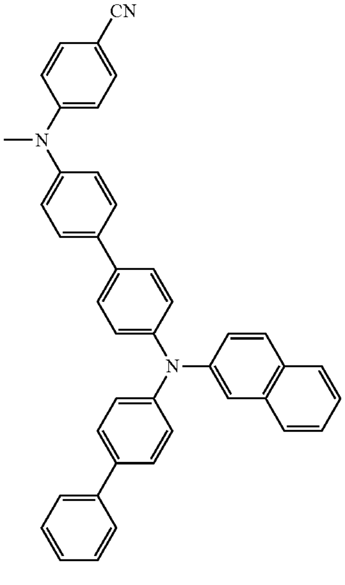

-continued
494
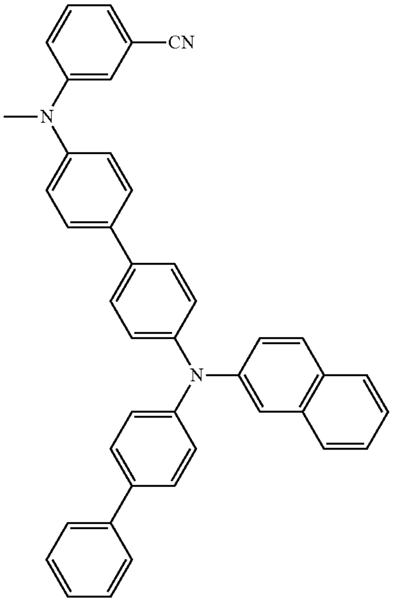
496
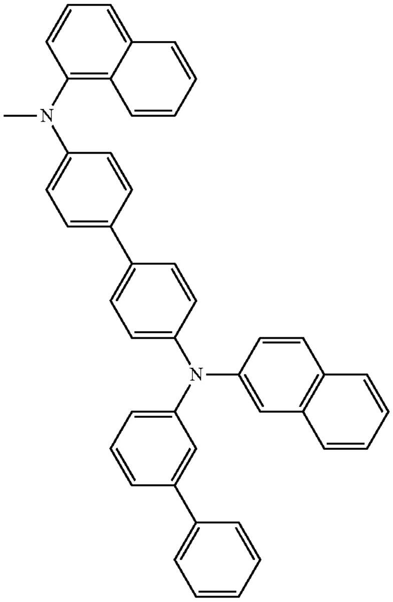
495
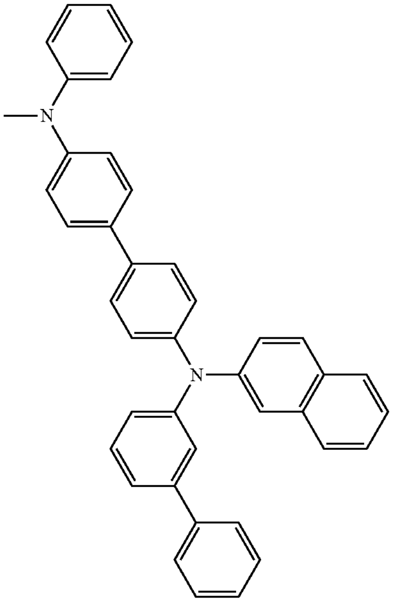
497
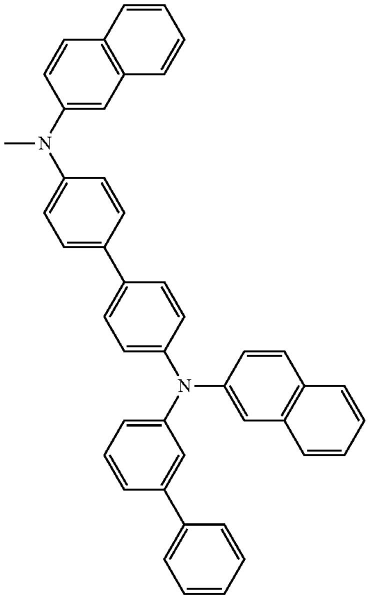

-continued
498
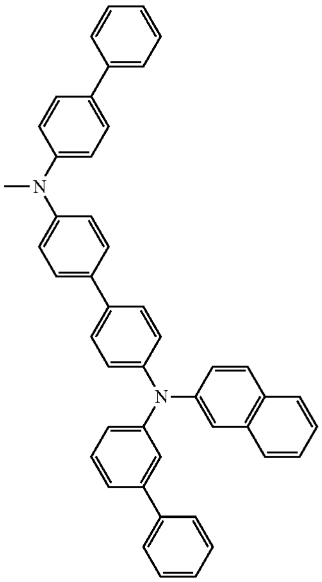
499
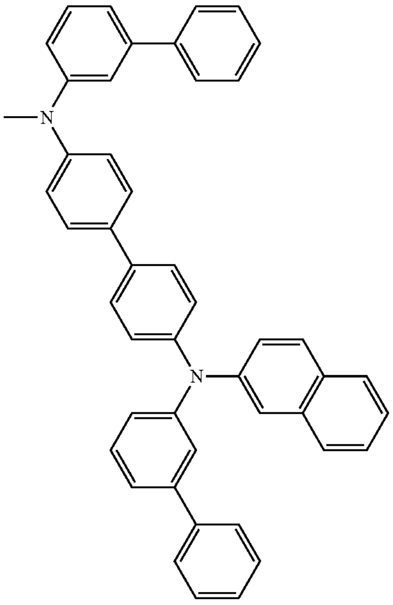
-continued
500
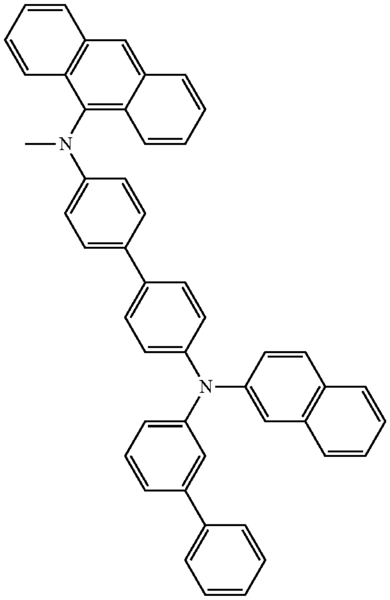
501
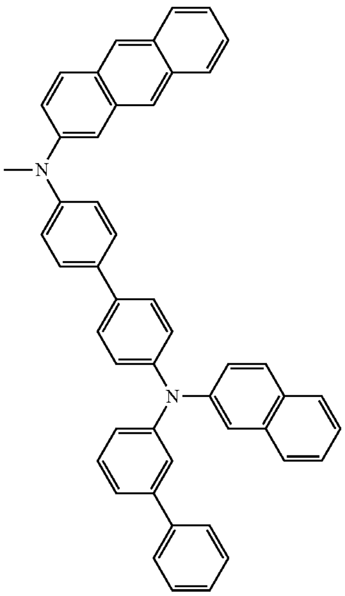

-continued
502
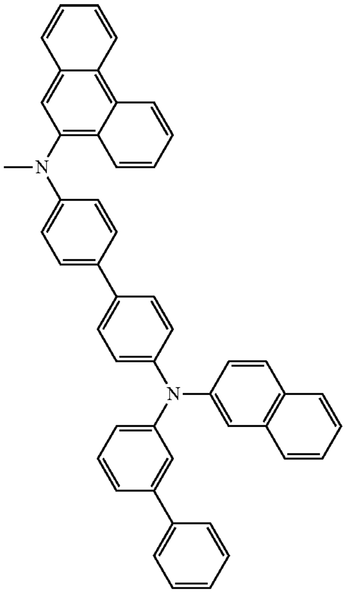
504
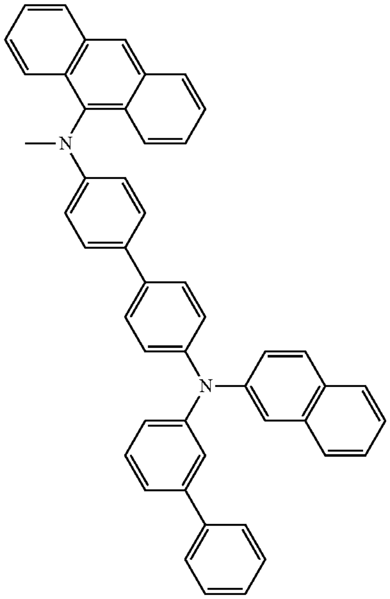
503
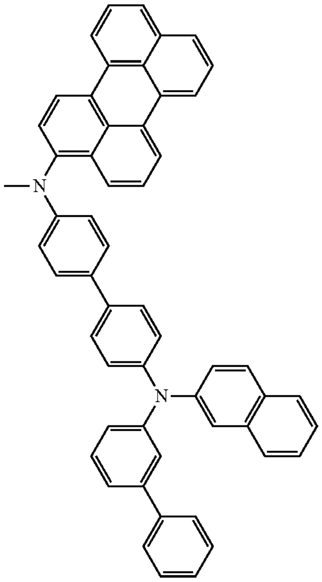
505
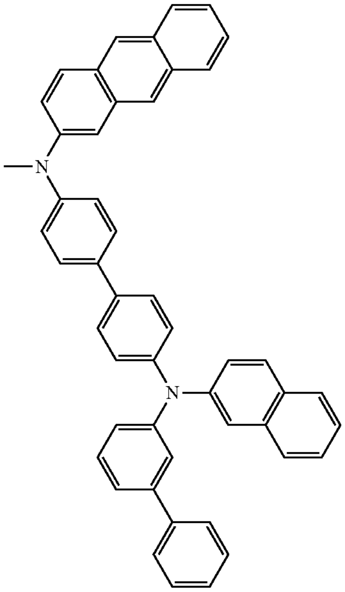

-continued
506
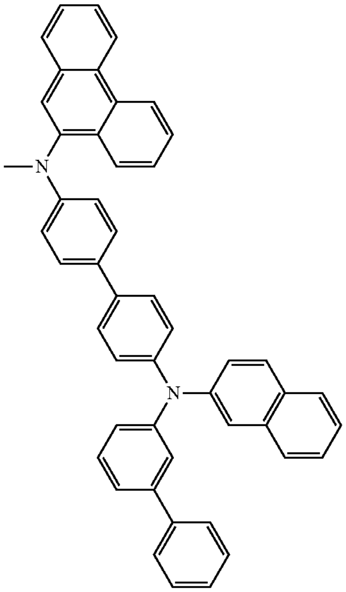
508
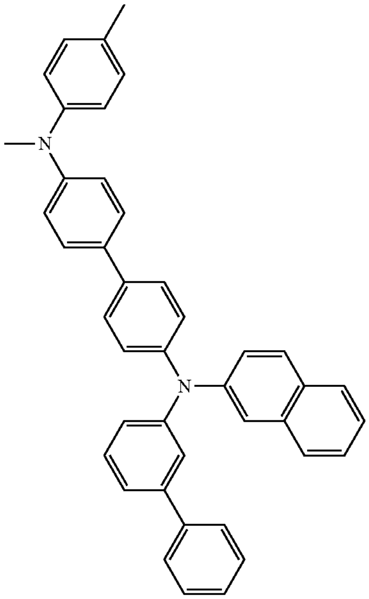
507
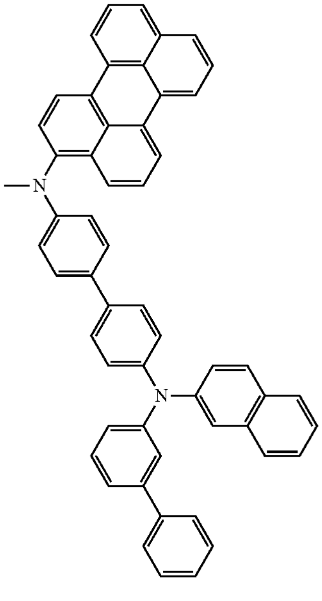
509
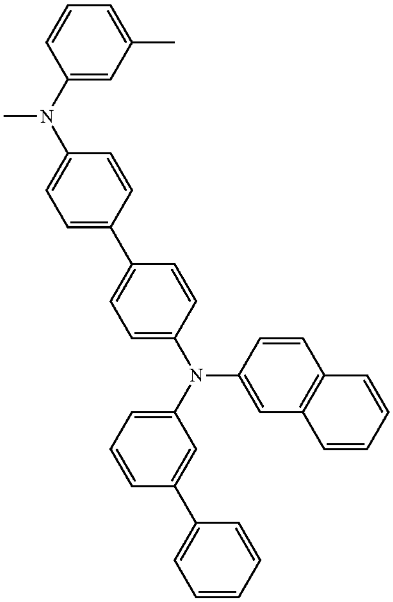

-continued
510
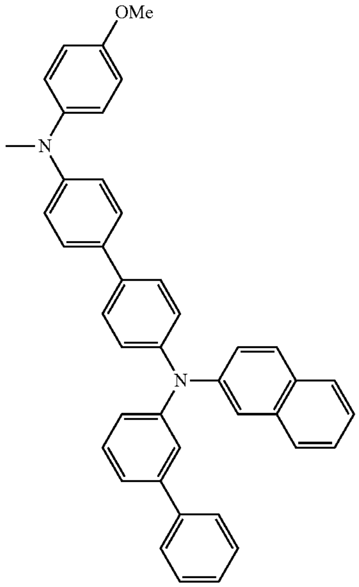
511
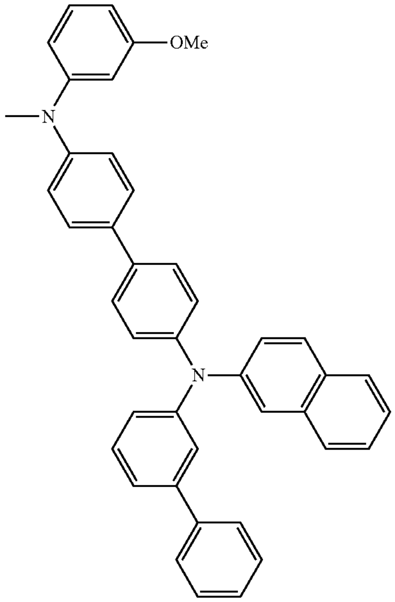
-continued
512
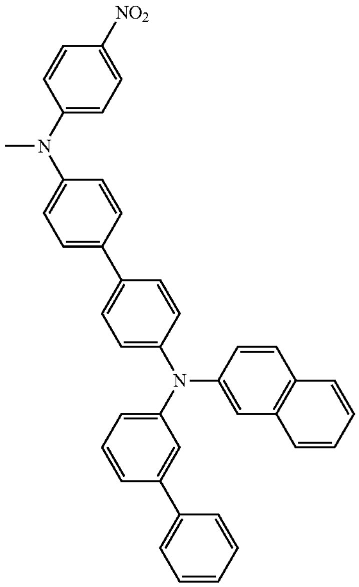
513
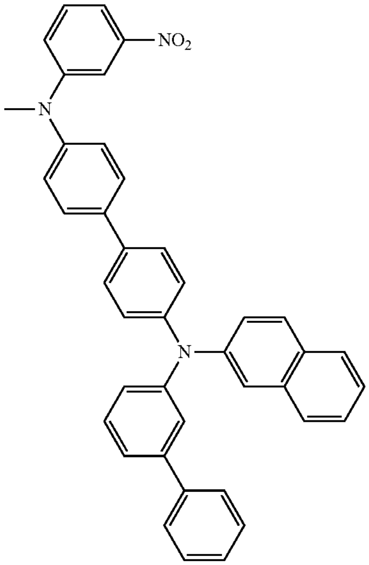

-continued
514
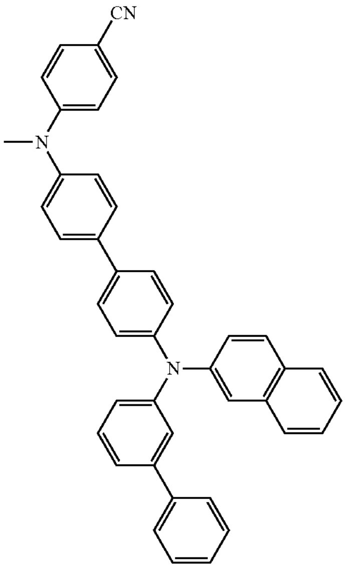
515
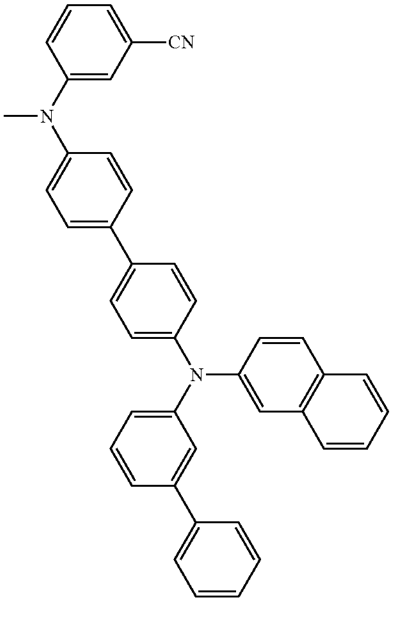
-continued
516
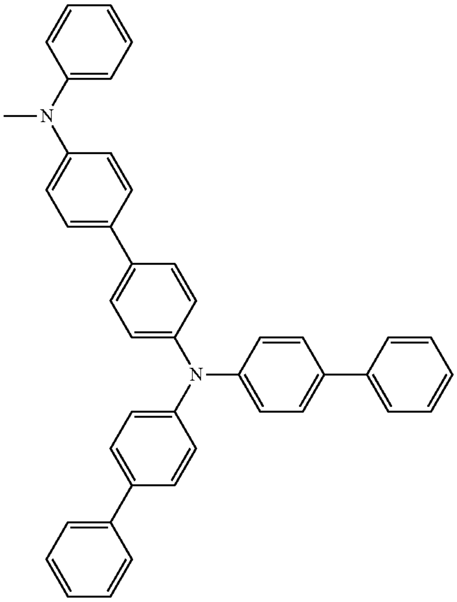
517
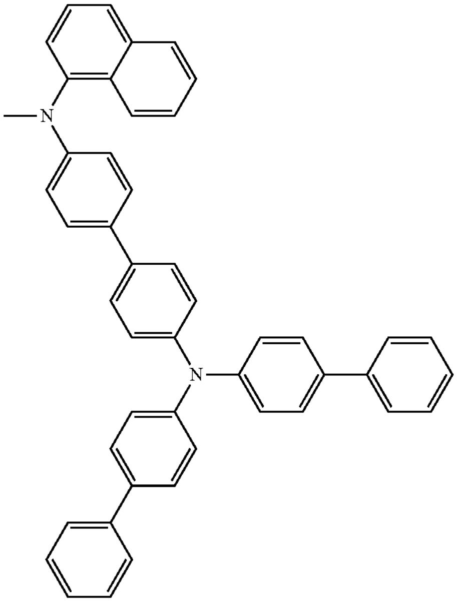

-continued
518
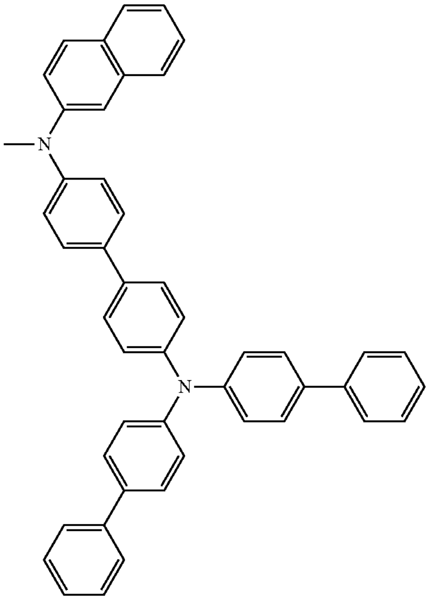
519
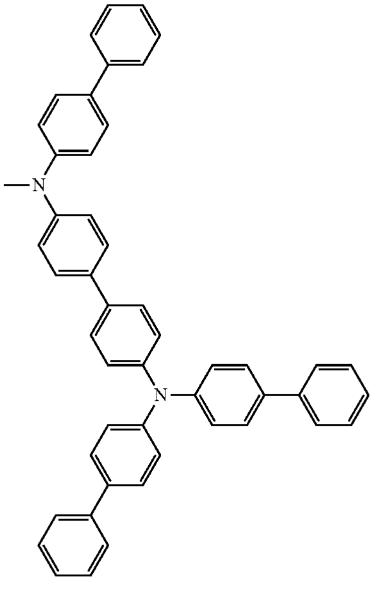
-continued
520
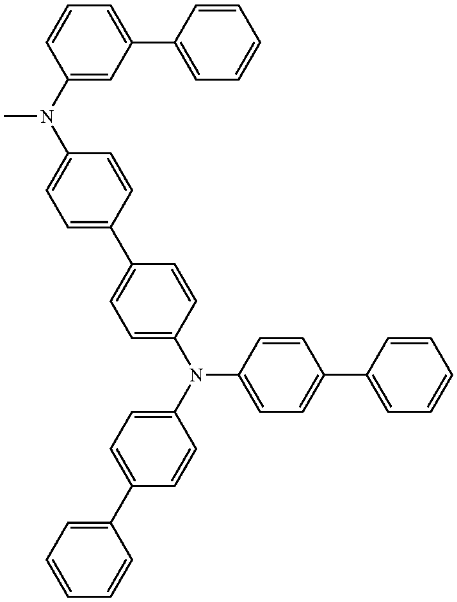
521
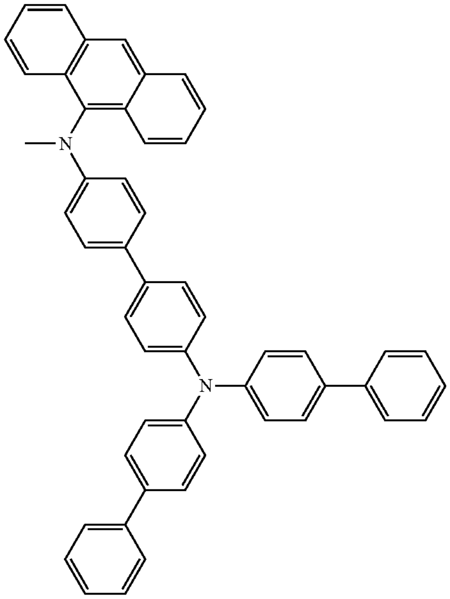

-continued
522
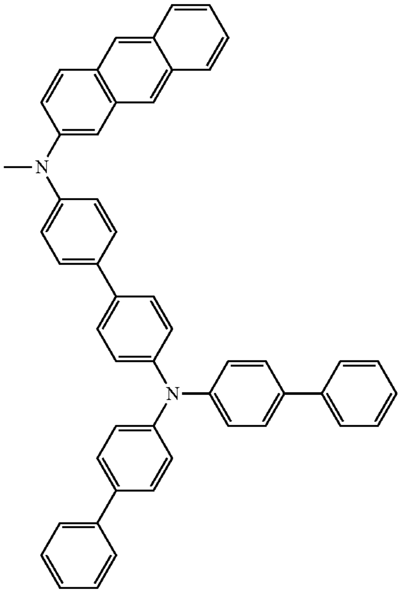
524
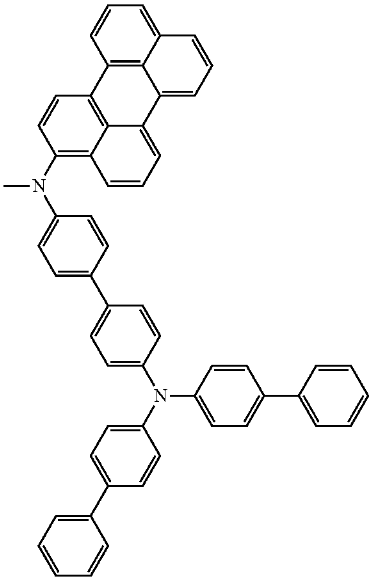
523
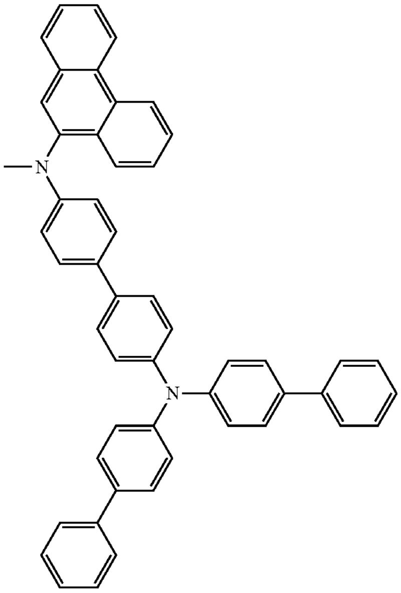
525
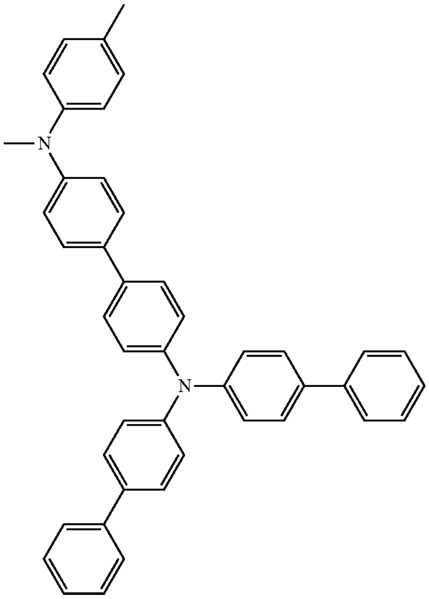

-continued
526
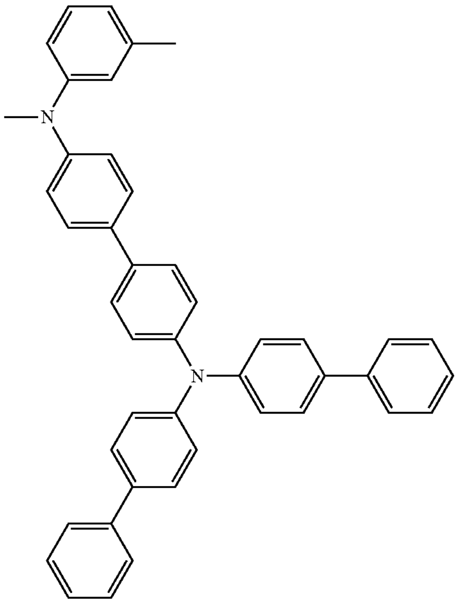
527
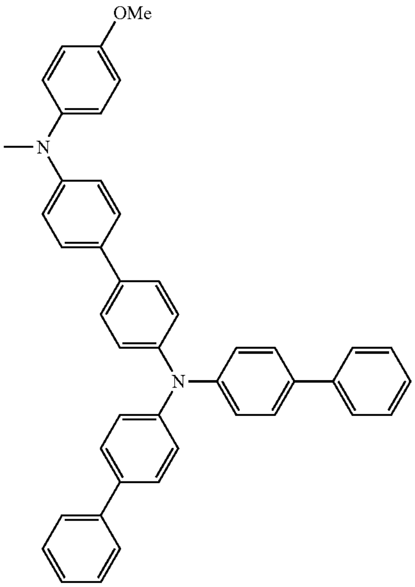
-continued
528
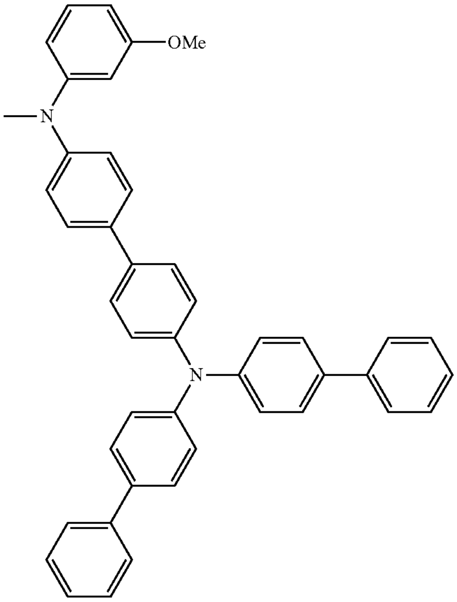
529
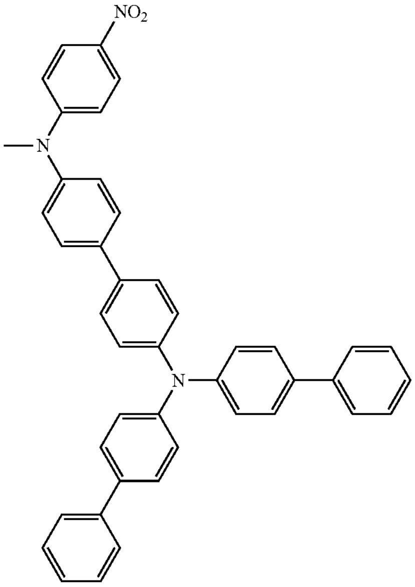

-continued
530
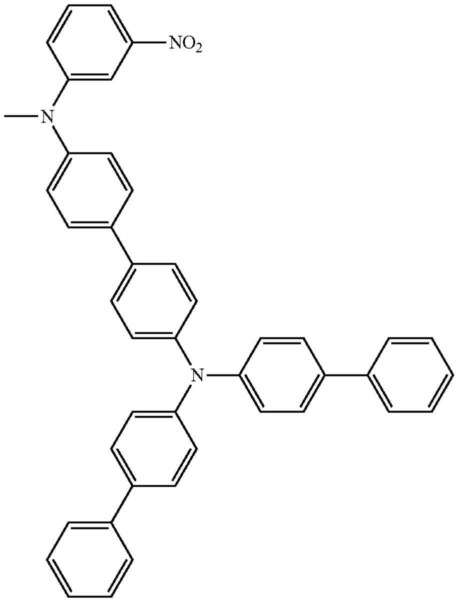
532
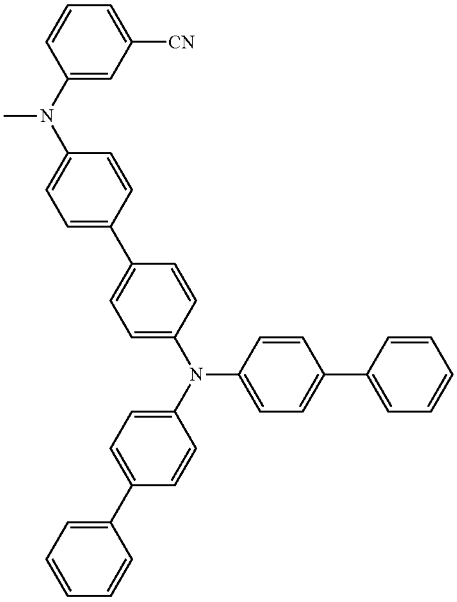
531
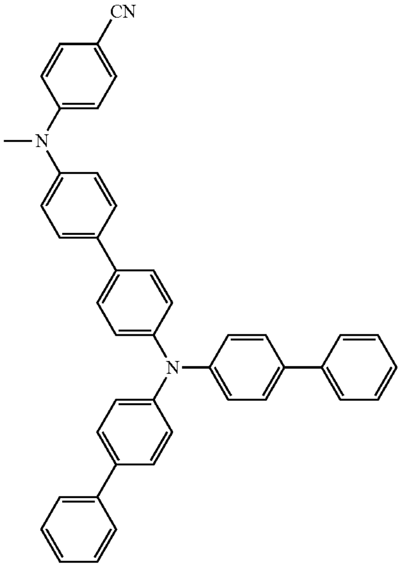
533
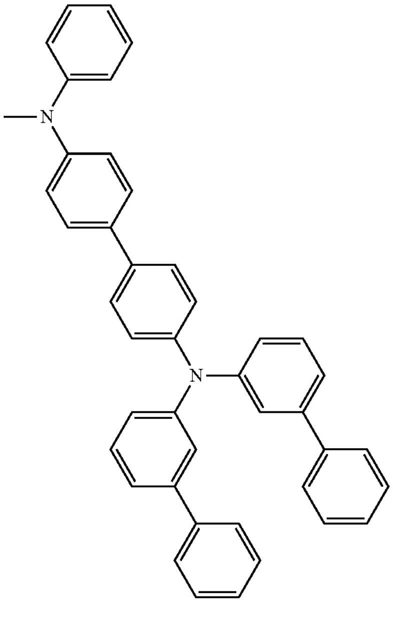

-continued
534
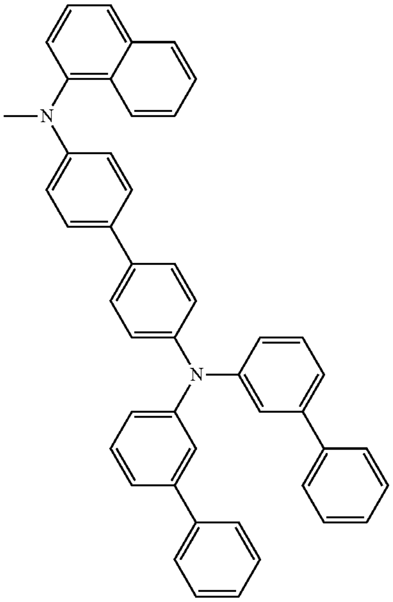
535
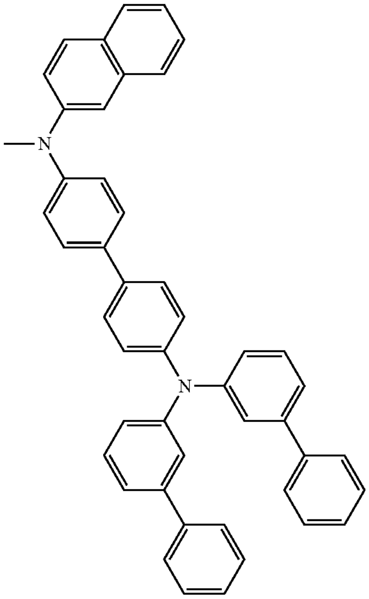
-continued
536
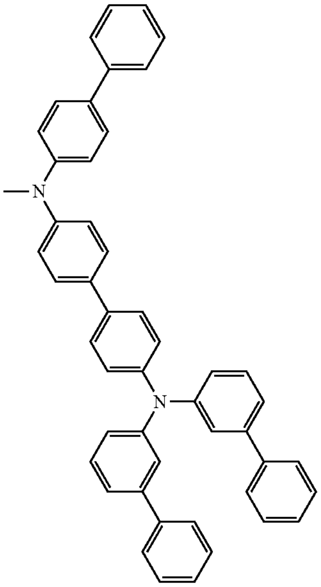
537
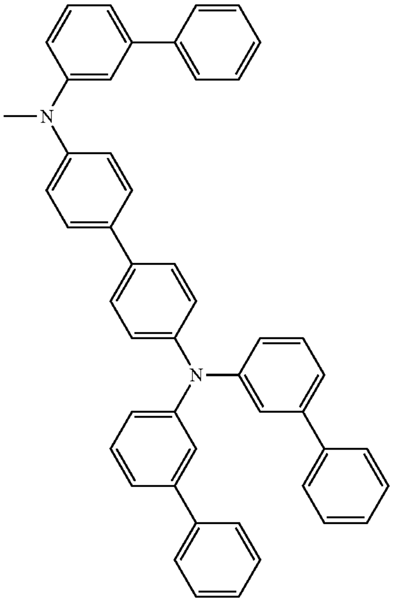

-continued
538
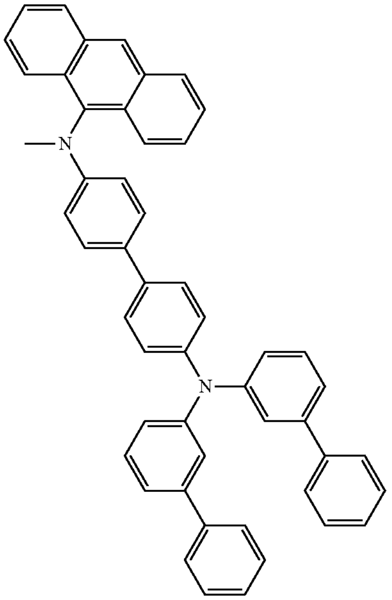
540
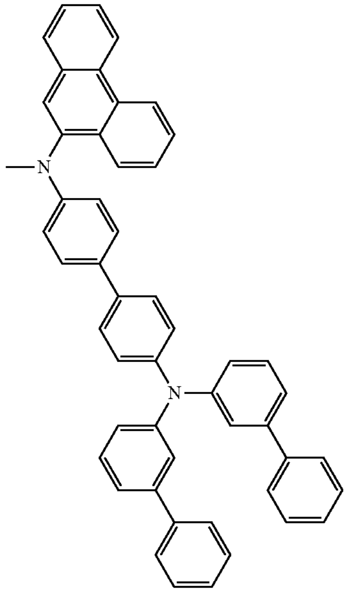
539
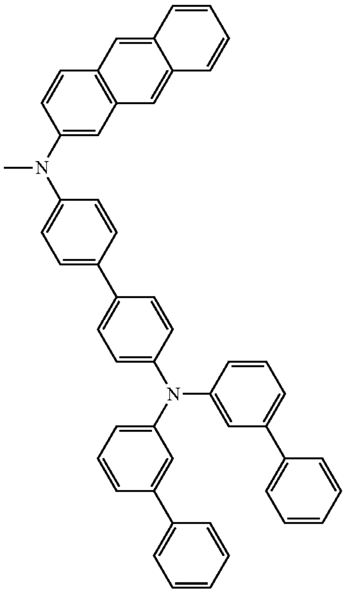
541
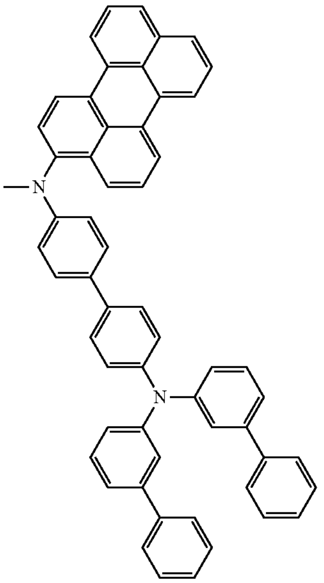

-continued
542
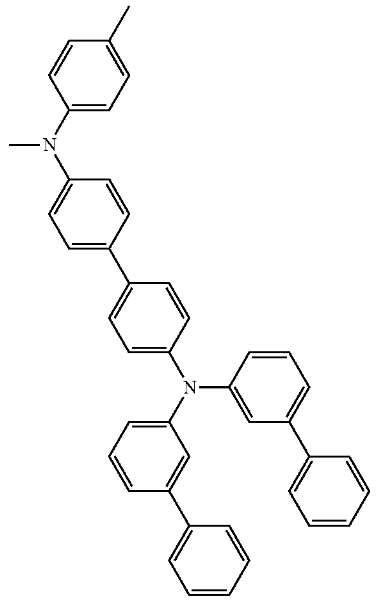
543
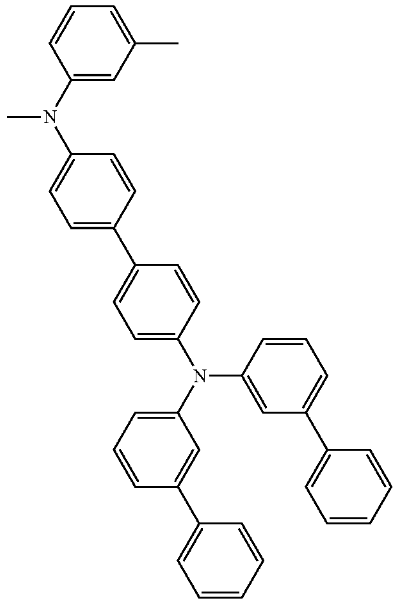
-continued
544
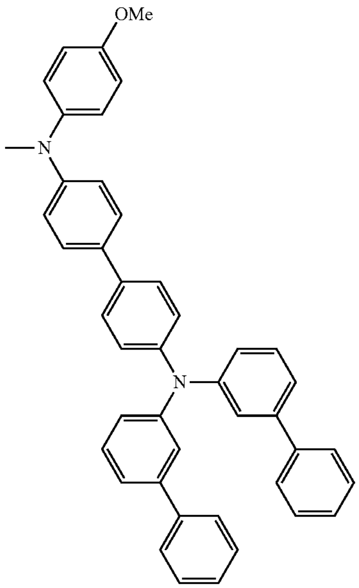
545
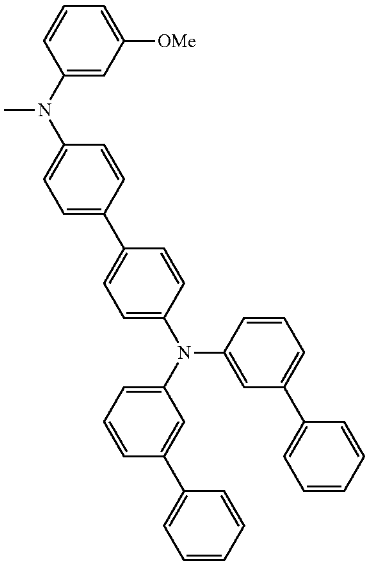

-continued
546
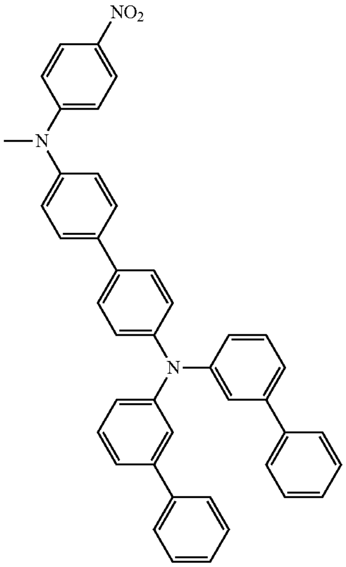
547
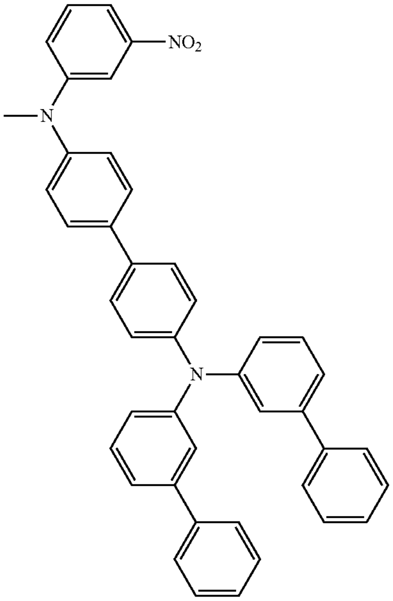
-continued
548
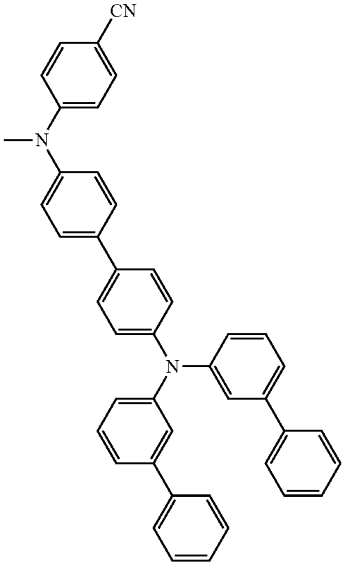
549
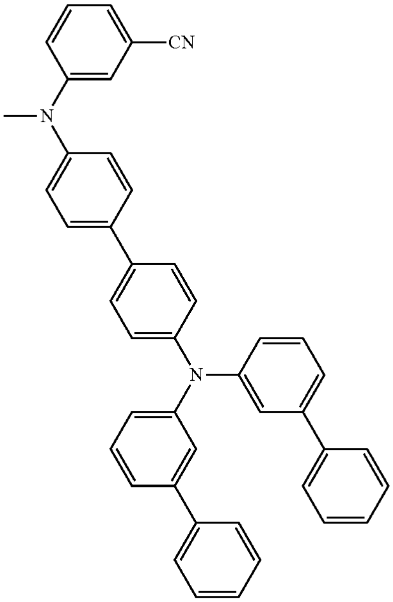
Ar may be preferably phenylene.
The compound of Formula 1 may be preferably a compound that is represented by the following Formula 4 to Formula 12.

[Formula 4]
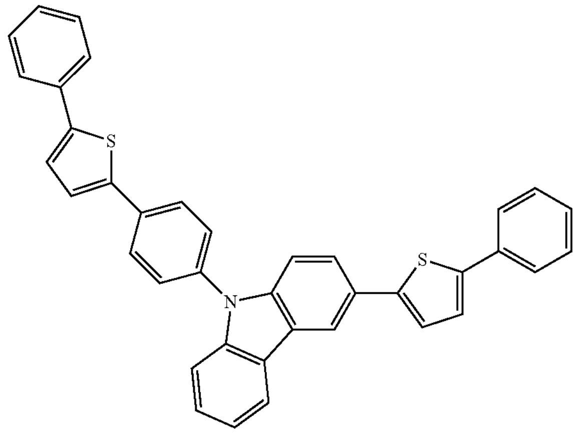
[Formula 5]
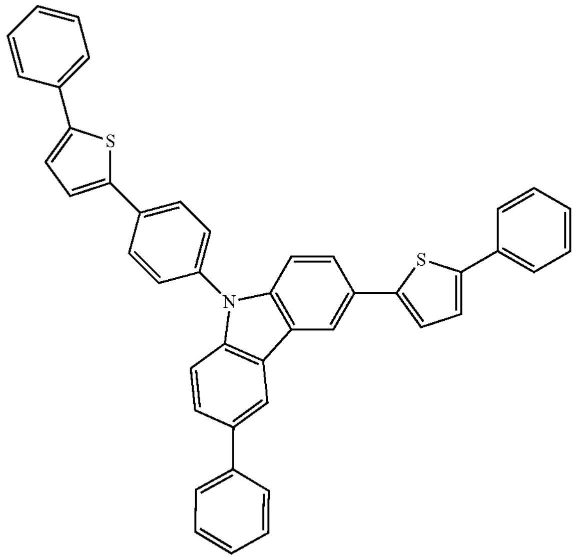
[Formula 6]
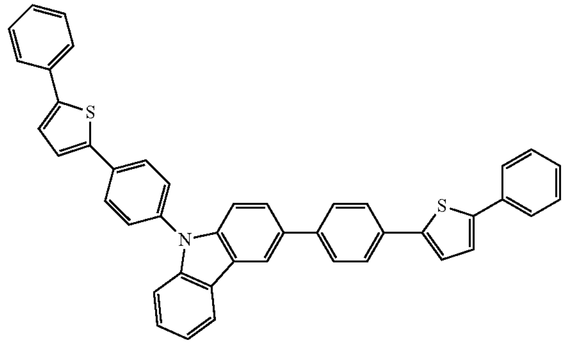
[Formula 7]
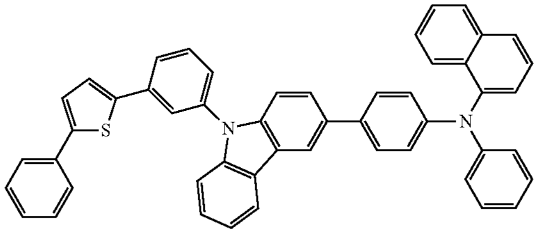
[Formula 8]
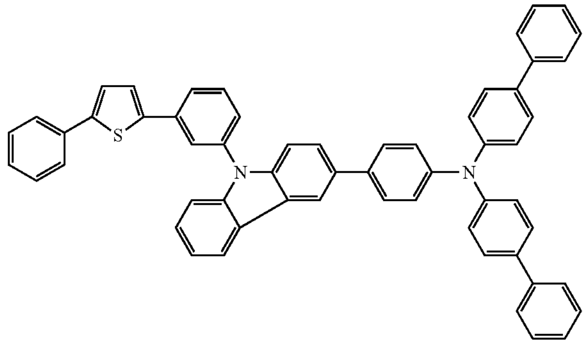
[Formula 9]
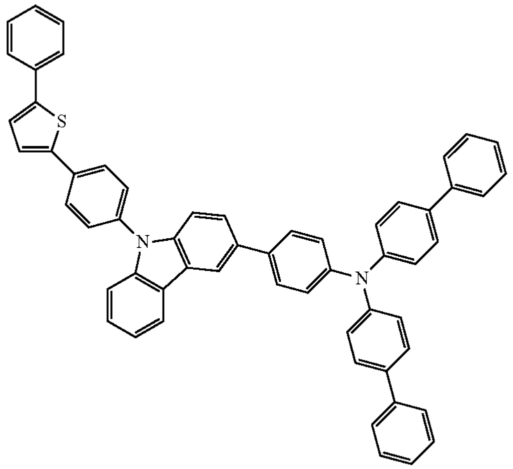

-continued
[Formula 10]
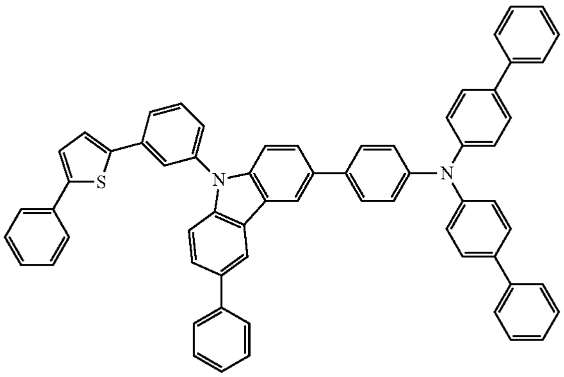
[Formula 11]
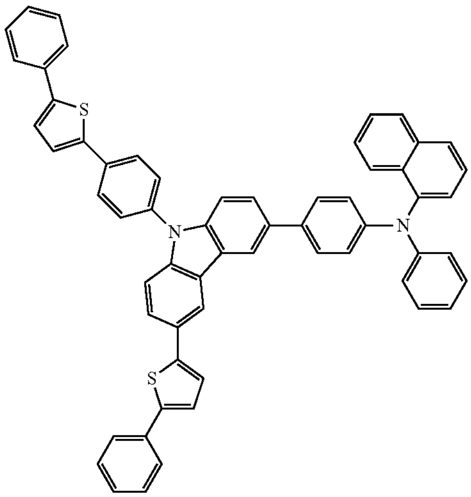
[Formula 12]
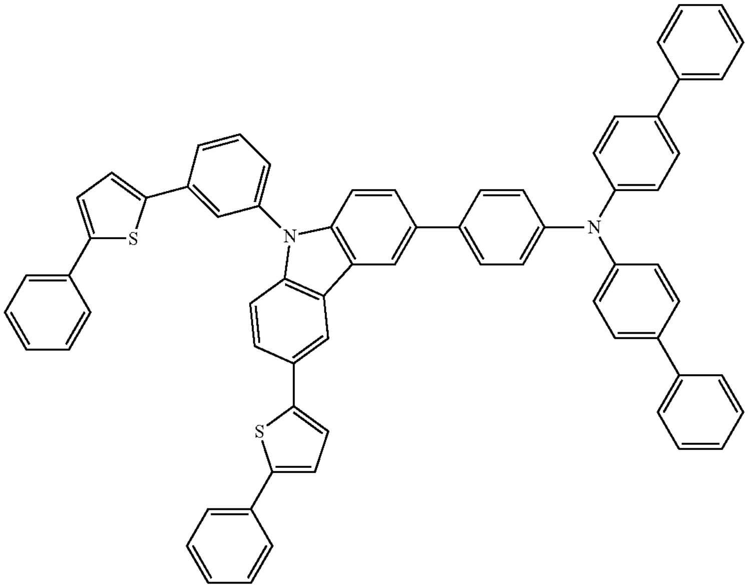
[Formula 13]
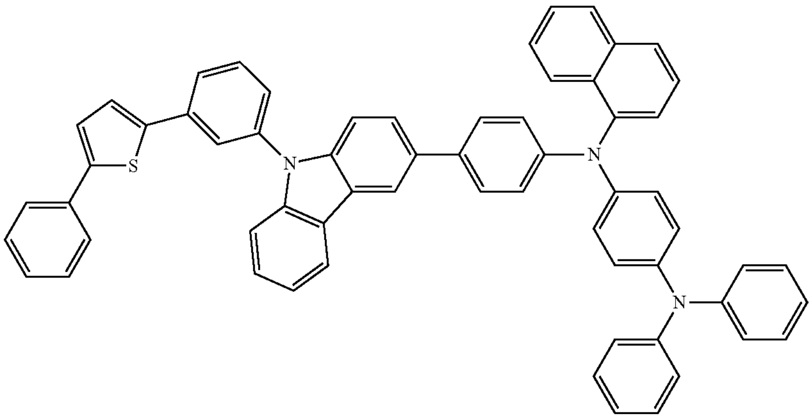

-continued

[Formula 14]

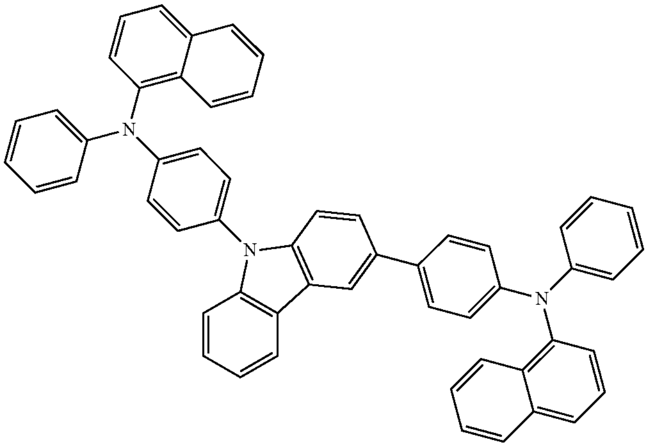

[Formula 15]

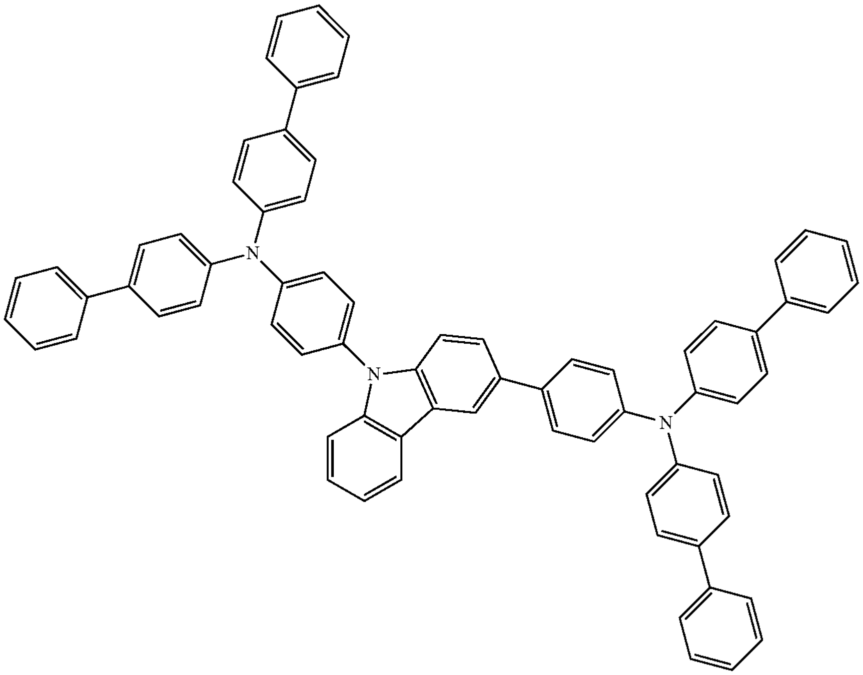

The compound of Formula 1 may have a property that is required when it is used as an organic material layer used in an organic light emitting device by using a core structure which is shown in Formula 1, that is, a structure in which arylene is substituted at a carbon position between R5 and R6 of carbazole as a core structure and introducing various substituents into the core structure including a structure that includes each independently hydrogen, heavy hydrogen; aliphatic hydrocarbon having 1-20 carbon atoms; aromatic hydrocarbon; aromatic hydrocarbon which is substituted with one or more substituent groups selected from the group consisting of nitro, nitrile, halogen, an alkyl group, an alkoxy group, an amino group, an aromatic hydrocarbon and a hetero ring group; a silicon group which is substituted with aromatic hydrocarbon; a hetero ring group; a hetero ring group which is substituted with one or more substituent groups selected from the group consisting of nitro, nitrile, halogen, an alkyl group, an alkoxy group, an amino group, an aromatic hydrocarbon and a hetero ring group; a thiophene group which is substituted with hydrocarbon having 1-20 carbon atoms or aromatic hydrocarbon having 6-20 carbon atoms; or a boron group which is substituted with an aromatic hydrocarbon.

The conjugation length of the compound has a close relationship with an energy band gap. In detail, the energy band gap is reduced as the conjugation length of the compound increases. As described above, since a conjugation structure is limited in the core structure of the compound of Formula 1, the core structure has a large energy band gap.

As described above, in the present invention, various substituent groups are introduced to R1 to R7 and X and Y positions of the core structure having the large energy band gap so as to produce compounds having various energy band gaps. Generally, it is easy to control an energy band gap by introducing substituent groups into a core structure having a large energy band gap, but it is difficult to significantly control the energy band gap by introducing substituent groups into a core structure having a small energy band gap. Furthermore, in the present invention, it is possible to control HOMO and LUMO energy levels of the compound by introducing various substituent groups into R1 to R7 and X and Y of the core structure.

Additionally, by introducing various substituent groups into the core structure, compounds having intrinsic characteristics of the substituent groups may be obtained. For example, substituent groups, which are frequently applied to hole injection layer material, hole transport layer material, light emitting layer material, and electron transport layer materials during the production of the organic light emitting device, are introduced into the core structure so as to produce substances capable of satisfying the requirements of each organic material layer.

Since the core structure of the compound of Formula 1 includes the amine structure, it has an energy level suitable for the hole injection and/or hole transport materials in the organic light emitting device. In the present invention, the compound having the proper energy level is selected depending on the substituent group among the compounds represented by Formula 1 to be used in the organic light emitting device, thereby it is possible to realize a device having a low driving voltage and a high light efficiency.

Furthermore, various substituent groups are introduced into the core structure so as to precisely control the energy band gap, and to improve interfacial characteristics with organic materials, thereby apply the compound to various fields.

In addition, by controlling the number of amine that is included in the substitutent group B, HOMO and LUMO energy levels and the energy band gap are capable of being precisely controlled, and interfacial characteristics with organic materials are improved, thereby apply the compound to various fields.

Meanwhile, since the compound of Formula 1 has a high glass transition temperature (Tg), it has excellent thermal stability. Such increase in thermal stability is an important factor providing driving stability to the device.

Furthermore, the compound of Formula 1 may be used to form the organic material layer using a vacuum deposition process or a solution coating process during the production of the organic light emitting device. In connection with this, illustrative, but non-limiting, examples of the solution coating process include a spin coating process, a dip coating process, an inkjet printing process, a screen printing process, a spray process, and a roll coating process.

The organic light emitting device of the present invention may be produced using known materials through a known process, modified only in that at least one layer of organic material layer(s) include the compound of the present invention, that is, the compound of Formula 1.

The organic material layer(s) of the organic light emitting device according to the present invention may have a single layer structure, or alternatively, a multilayered structure in which at least two organic material layers are layered. For example, the organic light emitting device of the present invention may comprise a hole injection layer, a hole transport layer, a light emitting layer, an electron transport layer, and an electron injection layer as the organic material layer(s). However, the structure of the organic light emitting device is not limited to this, but may comprise a smaller number of organic material layers.

Furthermore, the organic light emitting device of the present invention may be produced, for example, by sequentially layering a first electrode, organic material layer(s), and a second electrode on a substrate. In connection with this, a physical vapor deposition (PVD) method, such as a sputtering method or an e-beam evaporation method, may be used, but the method is not limited to these.

MODE FOR INVENTION

A better understanding of a method of manufacturing an compound represented by Formula 1 may be obtained in light of the following Preparation Examples. However, the Following Preparation Examples and Experimental Examples are set forth to illustrate, but are not to be construed to limit the present invention.

Preparation Example 1

Manufacturing of the Compound Represented by Formula 4

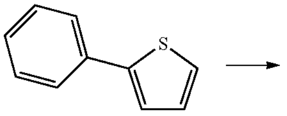

compound A

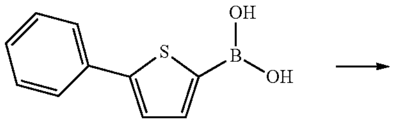

compound B

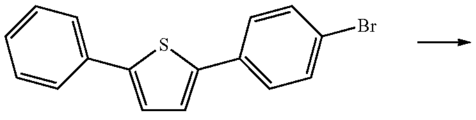

compound C

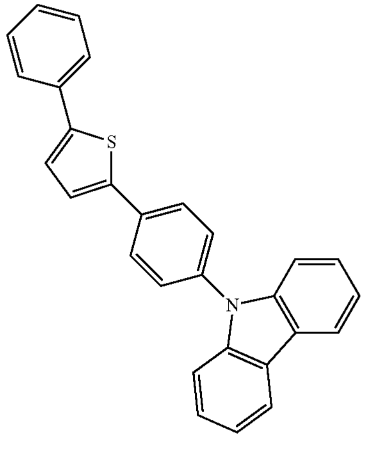

compound D

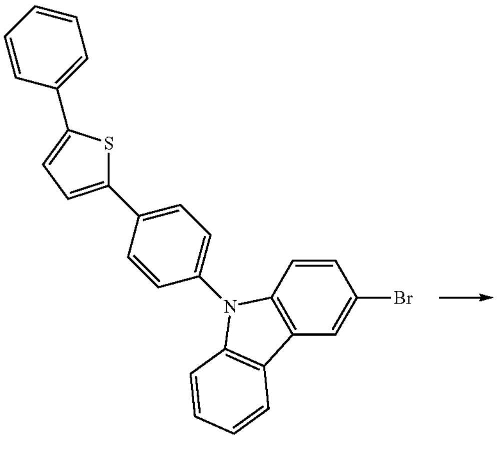

compound E

-continued

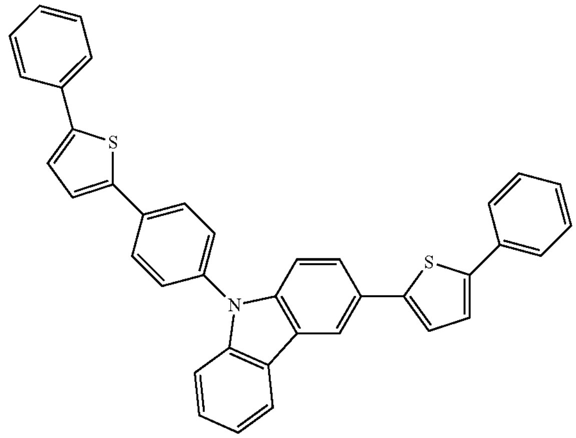

Formula 4

Preparation Example 1-1

Manufacturing of the Compound A

After 2-bromothiopene (20 g, 122.7 mmol) and phenyl boronic acid (18 g, 147.6 mmol) were dissolved in tetrahydrofuran (300 ml), 4N potassium carbonate aqueous solution (130 mL) and tetrakis(triphenylphosphine)palladium (0) (2.9 g, 2.5 mmol) and were put thereinto and heated while being agitated. After the reaction was finished, the organic layer was separated and dried by using anhydrous magnesium sulfate. After it was distilled under the reduced pressure, it was recrystallized by using hexane to obtain a compound A (14.6 g, yield 74%; $[M+H]^+$=161).

Preparation Example 1-2

Manufacturing of the Compound B

The compound A (18 g, 112.3 mmol) that was manufactured in Preparation Example 1-1 was dissolved in anhydrous tetrahydrofuran, n-butyl lithium (2.5M hexane solution, 49.4 mL, 123.5 mmol) was added dropwise at −78° C., and agitated for 1 hour. Trimethyl borate (15.1 g, 145.3 mmol) was put thereinto, agitated for 1 hour, 2N hydrochloric acid aqueous solution (80 mL) was put thereinto, and it was heated to normal temperature. After the organic layer was separated, it was dried by using anhydrous magnesium sulfate. After it was distilled under the reduced pressure, it was recrystallized by using hexane to obtain a compound B (15.2 g, yield 66%; $[M+H]^+$=205).

Preparation Example 1-3

Manufacturing of the Compound C

The compound B (15 g, 73.5 mmol) that was manufactured in Example 1-2 and 4-bromo-3-iodobenzene (20.8 g, 73.5 mmol) were dissolved in tetrahydrofuran (250 ml), 4N potassium carbonate aqueous solution (75 mL) and tetrakis(triphenylphosphine)palladium (0) (1.7 g, 1.5 mmol) and were put thereinto and heated while being agitated. After the reaction was finished, the organic layer was separated and dried by using anhydrous magnesium sulfate. After it was distilled under the reduced pressure, it was recrystallized by using ethanol to obtain a compound C (14.8 g, yield 64%; $[M+H]^+$= 316).

Preparation Example 1-4

Manufacturing of the Compound D

After the compound C (14 g, 44.4 mmol) that was manufactured in Preparation Example 1-3, carbazole (7.5 g, 44.9 mmol), sodium-tertiary-butoxide (5.5 g, 57.2 mmol) and bis (tri tertiary-butyl phosphine)palladium (0) (0.23 g, 0.45 mmol) were suspended in xylene (300 ml), they were refluxed while being agitated. After the reaction was finished, it was cooled to normal temperature, and the manufactured solid was filtered. It was sequentially washed by using water and ethanol to obtain a compound D (14.7 g, yield 82%; $[M+H]^+$= 402)<

Preparation Example 1-5

Manufacturing of the Compound E

The compound D (14 g, 34.9 mmol) that was manufactured in Preparation Example 1-4 was dissolved in chloroform (300 mL), N-bromosuccinimide (6.3 g, 35.4 mmol) was added thereto, and they were agitated at normal temperature. After the reaction was finished, water was poured thereon, and the organic layer was separated, and it was dried by using anhydrous magnesium sulfate. It was distilled under the reduced pressure, and recrystallized by using tetrahydrofuran and ethanol to obtain a compound E (14.3 g, yield 85%; $[M+H]^+$= 481)

Preparation Example 1-6

Manufacturing of Formula 4

The compound E (13 g, 27 mmol) that was manufactured in Example 1-5 and the compound B (5.5 g, 27 mmol) that was manufactured in Example 1-2 were dissolved in tetrahydrofuran (200 ml), 4N potassium carbonate aqueous solution (30 mL) and tetrakis(triphenylphosphine)palladium (0) (0.62 g, 0.54 mmol) and were put thereinto and heated while being agitated. After the reaction was finished, the organic layer was separated and dried by using anhydrous magnesium sulfate. After it was distilled under the reduced pressure, it was recrystallized by using tetrahydrofuran and ethanol to obtain Formula 4 (10.7 g, yield 71%; $[M+H]^+=560$).

Preparation Example 2

Manufacturing of the Compound Represented by Formula 5

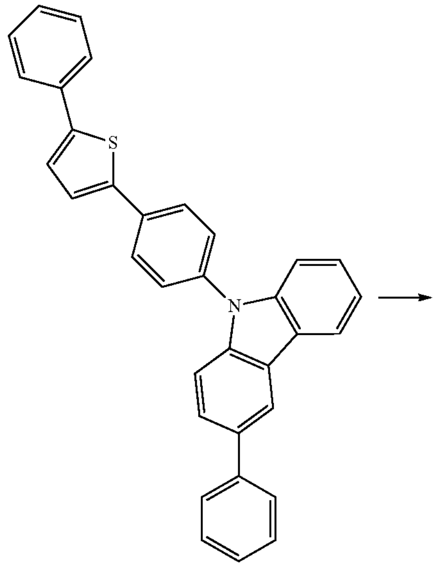

compound A

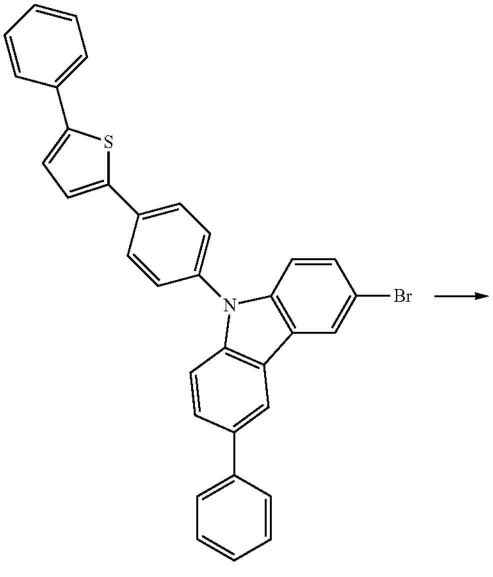

compound B

-continued

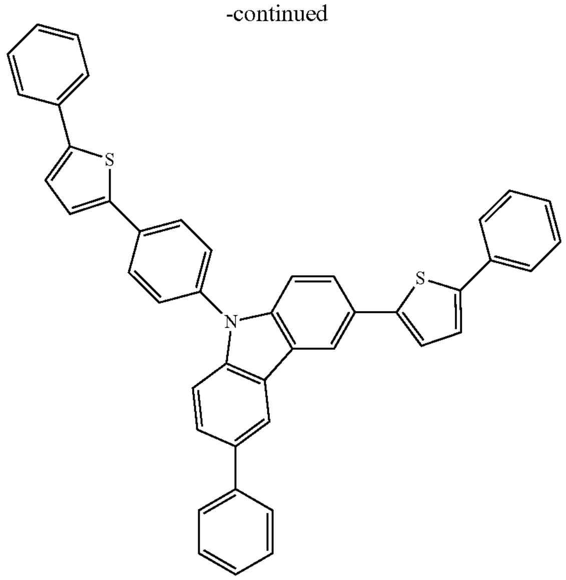

Formula 5

Preparation Example 2-1

Manufacturing of the Compound A

After the compound E (10 g, 20.8 mmol) of Preparation Example 1-5, and phenyl boronic acid (2.7 g, 22.1 mmol) were dissolved in tetrahydrofuran (300 ml), 4N potassium carbonate aqueous solution (25 mL) and tetrakis(triphenylphosphine)palladium (0) (0.49 g, 0.42 mmol) and were put thereinto and heated while being agitated. After the reaction was finished, the organic layer was separated and dried by using anhydrous magnesium sulfate. After it was distilled under the reduced pressure, it was recrystallized by using tetrahydrofuran and hexane to obtain a compound A (8.2 g, yield 83%; $[M+H]^+=478$).

Preparation Example 2-2

Manufacturing of the Compound B

The compound A (8 g, 16.7 mmol) that was manufactured in Preparation Example 2-1 was dissolved in chloroform (200 mL), N-bromosuccinimide (3 g, 16.9 mmol) was added thereto, and they were agitated at normal temperature. After the reaction was finished, water was poured thereon and the manufactured solid was filtered. It was sequentially washed by using water and ethanol to obtain a compound B (8.2 g, yield 88%; $[M+H]^+=557$).

Preparation Example 2-3

Manufacturing of Formula 5

The compound B (5 g, 9 mmol) that was manufactured in Preparation Example 2-2 and the compound B (1.9 g, 9.3 mmol) that was manufactured in Preparation Example 1-2 were dissolved in tetrahydrofuran (150 ml), 4N potassium carbonate aqueous solution (12 mL) and tetrakis(triphenylphosphine)palladium (0) (0.2 g, 0.18 mmol) and were put thereinto and heated while being agitated. After the reaction was finished, the organic layer was separated and dried by using anhydrous magnesium sulfate. After it was distilled under the reduced pressure, it was recrystallized by using tetrahydrofuran and ethanol to obtain Formula 5 (3.9 g, yield 68%; $[M+H]^+$=636).

Preparation Example 3

Manufacturing of the Compound Represented by Formula 6

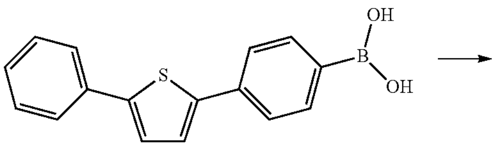

compound A

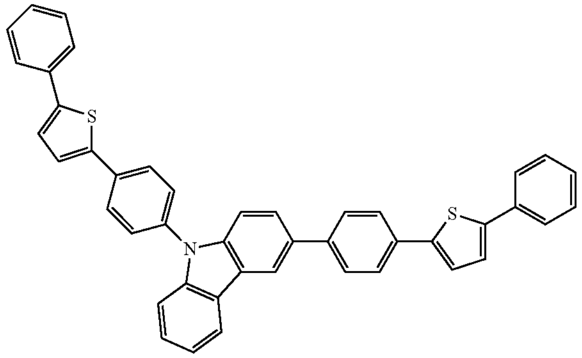

Formula 6

Preparation Example 3-1

Manufacturing of the Compound A

The compound C (10 g, 31.7 mmol) that was manufactured in Preparation Example 1-3 was dissolved in anhydrous tetrahydrofuran, n-butyl lithium (2.5M hexane solution, 13.8 mL, 34.5 mmol) was added dropwise at −78° C., and agitated for 1 hour. Trimethyl borate (4.3 g, 41.4 mmol) was put thereinto, agitated for 1 hour, 2N hydrochloric acid aqueous solution (20 mL) was put thereinto, and it was heated to normal temperature. After the organic layer was separated, it was dried by using anhydrous magnesium sulfate. After it was distilled under the reduced pressure, it was recrystallized by using hexane to obtain a compound A (5.4 g, yield 61%; $[M+H]^+$=281).

Preparation Example 3-2

Manufacturing of Formula 6

The compound A (5 g, 17.8 mmol) that was manufactured in Preparation Example 3-1 and the compound E (8.5 g, 17.7 mmol) that was manufactured in Preparation Example 1-5 were dissolved in tetrahydrofuran (150 ml), 4N potassium carbonate aqueous solution (20 mL) and tetrakis(triphenylphosphine)palladium (0) (0.42 g, 0.36 mmol) and were put thereinto and heated while being agitated. After the reaction was finished, the organic layer was separated and dried by using anhydrous magnesium sulfate. After it was distilled under the reduced pressure, it was recrystallized by using tetrahydrofuran and ethanol to obtain Formula 6 (8.2 g, yield 73%; $[M+H]^+$=636).

Preparation Example 4

Manufacturing of the Compound Represented by Formula 7

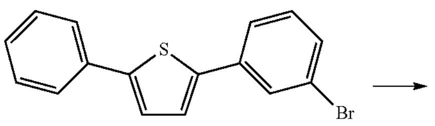

compound A

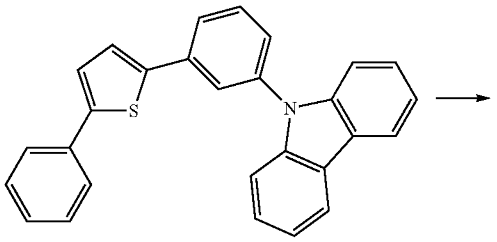

compound B

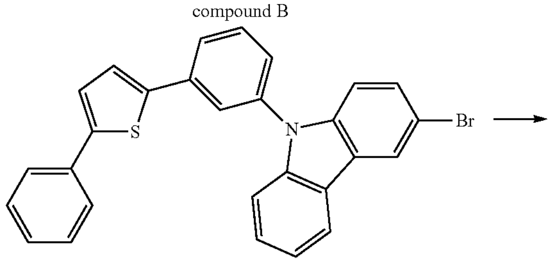

compound C

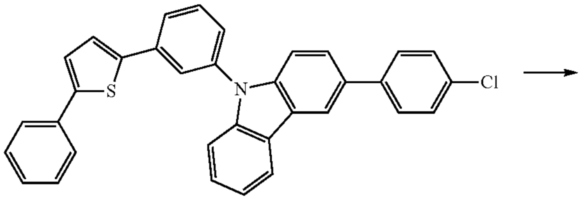

compound D

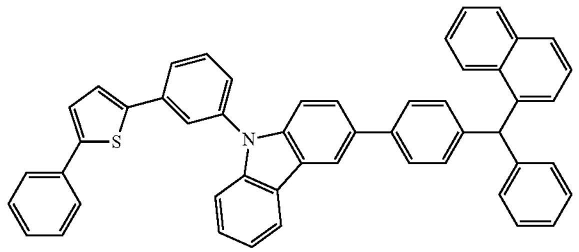

Formula 7

Preparation Example 4-1

Manufacturing of the Compound A

The compound B (15 g, 73.5 mmol) that was manufactured in Preparation Example 1-2 and 3-bromo-1-iodobenzene (20.8 g, 73.5 mmol) were dissolved in tetrahydrofuran (180 ml), 4N potassium carbonate aqueous solution (75 mL) and tetrakis(triphenylphosphine)palladium (0) (1.7 g, 1.5 mmol) and were put thereinto and heated while being agitated. After the reaction was finished, the organic layer was separated and dried by using anhydrous magnesium sulfate. After it was distilled under the reduced pressure, it was subjected to the column separation by using a tetrahydrofuran/hexane=1/10 solvent to obtain a compound A (14.4 g, yield 62%; $[M+H]^+$=316).

Preparation Example 4-2

Manufacturing of the Compound B

After the compound A (14 g, 44.4 mmol) that was manufactured in Preparation Example 4-1, carbazole (7.5 g, 44.9 mmol), sodium-tertiary-butoxide (5.5 g, 57.2 mmol) and bis(tri tertiary-butyl phosphine)palladium (0) (0.23 g, 0.45 mmol) were suspended in xylene (300 ml), they were refluxed while being agitated. After the reaction was finished, it was cooled to normal temperature, and the manufactured solid was filtered. It was sequentially washed by using water and ethanol to obtain a compound B (15.1 g, yield 85%; $[M+H]^+$=402).

Preparation Example 4-3

Manufacturing of the Compound C

The compound B (15 g, 37.4 mmol) that was manufactured in Preparation Example 4-2 was dissolved in chloroform (300 mL), N-bromosuccinimide (6.7 g, 37.6 mmol) was added thereto, and they were agitated at normal temperature. After the reaction was finished, water was poured thereon, the organic layer was separated, and they were dried by using anhydrous magnesium sulfate. It was distilled under the reduced pressure and recrystallized by using tetrahydrofuran and ethanol to obtain a compound C (14.2 g, yield 79%; $[M+H]^+$=481).

Preparation Example 4-4

Manufacturing of the Compound D

The compound C (13 g, 27 mmol) that was manufactured in Preparation Example 4-3 and 4-chlorophenyl borate (4.3 g, 27.5 mmol) were dissolved in tetrahydrofuran (300 ml), 4N potassium carbonate aqueous solution (33 mL) and tetrakis(triphenylphosphine)palladium (0) (0.62 g, 0.54 mmol) and were put thereinto and heated while being agitated. After the reaction was finished, the organic layer was separated and dried by using anhydrous magnesium sulfate. After it was distilled under the reduced pressure, it was recrystallized by using tetrahydrofuran and ethanol to obtain a compound D (9.5 g, yield 69%; $[M+H]^+$=512).

Preparation Example 4-5

Manufacturing of Formula 7

After the compound D (8 g, 15.6 mmol) that was manufactured in Preparation Example 4-4, N-phenyl-1-naphthyl amine (3.8 g, 17.3 mmol), sodium-tertiary-butoxide (2 g, 20.8 mmol) and bis(tri tertiary-butyl phosphine)palladium (0) (0.08 g, 0.16 mmol) were suspended in xylene (300 ml), they were refluxed while being agitated. After the reaction was finished, it was cooled to normal temperature, an acidic white clay was put thereinto, and they were agitated. After it was filtered, it was distilled under the reduced pressure, and subjected to the column separation by using a tetrahydrofuran/hexane=1/7 solvent to obtain Formula 7 (6.4 g, yield 59%; $[M+H]^+$=695).

Preparation Example 5

Manufacturing of the Compound Represented by Formula 8

Formula 8

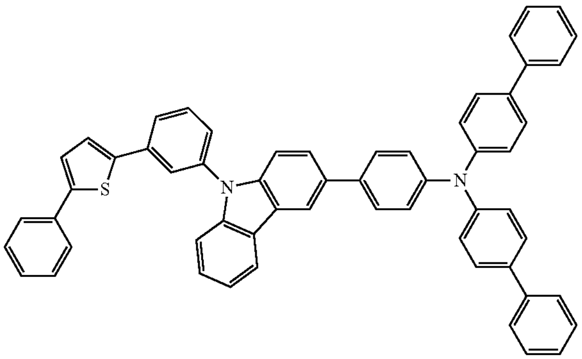

Preparation Example 5-1

Manufacturing of Formula 8

After the compound D (8 g, 15.6 mmol) that was manufactured in Preparation Example 4-4, bis(4-biphenylyl)amine (5.5 g, 17.1 mmol), sodium-tertiary-butoxide (2 g, 20.8 mmol) and bis(tri tertiary-butyl phosphine)palladium (0) (0.08 g, 0.16 mmol) were suspended in xylene (250 ml), they were refluxed while being agitated. After the reaction was finished, it was cooled to normal temperature, an acidic white clay was put thereinto, and they were agitated. After it was filtered, it was distilled under the reduced pressure, and recrystallized by using tetrahydrofuran and ethanol to obtain Formula 8 (7.8 g, yield 63%; $[M+H]^+=797$).

Preparation Example 6

Manufacturing of the Compound Represented by Formula 9

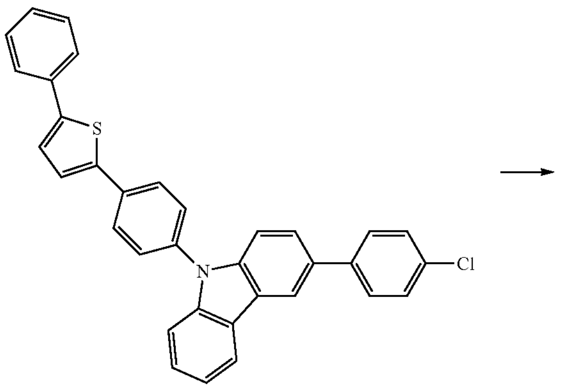

compound A

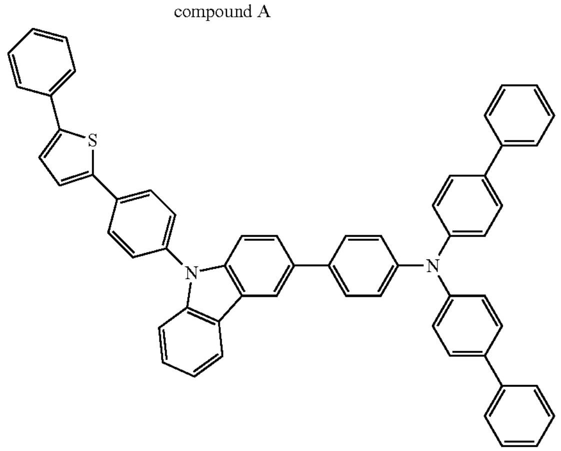

Formula 9

Preparation Example 6-1

Manufacturing of the Compound A

The compound E (10 g, 20.8 mmol) that was manufactured in Preparation Example 1-5 and 4-chlorophenyl borate (3.6 g, 23 mmol) were dissolved in tetrahydrofuran (250 ml), 4N potassium carbonate aqueous solution (22 mL) and tetrakis (triphenylphosphine)palladium (0) (0.49 g, 0.42 mmol) and were put thereinto and heated while being agitated. After the reaction was finished, the organic layer was separated and dried by using anhydrous magnesium sulfate. After it was distilled under the reduced pressure, it was recrystallized by using tetrahydrofuran and ethanol to obtain a compound A (7 g, yield 66%; $[M+H]^+=512$).

Preparation Example 6-2

Manufacturing of Formula 9

After the compound A (5 g, 9.7 mmol) that was manufactured in Preparation Example 6-1, bis(4-biphenylyl)amine (3.4 g, 10.6 mmol), sodium-tertiary-butoxide (1.2 g, 12.6 mmol) and bis (tri tertiary-butyl phosphine)palladium (0) (0.05 g, 0.1 mmol) were suspended in xylene (150 ml), they were refluxed while being agitated. After the reaction was finished, it was cooled to normal temperature, and the manufactured solide was filtered. After the filtered solide was dissolved in chloroform, an acidic white clay was put thereinto, and they were agitated. After it was filtered, it was distilled under the reduced pressure, and recrystallized by using tetrahydrofuran and ethanol to obtain Formula 9 (5.2 g, yield 67%; $[M+H]^+=797$).

Preparation Example 7

Manufacturing of the Compound Represented by Formula 10

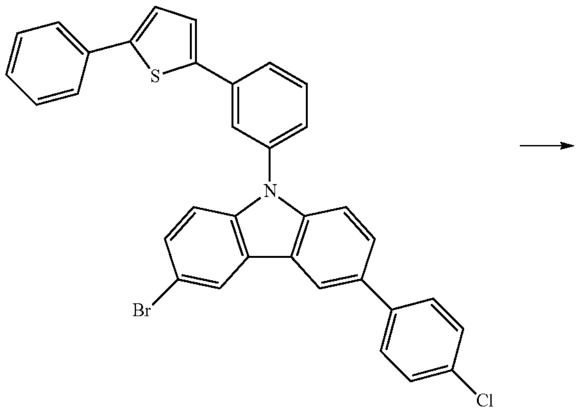

compound A

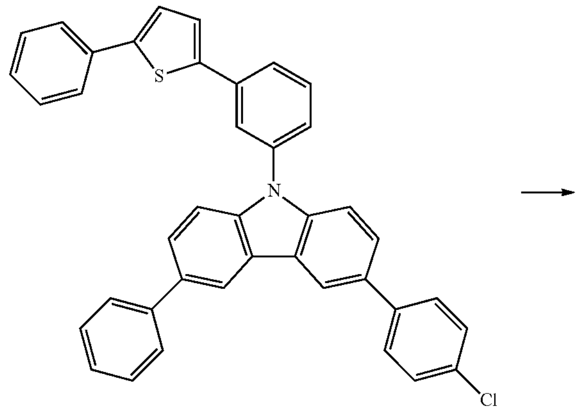

compound B

-continued

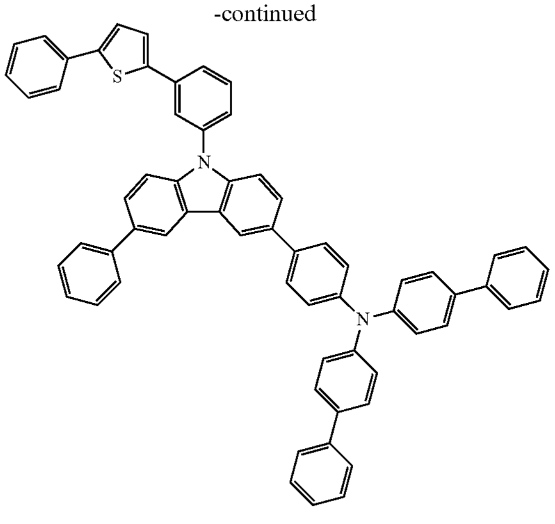

Formula 10

Preparation Example 7-1

Manufacturing of the Compound A

The compound D (10 g, 19.5 mmol) that was manufactured in Preparation Example 4-4 was dissolved in chloroform (300 mL), N-bromosuccinimide (3.7 g, 20.8 mmol) was added thereto, and they were agitated at normal temperature. After the reaction was finished, water was poured thereon, the organic layer was separated, and they were dried by using anhydrous magnesium sulfate. It was distilled under the reduced pressure and recrystallized by using tetrahydrofuran and ethanol to obtain a compound A (8.9 g, yield 77%; $[M+H]^+=591$).

Preparation Example 7-2

Manufacturing of the Compound B

The compound A (8 g, 13.5 mmol) that was manufactured in Preparation Example 7-1 and 4-chlorophenyl borate (2.3 g, 14.7 mmol) were dissolved in tetrahydrofuran (200 ml), 4N potassium carbonate aqueous solution (15 mL) and tetrakis (triphenylphosphine)palladium (0) (0.31 g, 0.27 mmol) and were put thereinto and heated while being agitated. After the reaction was finished, the manufactured solid was filtered. The filtered solid was recrystallized by using tetrahydrofuran and ethanol to obtain a compound B (5.2 g, yield 65%; $[M+H]^+=588$).

Preparation Example 7-3

Manufacturing of Formula 10

After the compound B (5 g, 8.5 mmol) that was manufactured in Preparation Example 7-2, bis(4-biphenylyl)amine (3 g, 9.3 mmol), sodium-tertiary-butoxide (1.1 g, 11.4 mmol) and bis(tri tertiary-butyl phosphine)palladium (0) (0.05 g, 0.1 mmol) were suspended in xylene (150 ml), they were refluxed while being agitated. After the reaction was finished, it was cooled to normal temperature, an acidic white clay was put thereinto, and they were agitated. After it was filtered, it was distilled under the reduced pressure, and recrystallized by using tetrahydrofuran and ethanol to obtain Formula 10 (4.5 g, yield 61%; $[M+H]^+=873$).

Preparation Example 8

Manufacturing of the Compound Represented by Formula 11

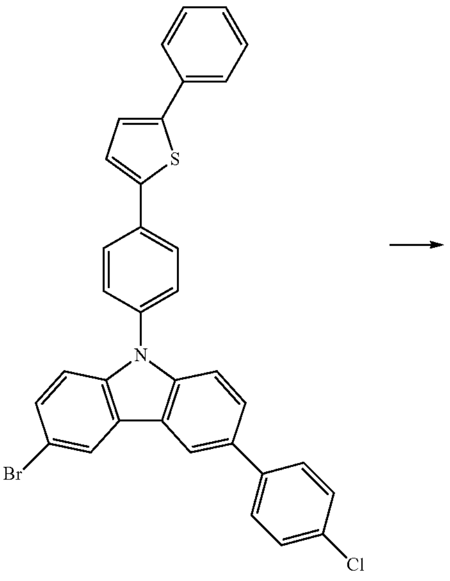

compound A

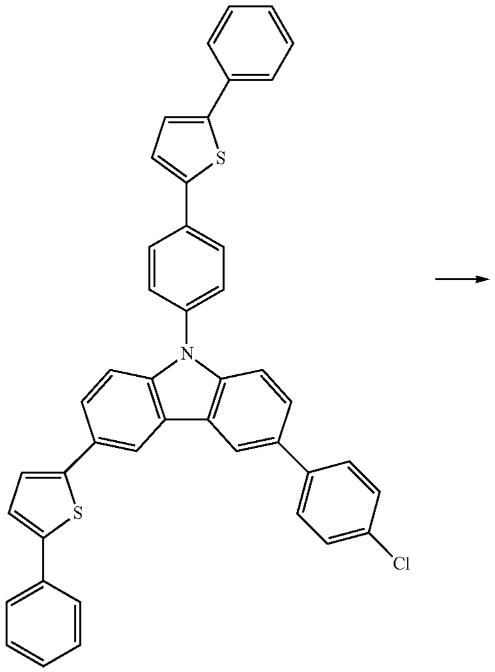

compound B

-continued

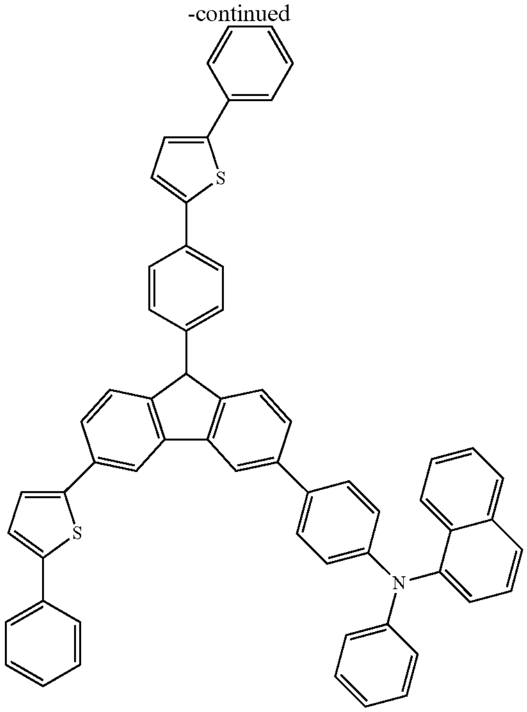

Formula 11

Preparation Example 8-1

Manufacturing of the Compound A

The compound A (10 g, 19.5 mmol) that was manufactured in Preparation Example 6-1 was dissolved in chloroform (300 mL), N-bromosuccinimide (3.7 g, 20.8 mmol) was added thereto, and they were agitated at normal temperature. After the reaction was finished, water was poured thereon, the organic layer was separated, and they were dried by using anhydrous magnesium sulfate. It was distilled under the reduced pressure and recrystallized by using tetrahydrofuran and ethanol to obtain a compound A (9.4 g, yield 82%; $[M+H]^+$=591).

Preparation Example 8-2

Manufacturing of the Compound B

The compound A (8 g, 13.5 mmol) that was manufactured in Preparation Example 8-1 and the compound B (3 g, 14.7 mmol) that was manufactured in Preparation Example 1-2 were dissolved in tetrahydrofuran (150 ml), 4N potassium carbonate aqueous solution (15 mL) and tetrakis(triphenylphosphine)palladium (0) (0.31 g, 0.27 mmol) and were put thereinto and heated while being agitated. After the reaction was finished, the manufactured solid was filtered. The filtered solid was recrystallized by using tetrahydrofuran and ethanol to obtain a compound B (6.2 g, yield 69%; $[M+H]^+$=670).

Preparation Example 8-3

Manufacturing of Formula 11

After the compound B (6 g, 9 mmol) that was manufactured in Preparation. Example 8-2, N-phenyl-1-naphthyl amine (2.1 g, 9.6 mmol), sodium-tertiary-butoxide (1.1 g, 11.7 mmol) and bis(tri tertiary-butyl phosphine)palladium (0) (0.05 g, 0.1 mmol) were suspended in xylene (100 ml), they were refluxed while being agitated. After the reaction was finished, it was cooled to normal temperature, an acidic white clay was put thereinto, and they were agitated. After it was filtered, it was distilled under the reduced pressure, and subjected to the column separation by using a tetrahydrofuran/hexane=1/6 solvent to obtain Formula 11 (3.8 g, yield 49%; $[M+H]^+$=853).

Preparation Example 9

Manufacturing of the Compound Represented by Formula 12

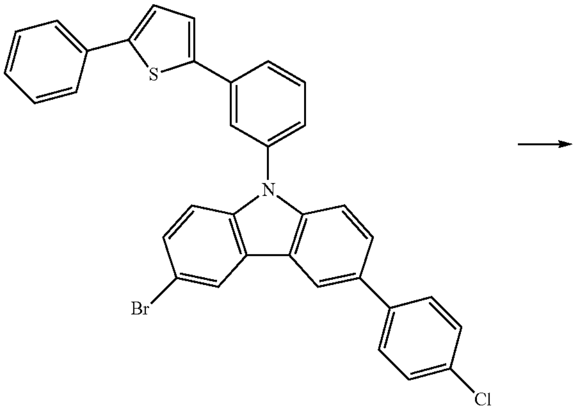

compound A

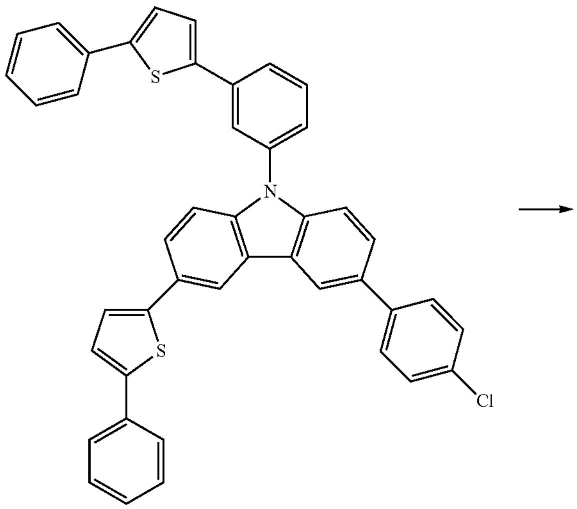

compound B

-continued

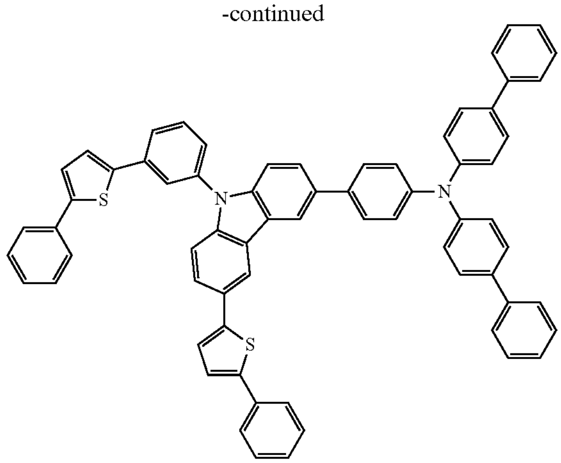

Formula 12

Preparation Example 9-1

Manufacturing of the Compound A

The compound D (10 g, 19.5 mmol) that was manufactured in Preparation Example 4-4 was dissolved in chloroform (300 mL), N-bromosuccinimide (3.7 g, 20.8 mmol) was added thereto, and they were agitated at normal temperature. After the reaction was finished, water was poured thereon, the organic layer was separated, and they were dried by using anhydrous magnesium sulfate. It was distilled under the reduced pressure and recrystallized by using tetrahydrofuran and ethanol to obtain a compound A (9.1 g, yield 79%; $[M+H]^+$=591).

Preparation Example 9-2

Manufacturing of the Compound B

The compound A (9 g, 15.2 mmol) that was manufactured in Preparation Example 9-1 and the compound B (3.4 g, 16.7 mmol) that was manufactured in Preparation Example 1-2 were dissolved in tetrahydrofuran (150 ml), 4N potassium carbonate aqueous solution (18 mL) and tetrakis(triphenylphosphine)palladium (0) (0.35 g, 0.3 mmol) and were put thereinto and heated while being agitated. After the reaction was finished, the manufactured solid was filtered. The filtered solid was recrystallized by using tetrahydrofuran and ethanol to obtain a compound B (7.3 g, yield 72%; $[M+H]^+$=670).

Preparation Example 9-3

Manufacturing of Formula 12

After the compound B (6 g, 9 mmol) that was manufactured in Preparation Example 9-2, bis(4-biphenylyl)amine (3 g, 9.3 mmol), sodium-tertiary-butoxide (1.1 g, 11.4 mmol) and bis (tri tertiary-butyl phosphine)palladium (0) (0.05 g, 0.1 mmol) were suspended in xylene (150 ml), they were refluxed while being agitated. After the reaction was finished, it was cooled to normal temperature, and the manufactured solid was filtered. The filtered solid was dissolved in chloroform, an acidic white clay was put thereinto, and they were agitated and filtered. After it was distilled under the reduced pressure, and recrystallized by using tetrahydrofuran and ethanol to obtain Formula 12 (5.6 g, yield 65%; $[M+H]^+$=955).

Preparation Example 10

Manufacturing of Formula 13

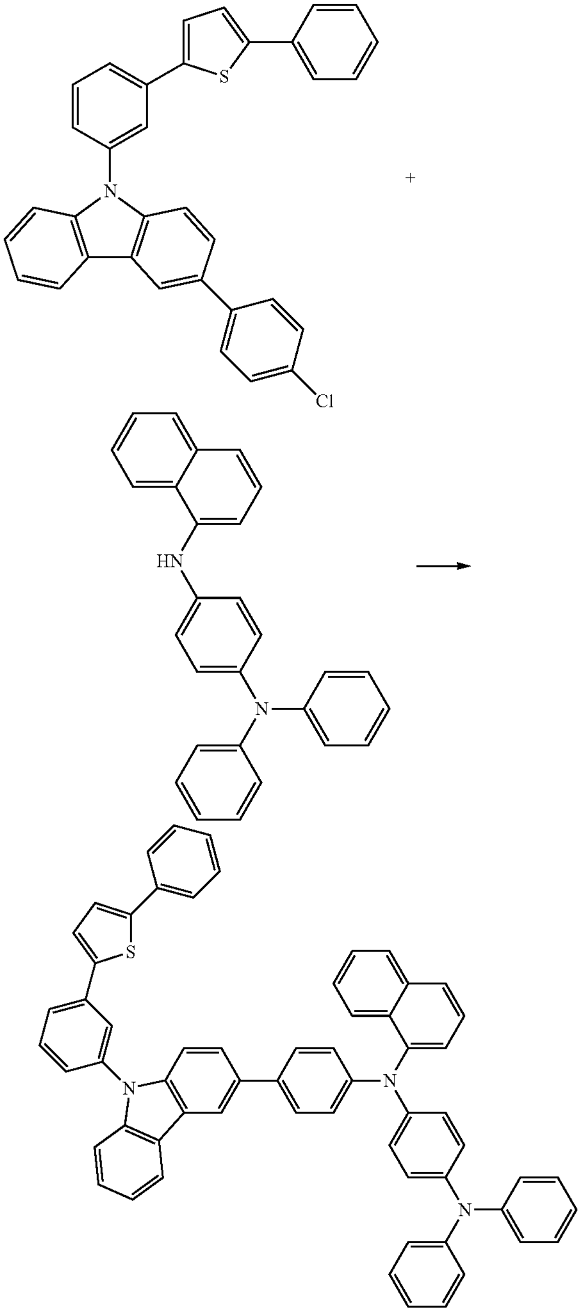

Formula 13

The compound A (4 g, 7.8 mmol) of the Preparation Example 6 and the amine compound (3.17 g, 8.2 mmol) were dissolved in 150 ml of xylene, sodium-tertiary-butoxide (1.9 g, 19.5 mmol), and 20 mg of $Pd[P(t-Bu)_3]_2$ (0.06 mmol) were added, and refluxed for 5 hours under the nitrogen atmosphere.

Distilled water was put in the reaction solution, the reaction was finished, and the organic layer was extracted. It was subjected to the column separation by using a normal-hexane/tetrahydrofuran=10/1 solvent, agitated in petroleum ether, and vacuum dried to obtain Formula 13 (3.4 g, yield 50%). MS: $[M+H]^+$=861

Preparation Example 11

Manufacturing of Formula 14

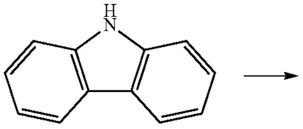

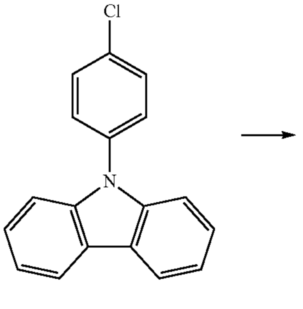

Formula A

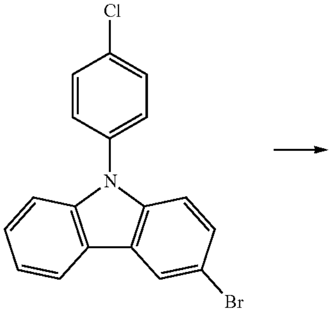

Formula B

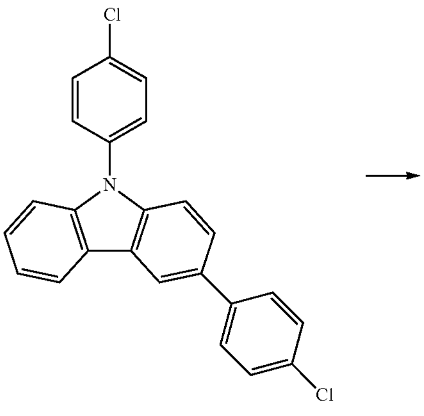

Formula C

-continued

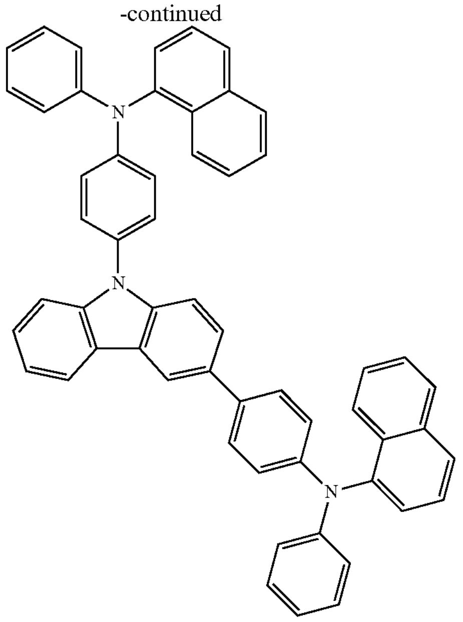

Formula 14

(1) Manufacturing of Formula A

Carbazole (17.5 g, 104.8 mmol) was dissolved in dimethylacetamide (100 mL), and 4-chloroiodobenzene (25 g, 104.8 mmol), Cu (13.3 g, 209.6 mmol), $K_2CO_3$ (43.5 g, 314.4 mmol) were put thereinto, and they were refluxed for 12 hours.

After the reaction solution was filtered, concentrated, and recrystallized by using EtOH to obtain Formula A (24.8 g, yield 85%). MS: $[M+H]^+$=278

(2) Manufacturing of Formula B

Formula A (24.8 g, 89.3 mmol) that was manufactured in step (1) was dissolved in chloroform (200 mL), N-bromosuccinic imide (15.9 g, 89.3 mmol) was added thereto, and they were agitated for 5 hours at normal temperature.

Distilled water was put thereinto the reaction solution, the reaction was finished, and the organic layer was extracted. After the reaction solution was concentrated, the next reaction was performed without the purification process. MS: $[M+H]^+$=357

(3) Manufacturing of Formula C

Formula B (31.7 g, 89 mmol) that was manufactured in step (2) and 4-chlorophenyl boronic acid (15.3 g, 97.9 mmol) were dissolved in THF (150 mL), and $Pd(PPh_3)_4$ (2.1 g, 1.78 mmol) and the $K_2CO_3/H_2O$ aqueous solution (6 g/100 mL, 356 mmol) were put thereinto, and they were refluxed for 24 hours.

Distilled water was put thereinto the reaction solution, the reaction was finished, and the organic layer was extracted. After the reaction solution was concentrated and subjected to the column separation by using a normal-hexane/tetrahydrofuran=10/1 solvent, they were agitated in EtOH, filtered, and vacuum dried to obtain Formula C (8.9 g, yield 26%). MS: $[M+H]^+$=388

(4) Manufacturing of Formula 14

Formula C (4.9 g, 12.6 mmol) that was manufactured in step (3) and N-phenyl-1-naphthyl amine (6.9 g, 31.5 mmol) were dissolved in 150 ml of xylene, sodium-tertiary-butoxide (3 g, 31.5 mmol), bisdibenzylidene acetone palladium (0) (0.28 g, 0.5 mmol), and 50 wt % tri-tertiary-butylphosphine toluene solution (0.24 ml, 0.5 mmol) were added thereto, and refluxed for 5 hours under the nitrogen atmosphere.

Distilled water was put in the reaction solution, the reaction was finished, and the organic layer was extracted. It was subjected to the column separation by using a normal-hexane/tetrahydrofuran=10/1 solvent, agitated in EtOH, filtered, and vacuum dried to obtain Formula 14 (1.8 g, yield 19%). MS: $[M+H]^+$=754

Preparation Example 12

Manufacturing of Formula 15

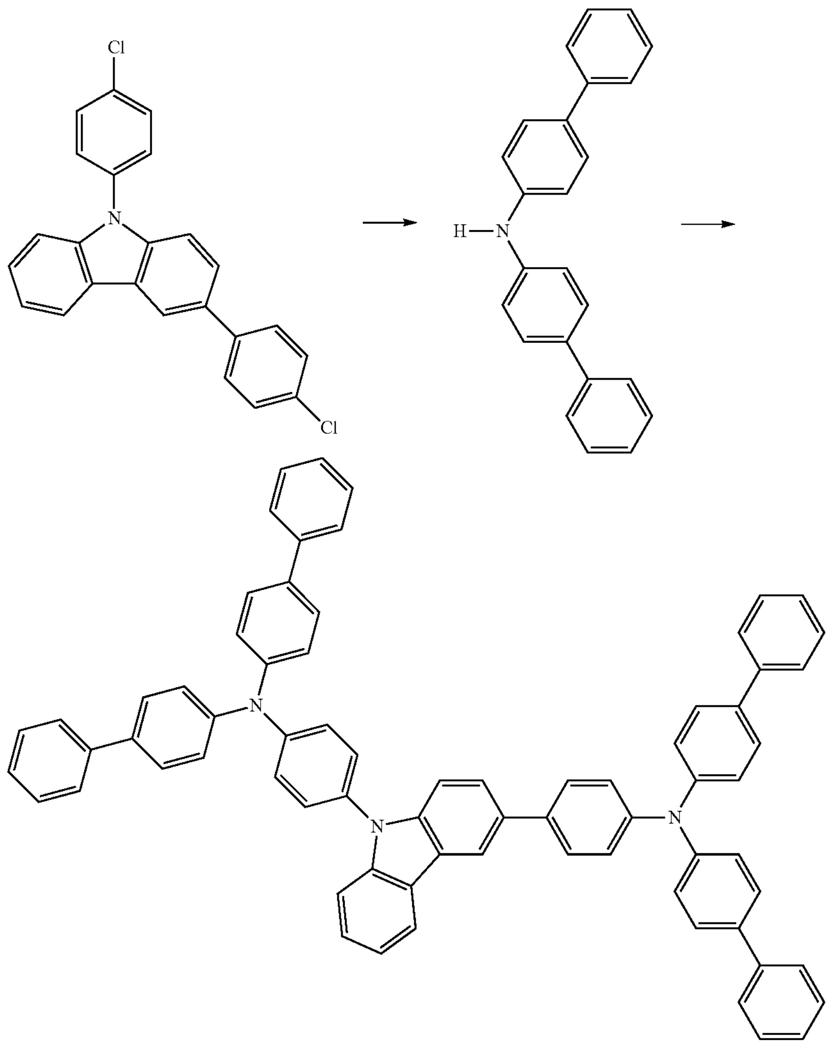

Formula 15

Formula C (4 g, 10.3 mmol) that was manufactured in step (3) of Preparation Example 11 and bisdiphenylamine (8.28 g, 25.8 mmol) were dissolved in 150 ml of xylene, sodium-tertiary-butoxide (2.47 g, 25.8 mmol), and $Pd[P(t\text{-}Bu)_3]_2$ (0.2 g, 0.4 mmol) were added thereto, and refluxed for 5 hours under the nitrogen atmosphere.

Distilled water was put in the reaction solution, the reaction was finished, and the organic layer was extracted. It was subjected to the column separation by using a normal-hexane/tetrahydrofuran=10/1 solvent, agitated in petroleum ether, and vacuum dried to obtain Formula 15 (6.9 g, yield 70%). MS: $[M+H]^+$=958

Experimental Example 1

A glass substrate, on which ITO (indium tin oxide) was applied to a thickness of 1500 Å to form a thin film, was put in distilled water, in which a detergent was dissolved, and washed using ultrasonic waves. In connection with this, a product manufactured by Fischer Inc. was used as the detergent, and distilled water was produced by filtering twice using a filter manufactured by Millipore Inc. After ITO was washed for 30 min, ultrasonic washing was conducted twice using distilled water for 10 min. After the washing using distilled water was completed, ultrasonic washing was conducted using isopropyl alcohol, acetone, and methanol solvents, and drying was then conducted. Next, it was transported to a plasma washing machine. In addition, the substrate was washed using oxygen plasma 85 W for 5 min, and then transported to a vacuum evaporator.

Hexanitrile hexaazatriphenylene (hereinafter, referred to as "HAT") of the following Formula was vacuum deposited to a thickness of 500 Å by heating on a transparent ITO electrode, which was prepared through the above procedure, so as to form a hole injection layer.

[HAT]

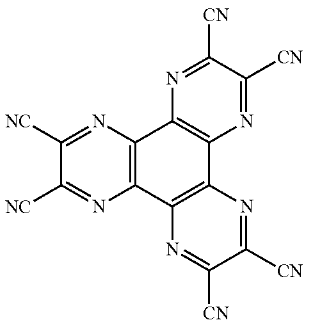

The compound of Formula 4, which was prepared in Example 1, was vacuum deposited to a thickness of 400 Å by heating on the hole injection layer so as to form a hole transport layer.

Subsequently, on the hole transport layer, GH and GD as described below were vacuum deposited to a film thickness of 300 Å at a film thickness ratio of 20:1 so as to form a light emitting layer.

[GH]

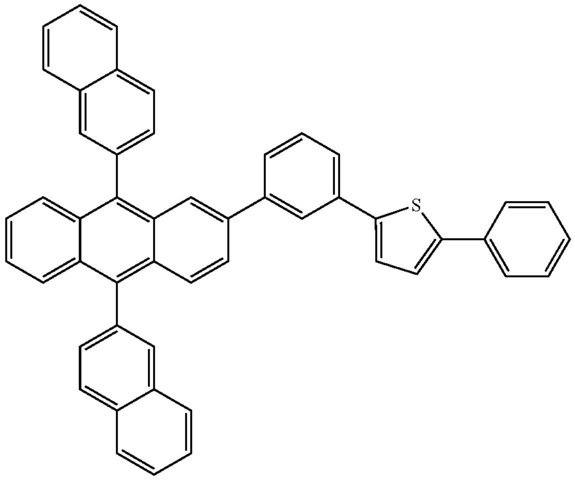

-continued

[GD]

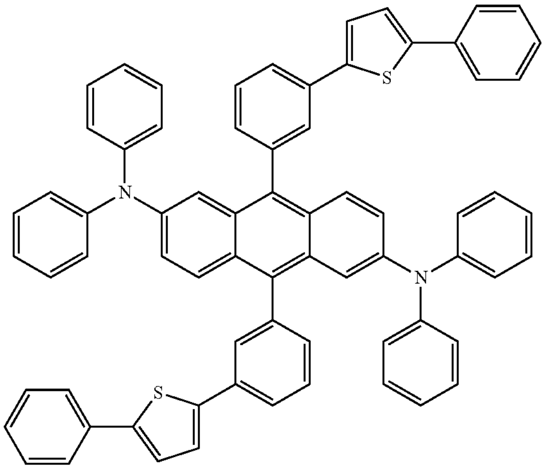

On the light emitting layer, the electron transport material as described below was vacuum deposited to a thickness of 200 Å so as to form an electron injection layer and a electron transport layer.

[Electron Transport Material]

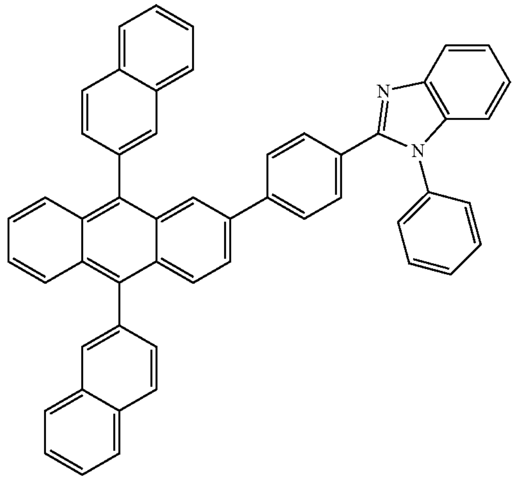 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

Lithium fluoride (LiF) having a thickness of 12 Å and aluminum having a thickness of 2000 Å were sequentially deposited on the electron injection layer and the electron transport layer to form a cathode.

In the above procedure, the deposition speed of an organic material was maintained at 0.4 to 0.7 Å/sec, lithium fluoride and aluminum were deposited at speeds of 0.3 Å/sec and 2 Å/sec, respectively, on the cathode, and in the deposition, a vacuum was maintained at $2\times10^{-7}$ to $5\times10^{-8}$ torr.

A forward current density of 4.8 V was applied to the light emitting device manufactured in the above, and as a result, the green light in which the color coordinate was (0.32, 0.66) at a current density of 50 $mA/cm^2$ was observed at 26 cd/A, and a life span to the luminance of 90% was 180 hours.

Experimental Example 2

The same process was performed to manufacture an organic EL device, except that the compound of Formula 5 was used instead of the compound of Formula 4 in Experimental Example 1.

A forward current density of 4.7 V was applied to the light emitting device manufactured in the above, and as a result, the green light in which the color coordinate was (0.33, 0.64) at a current density of 50 mA/cm$^2$ was observed at 27 cd/A, and a life span to the luminance of 90% was 200 hours.

Experimental Example 3

The same process was performed to manufacture an organic EL device, except that the compound of Formula 6 was used instead of the compound of Formula 4 in Experimental Example 1.

A forward current density of 4.8 V was applied to the light emitting device manufactured in the above, and as a result, the green light in which the color coordinate was (0.33, 0.65) at a current density of 50 mA/cm$^2$ was observed at 29 cd/A, and a life span to the luminance of 90% was 210 hours.

Experimental Example 4

The same process was performed to manufacture an organic EL device, except that the compound of Formula 7 was used instead of the compound of Formula 4 in Experimental Example 1.

A forward current density of 4.6 V was applied to the light emitting device manufactured in the above, and as a result, the green light in which the color coordinate was (0.32, 0.65) at a current density of 50 mA/cm$^2$ was observed at 28 cd/A, and a life span to the luminance of 90% was 190 hours.

Experimental Example 5

The same process was performed to manufacture an organic EL device, except that the compound of Formula 8 was used instead of the compound of Formula 4 in Experimental Example 1.

A forward current density of 4.7 V was applied to the light emitting device manufactured in the above, and as a result, the green light in which the color coordinate was (0.32, 0.64) at a current density of 501 mA/cm$^2$ was observed at 30 cd/A, and a life span to the luminance of 90% was 250 hours.

Experimental Example 6

The same process was performed to manufacture an organic EL device, except that the compound of Formula 9 was used instead of the compound of Formula 4 in Experimental Example 1.

A forward current density of 4.6 V was applied to the light emitting device manufactured in the above, and as a result, the green light in which the color coordinate was (0.31, 0.65) at a current density of 50 mA/cm$^2$ was observed at 29 cd/A, and a life span to the luminance of 90% was 240 hours.

Experimental Example 7

The same process was performed to manufacture an organic EL device, except that the compound of Formula 10 was used instead of the compound of Formula 4 in Experimental Example 1.

A forward current density of 4.5 V was applied to the light emitting device manufactured in the above, and as a result, the green light in which the color coordinate was (0.32, 0.65) at a current density of 50 mA/cm$^2$ was observed at 31 cd/A, and a life span to the luminance of 90% was 270 hours.

Experimental Example 8

The same process was performed to manufacture an organic EL device, except that the compound of Formula 11 was used instead of the compound of Formula 4 in Experimental Example 1.

A forward current density of 4.4 V was applied to the light emitting device manufactured in the above, and as a result, the green light in which the color coordinate was (0.32, 0.66) at a current density of 50 mA/cm$^2$ was observed at 31 cd/A, and a life span to the luminance of 90% was 270 hours.

Experimental Example 9

The same process was performed to manufacture an organic EL device, except that the compound of Formula 12 was used instead of the compound of Formula 4 in Experimental Example 1.

A forward current density of 4.4 V was applied to the light emitting device manufactured in the above, and as a result, the green light in which the color coordinate was (0.33, 0.65) at a current density of 50 mA/cm$^2$ was observed at 32 cd/A, and a life span to the luminance of 90% was 280 hours.

Comparative Example 1

The same process was performed to manufacture an organic EL device, except that 4,4'-bis[N-(1-naphthyl)-N-phenylamino]biphenyl (NPB) of the following Formula was used instead of the compound of Formula 4 in Experimental Example 1.

[NPB]

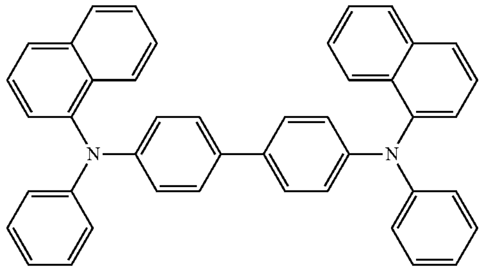

A forward current density of 4.6 V was applied to the light emitting device manufactured in the above, and as a result, the green light in which the color coordinate was (0.32, 0.64) at a current density of 50 mA/cm$^2$ was observed at 26 cd/A, and a life span to the luminance of 90% was 140 hours.

INDUSTRIAL APPLICABILITY

A compound according to the present invention is configured so that stability in respects to a hole and an electron is increased while properties of carbazole are not largely changed by introducing heavy hydrogen to carbazole. These compounds may be used as an organic material layer material, particularly, a hole injection material and/or a hole transport material in an organic light emitting device, and in the case of when it is used in the organic light emitting device, a driving voltage of the device may be reduced, light efficiency may be improved, and a life span property of the device may be improved because of thermal stability of the compound.

The invention claimed is:

1. A compound of the following Formula 1:

[Formula 1]

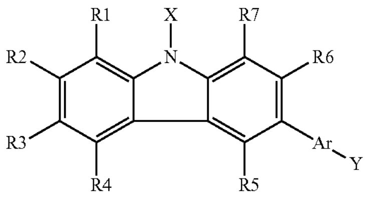

wherein X is $-(A)_m-(B)_n$,

Y is an arylamine group, which is substituted or unsubstituted with one or more substituent groups selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted hetero ring group, a nitrile group and an acetylene group; or a hetero ring group including O, N or S as a heteroatom, which is substituted or unsubstituted with one or more substituent groups selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted hetero ring group, a nitrile group and an acetylene group, Ar is an arylene group having 6 to 40 carbon atoms, which is substituted or unsubstituted with one or more substituent groups selected from the group consisting of nitro, nitrile, halogen, an alkyl group, an alkoxy group and an amino group, or a divalent hetero ring group, which is substituted or unsubstituted with one or more substituent groups selected from the group consisting of nitro, nitrile, halogen, an alkyl group, an alkoxy group and an amino group;

A is an aryl group, which is substituted or unsubstituted with one or more substituent groups selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted hetero ring group, a nitrile group and an acetylene group, B is a hetero ring group including O or S as a heteroatom, which is substituted or unsubstituted with one or more substituent groups selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted hetero ring group, a nitrile group and an acetylene group, m and n are integers in the range of 1 to 10, and R1 to R7 are each independently selected from the group consisting of hydrogen; an alkyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a nitrile group and an acetylene group; an alkoxy group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a nitrile group and an acetylene group; an aryl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a nitrile group and an acetylene group; an amino group, which is substituted with one or more substituent groups selected from the group consisting of an alkyl group, an alkenyl group, a substituted or unsubstituted aryl group, a substituted or unsubstituted arylalkyl group, and a substituted or unsubstituted arylalkenyl group; a nitro group; and a halogen group, and said R1 to R7 may form an aliphatic or hetero condensation ring in conjunction with adjacent groups.

2. The compound of Formula 1 as set forth in claim 1, wherein A of Formula 1 is selected from the group consisting of a phenyl group, a biphenyl group, a terphenyl group, a stilbene group, a naphthyl group, an anthracenyl group, a phenanthrene group, a pyrenyl group and a perylenyl group.

3. The compound of Formula 1 as set forth in claim 1, wherein B of Formula 1 is a hetero ring-selected from the group consisting of a thiophene group and a furan group, and Y of Formula 1 is a hetero ring selected from the group consisting of a thiophene group, a furan group, a pyrrolyl group, an imidazolyl group, a thiazolyl group, an oxazolyl group, an oxadiazolyl group, a triazolyl group, a pyridyl group, a pyridazine group, a quinolinyl group, an isoquinoline group, and an acridyl group.

4. The compound of Formula 1 as set forth in claim 1, wherein the compound of Formula 1 is represented by any one of the following Formula 2 and Formula 3:

[Formula 2]

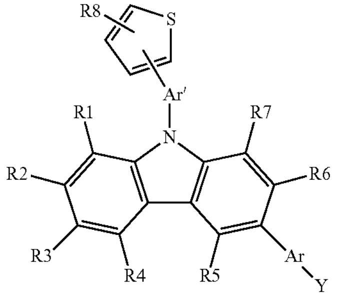

-continued

[Formula 3]

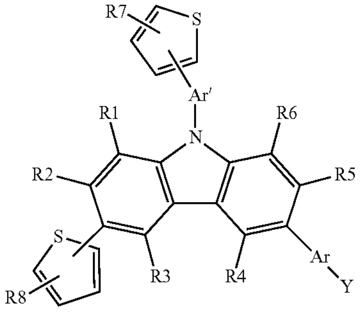

wherein Ar's are each independently selected from the group consisting of a phenyl group, a biphenyl group, a terphenyl group, a stilbene group, a naphthyl group, an anthracenyl group, a phenanthrene group, a pyrenyl group, a perylenyl group, and Ar, Y and R1 to R8 are the same as the definitions in respect to Ar, Y and R1 to R7 of Formula 1.

5. The compound of Formula 1 as set forth in claim 1, wherein the compound of Formula 1 is represented by any one of the following Formula 2-1 and Formula 3-1:

[Formula 2-1]

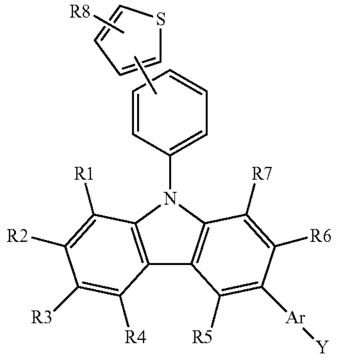

[Formula 3-1]

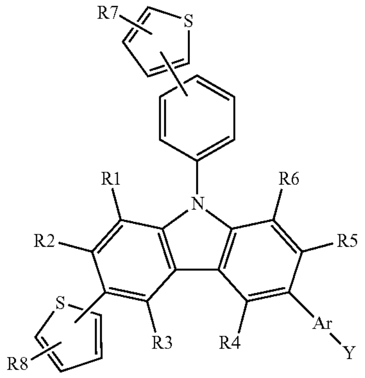

wherein Ar, Y and R1 to R8 are the same as the definitions in respect to Ar, Y and R1 to R7 of Formula 1.

6. The compound of Formula 1 as set forth in claim 1, wherein the compound of Formula 1 is represented by any one of the following Formula 2-2 and Formula 3-2:

[Formula 2-2]

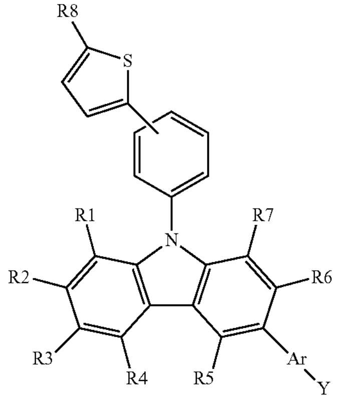

[Formula 3-2]

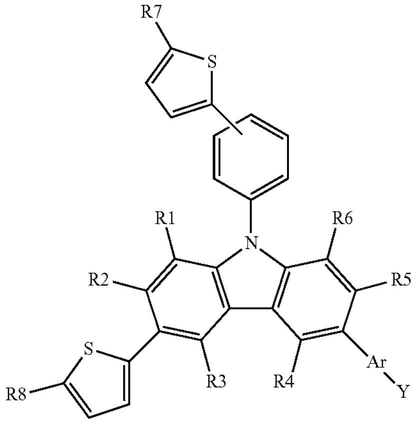

wherein Ar, Y and R1 to R8 are the same as the definitions in respect to Ar, Y and R1 to R7 of Formula 1.

7. The compound of Formula 1 as set forth in claim 1, wherein when Y of Formula 1 is arylamine, it is any one of the following groups:

1

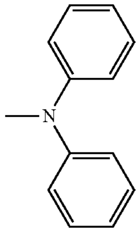

2

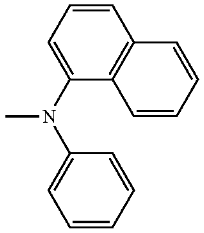

-continued
3
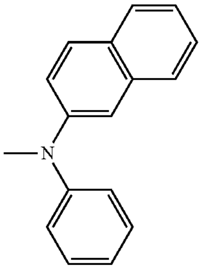
4
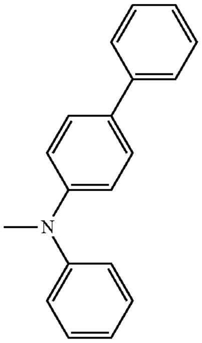
5
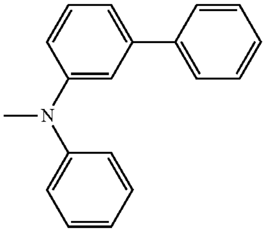
6
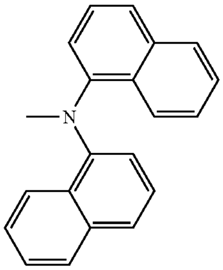
7
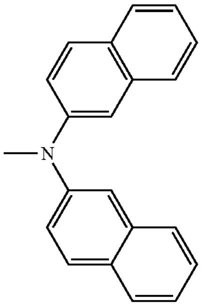
-continued
8
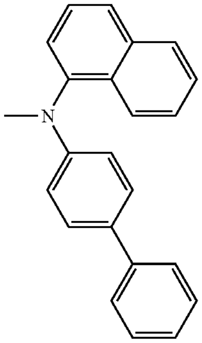
9
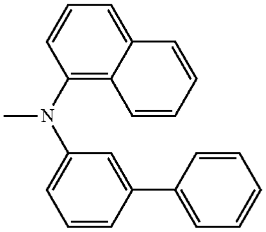
10
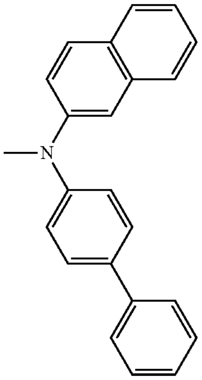
11
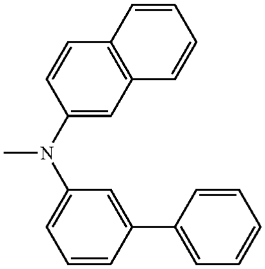

-continued
12
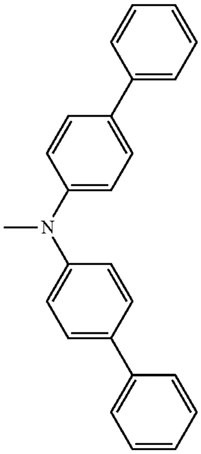
13
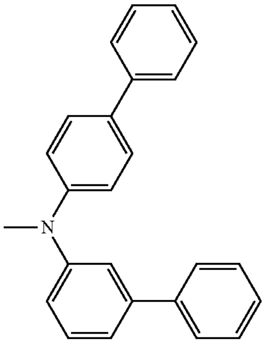
14
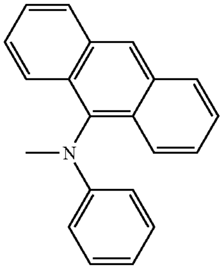
15
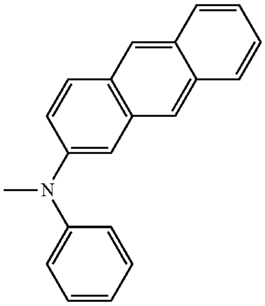
-continued
16
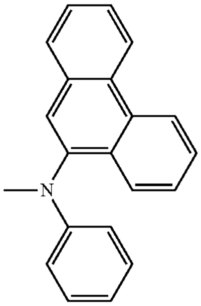
17
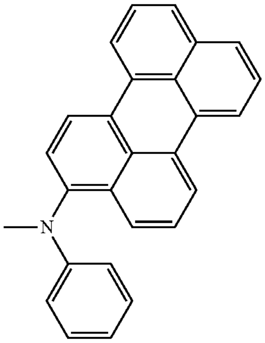
18
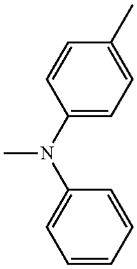
19
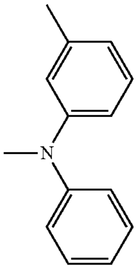
20
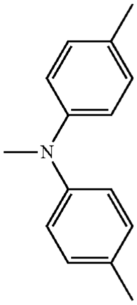

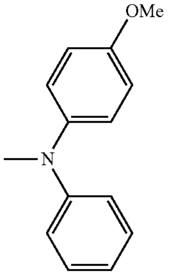
21
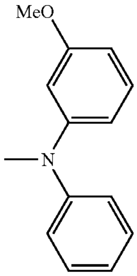
22
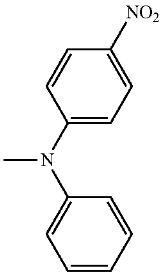
23
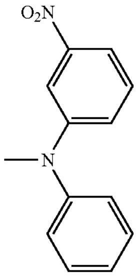
24
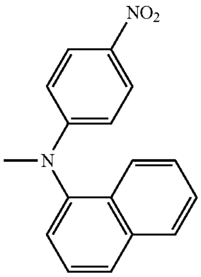
25
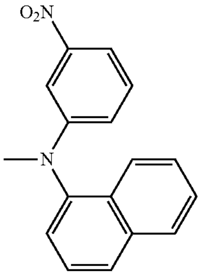
26
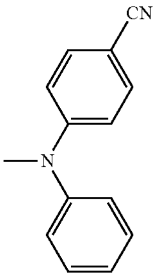
27
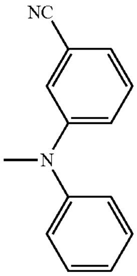
28
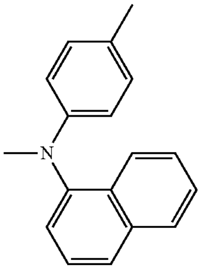
29
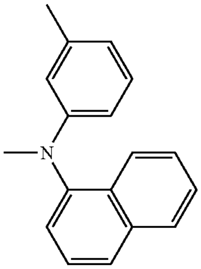
30

-continued
31
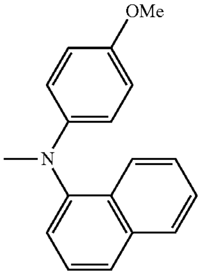
32
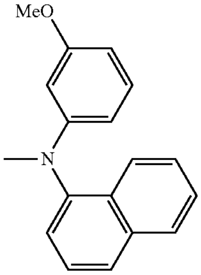
33
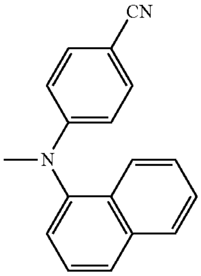
34
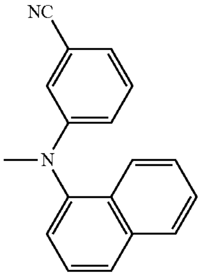
35
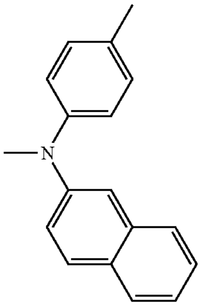
-continued
36
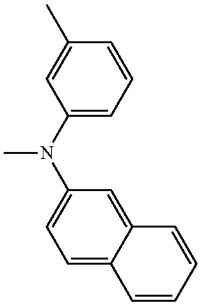
37
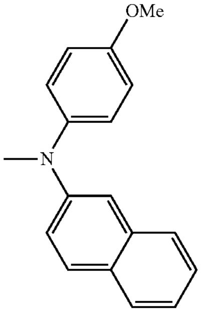
38
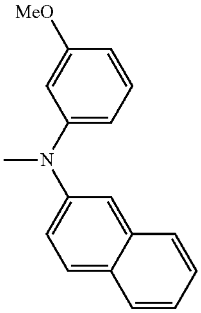
39
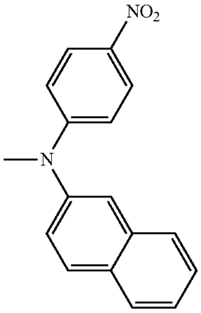
40
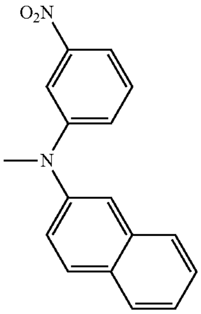

-continued
41
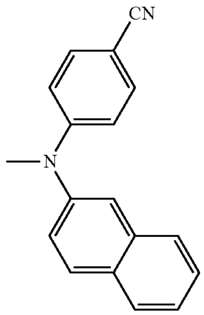
42
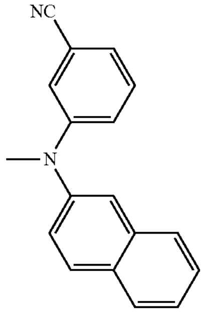
43
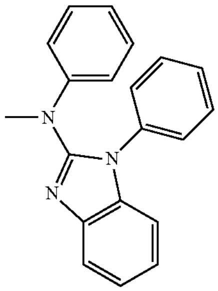
44
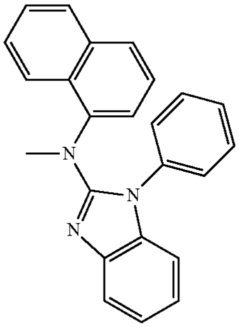
-continued
45
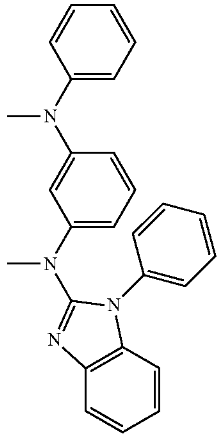
46
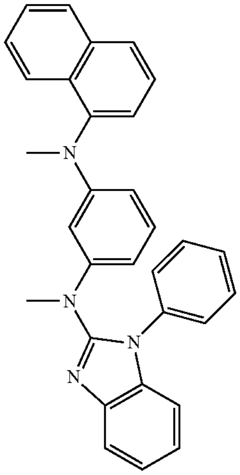
47
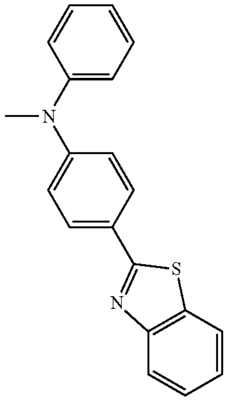

-continued
48
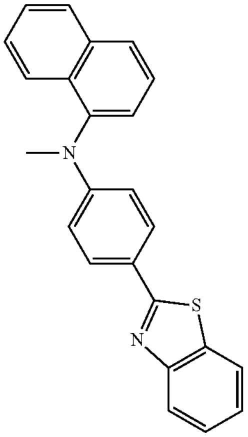
49
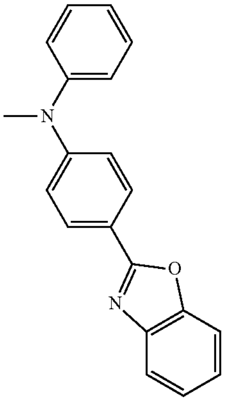
50
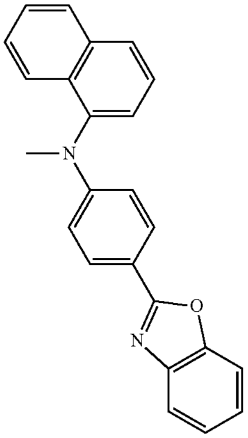
51
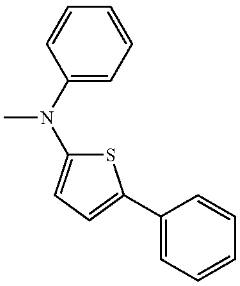
-continued
52
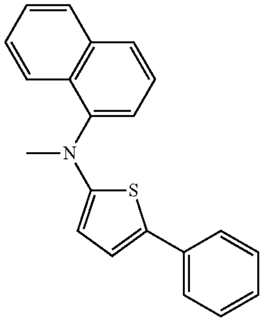
53
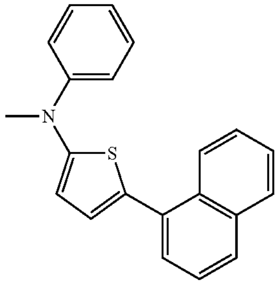
54
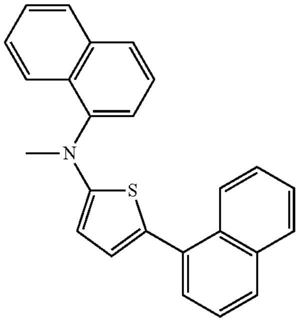
55
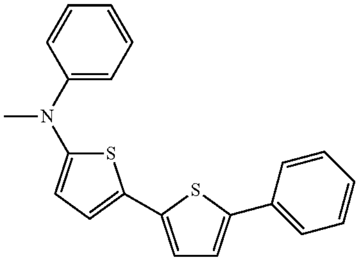
56
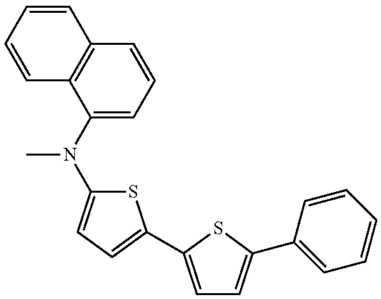

-continued
57
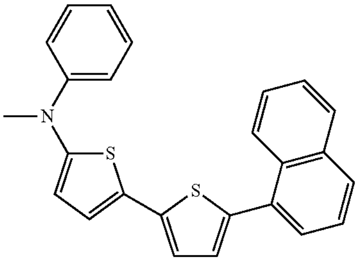
58
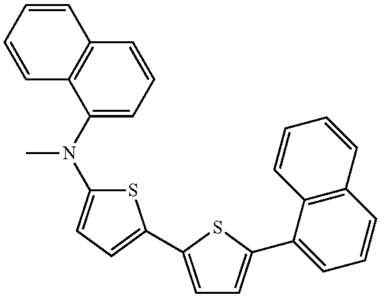
59
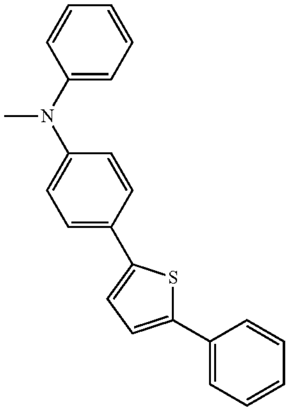
60
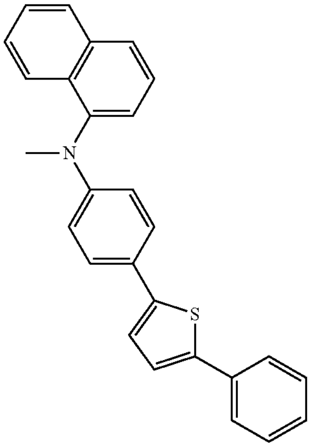
-continued
61
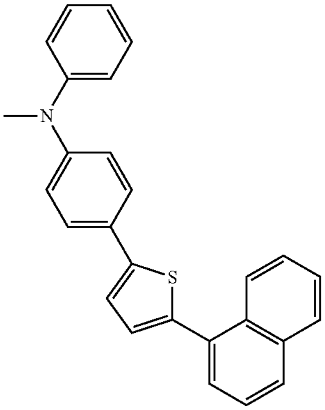
62
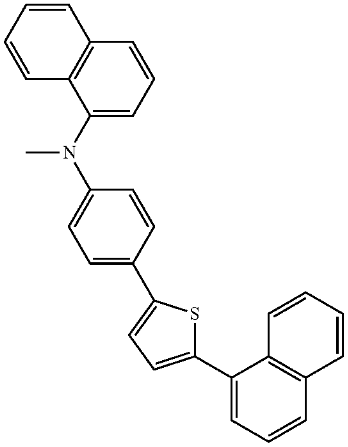
63
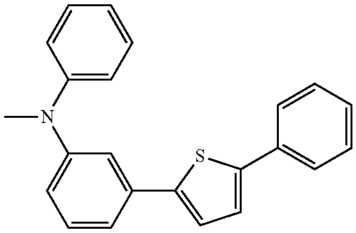
64
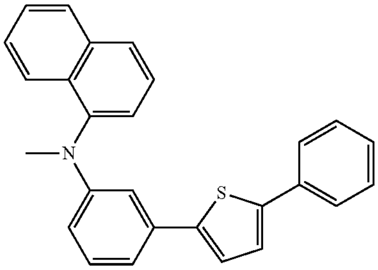
65
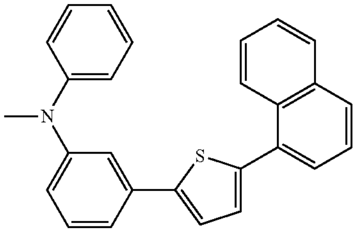

-continued
66
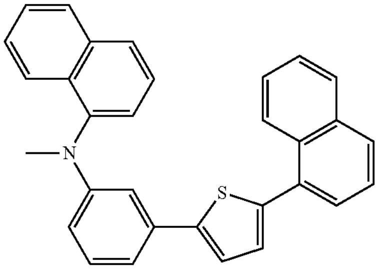
67
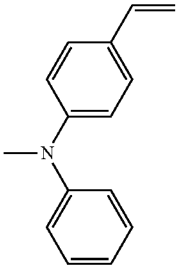
68
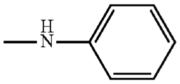
69
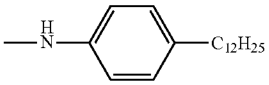
70
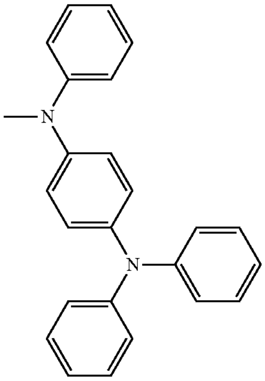
71
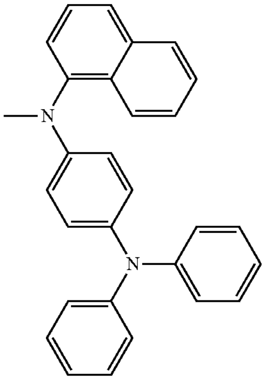
-continued
72
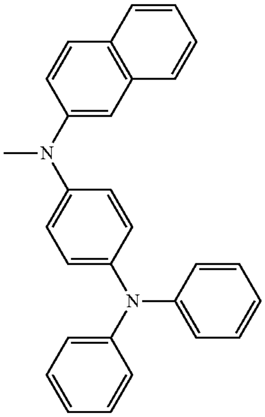
73
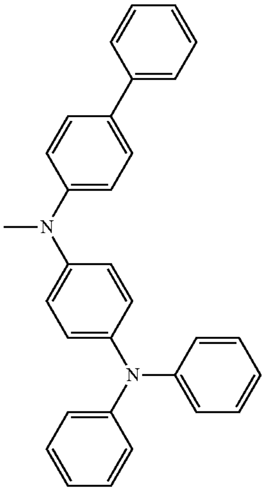
74
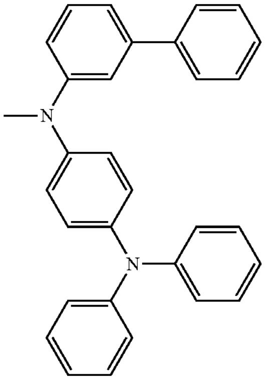

-continued
75
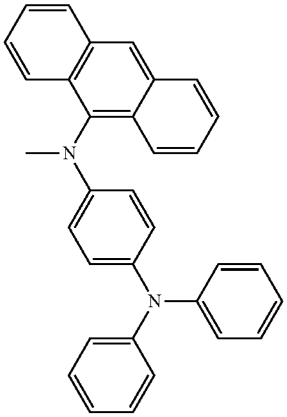
76
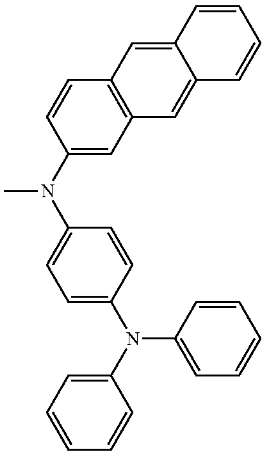
77
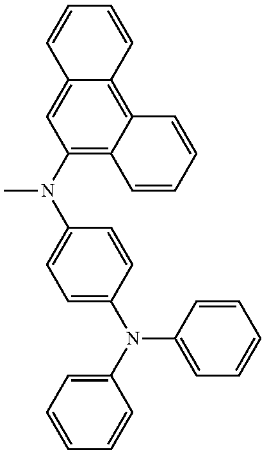
-continued
78
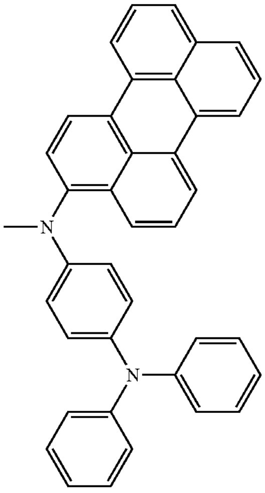
79
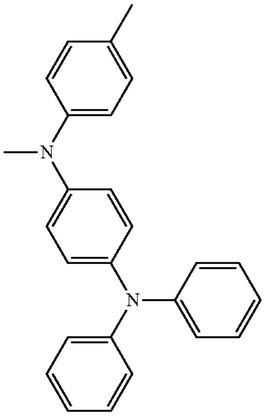
80
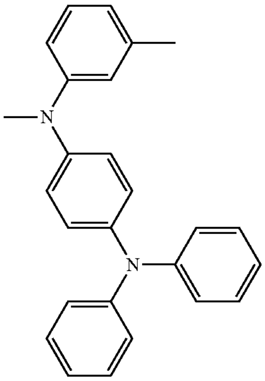

-continued
81
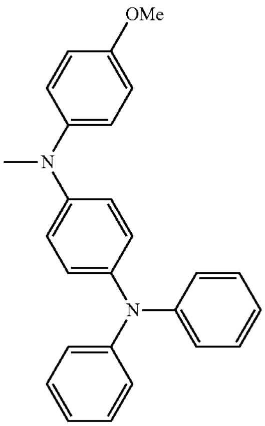
82
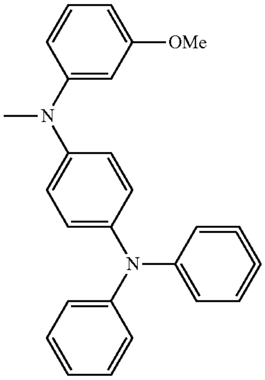
83
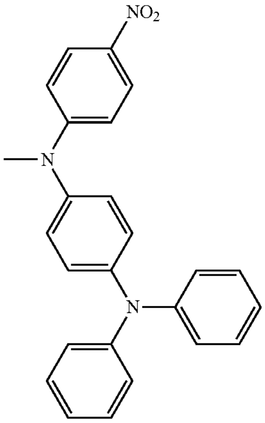
84
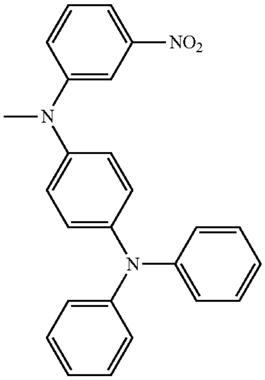
-continued
85
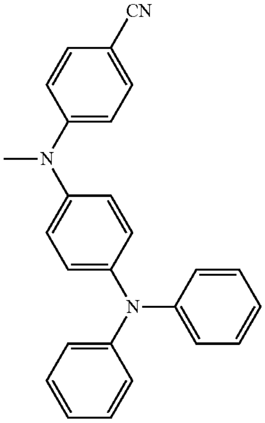
86
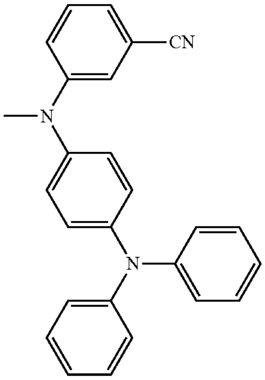
87
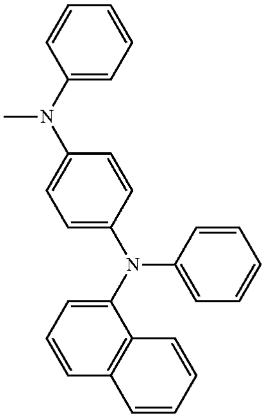
88
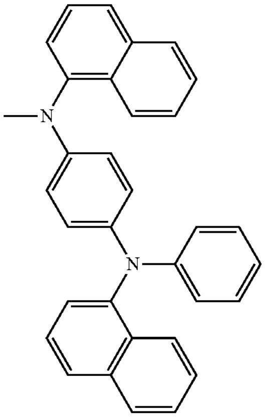

-continued
89
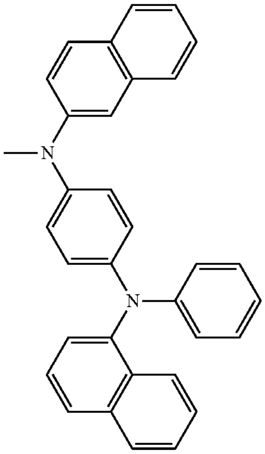
90
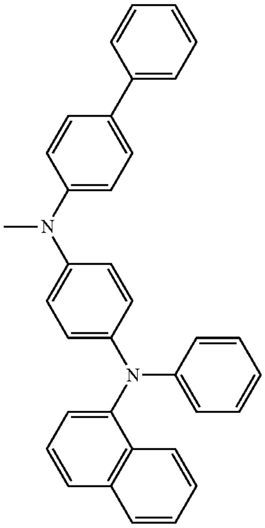
91
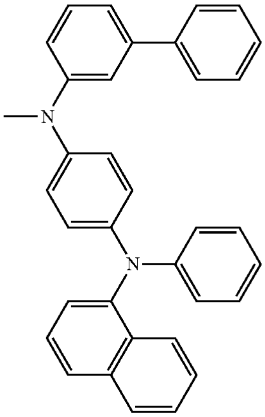
-continued
92
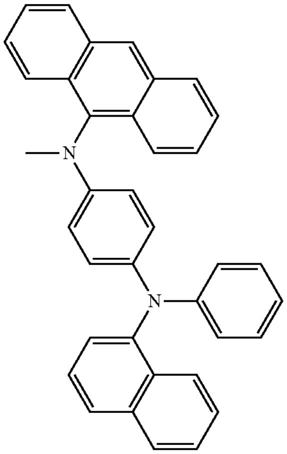
93
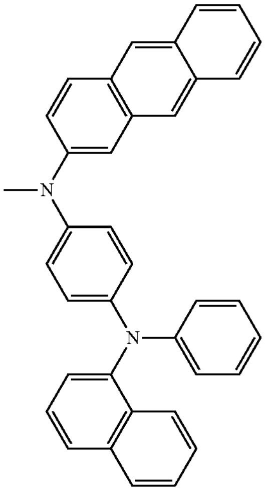
94
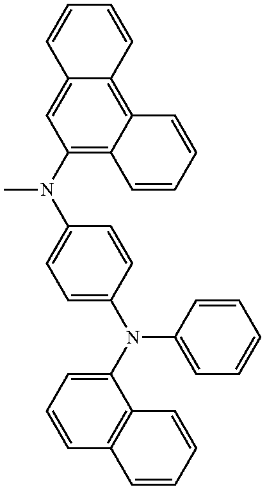

-continued
95
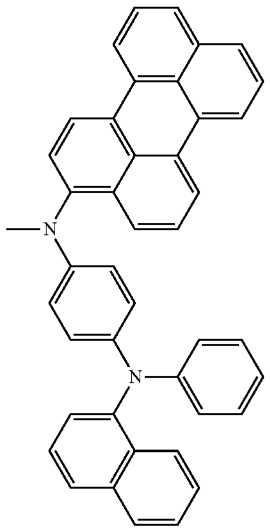
96
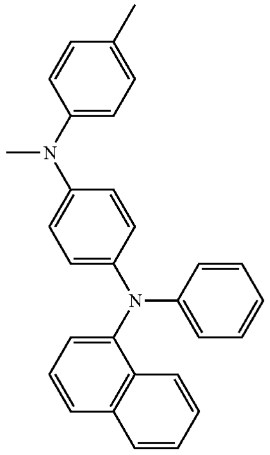
97
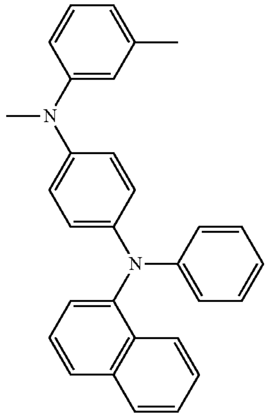
-continued
98
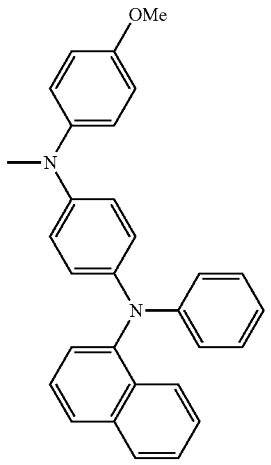
99
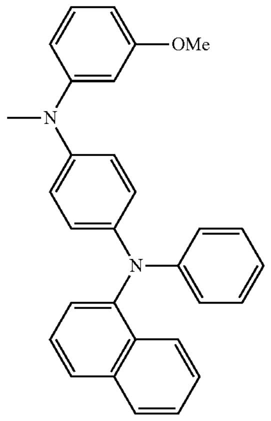
100
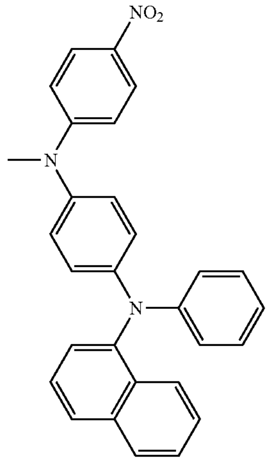

-continued
101
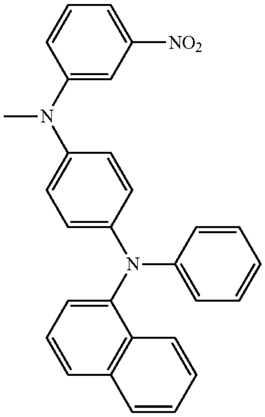
102
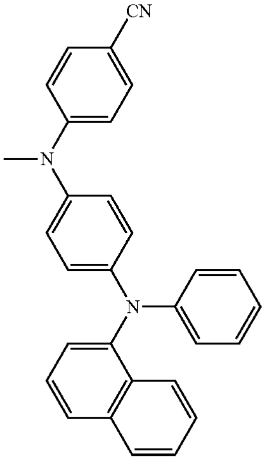
103
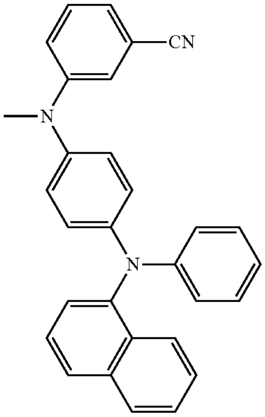
-continued
104
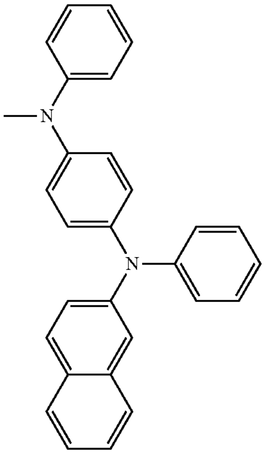
105
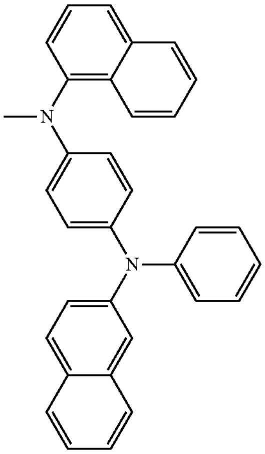
106
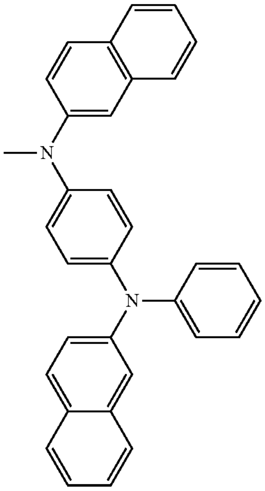

-continued
107
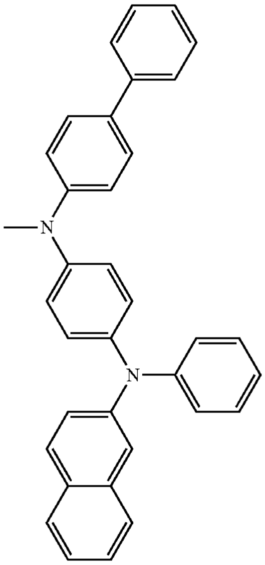
108
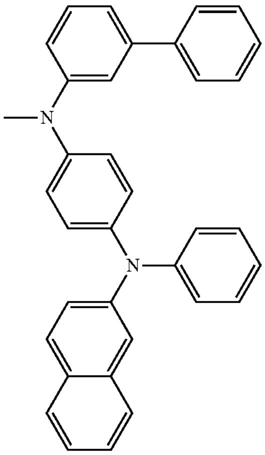
109
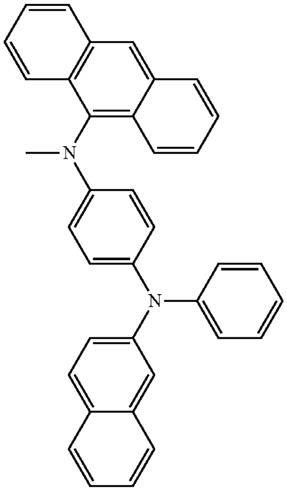
-continued
110
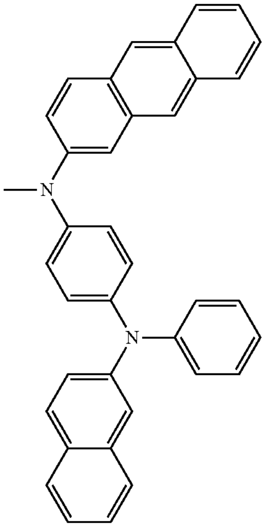
111
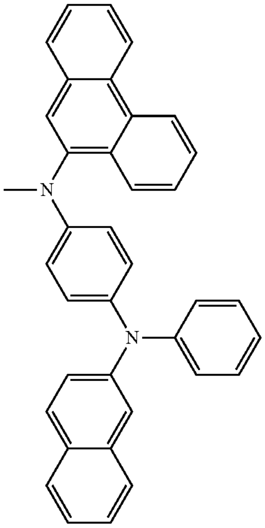
112
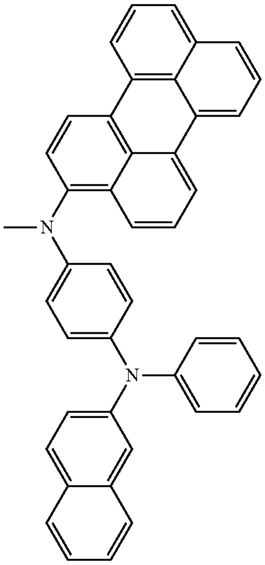

-continued
113
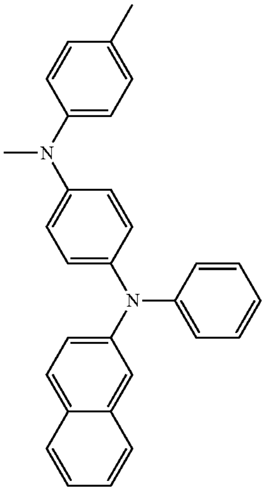
114
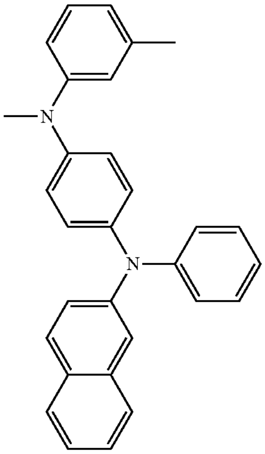
115
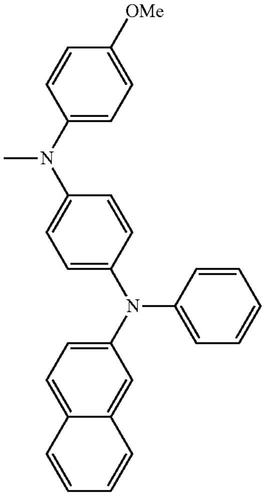
-continued
116
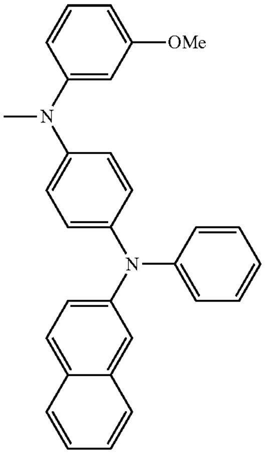
117
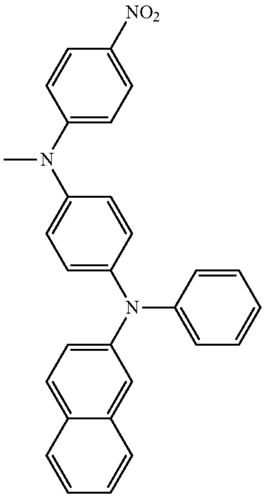
118
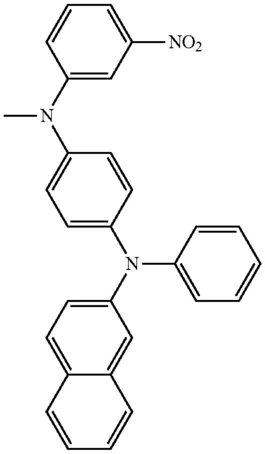

-continued
119
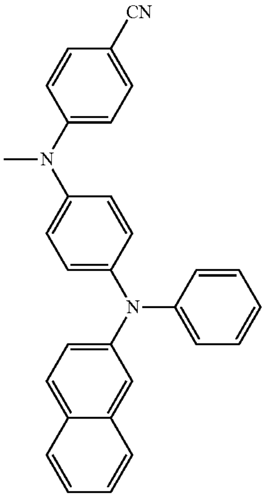
120
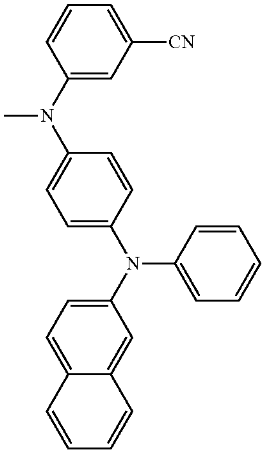
121
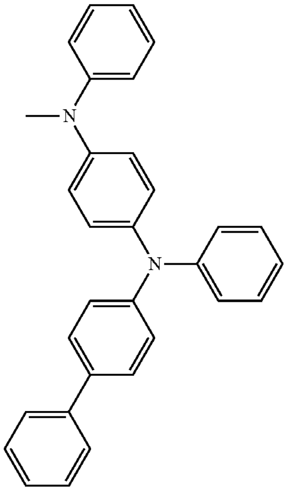
-continued
122
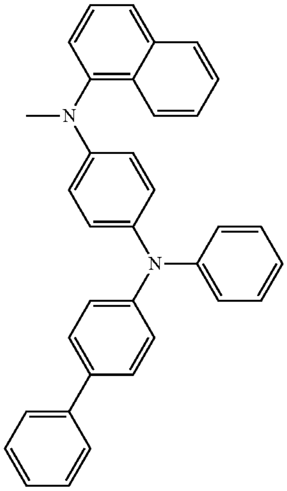
123
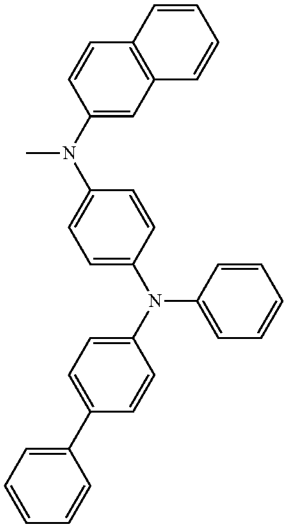
124
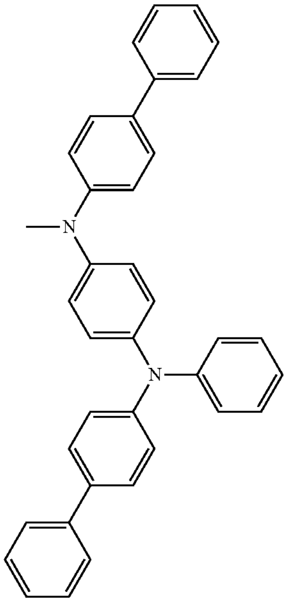

-continued
125
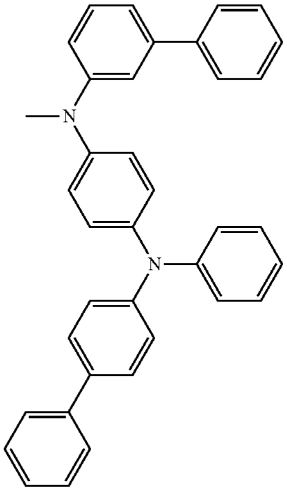
126
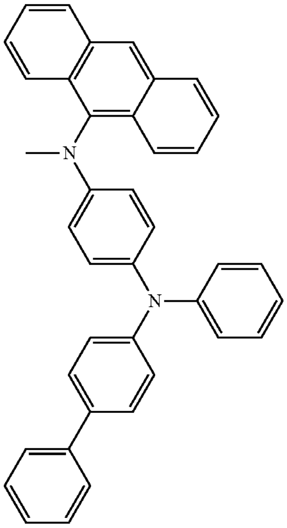
127
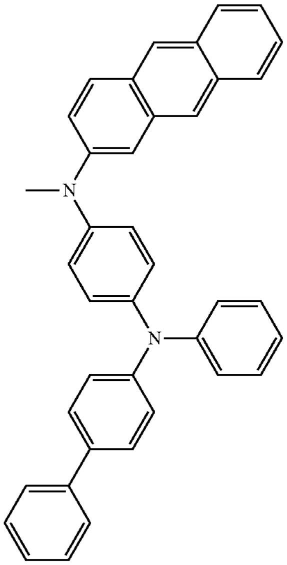
-continued
128
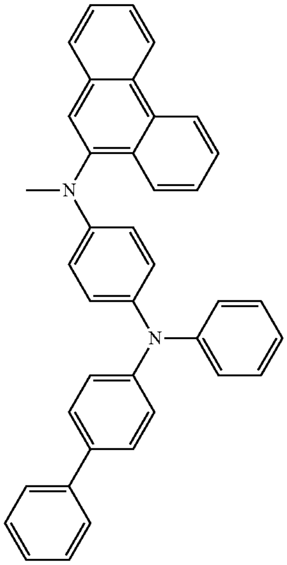
129
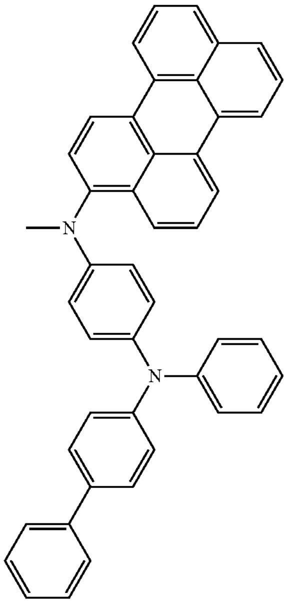

-continued
130
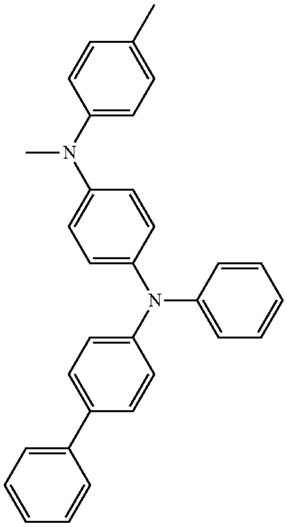
131
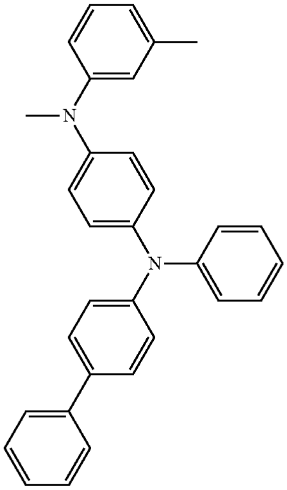
132
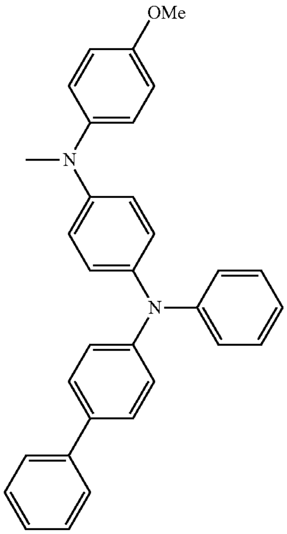
-continued
133
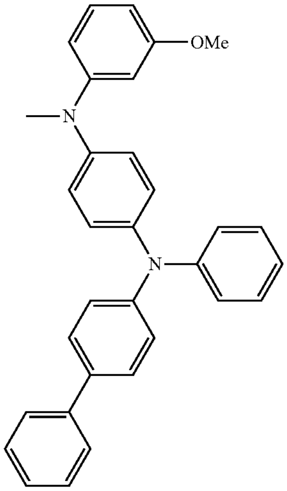
134
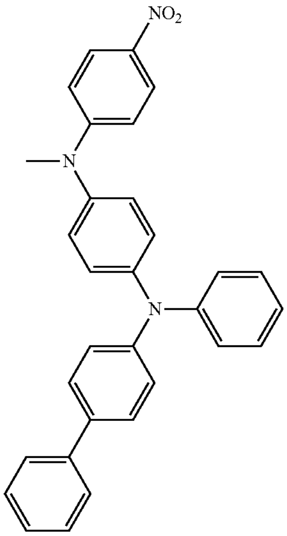
135
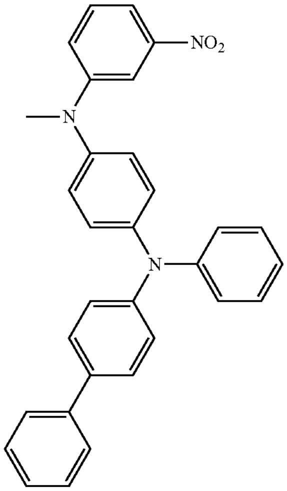

-continued
136
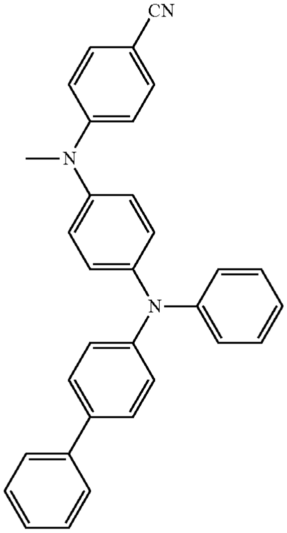
137
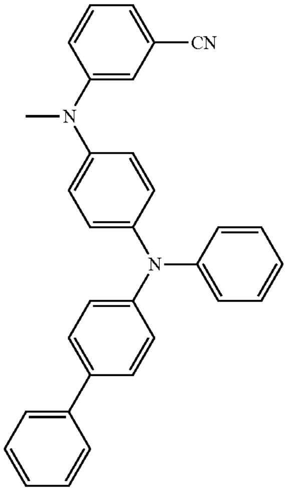
138
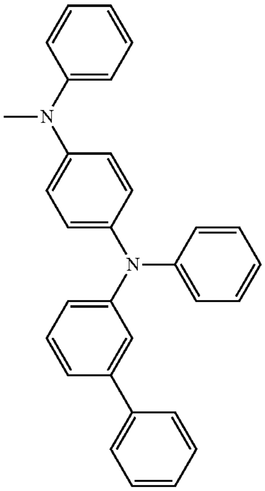
-continued
139
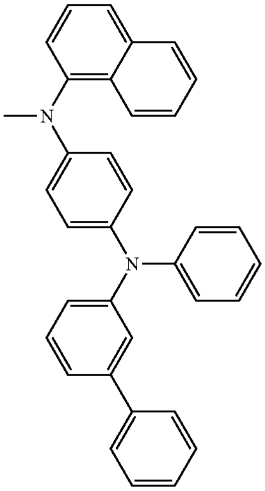
140
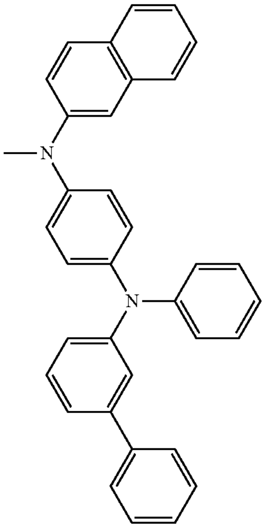
141
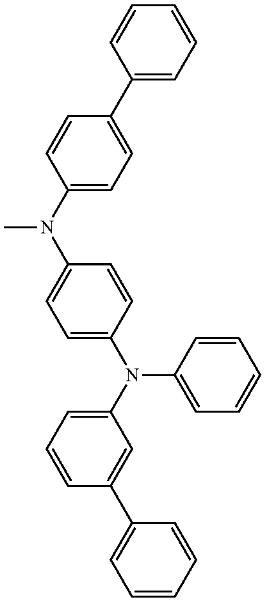

-continued
142
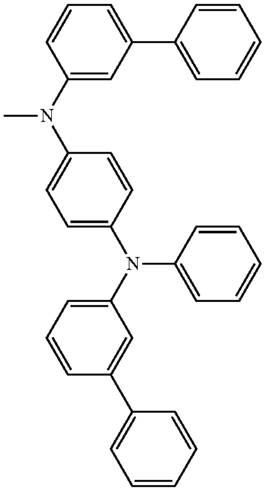
143
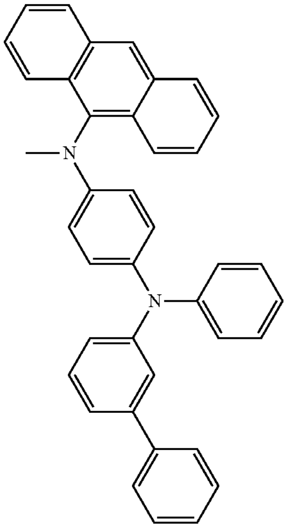
144
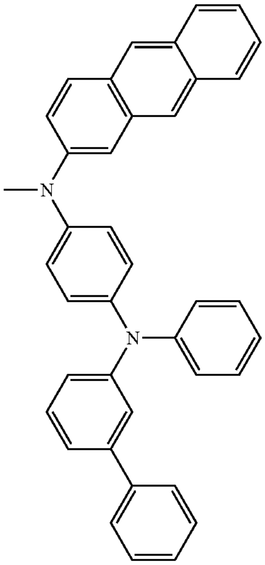
-continued
145
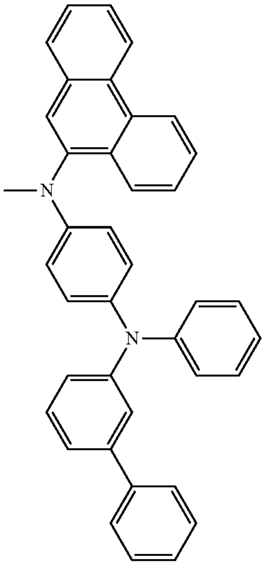
146
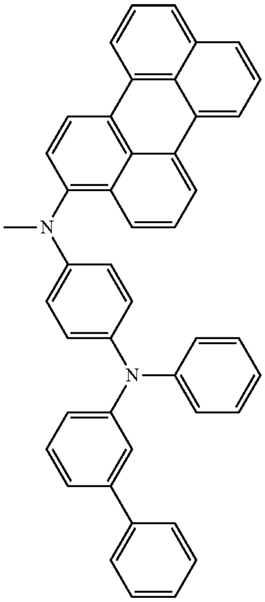

-continued
147
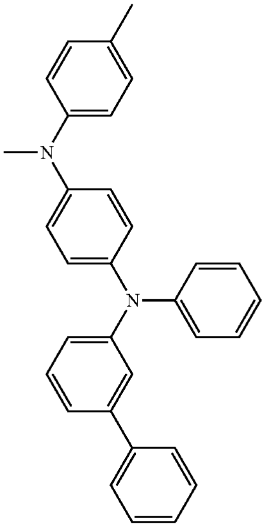
148
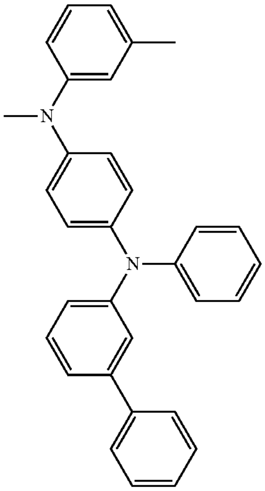
149
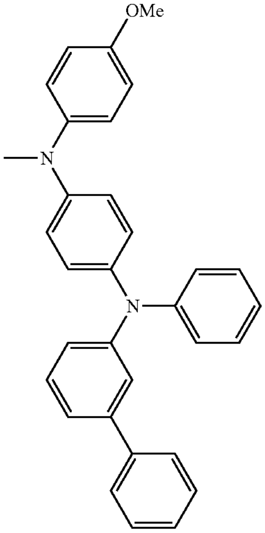
-continued
150
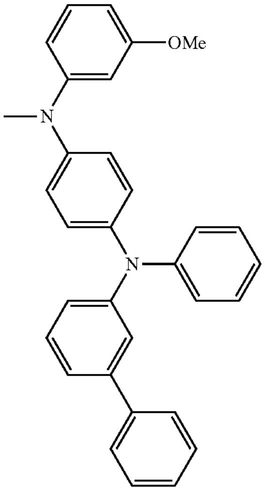
151
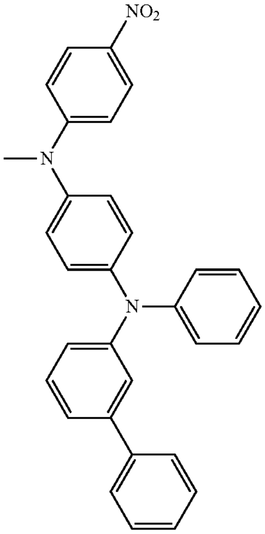
152
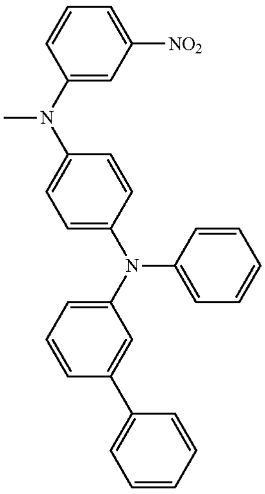

-continued
153
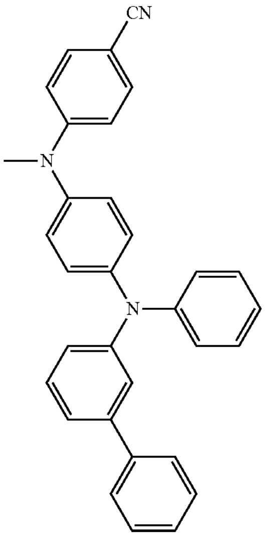
154
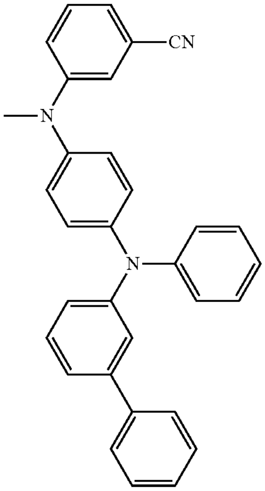
155
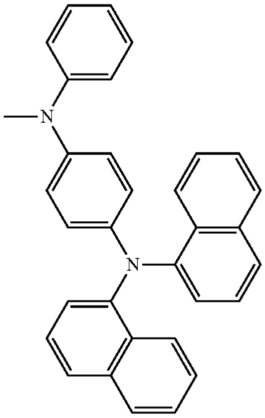
-continued
156
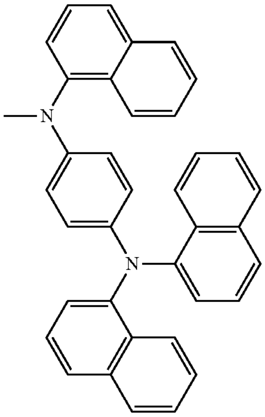
157
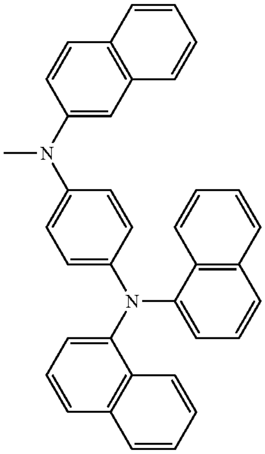
158
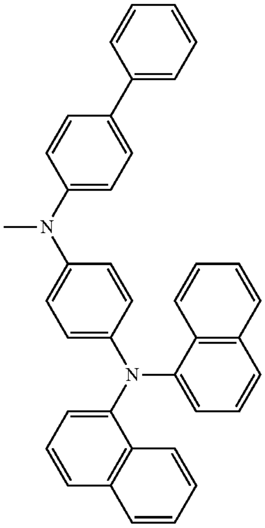

-continued
159
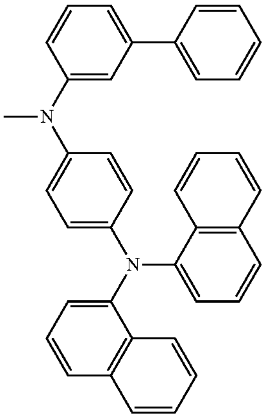
160
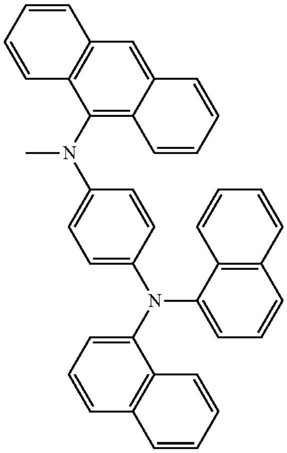
161
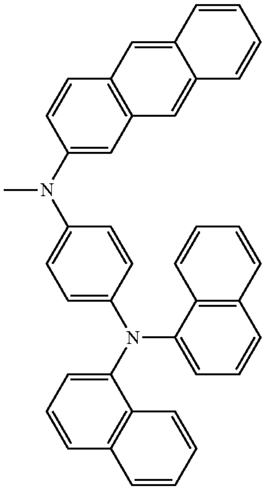
-continued
162
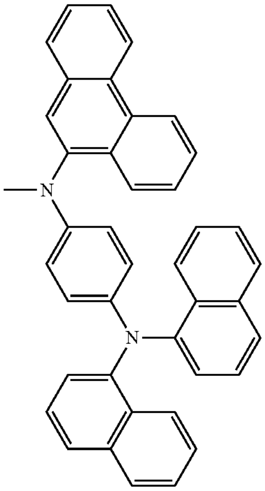
163
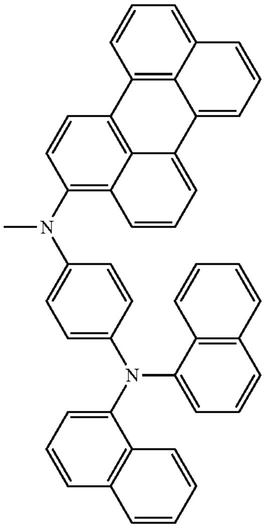
164
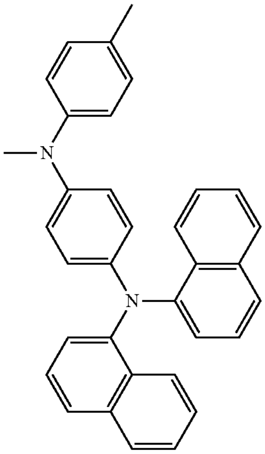

-continued
165
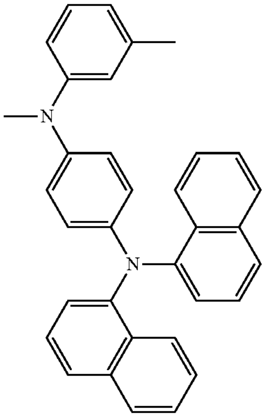
166
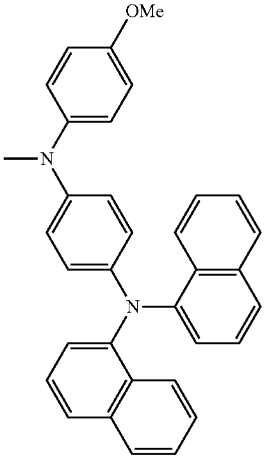
167
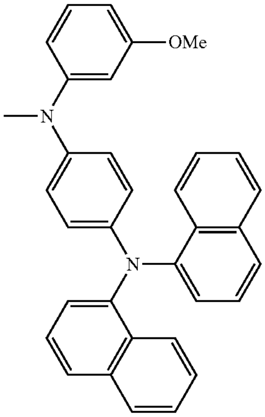
-continued
168
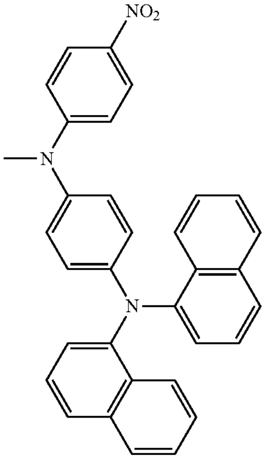
169
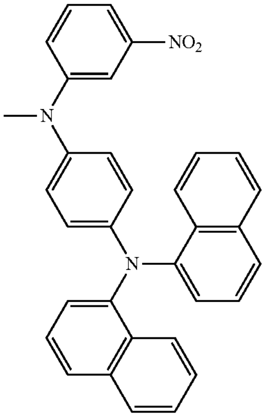
170
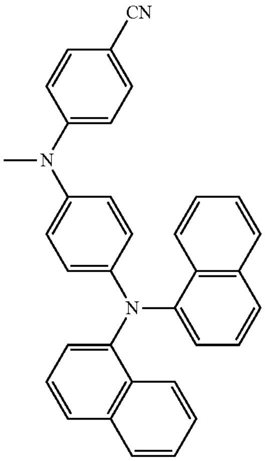

-continued
171
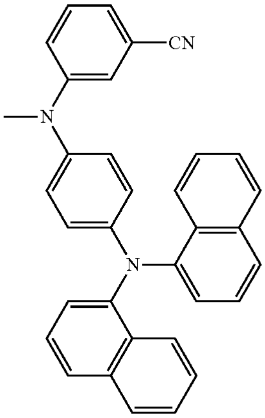
172
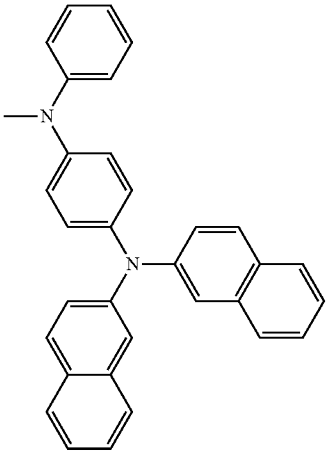
173
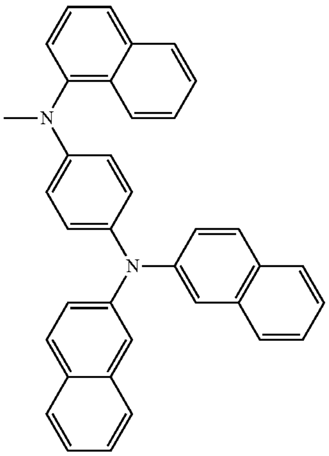
-continued
174
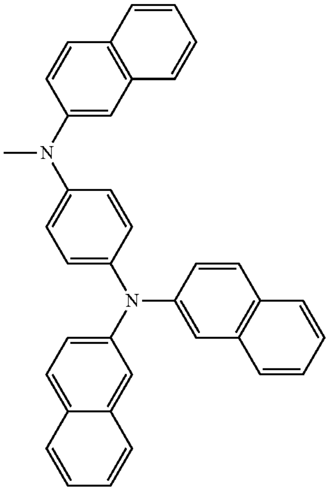
175
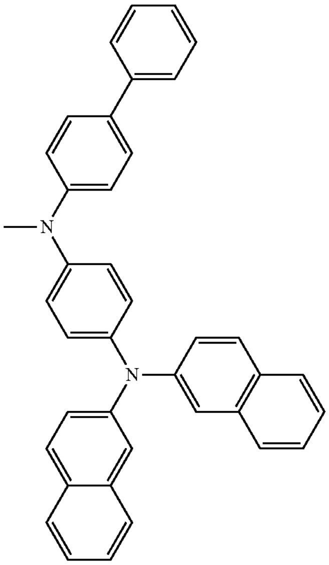
176
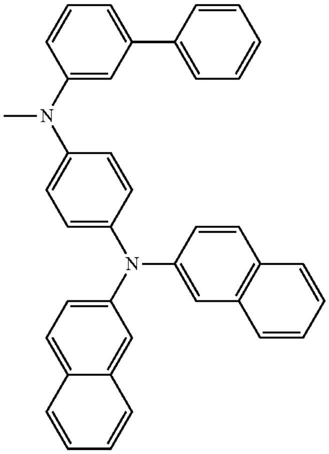

-continued
177
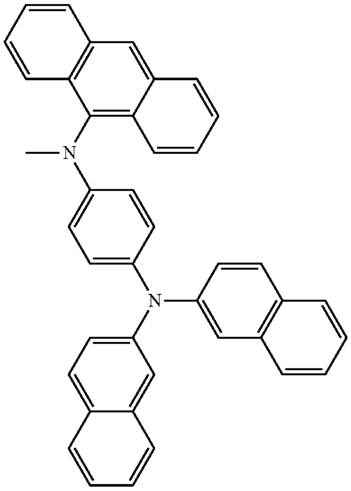
178
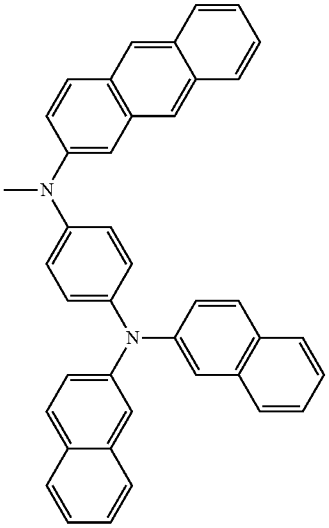
179
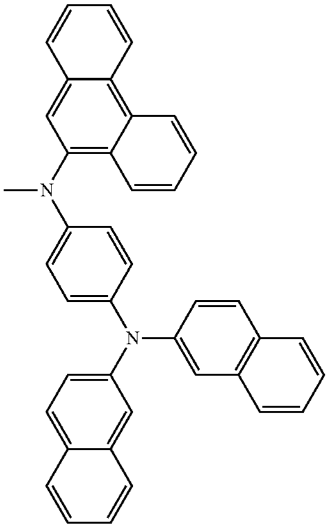
-continued
180
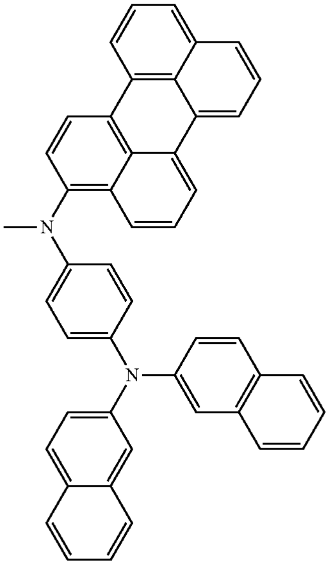
181
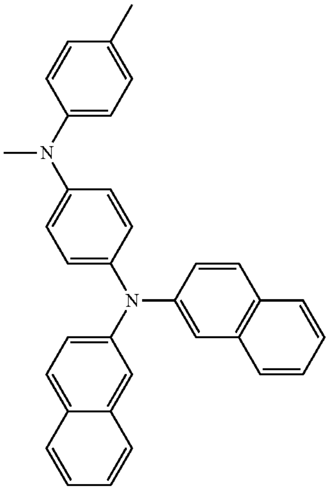
182
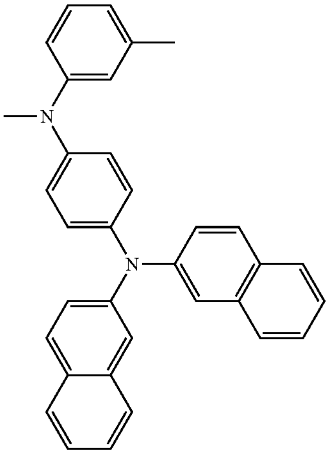

-continued
183
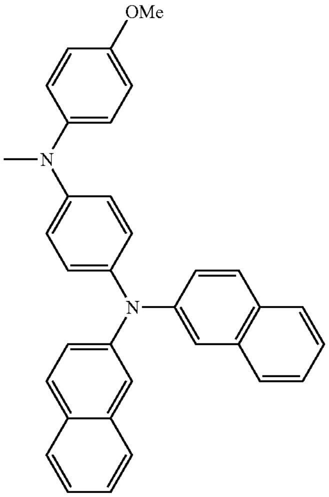
184
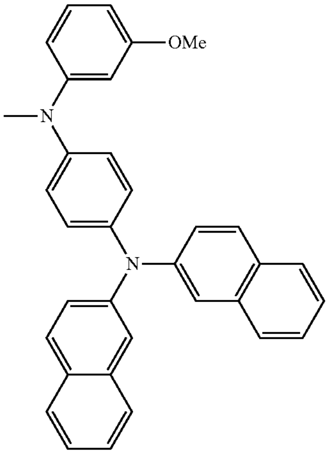
185
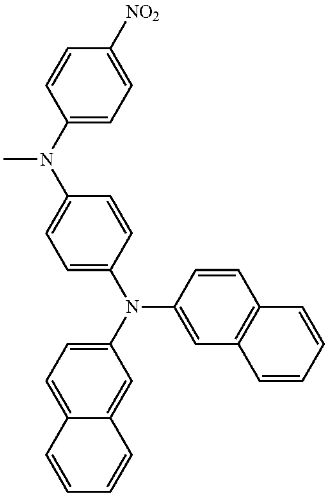
-continued
186
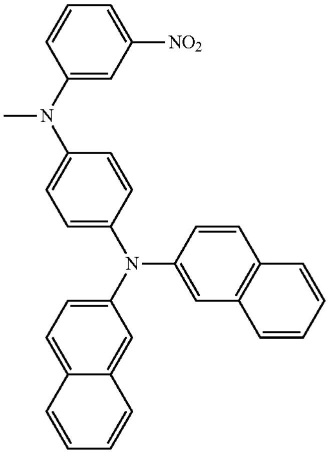
187
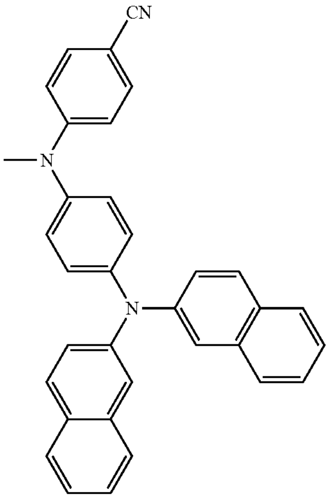
188
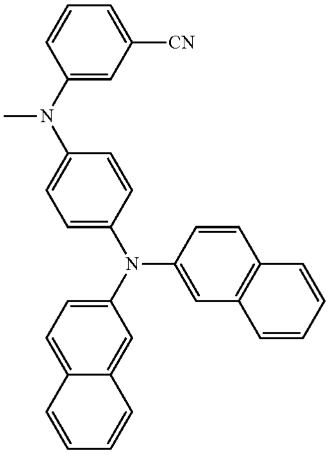

189
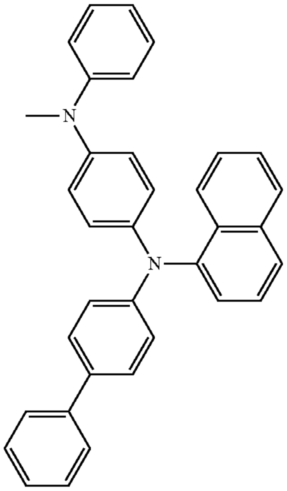
190
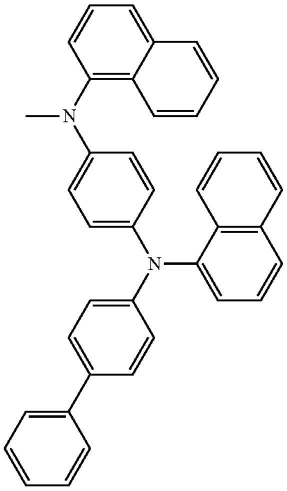
191
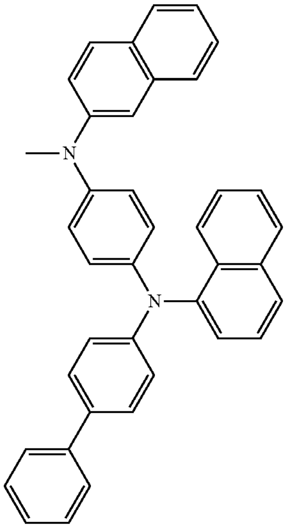
192
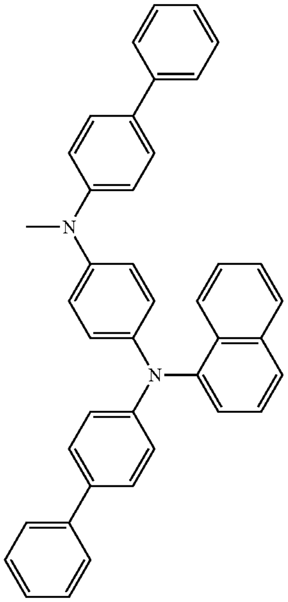
193
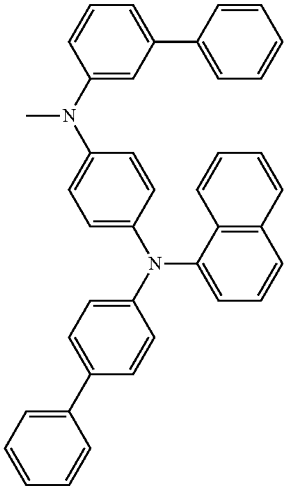
194
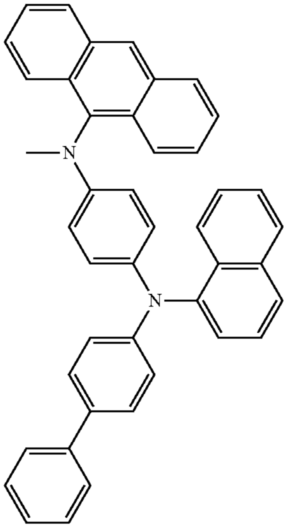

195
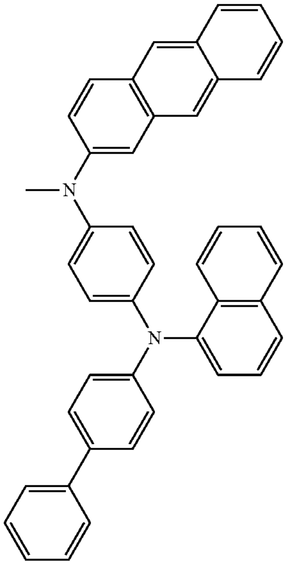
196
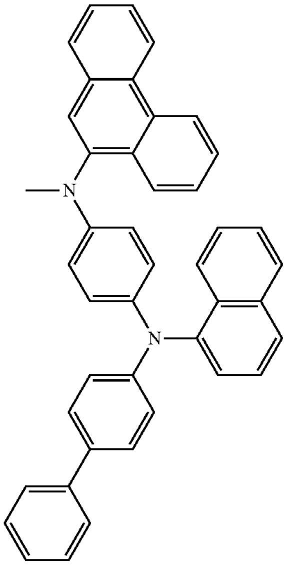
197
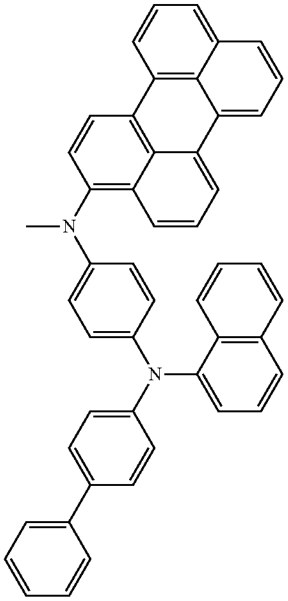
198
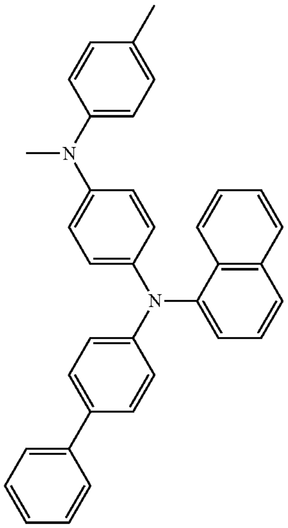
199
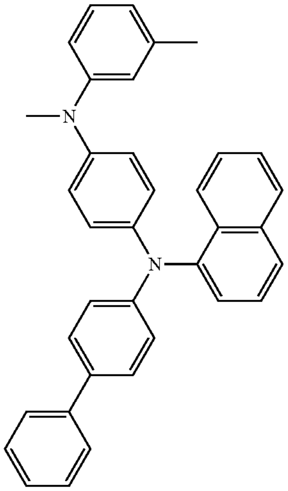

-continued
200
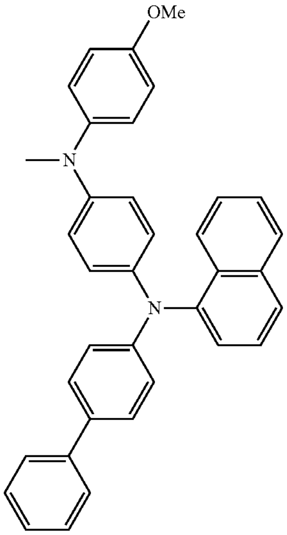
201
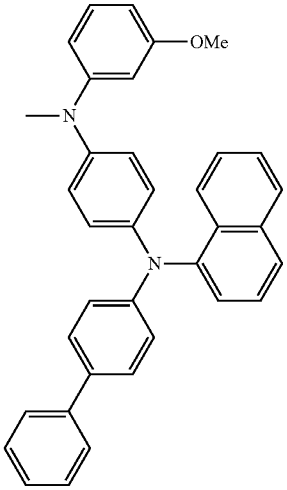
202
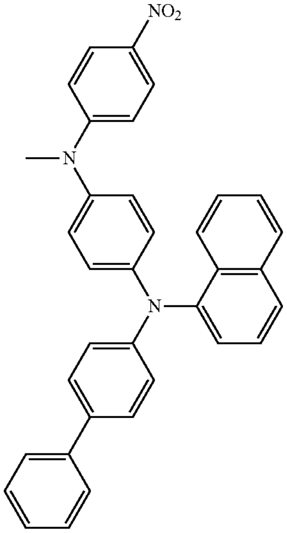
-continued
203
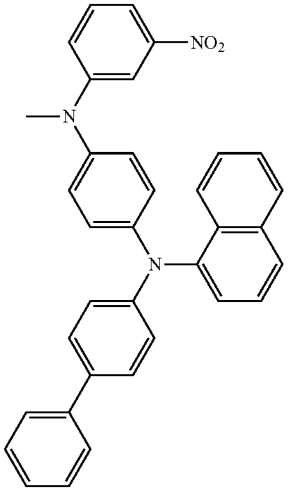
204
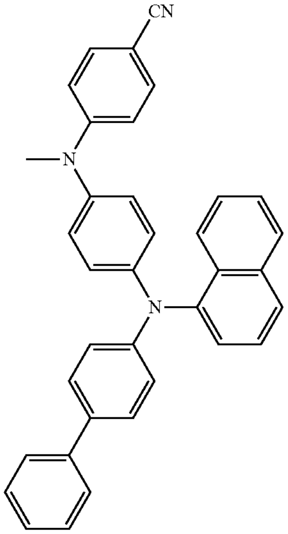
205
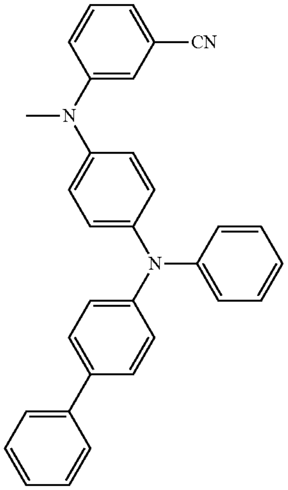

206
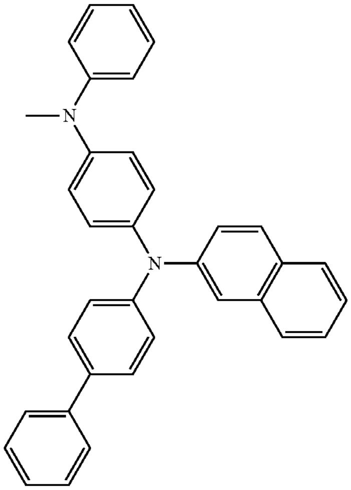
207
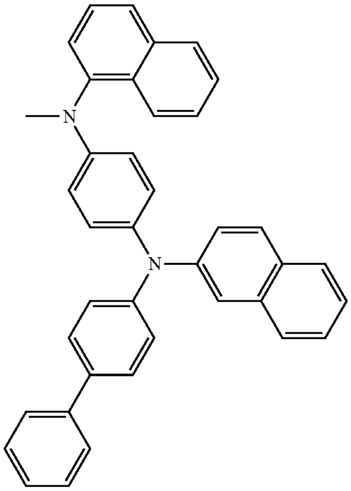
208
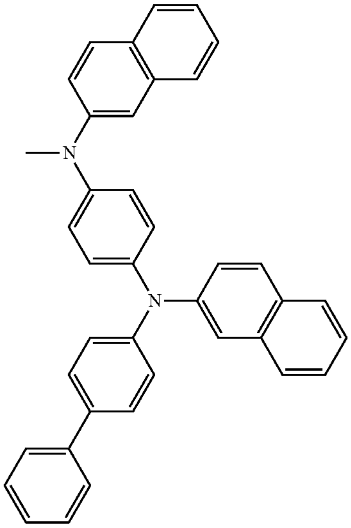
209
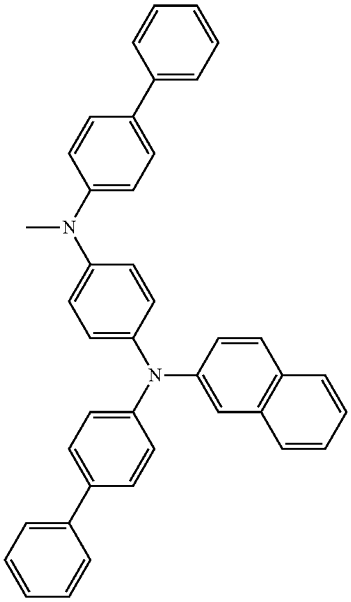
210
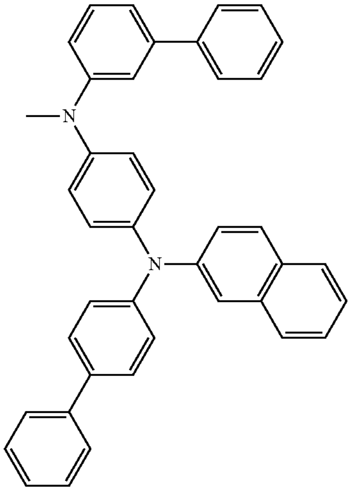
211
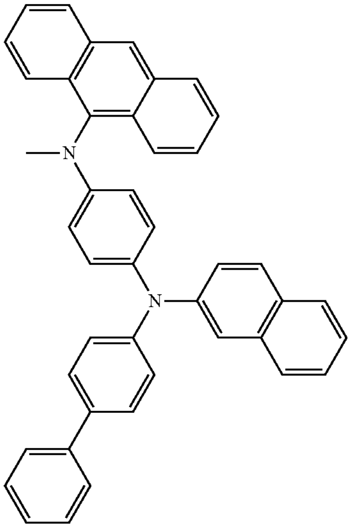

212
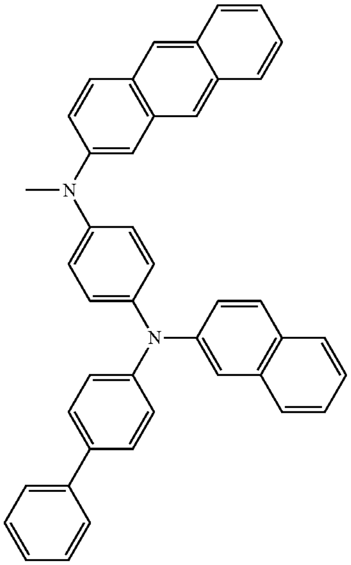
213
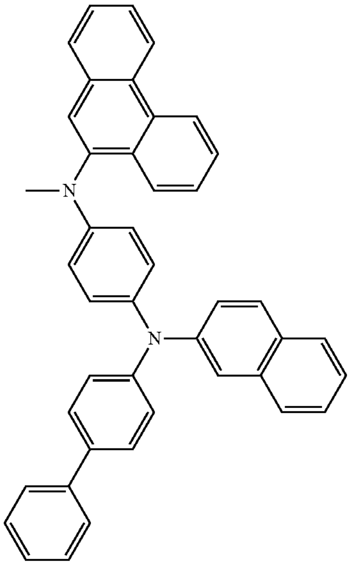
214
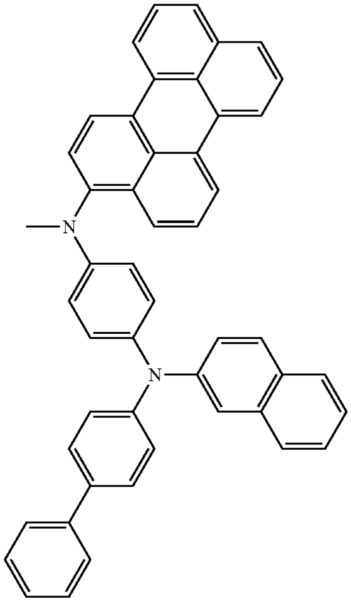
215
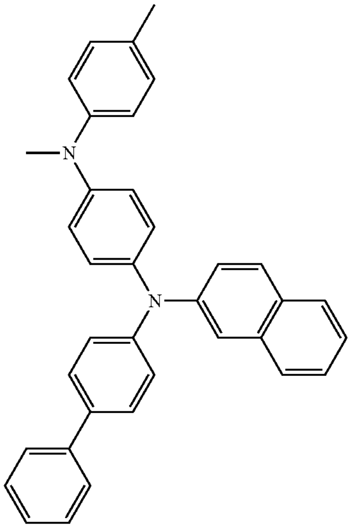
216
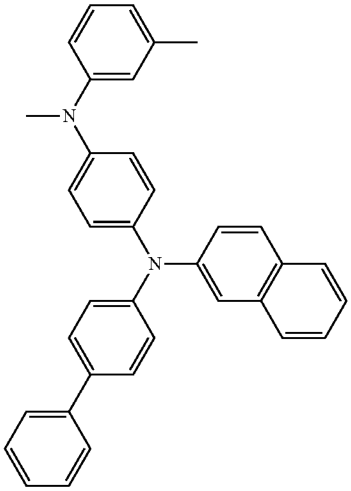

-continued
217
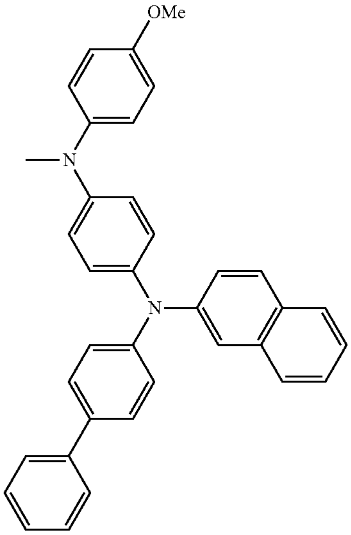
218
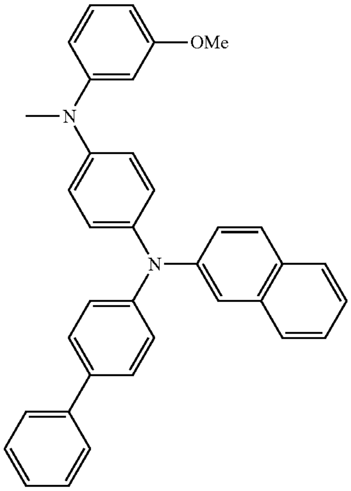
219
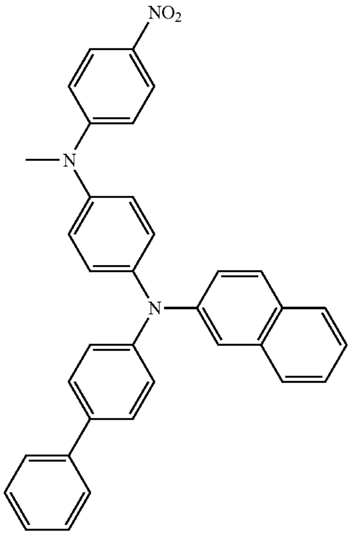
-continued
220
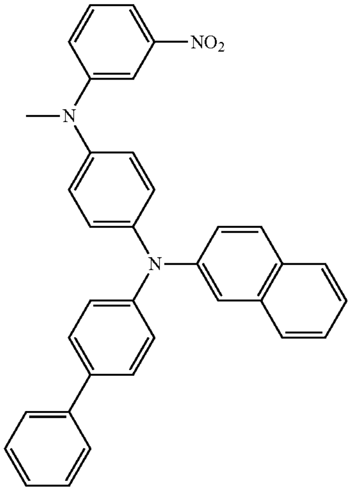
221
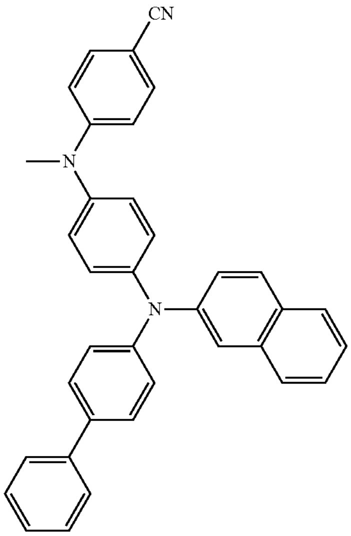
222
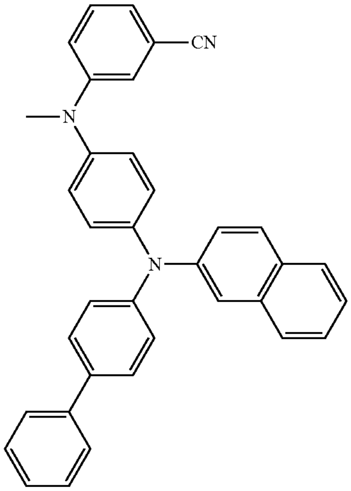

-continued
223
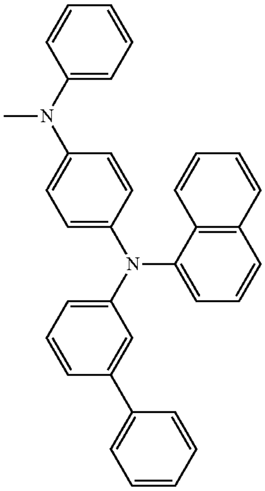
224
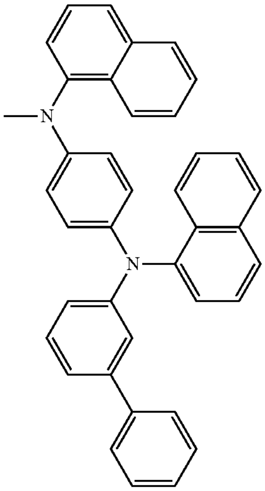
225
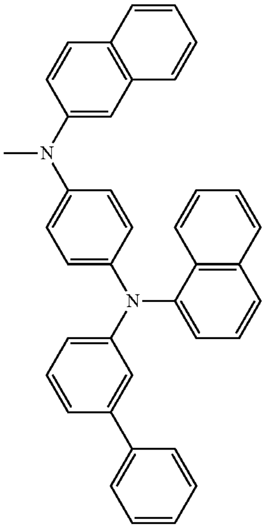
-continued
226
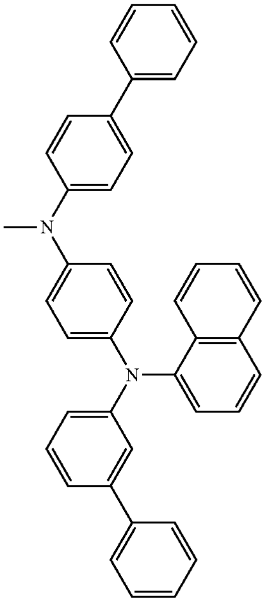
227
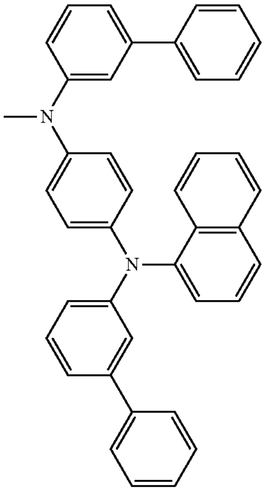
228
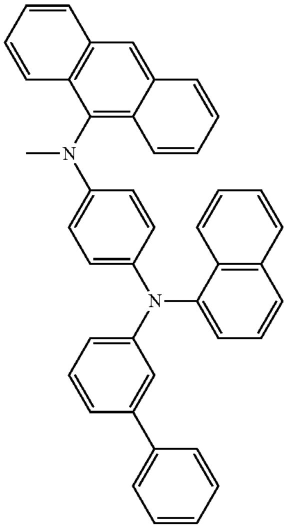

-continued
229
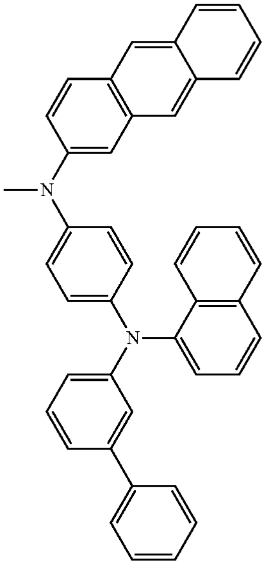
230
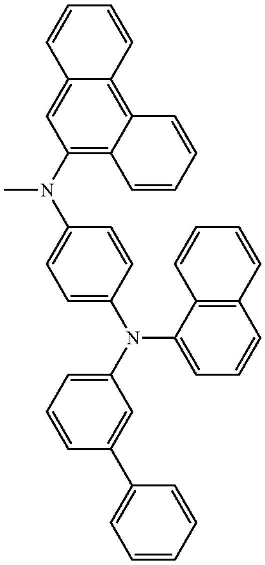
-continued
231
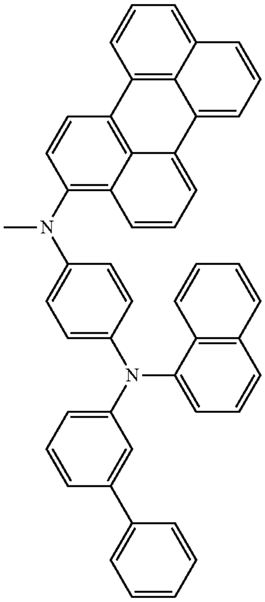
232
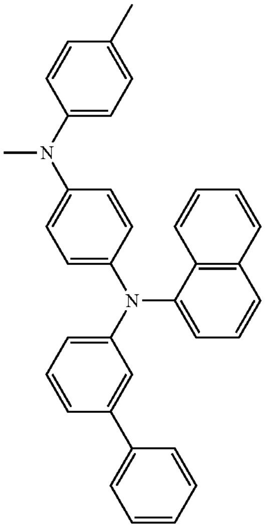
233
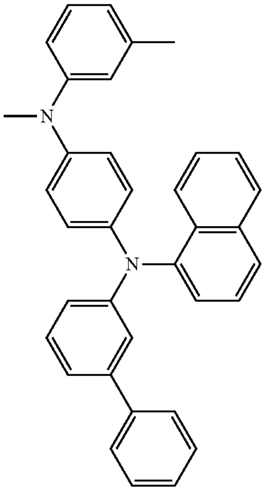

-continued
234
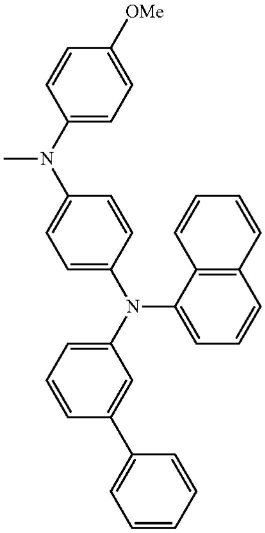
235
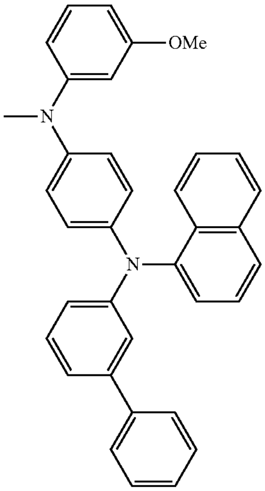
236
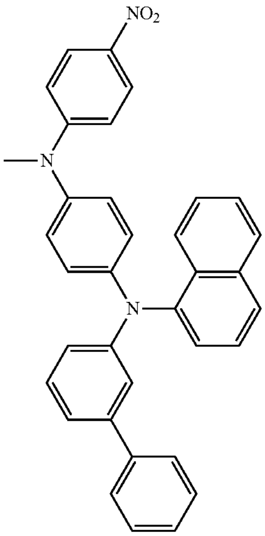
-continued
237
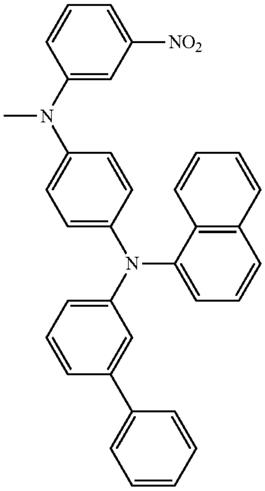
238
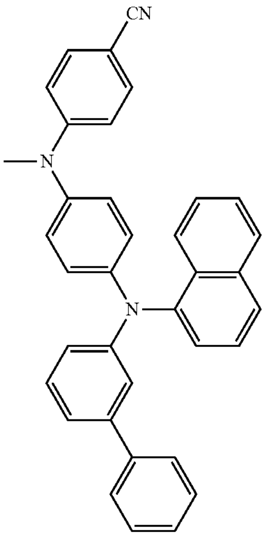
239
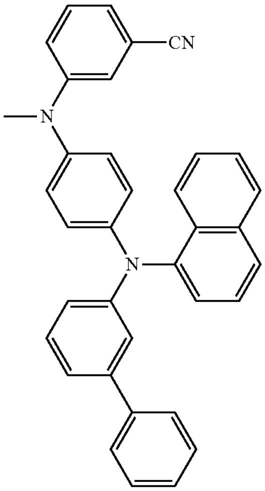

-continued
240
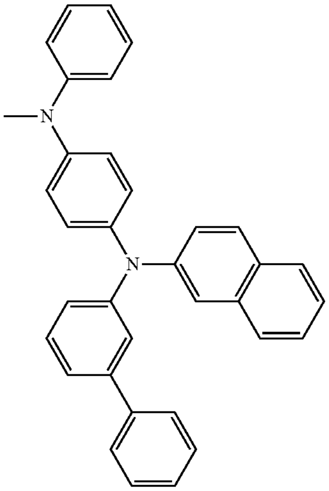
241
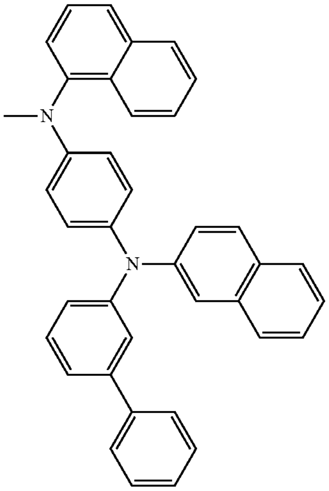
242
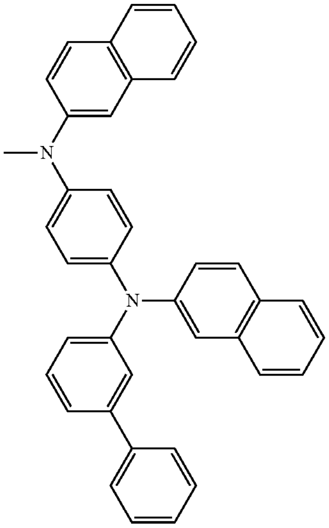
-continued
243
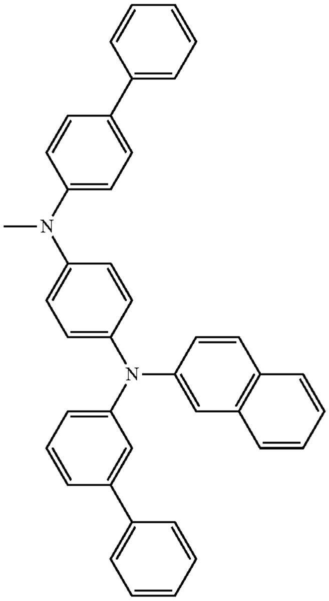
244
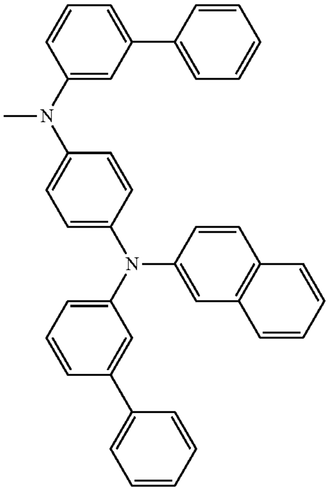
245
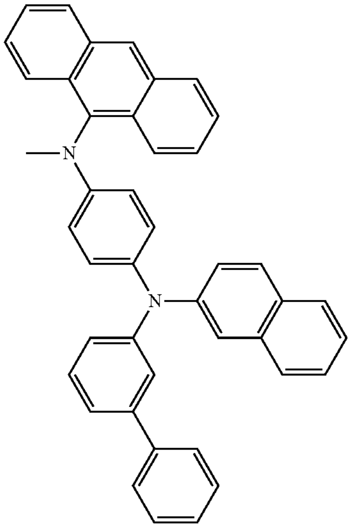

-continued
246
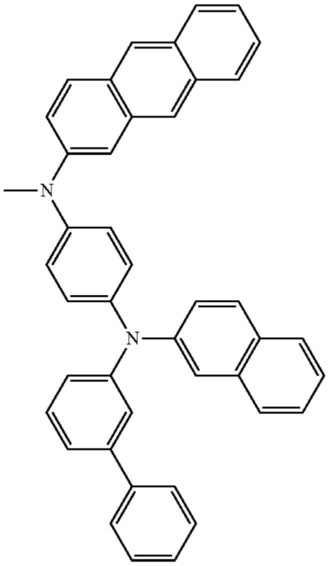
247
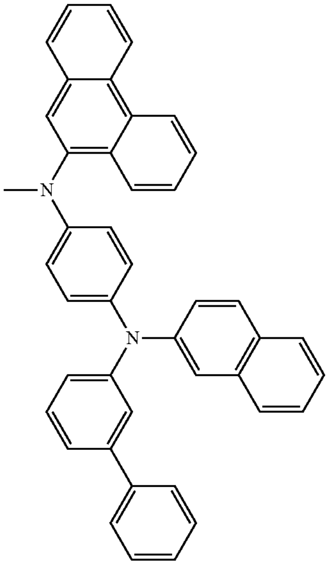
-continued
248
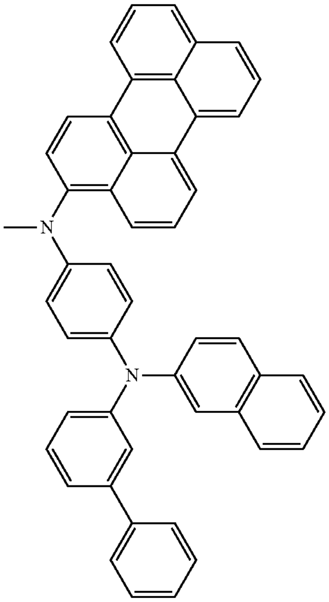
249
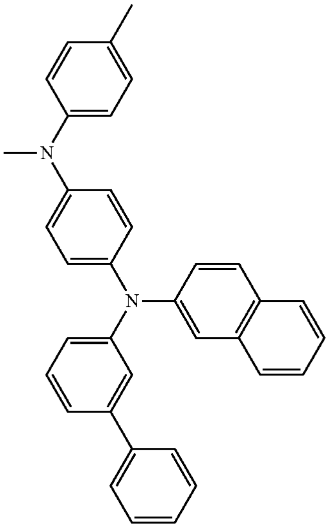
250
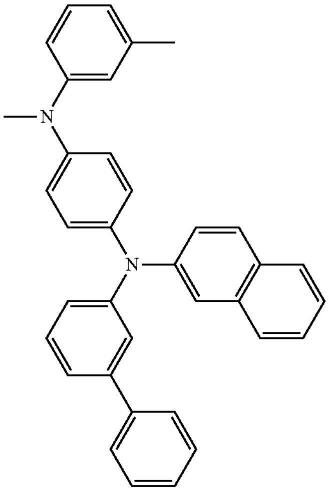

-continued
251
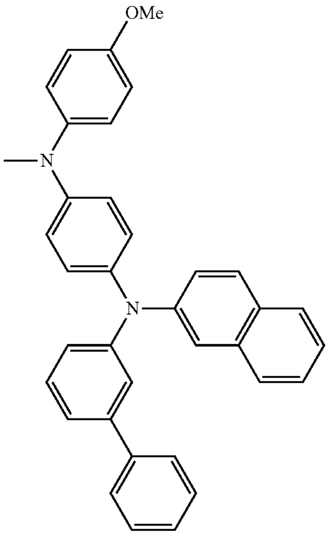
252
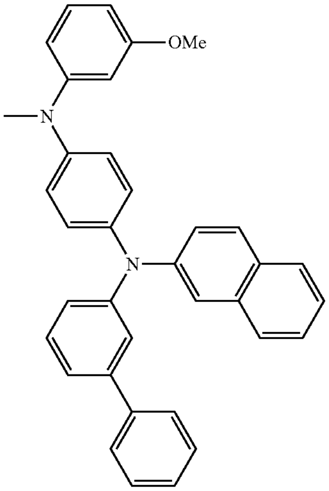
253
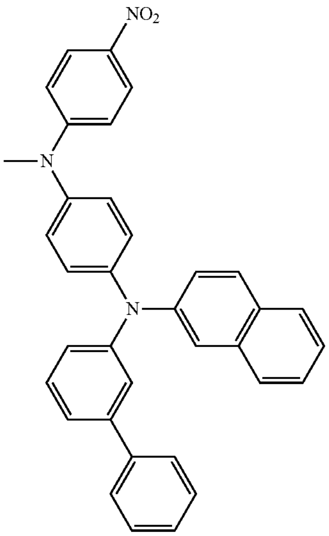
-continued
254
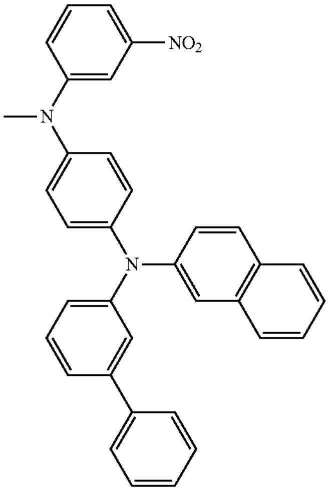
255
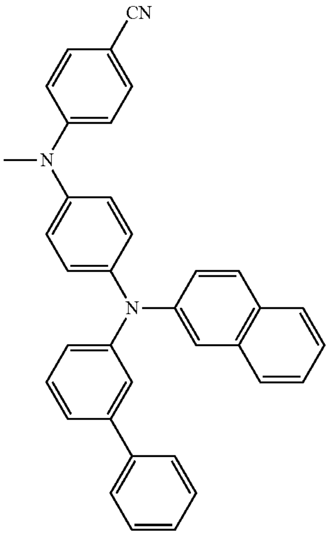
256
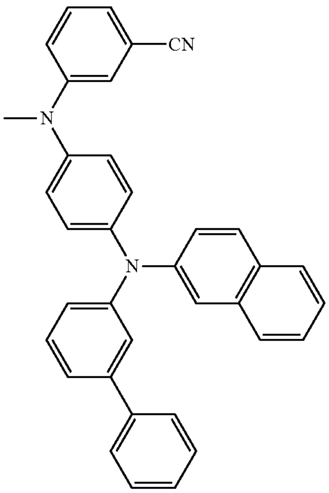

-continued
257
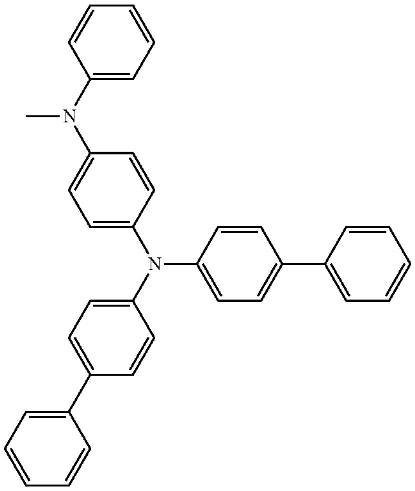
258
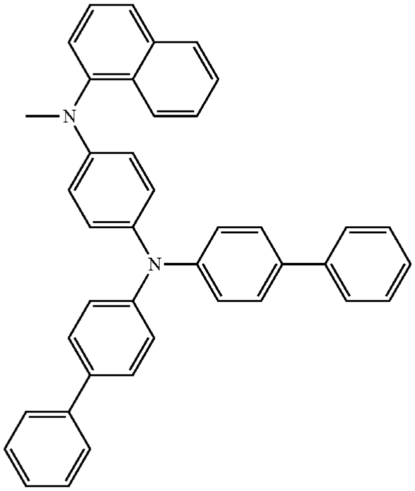
259
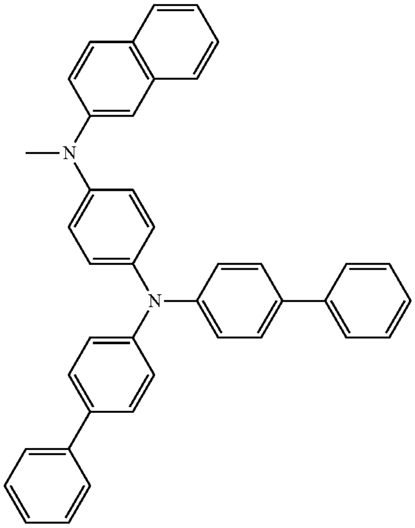
-continued
260
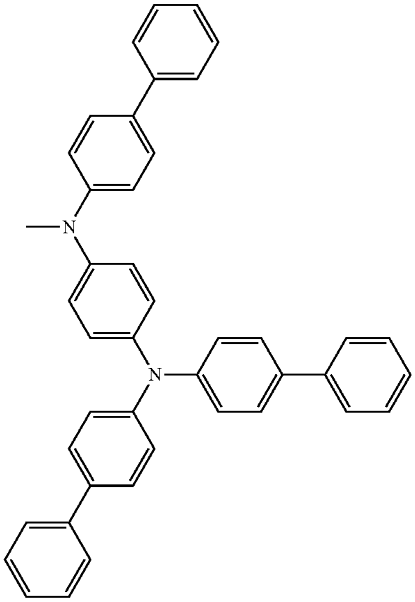
261
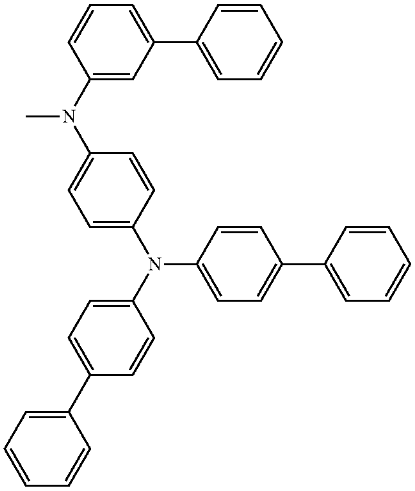
262
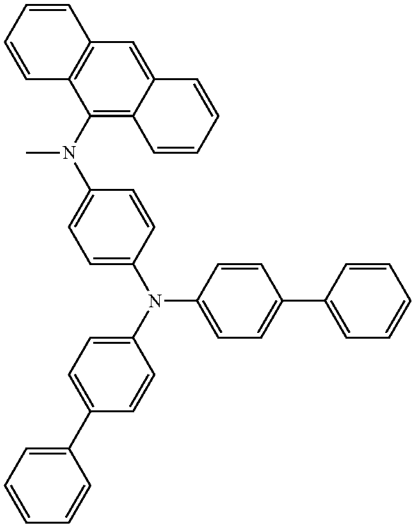

263
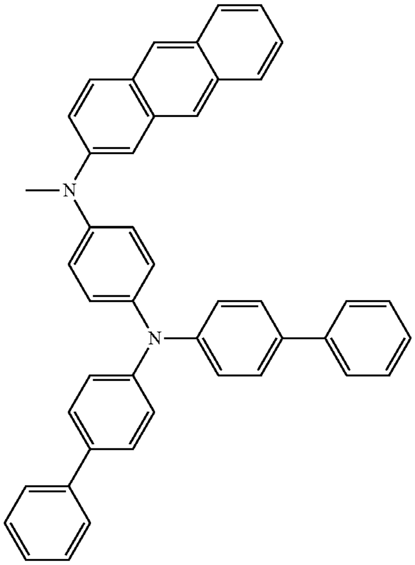
264
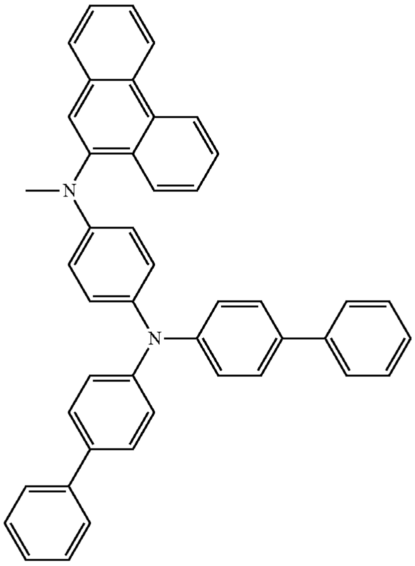
265
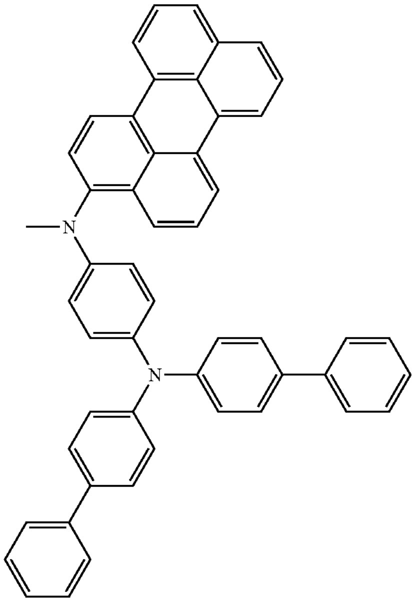
266
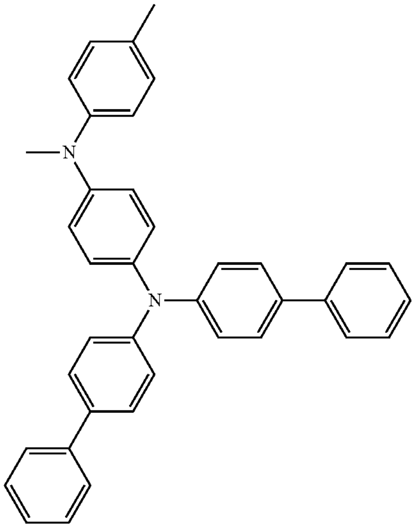
267
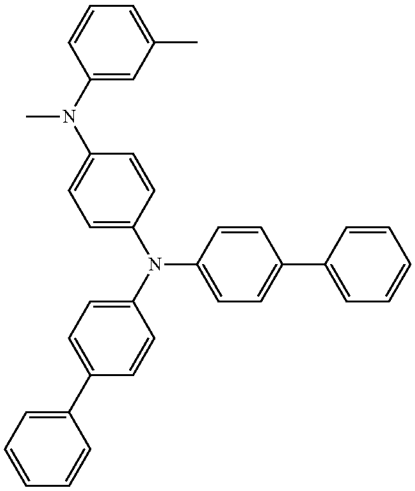

-continued
268
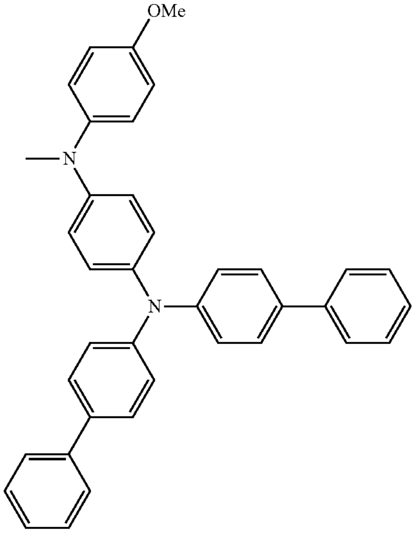
269
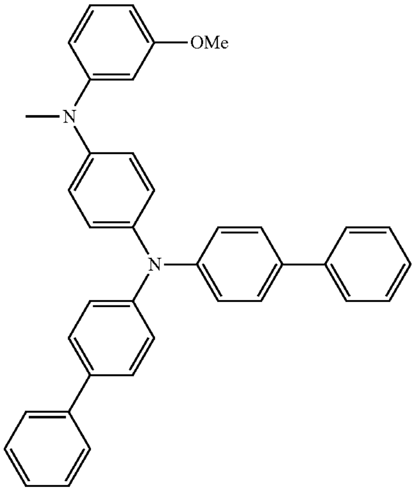
270
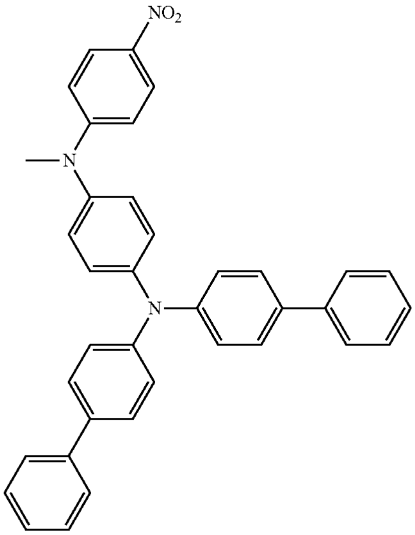
-continued
271
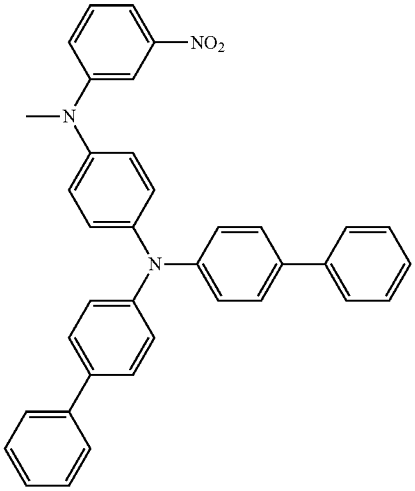
272
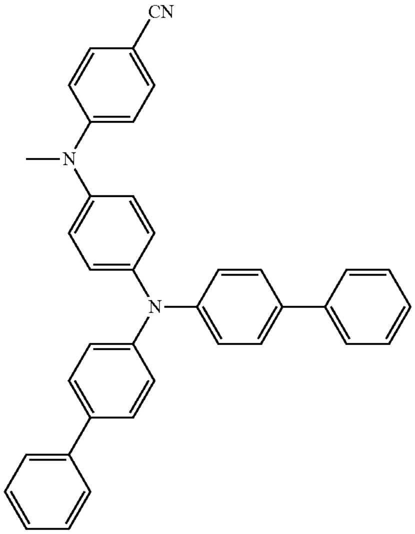
273
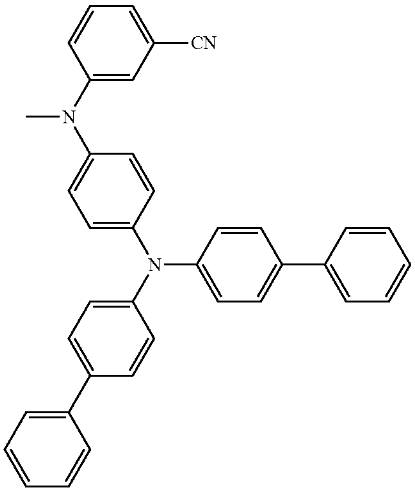

-continued
274
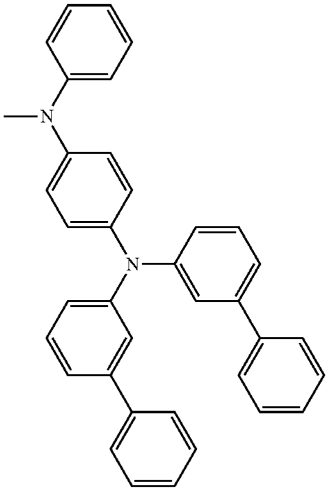
275
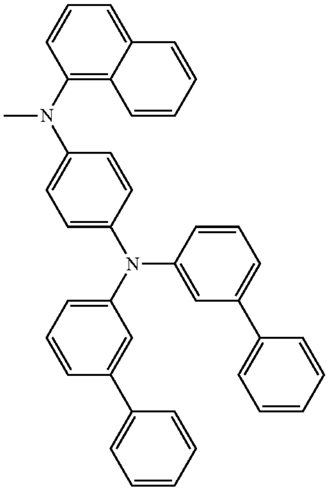
276
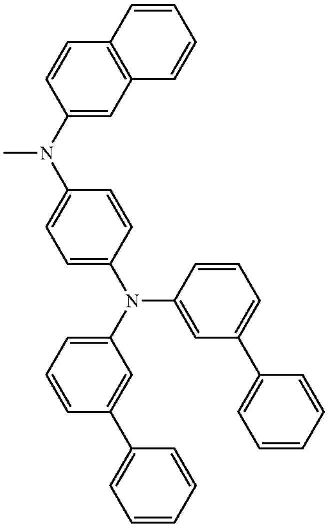
-continued
277
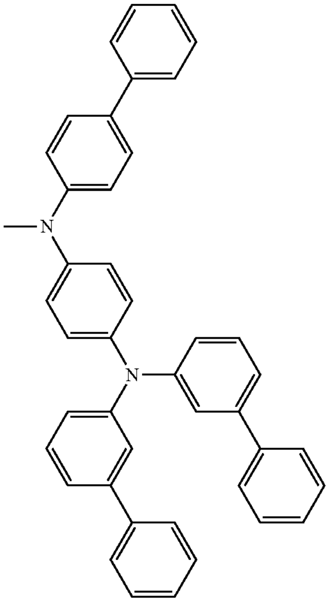
278
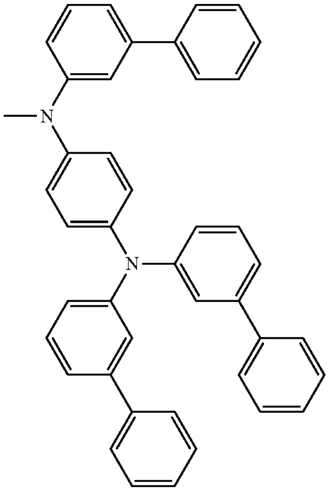
279
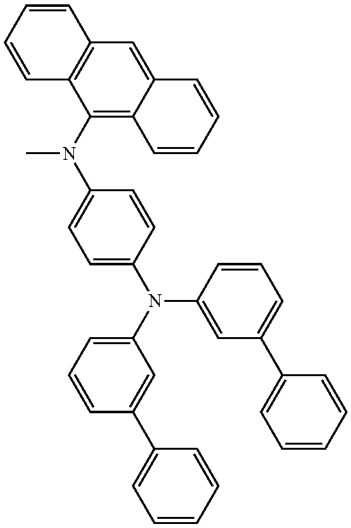

-continued
280
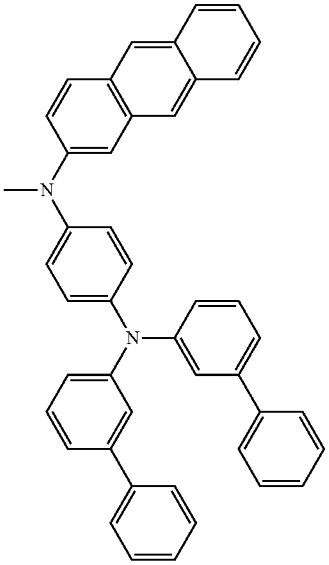
281
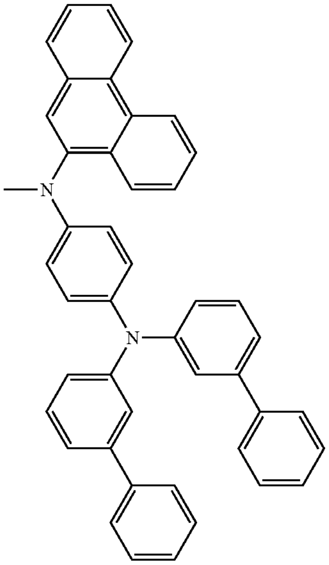
-continued
282
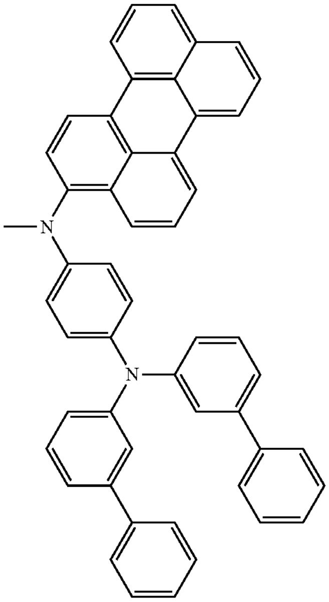
283
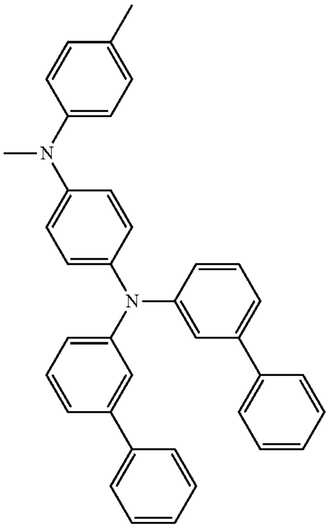
284
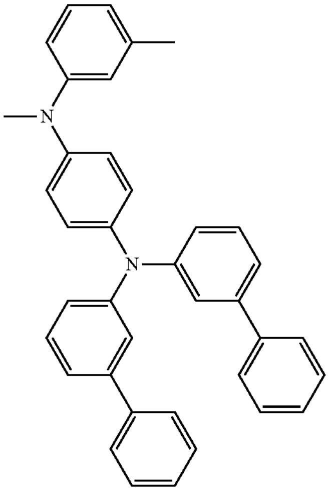

-continued
285
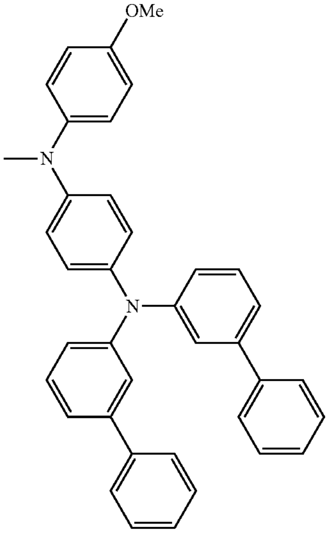
286
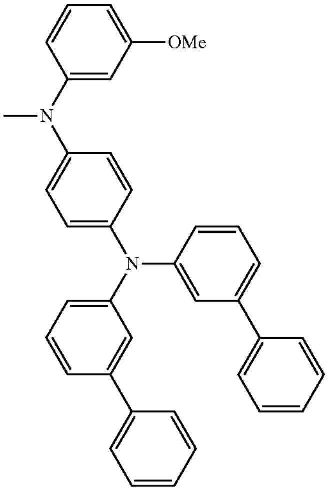
287
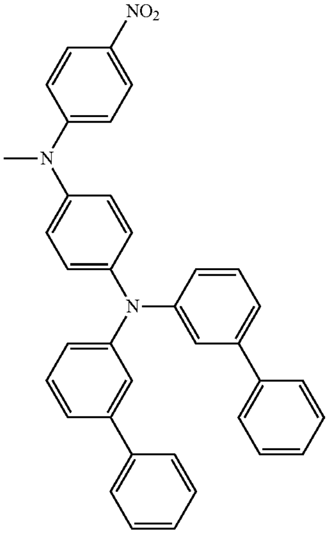
-continued
288
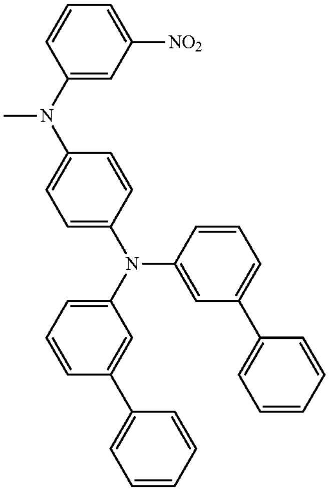
289
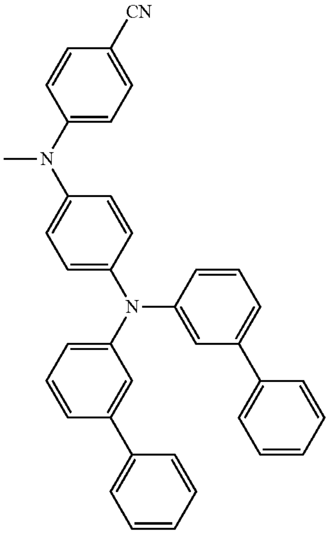
290
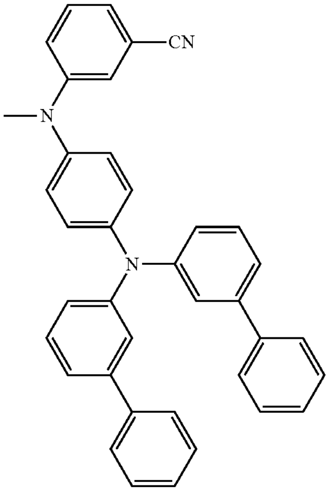

-continued
291
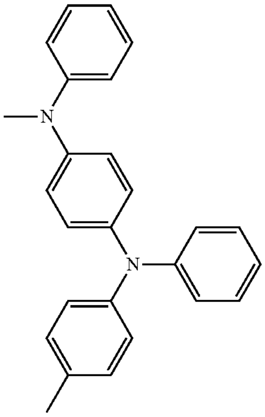
292
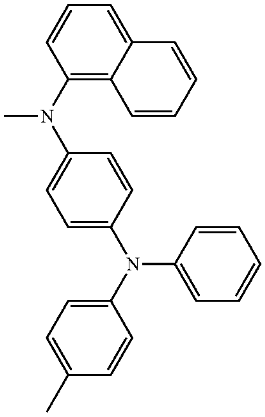
293
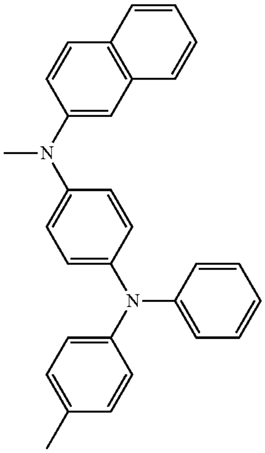
-continued
294
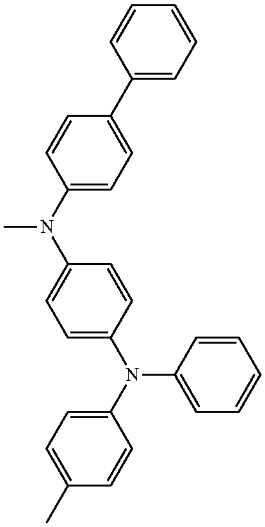
295
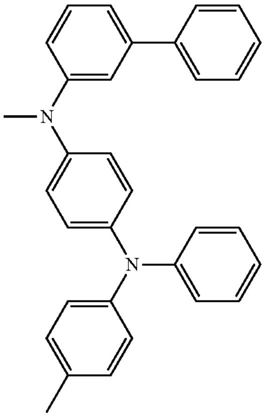
296
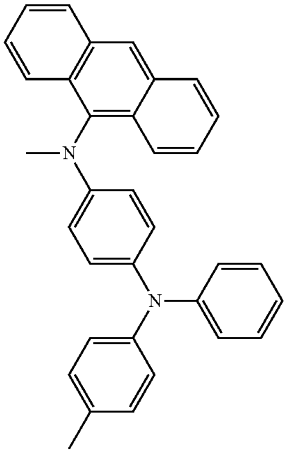

-continued
297
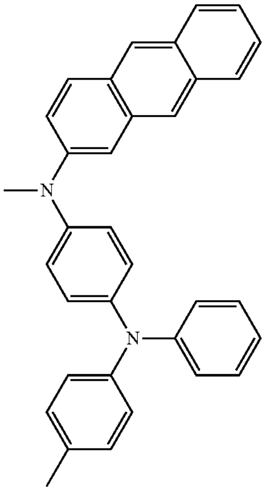
298
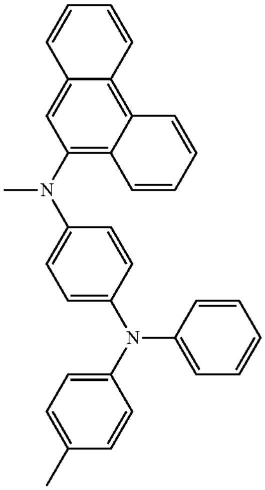
299
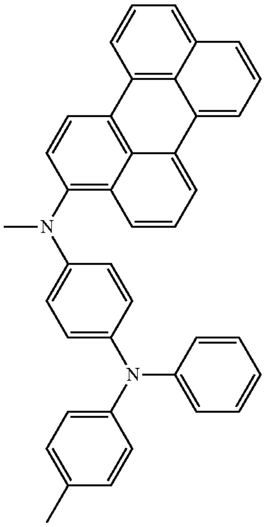
-continued
300
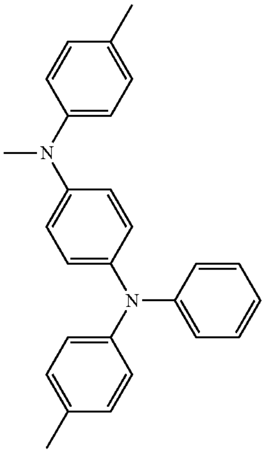
301
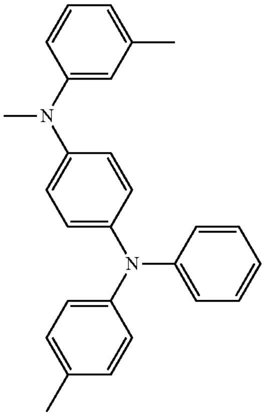
302
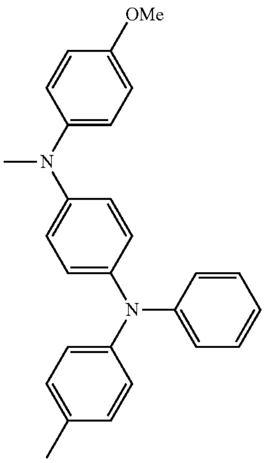

-continued
303
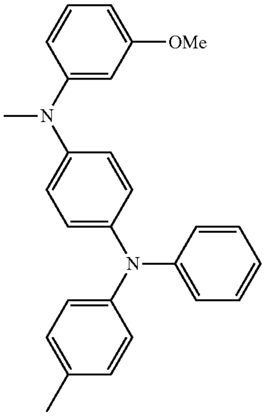
304
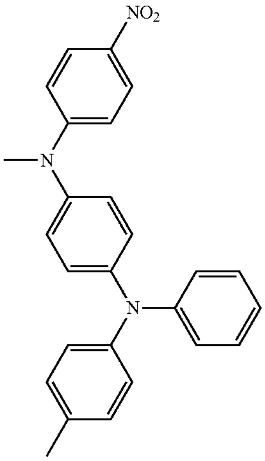
305
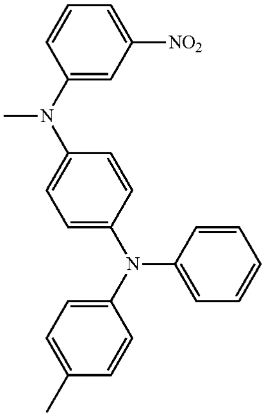
-continued
306
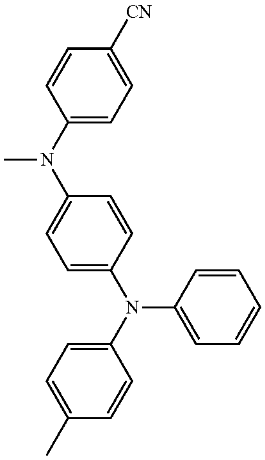
307
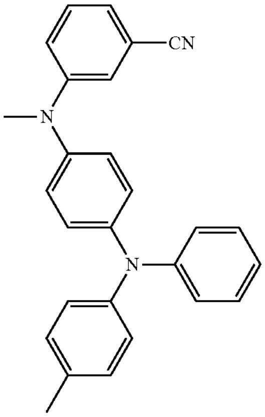
308
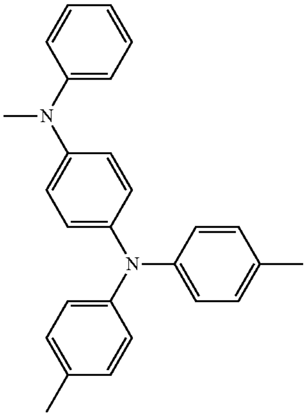

309
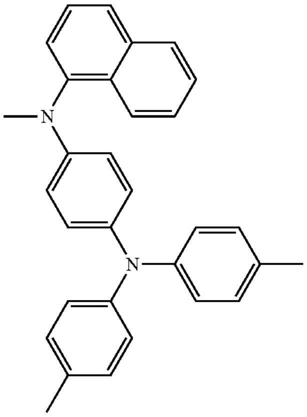
310
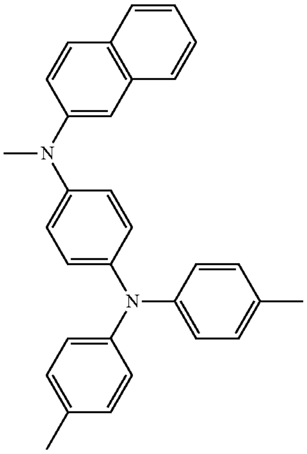
311
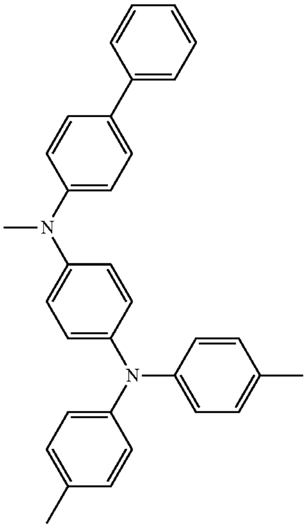
312
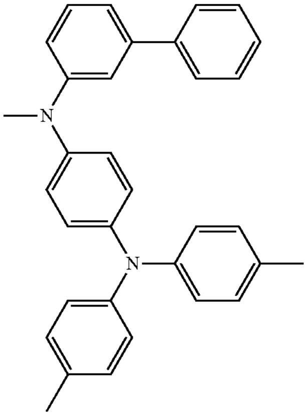
313
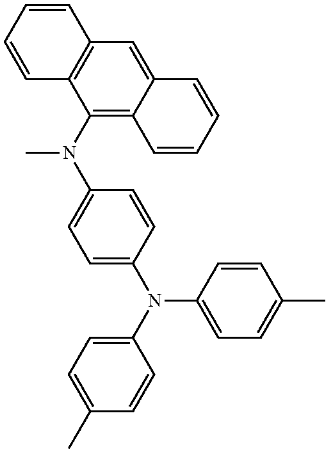
314
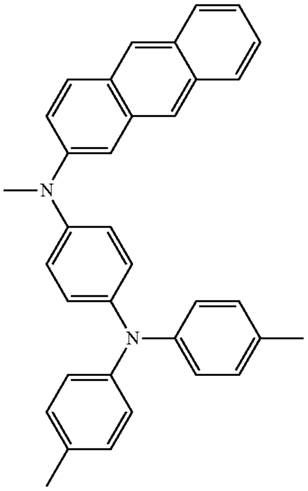

-continued
315
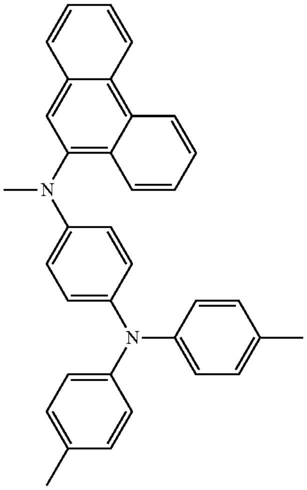
316
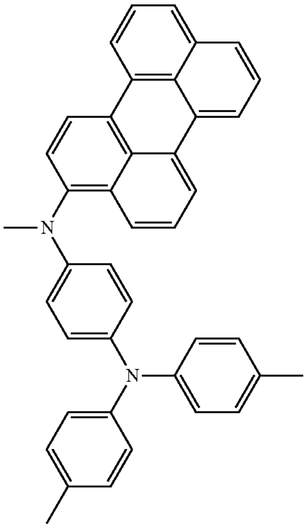
317
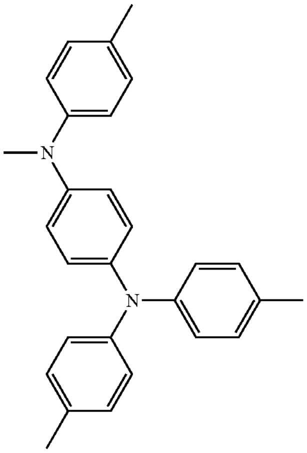
-continued
318
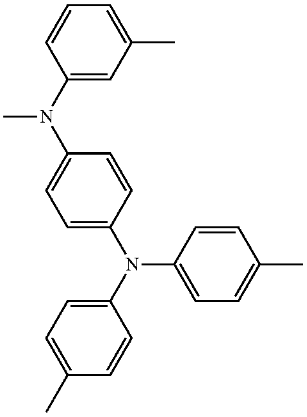
319
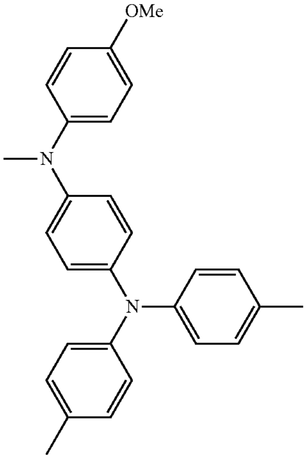
320
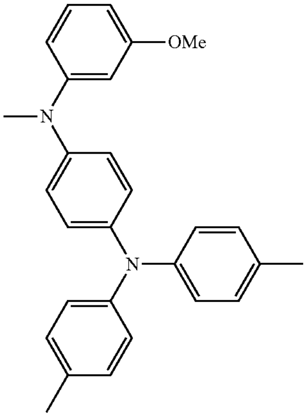

-continued
321
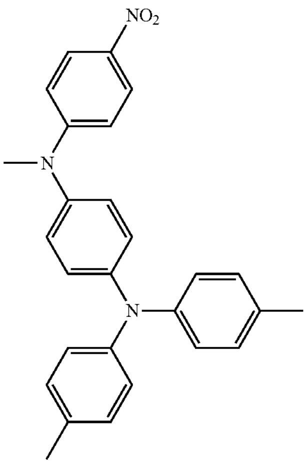
322
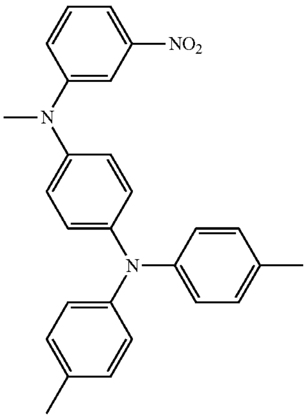
323
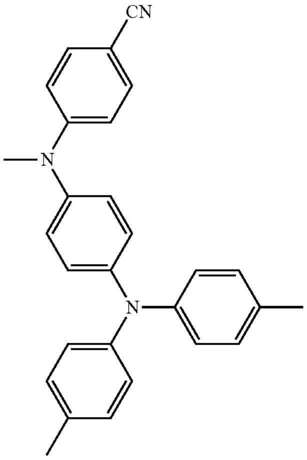
-continued
324
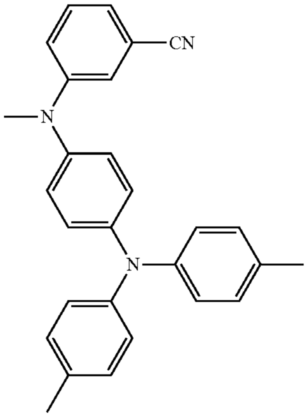
325
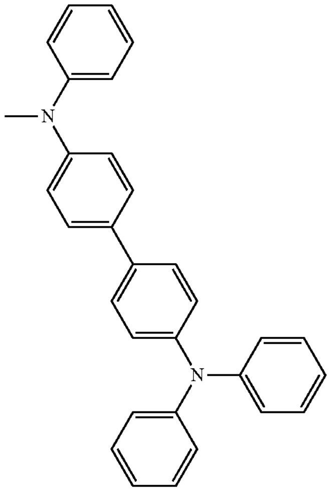
326
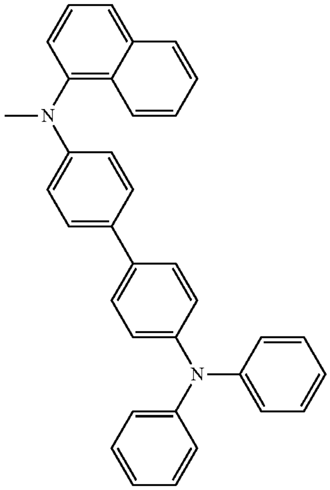

-continued
327
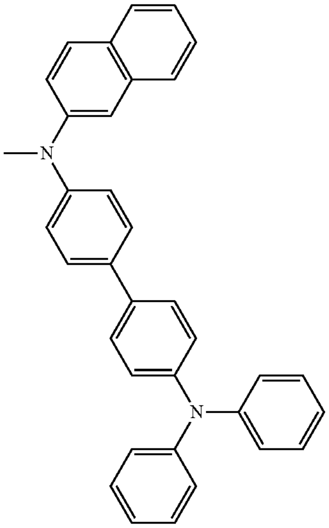
328
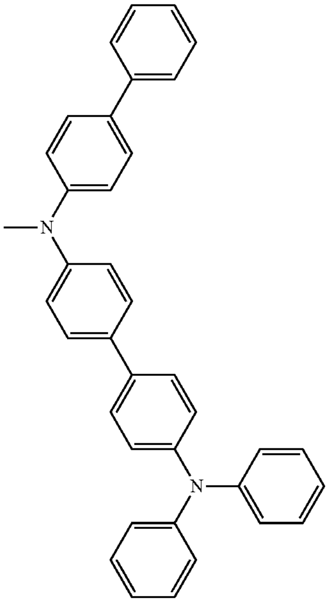
329
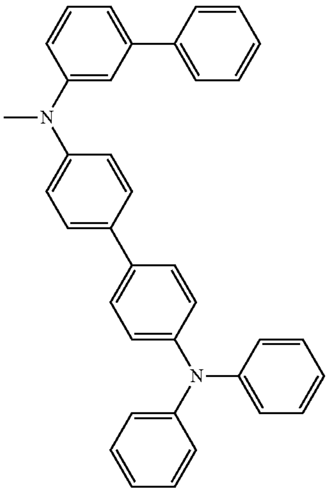
-continued
330
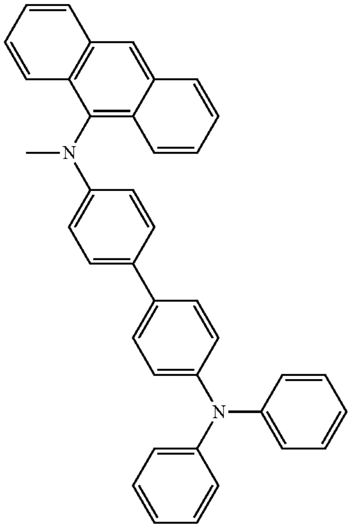
331
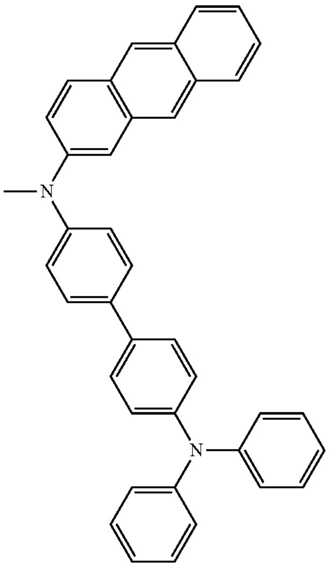
332
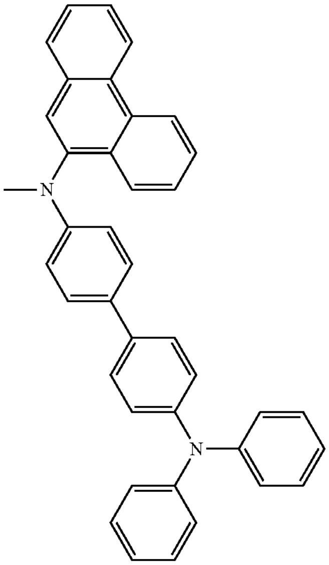

-continued
333
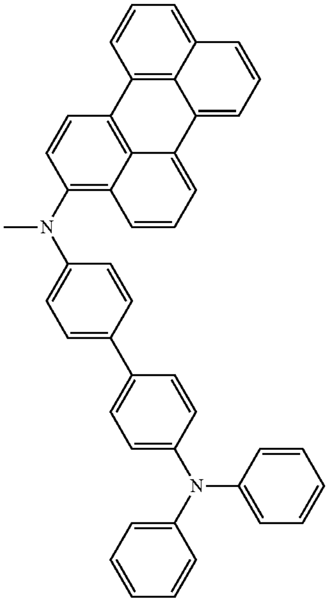
334
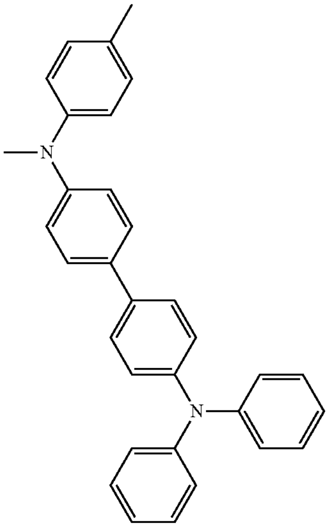
335
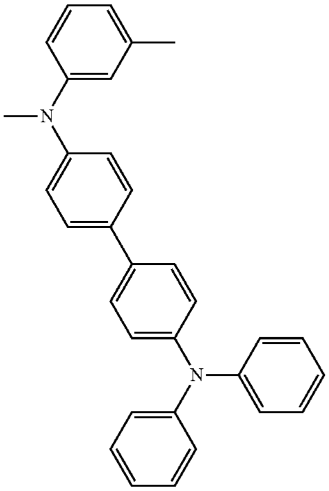
-continued
336
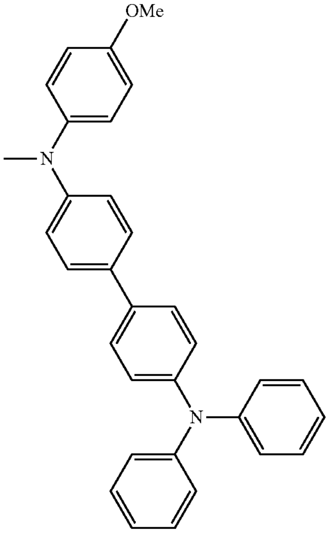
337
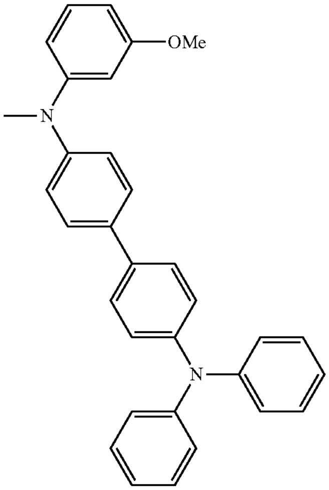
338
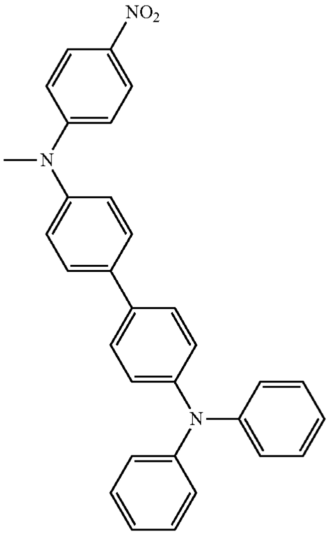

-continued
339
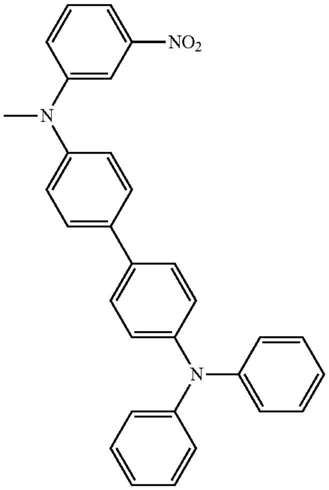
340
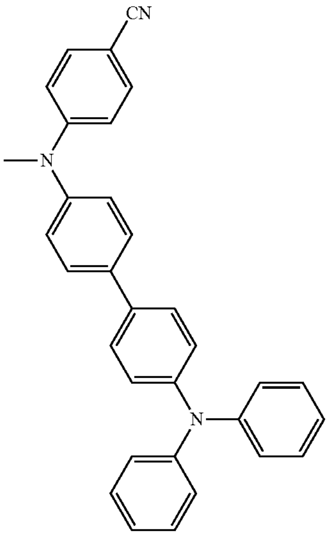
341
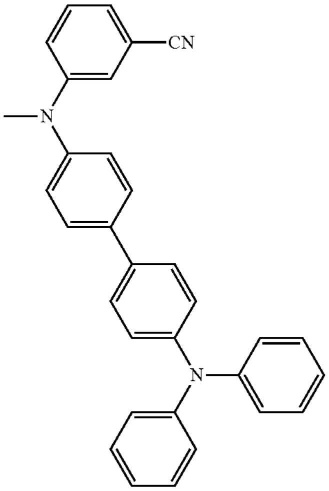
-continued
342
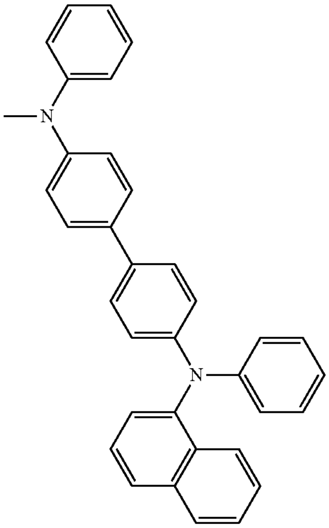
343
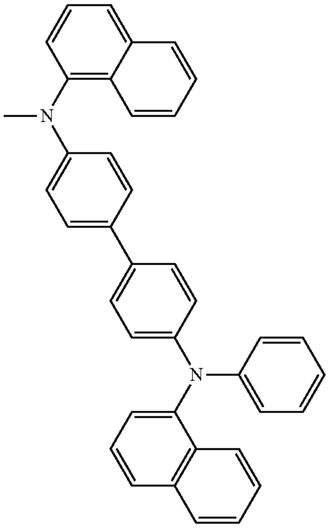
344
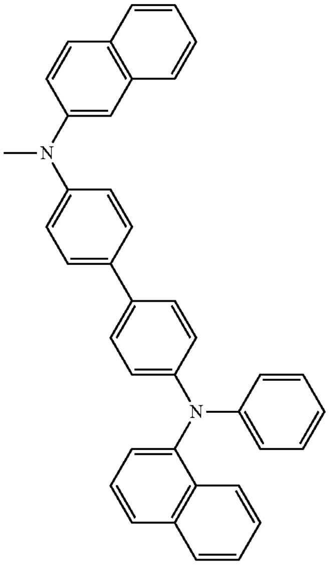

-continued
345
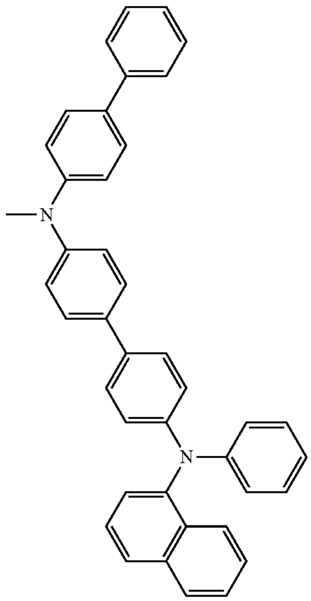
-continued
347
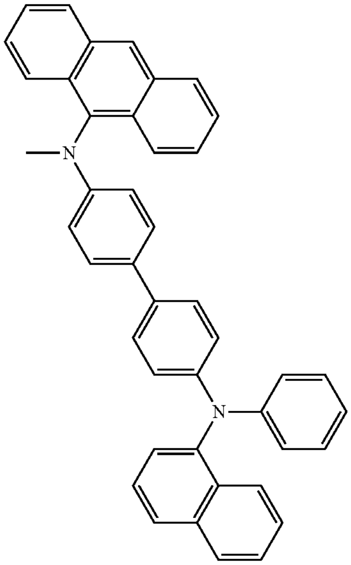
346
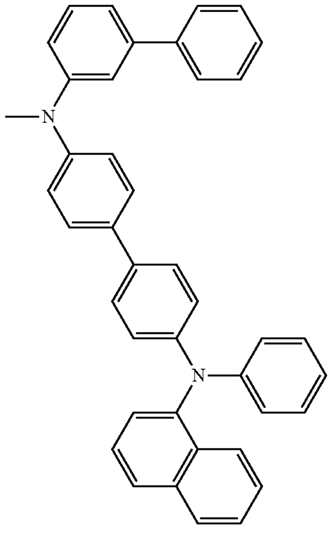
348
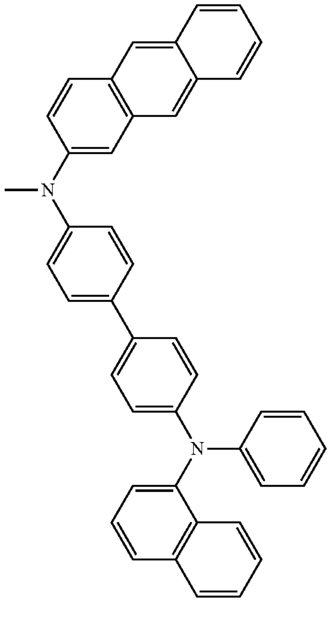

-continued
349
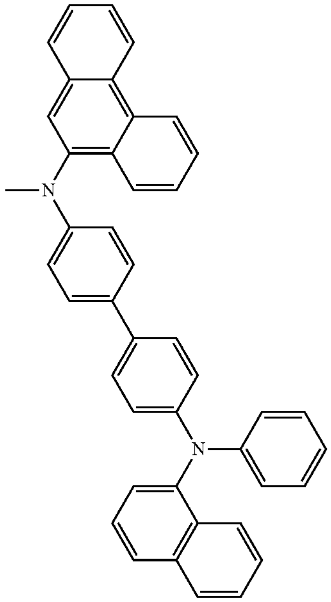
350
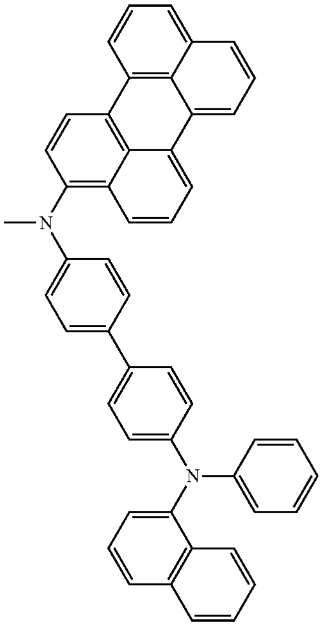
-continued
351
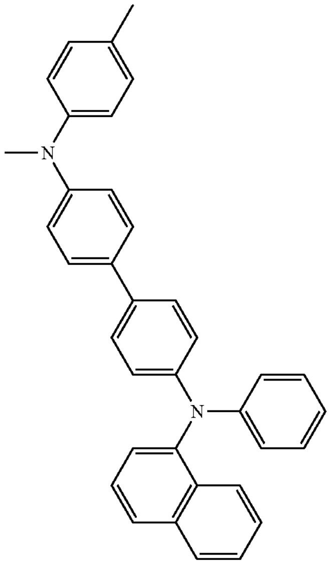
352
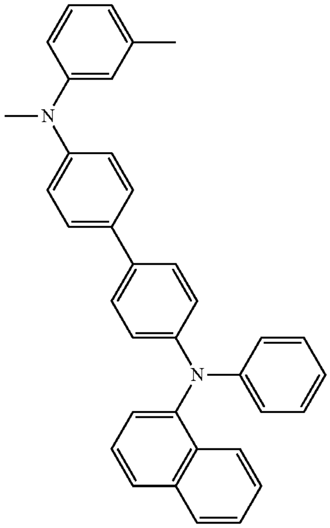
353
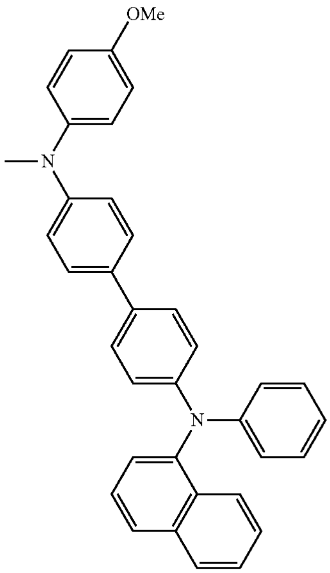

-continued
354
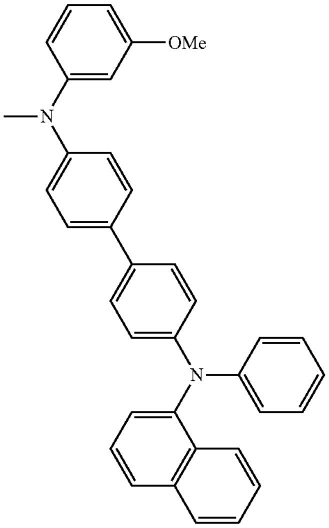
355
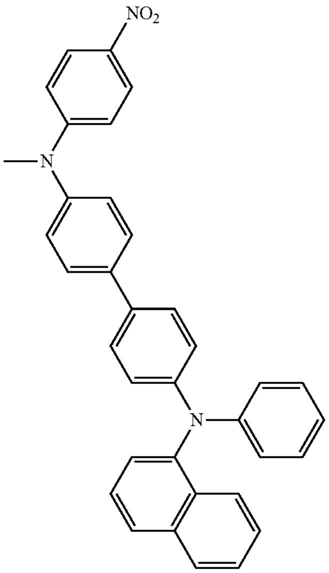
356
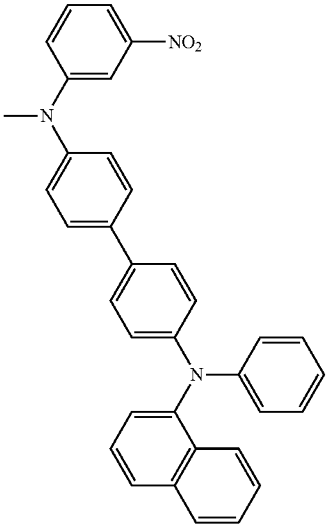
-continued
357
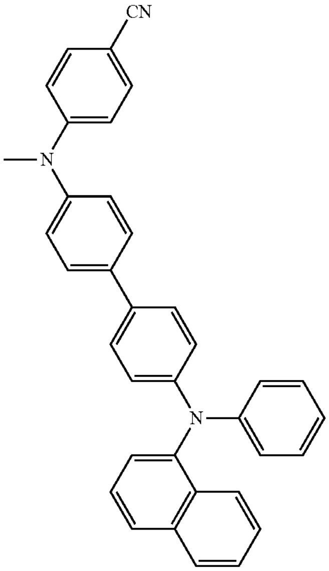
358
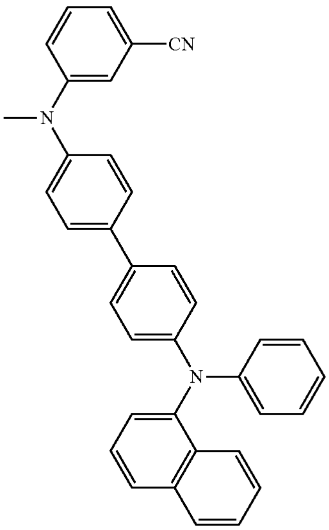
359
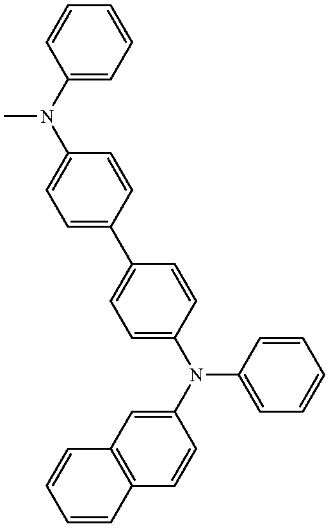

-continued
360
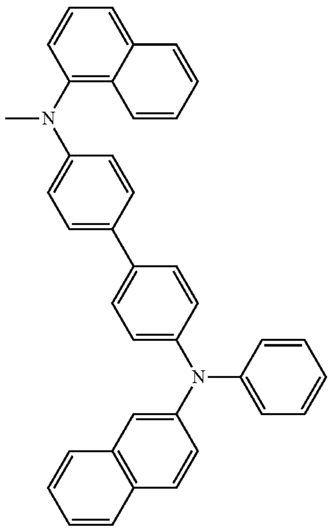
361
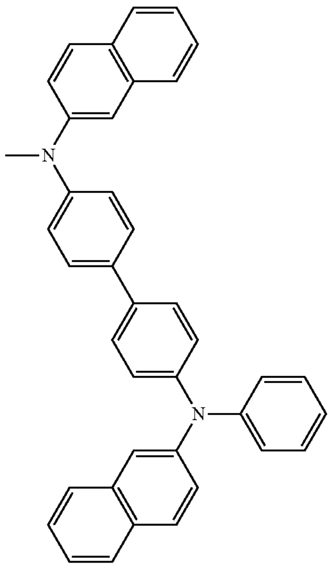
-continued
362
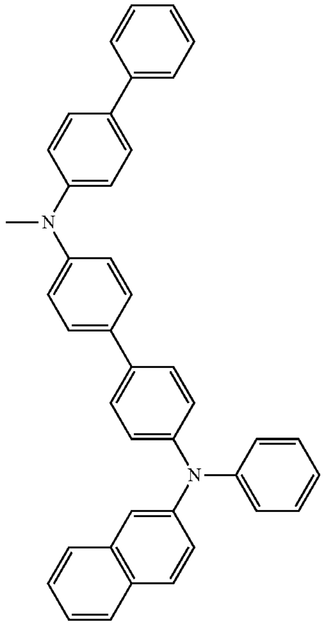
363
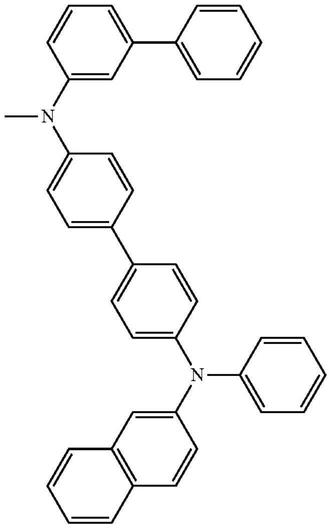

-continued
364
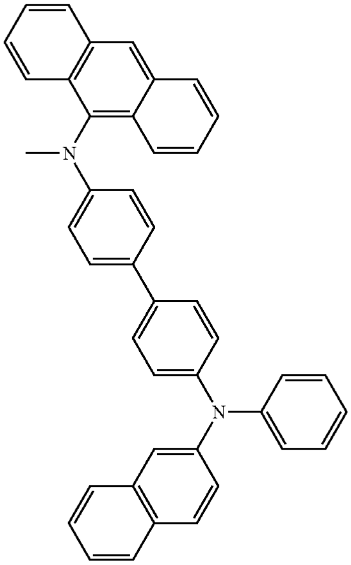
366
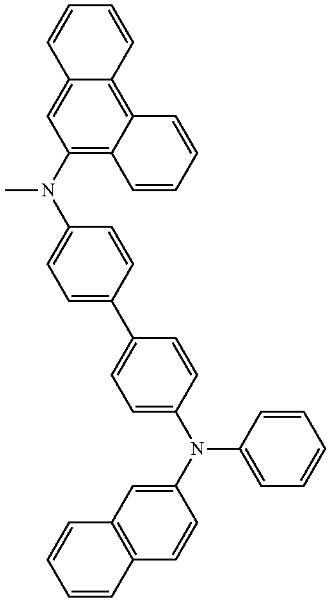
365
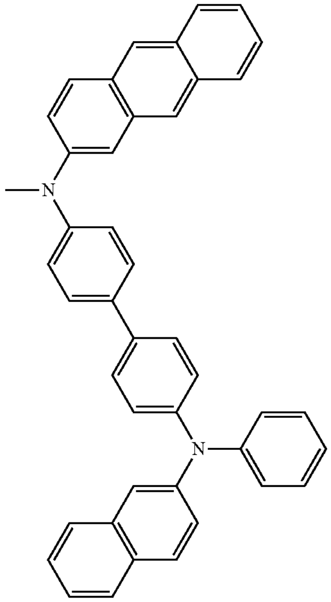
367
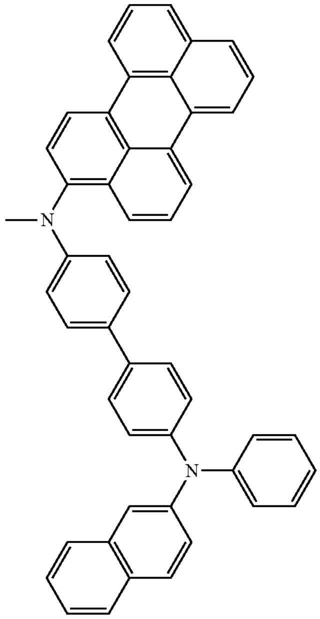

-continued
368
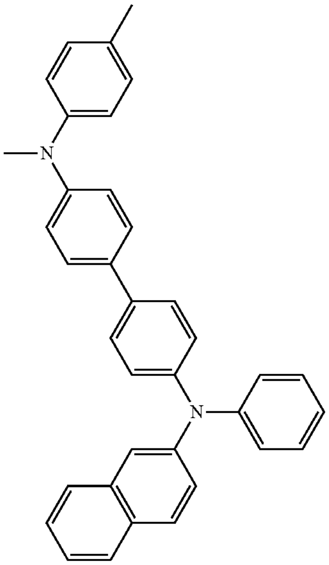
369
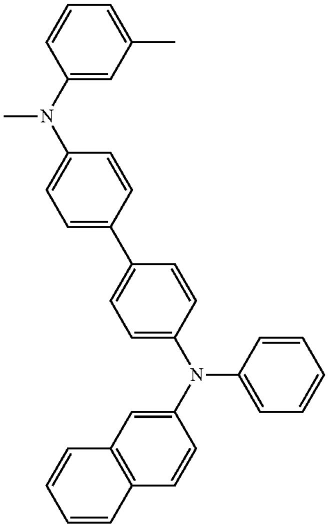
370
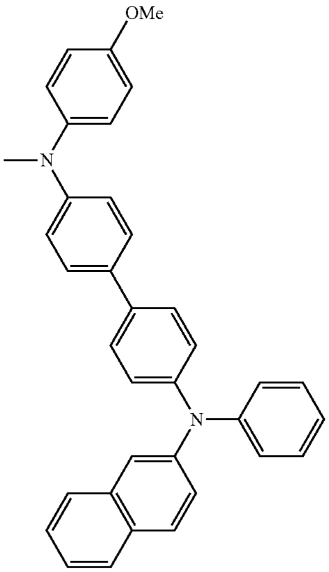
-continued
371
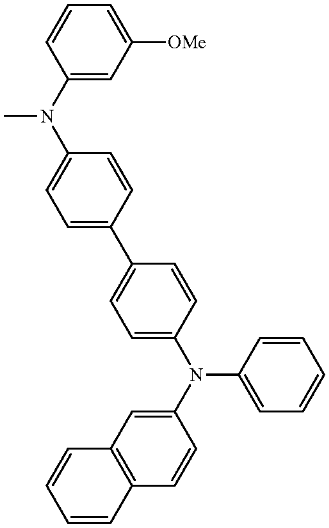
372
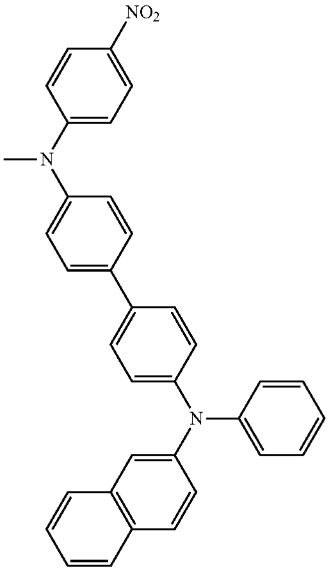
373
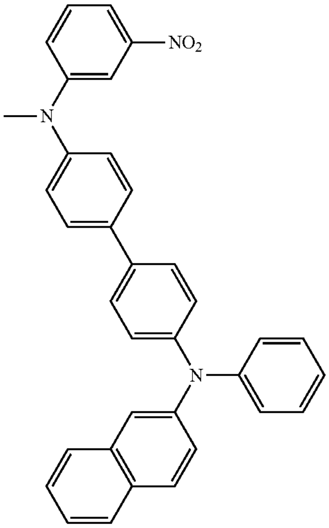

-continued
374
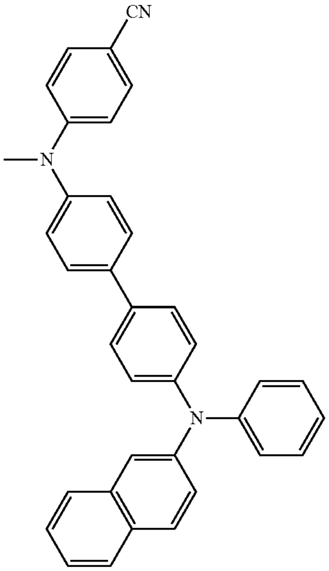
375
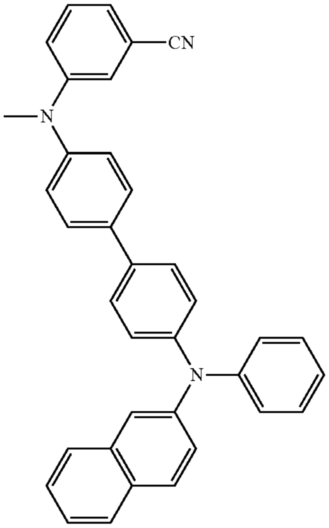
-continued
376
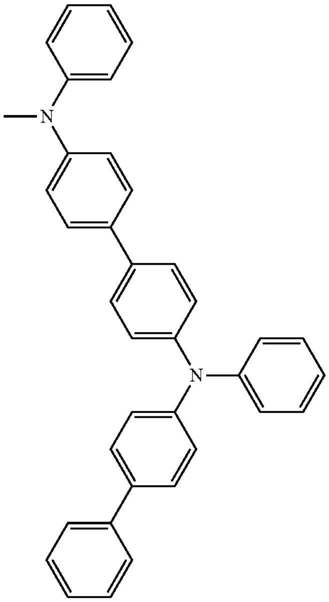
377
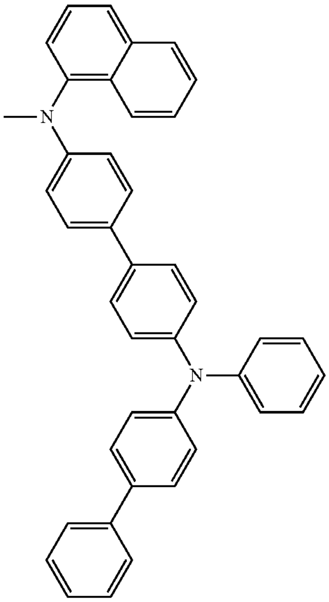

-continued
378
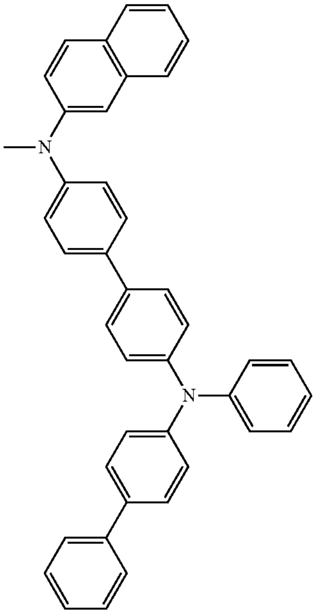
380
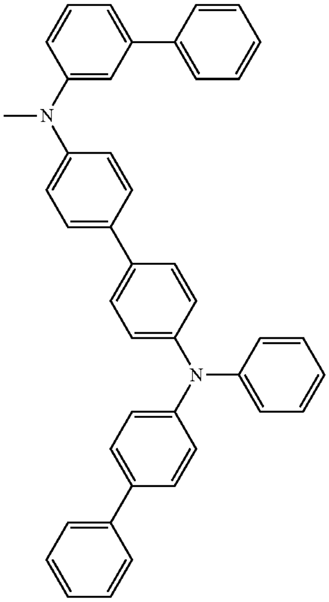
379
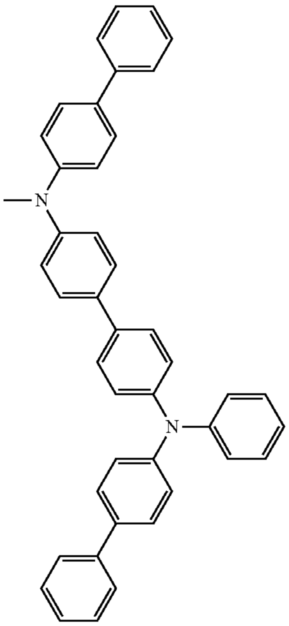
381
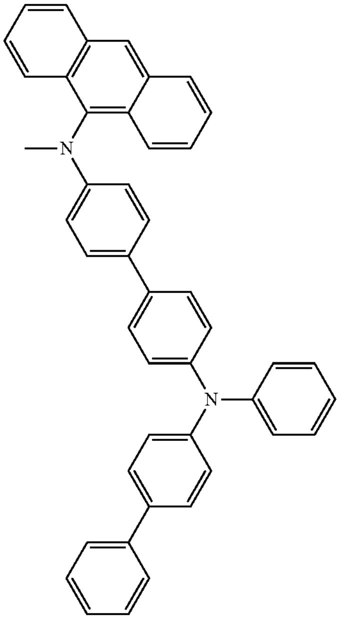

-continued
382
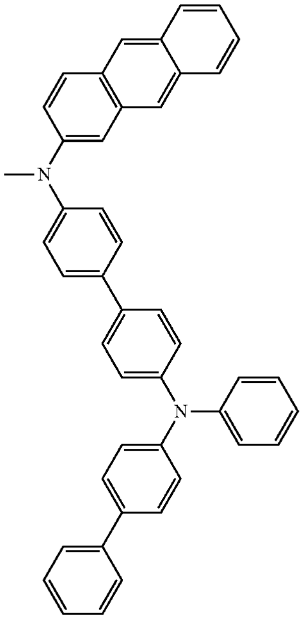
383
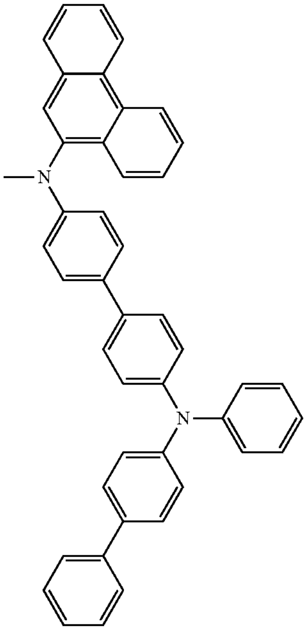
-continued
384
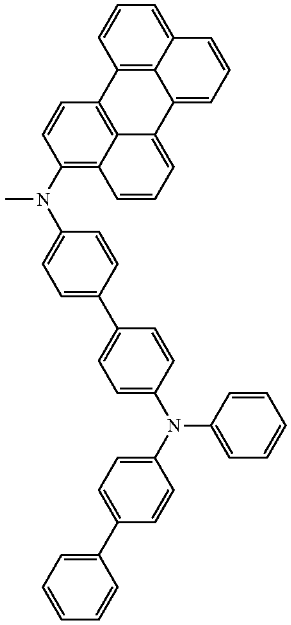
385
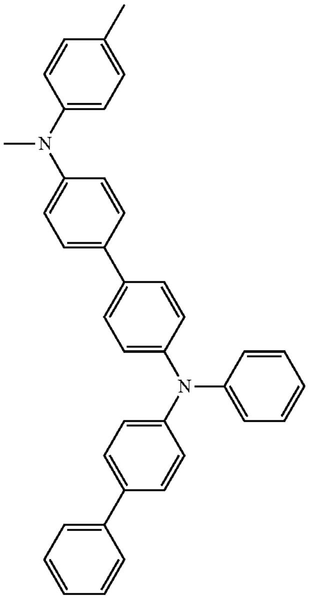

-continued
386
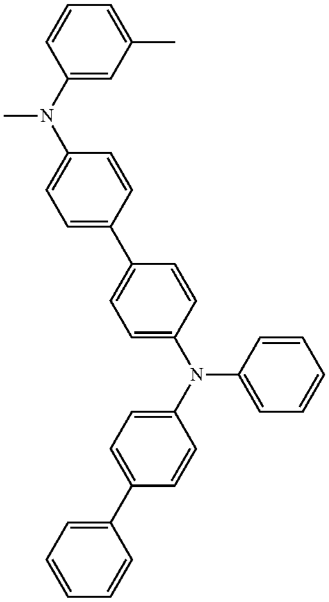
387
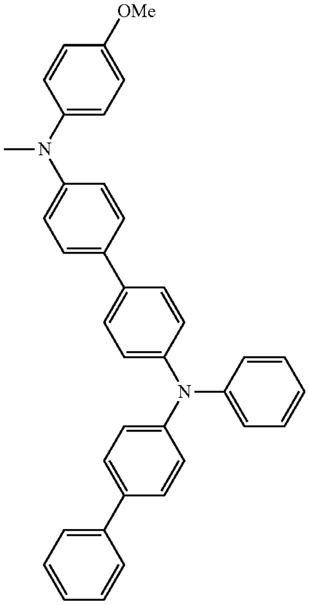
-continued
388
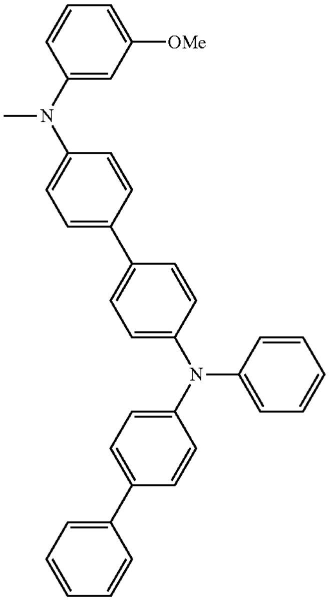
389
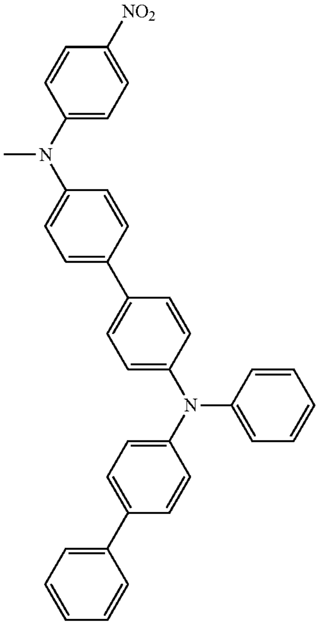

-continued
390
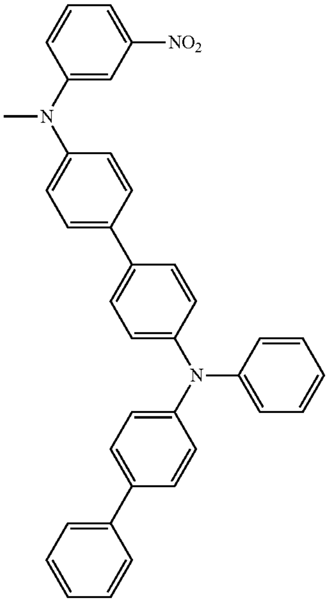
391
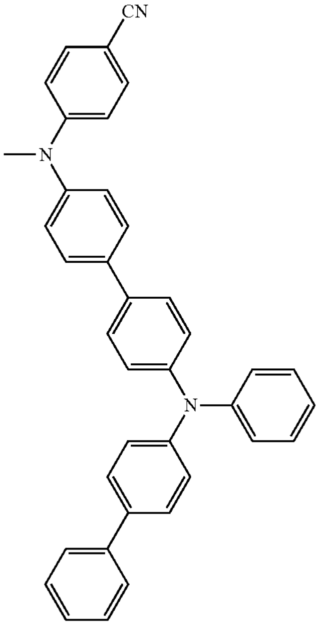
-continued
392
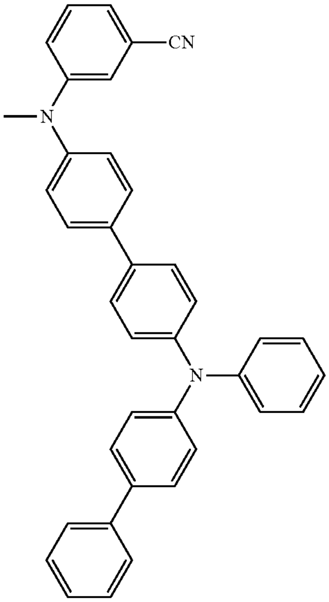
393
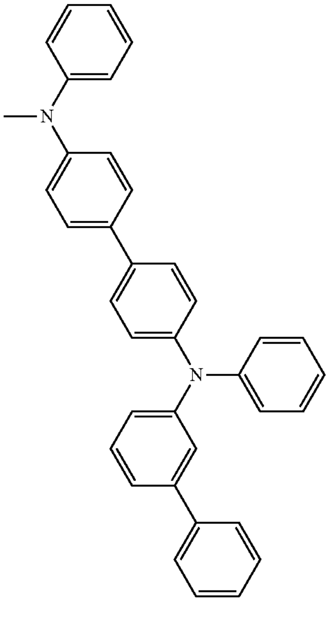

394
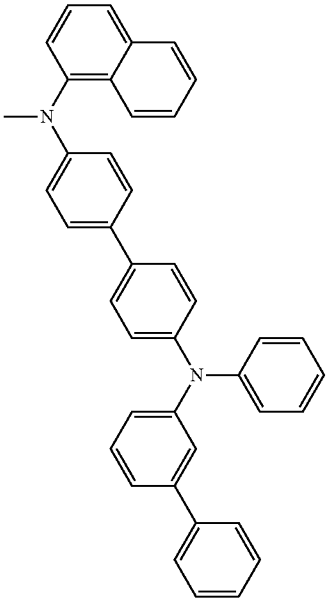
395
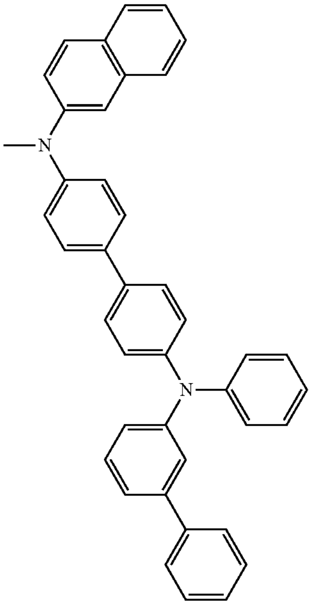
396
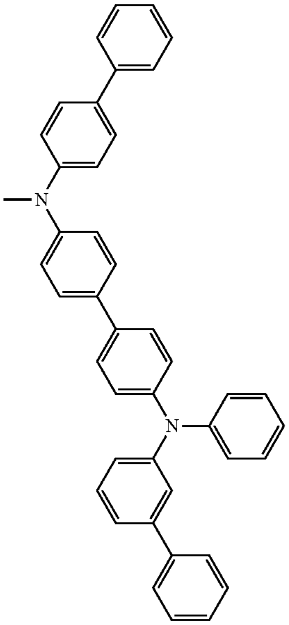
397
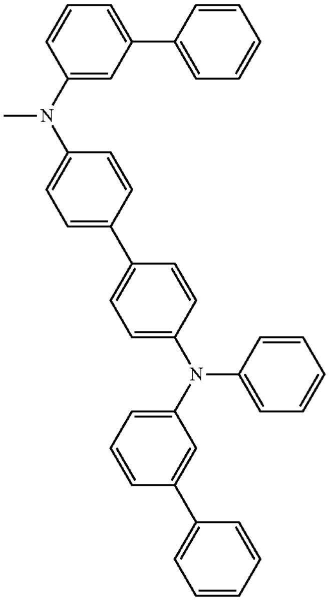

-continued
398
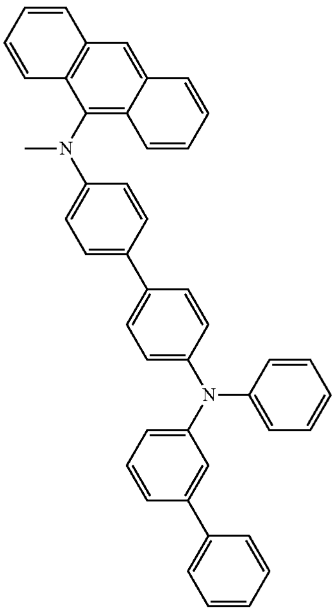
400
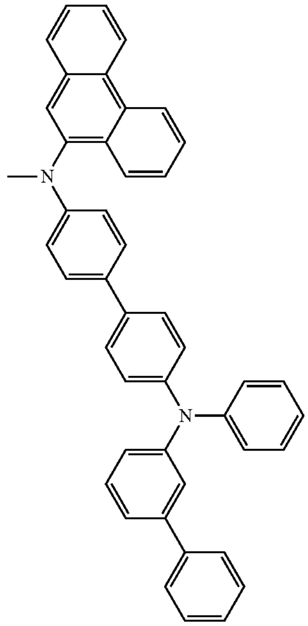
399
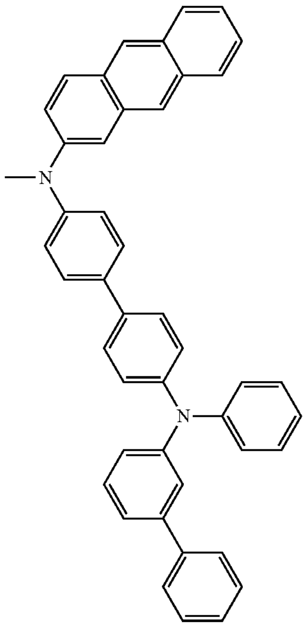
401
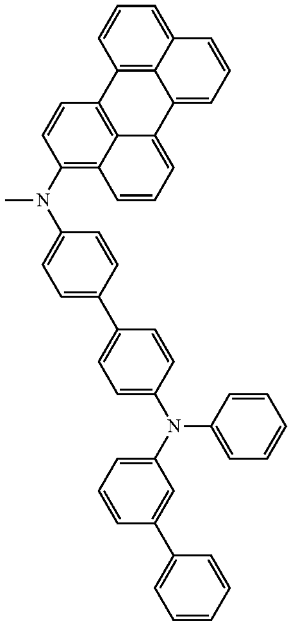

-continued
402
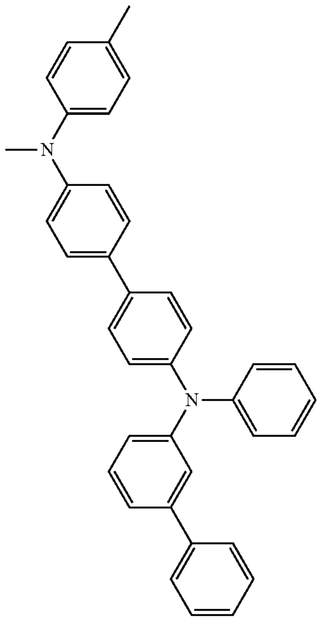
403
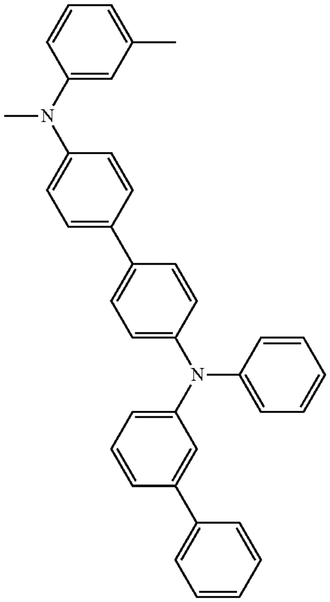
-continued
404
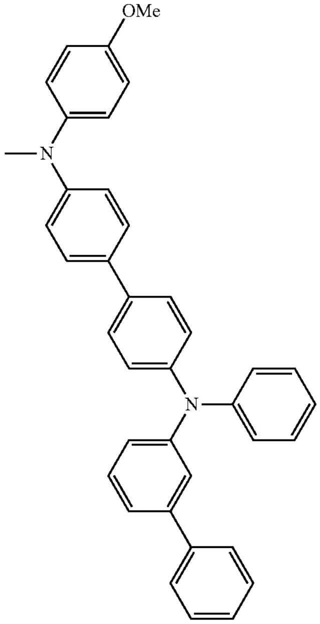
405
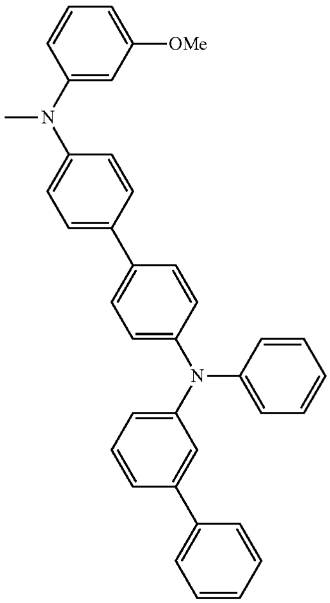

-continued
406
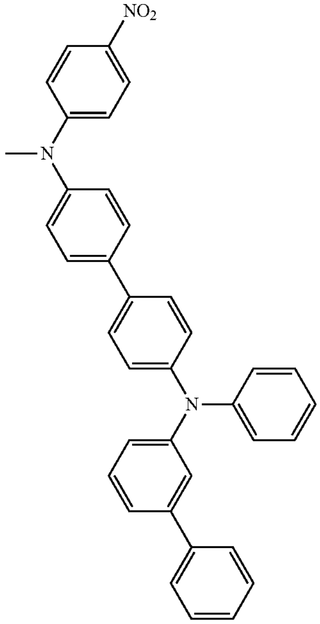
407
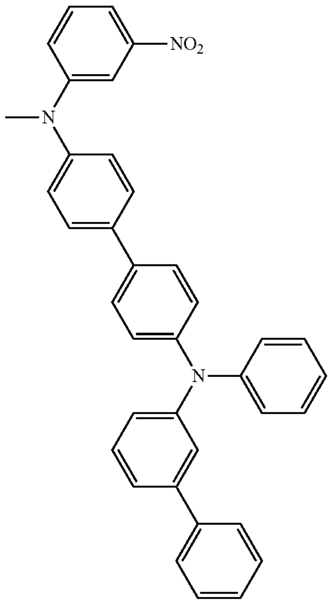
-continued
408
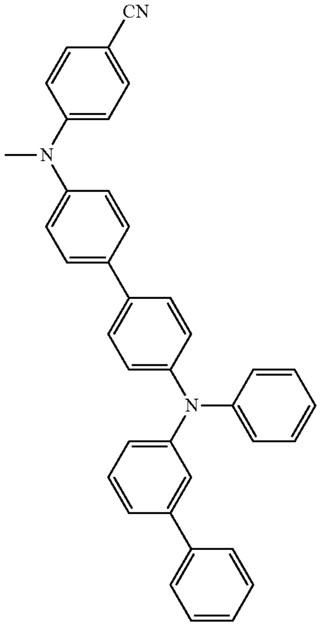
409
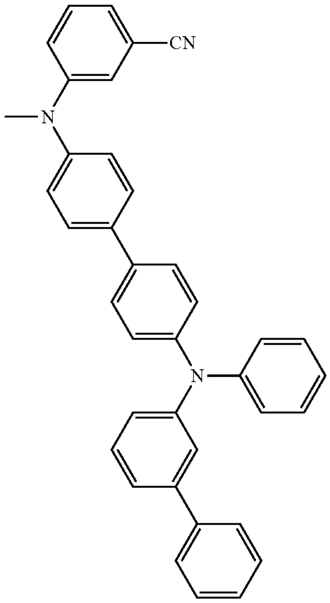

-continued
410
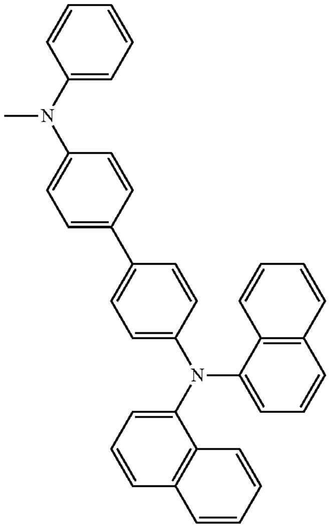
411
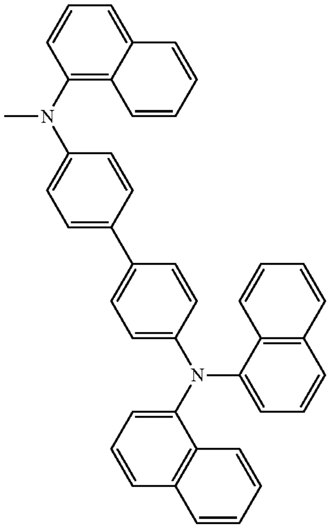
412
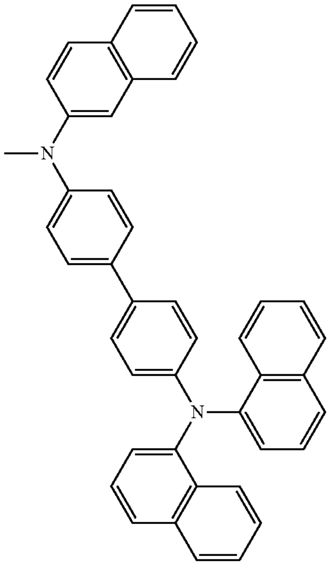
-continued
413
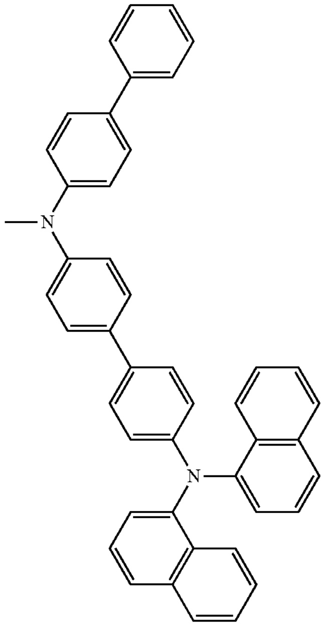
414
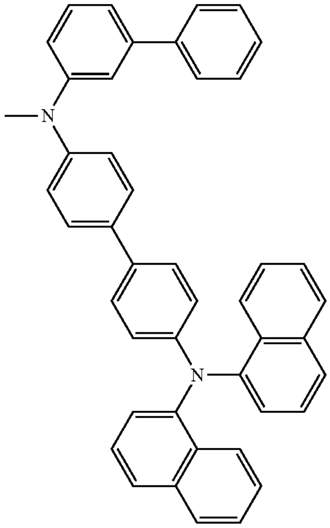

-continued
415
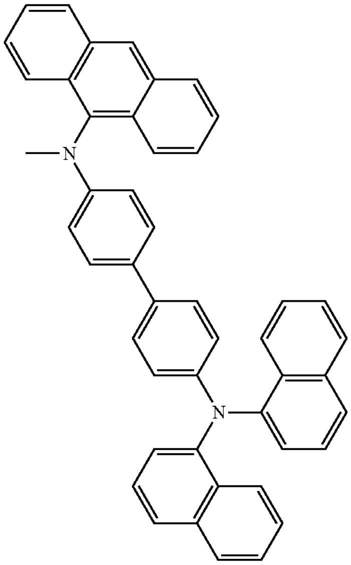
417
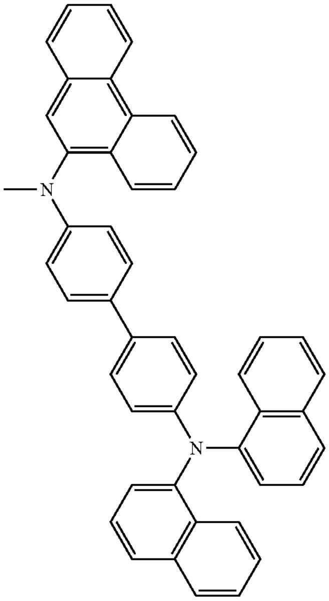
416
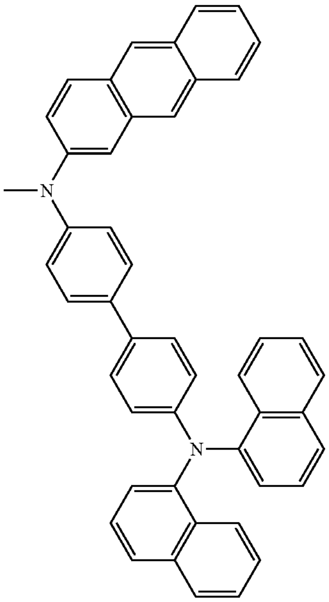
418
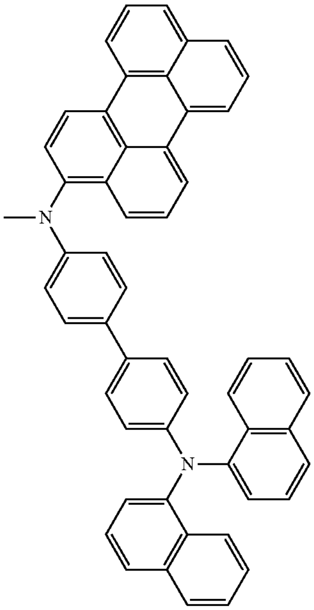

-continued
419
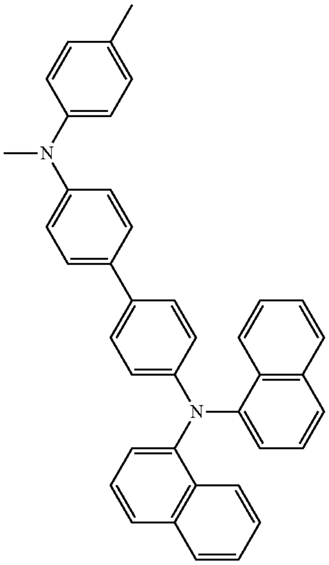
420
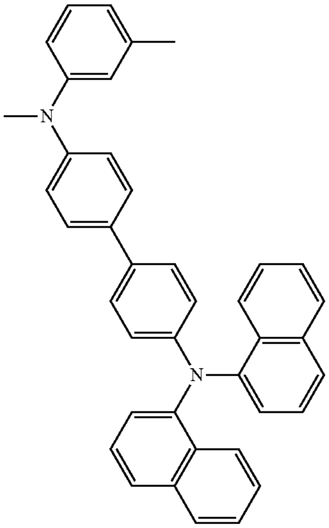
421
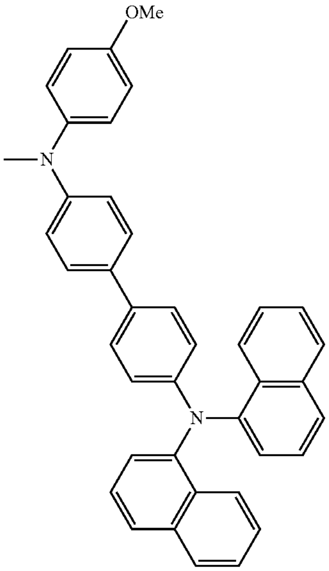
-continued
422
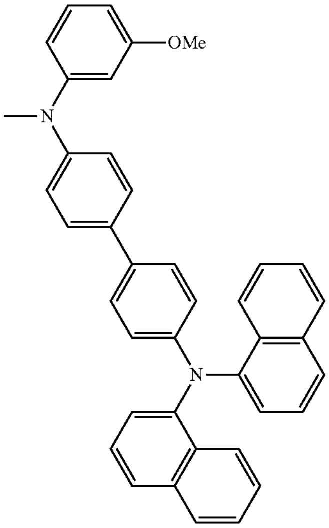
423
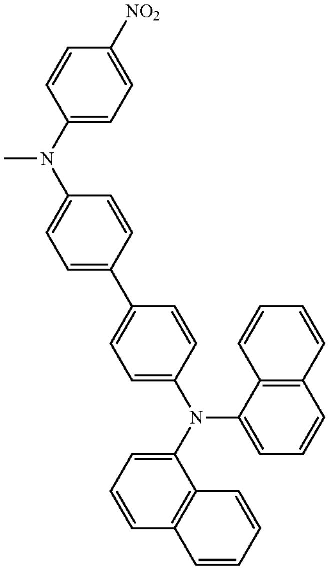
424
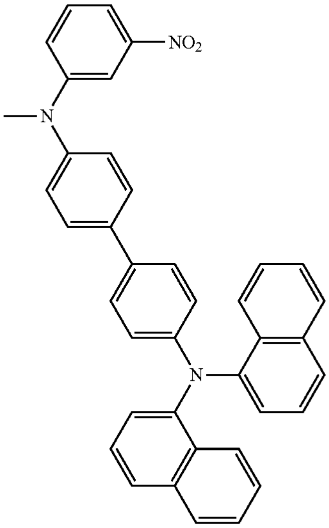

-continued
425
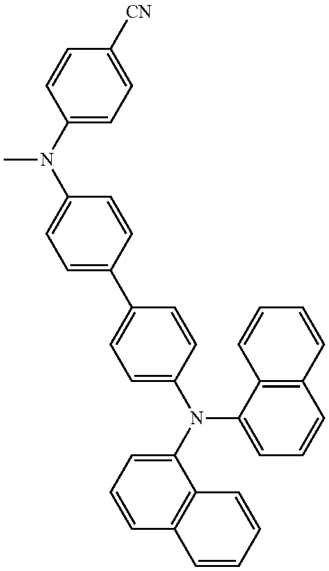
426
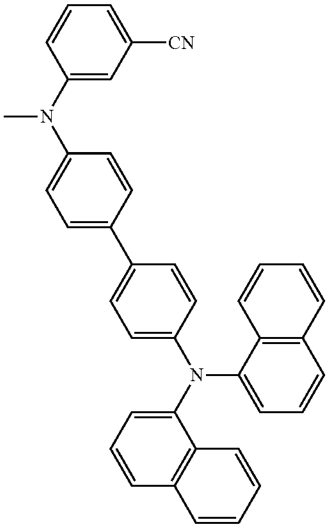
427
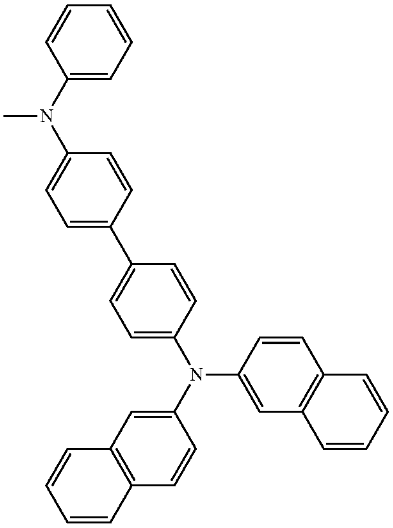
-continued
428
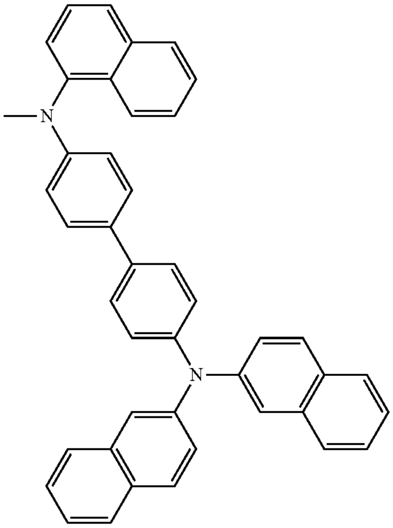
429
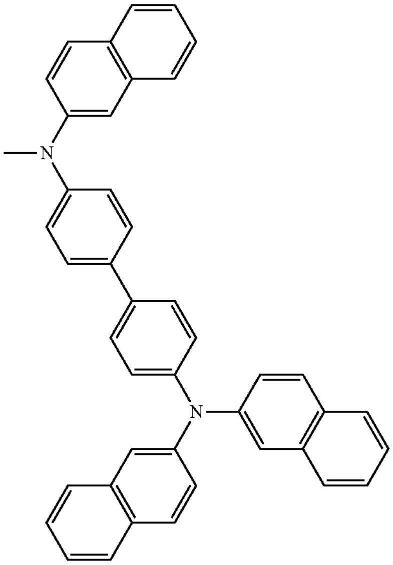

-continued
430
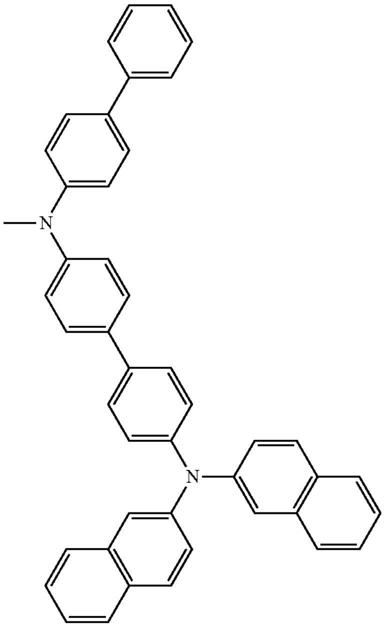
431
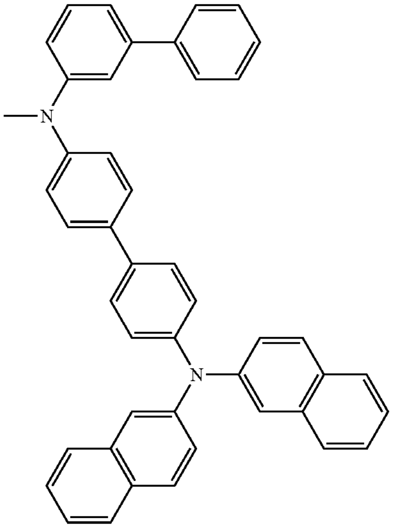
-continued
432
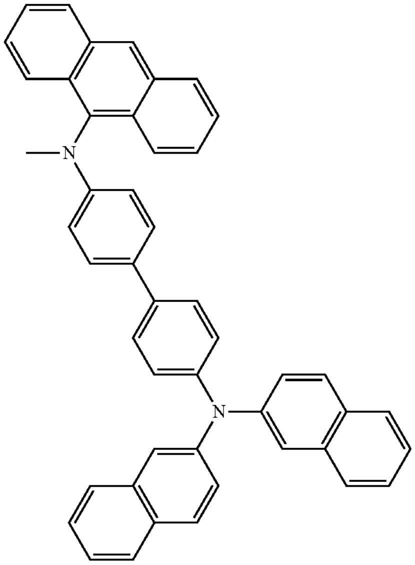
433
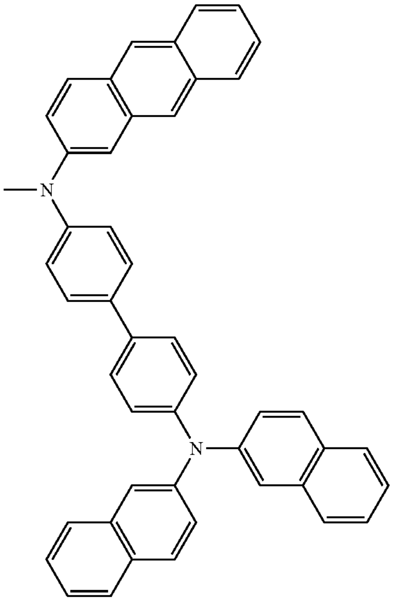

-continued
434
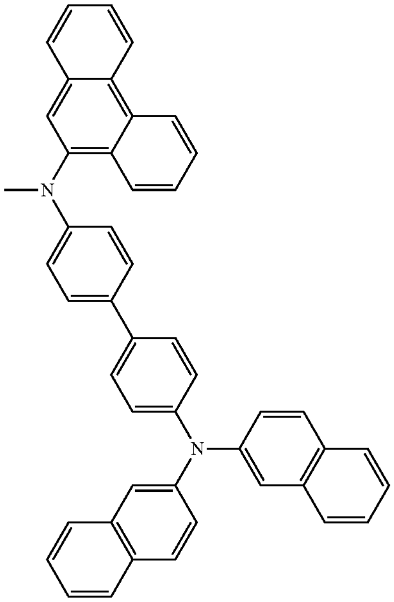
435
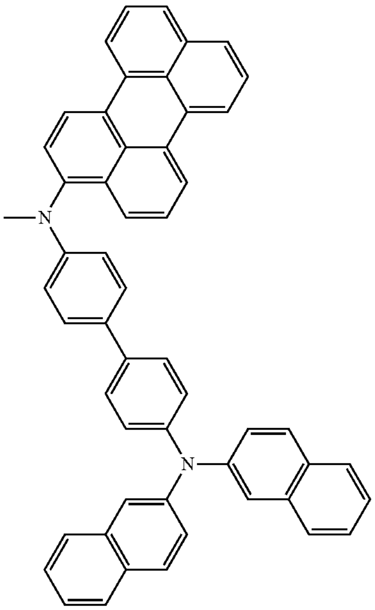
-continued
436
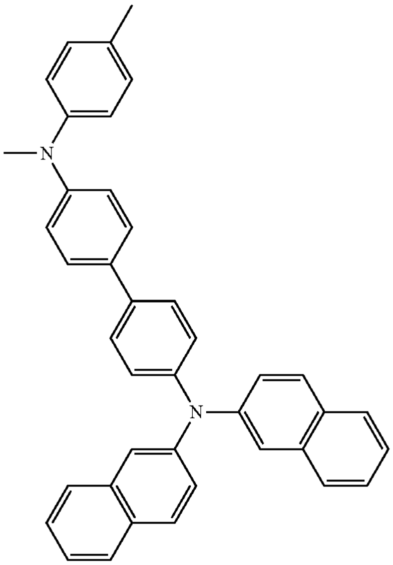
437
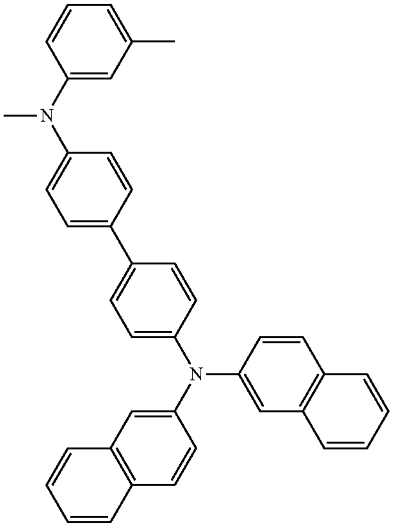
438
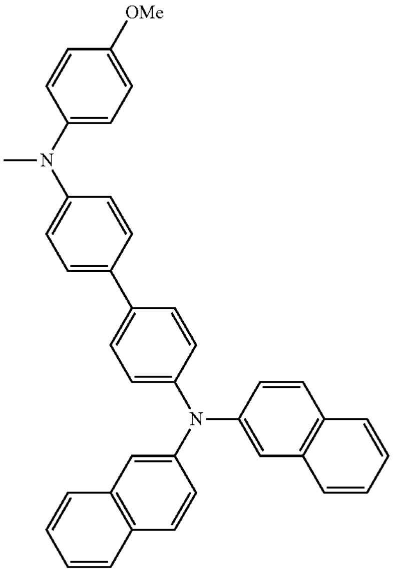

439
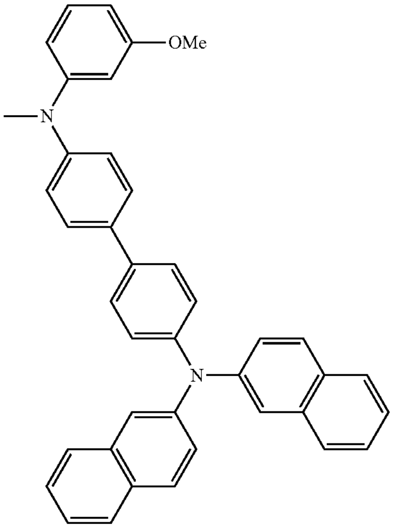
440
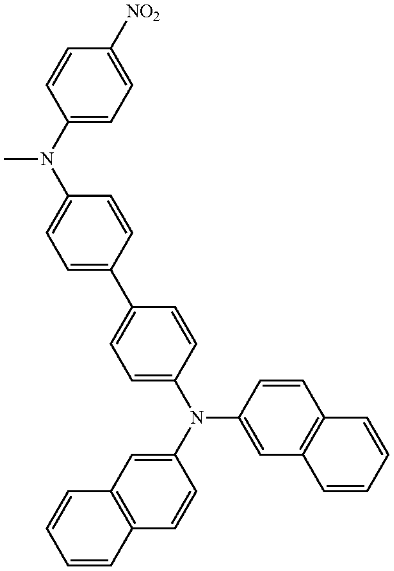
441
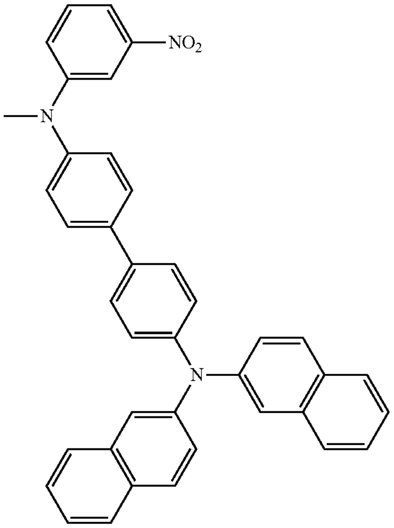
442
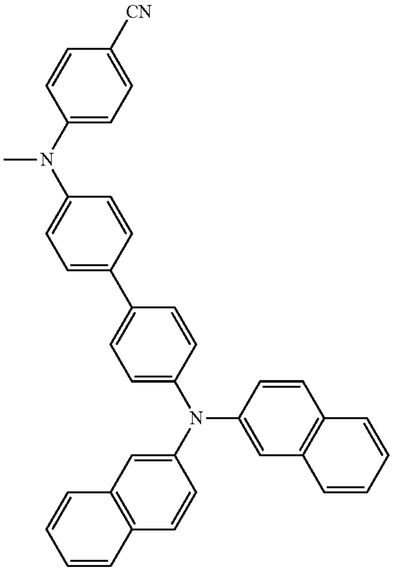
443
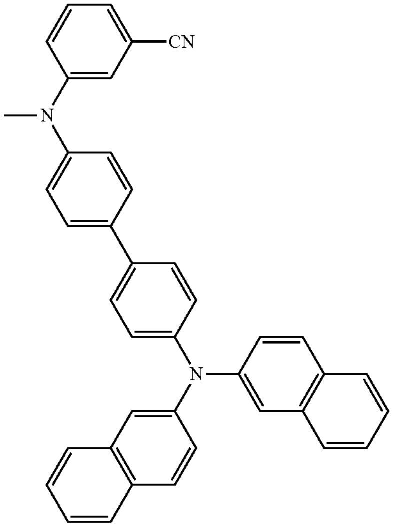

-continued
444
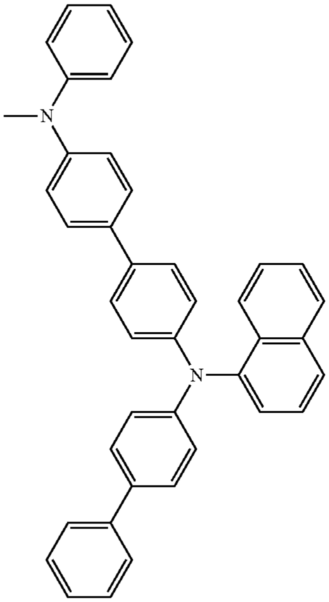
446
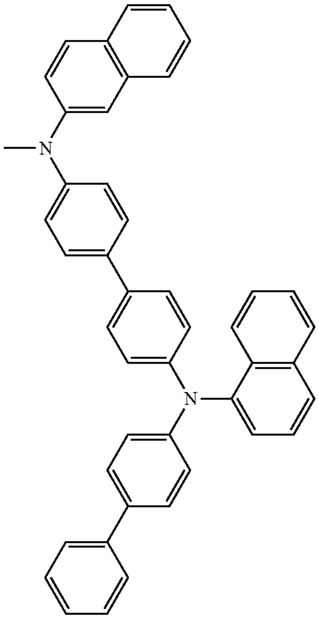
445
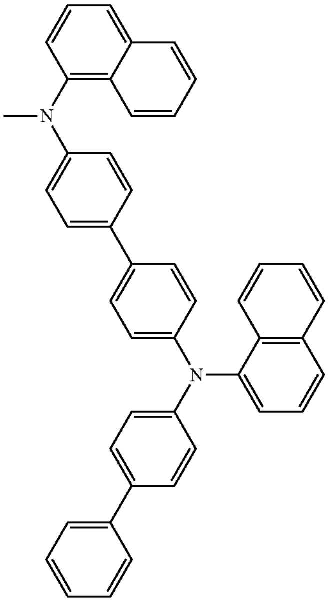
447
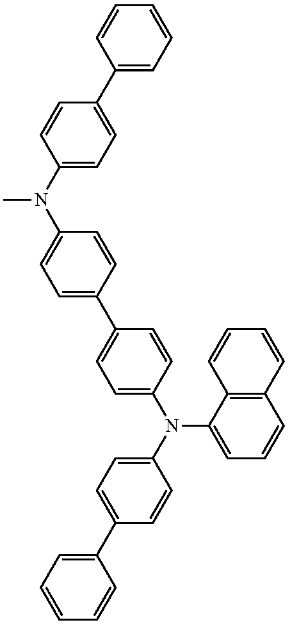

-continued
448
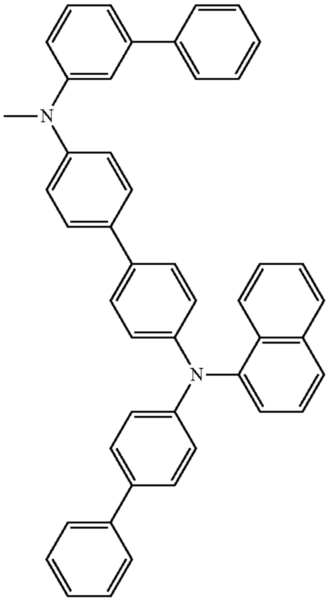
-continued
450
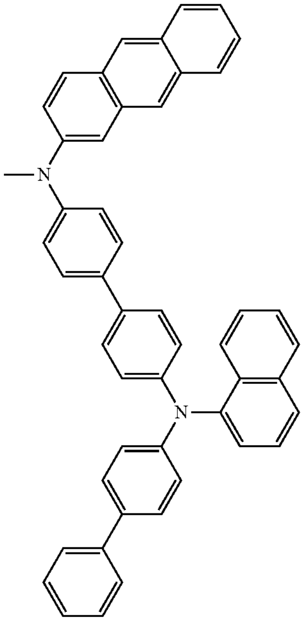
449
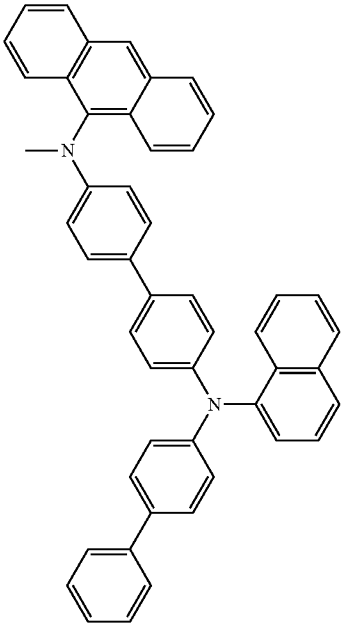
451
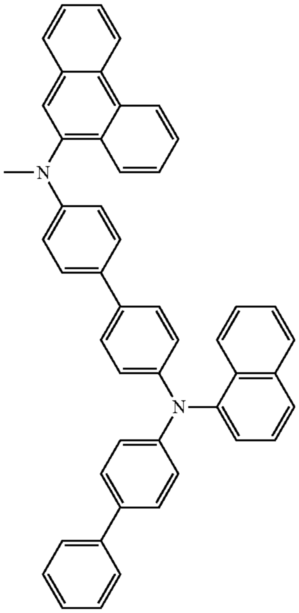

-continued
452
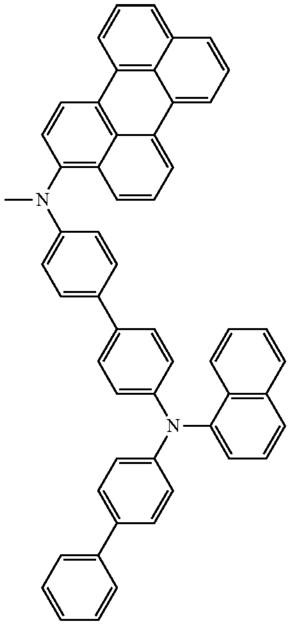
453
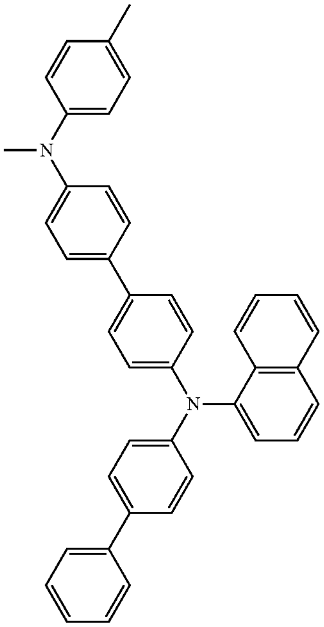
-continued
454
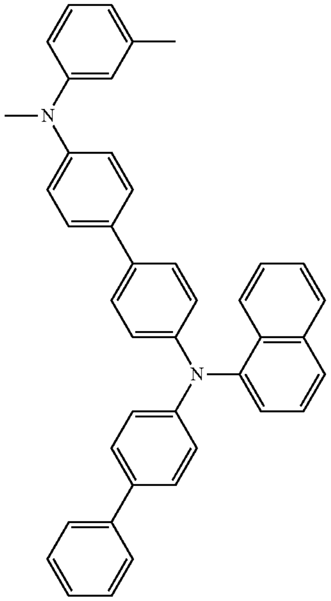
455
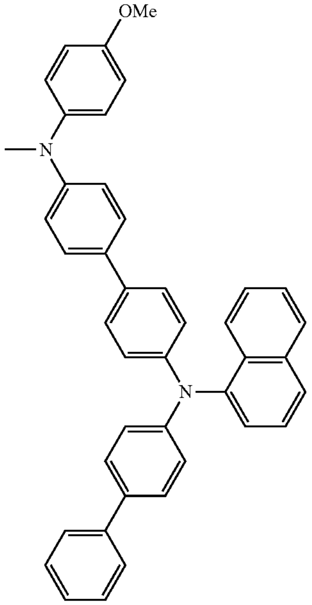

456
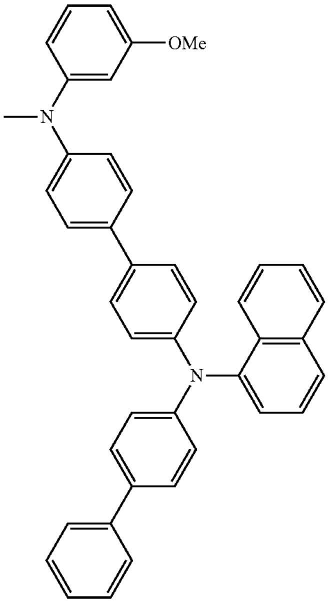
458
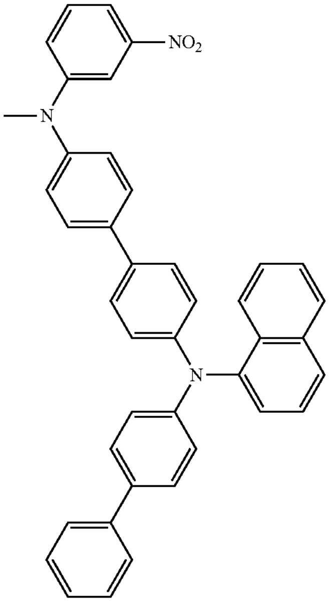
457
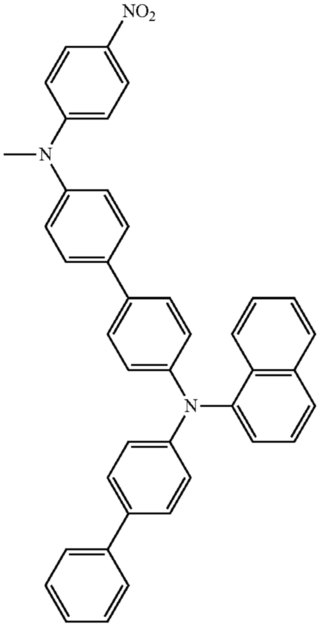
459
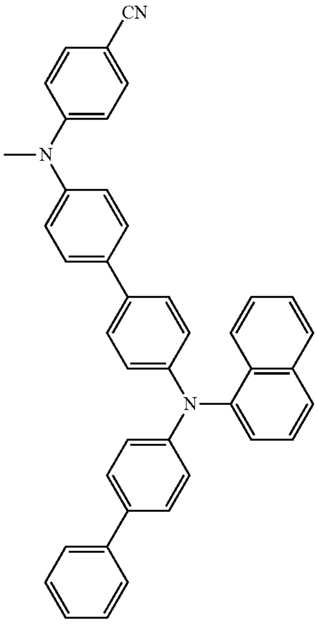

-continued
460
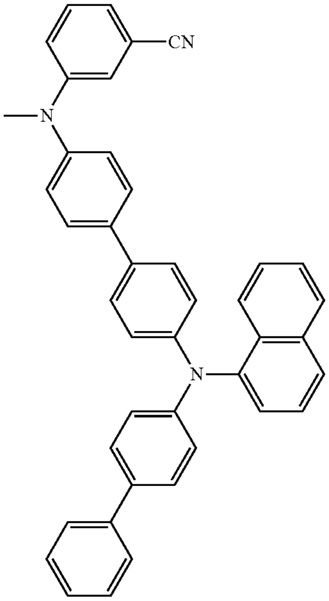
462
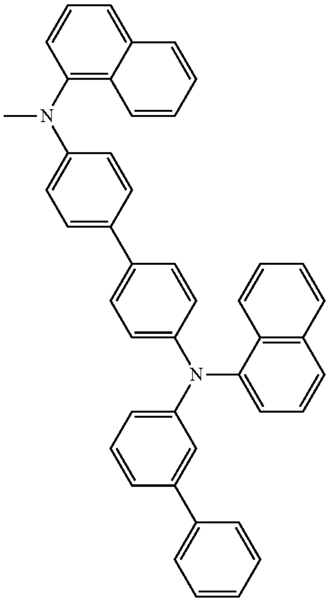
461
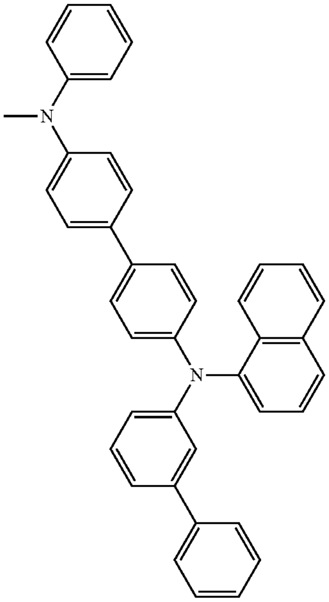
463
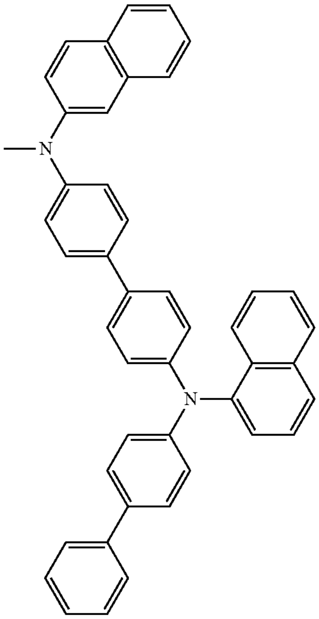

464
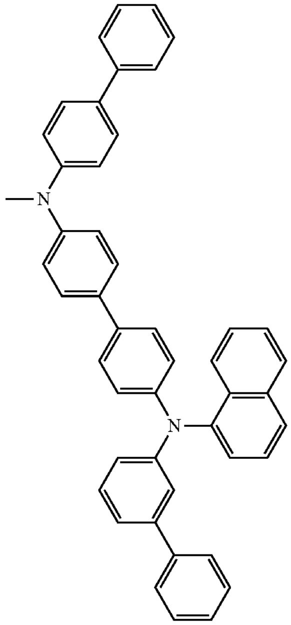
466
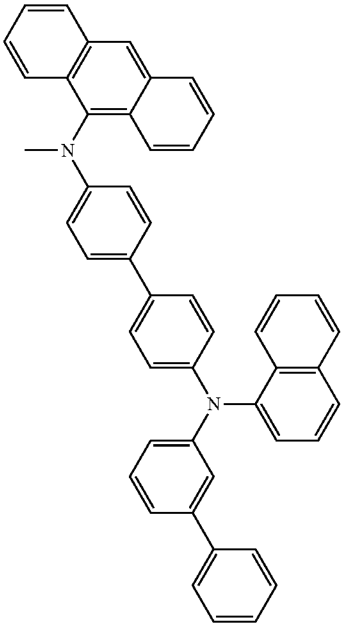
465
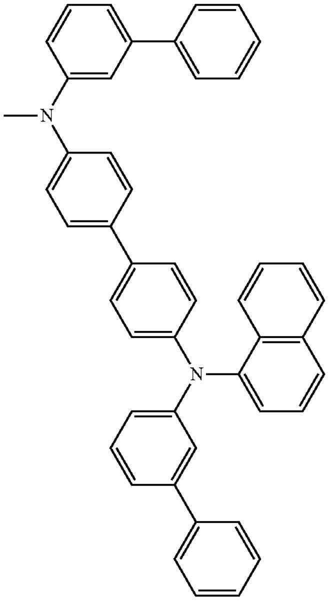
467
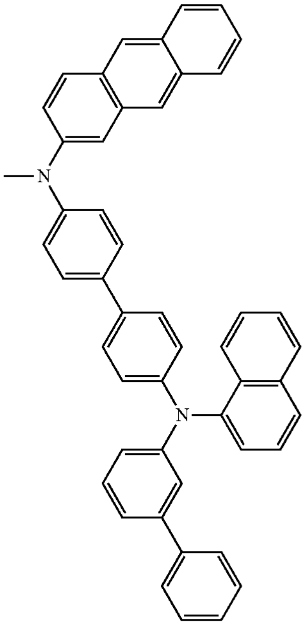

-continued
468
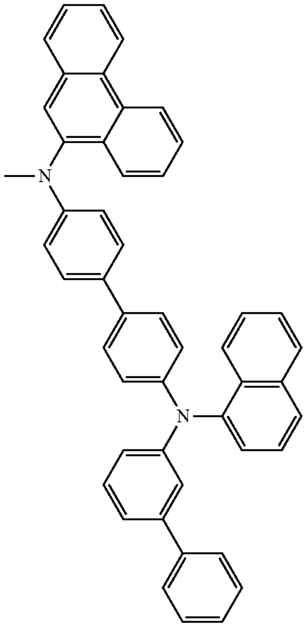
469
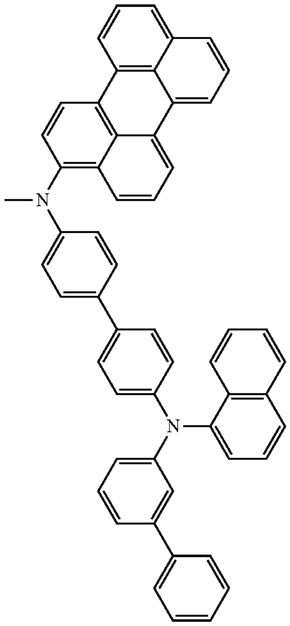
-continued
470
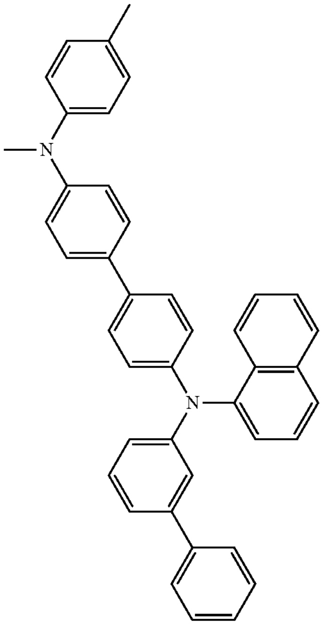
471
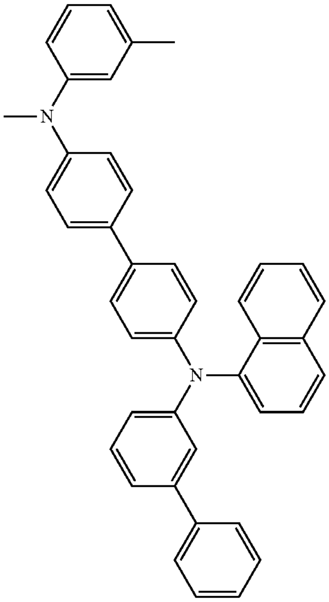

-continued
472
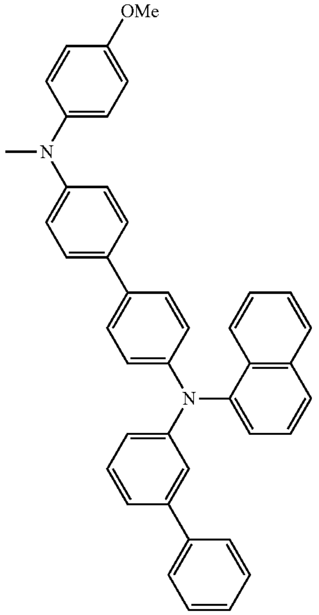
473
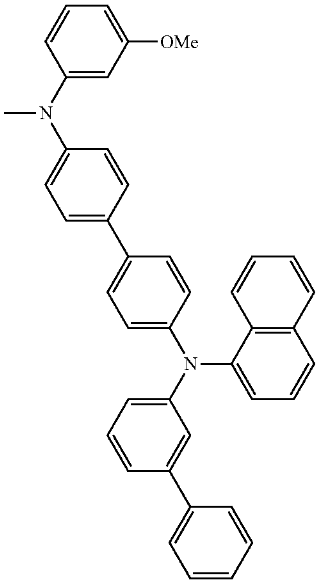
-continued
474
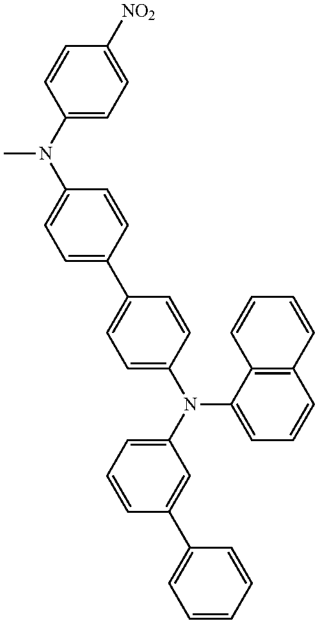
475
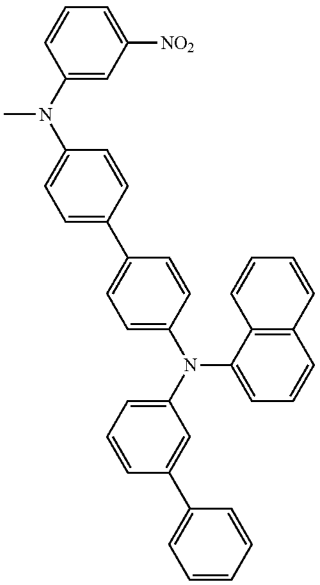

-continued
476
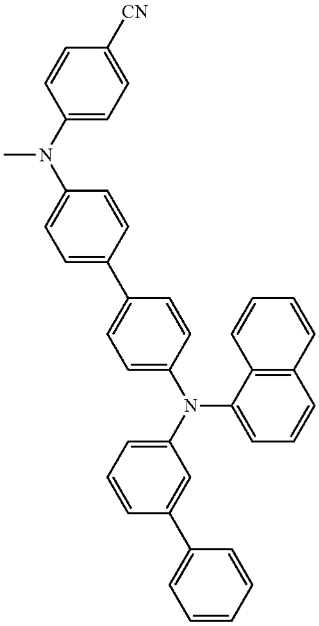
477
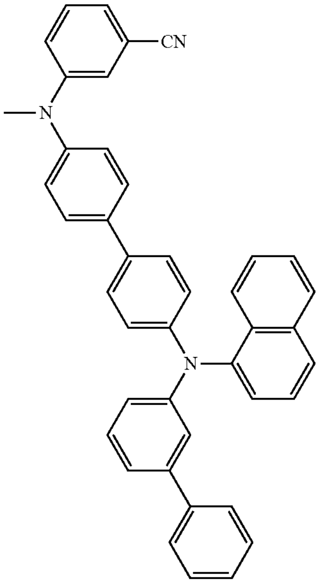
-continued
478
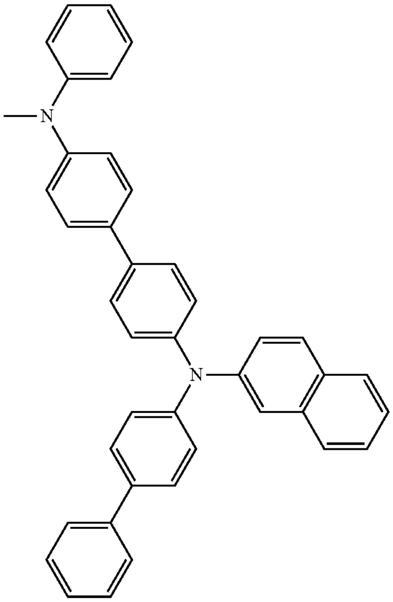
479
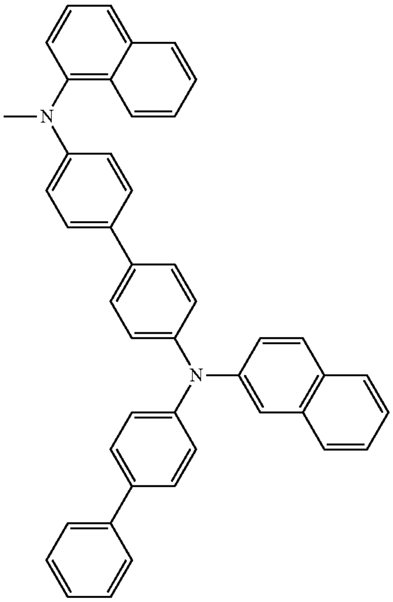

-continued
480
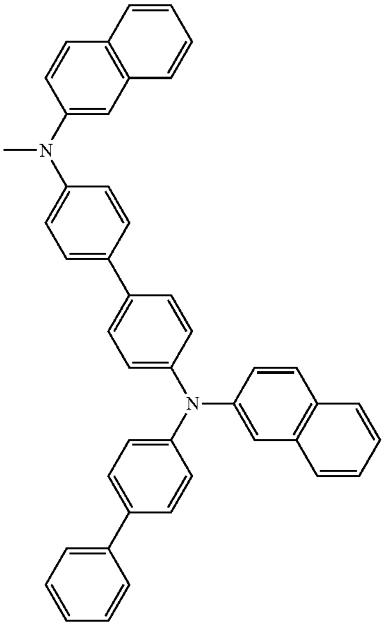
482
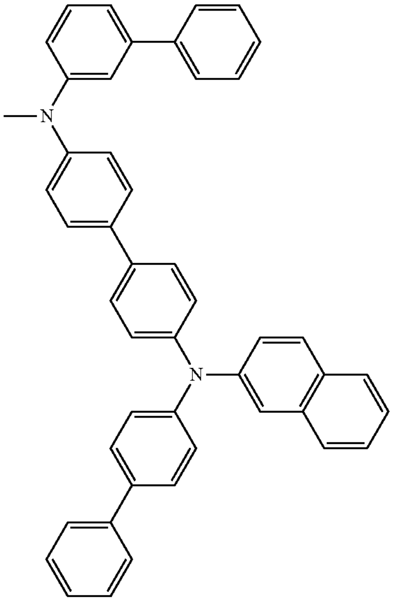
481
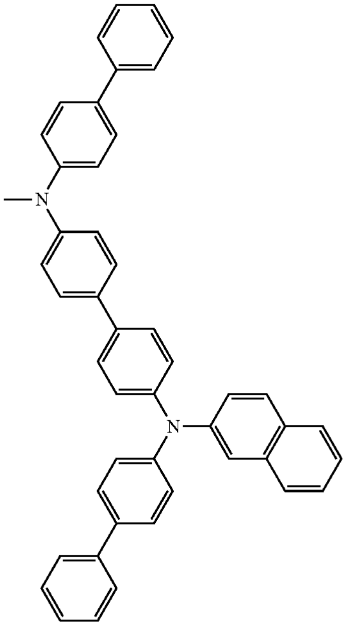
483
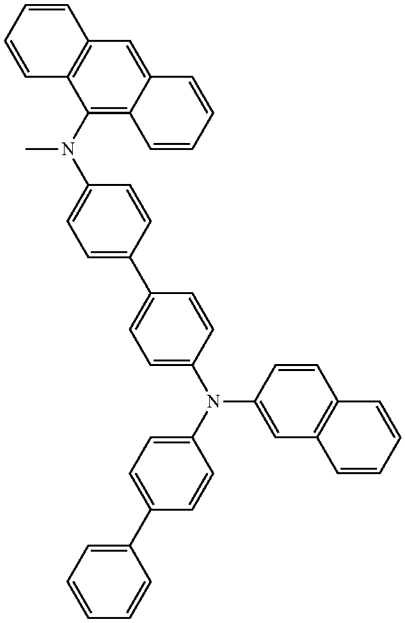

-continued
484
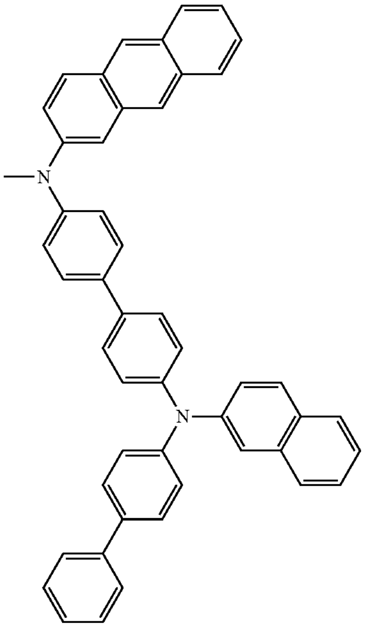
-continued
486
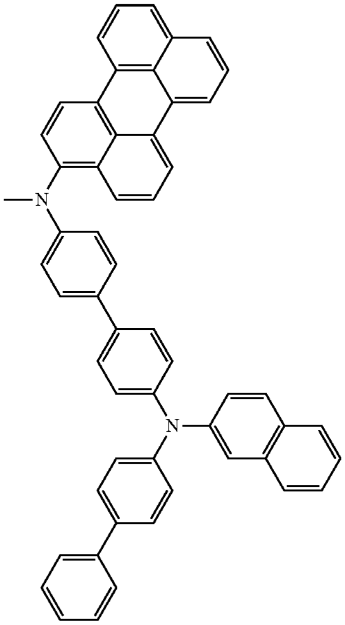
485
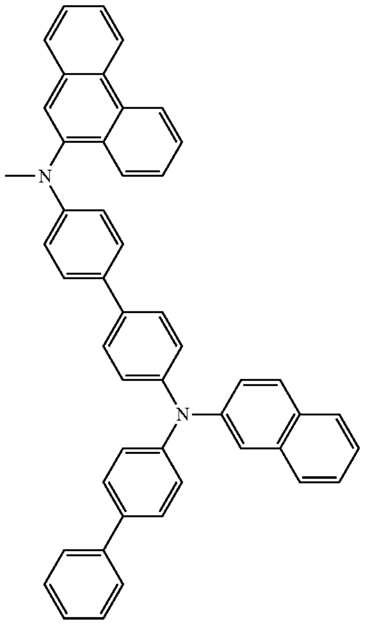
487
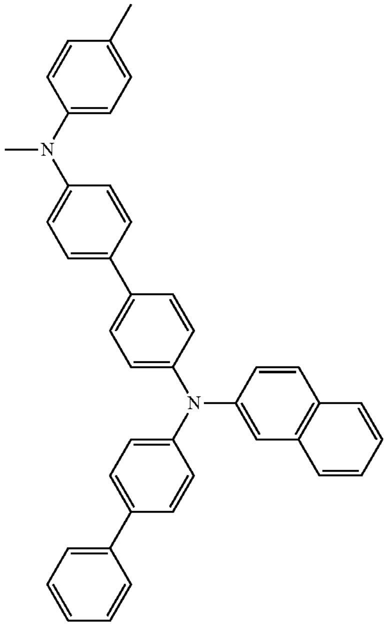

-continued
488
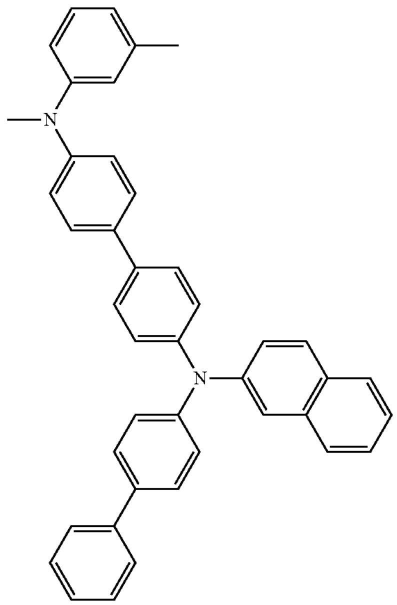
489
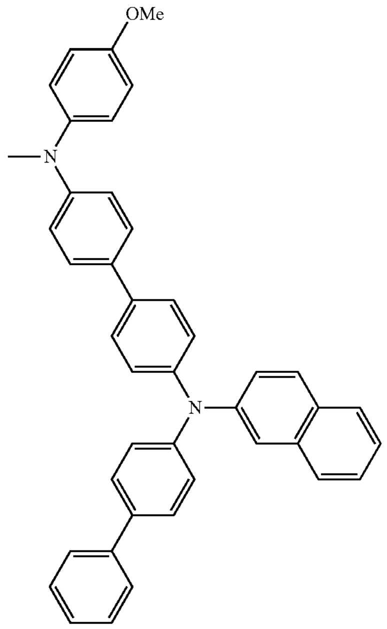
-continued
490
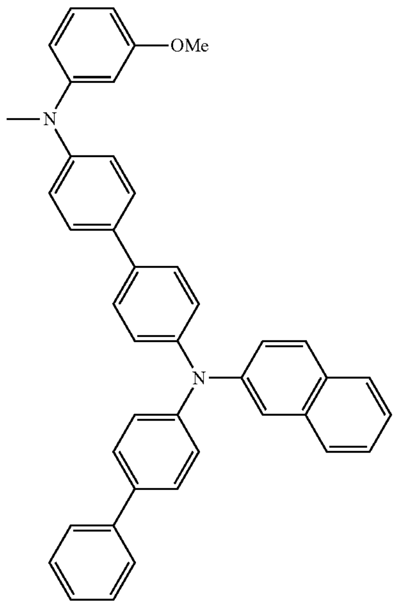
491
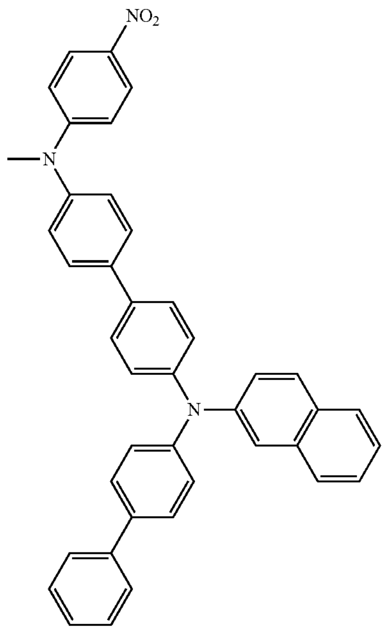

-continued
492
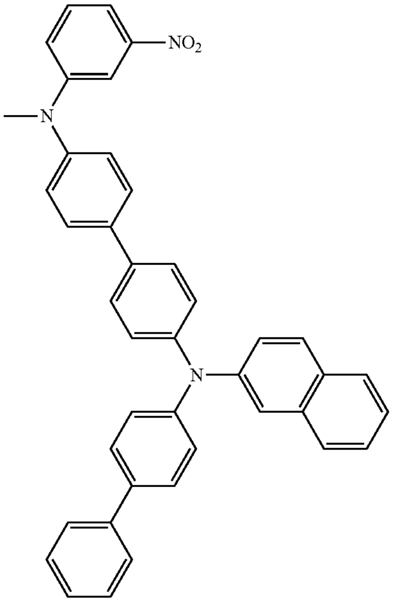
493
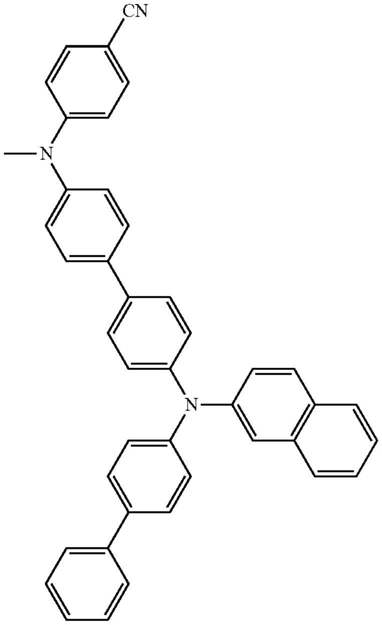
-continued
494
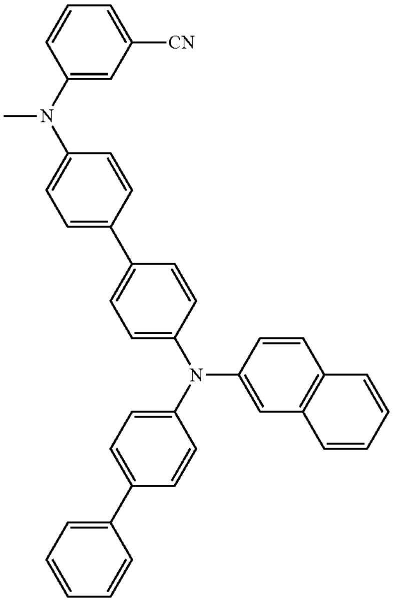
495
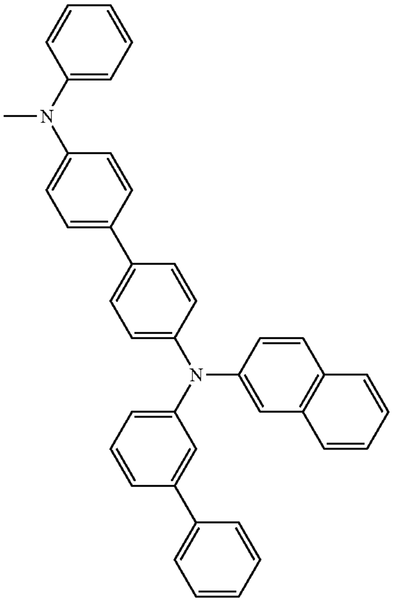

-continued
496
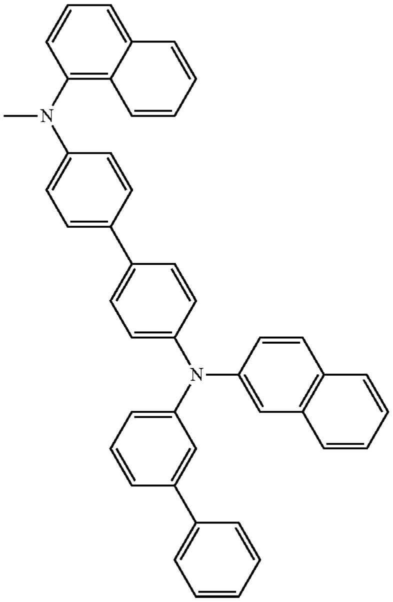
497
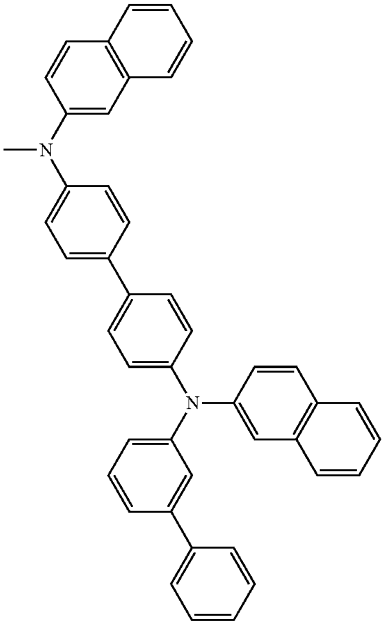
-continued
498
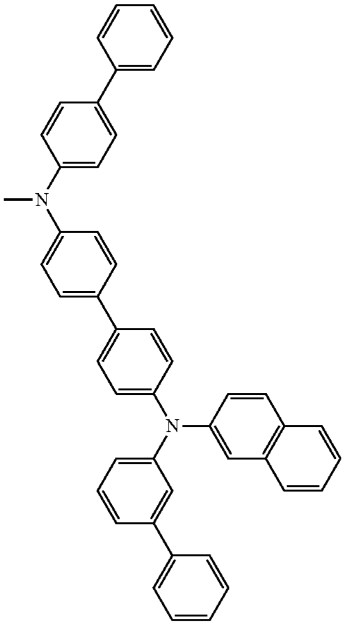
499
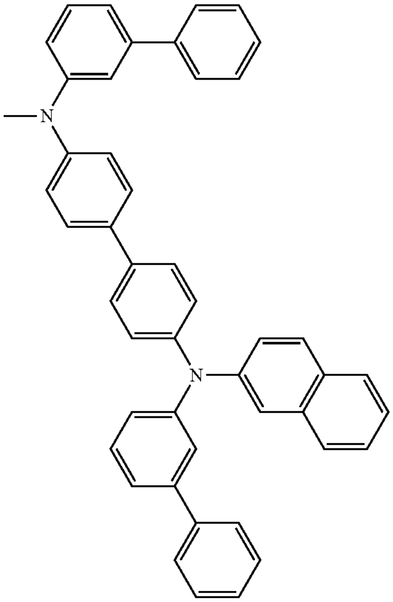

-continued
500
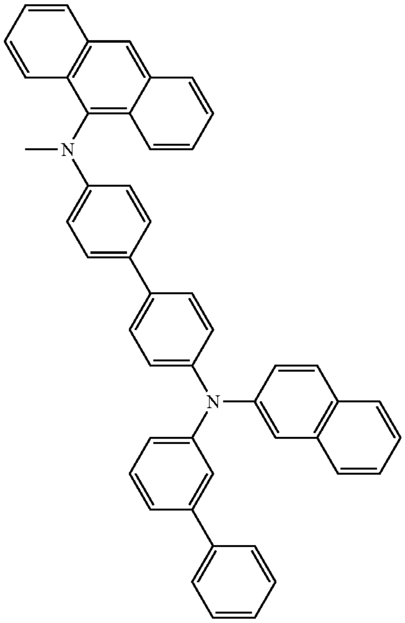
501
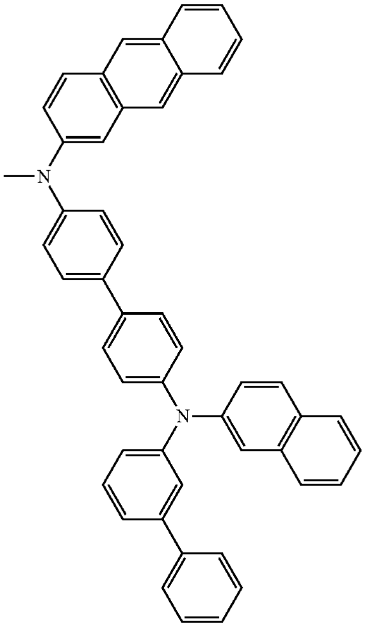
-continued
502
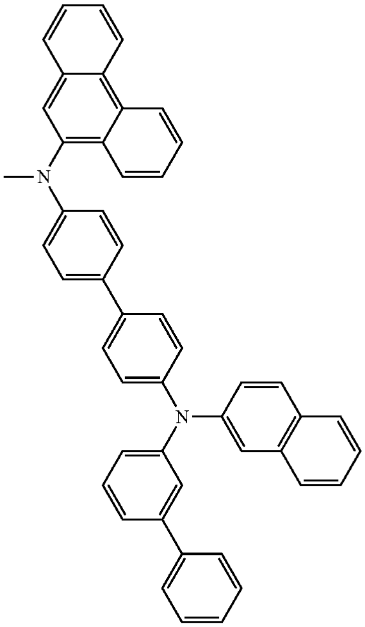
503
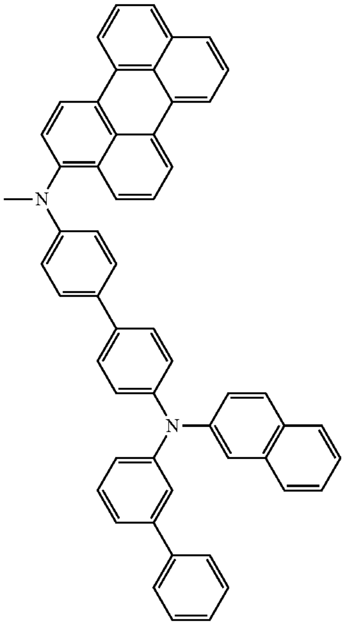

-continued
504
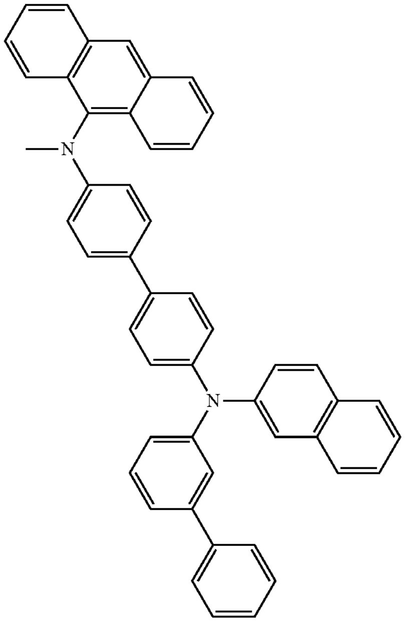
505
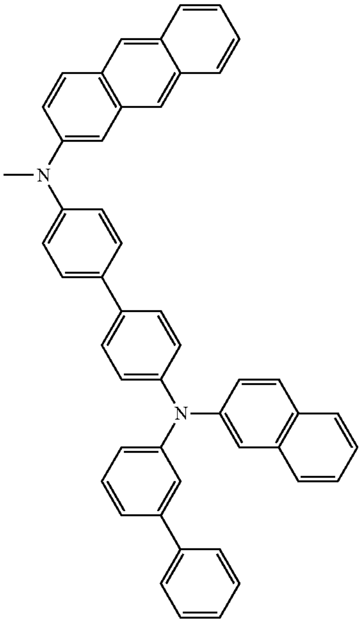
-continued
506
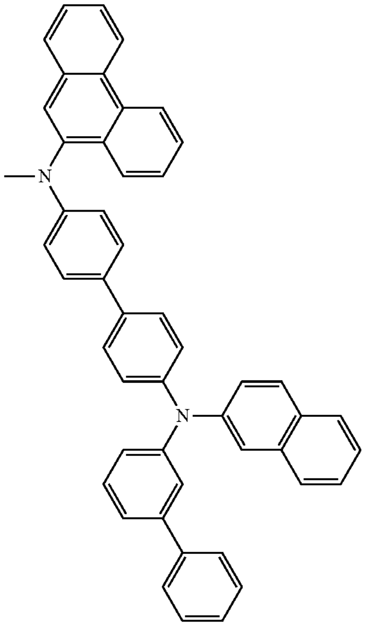
507
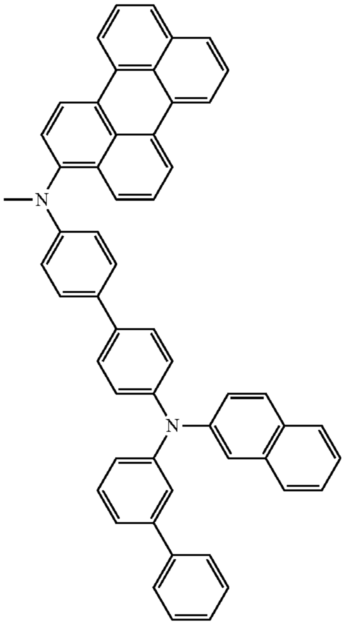

-continued
508
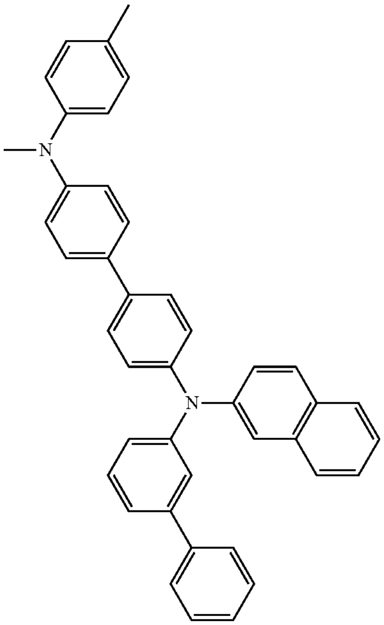
509
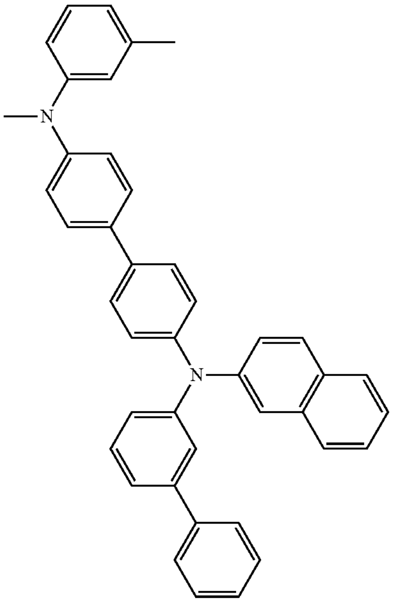
-continued
510
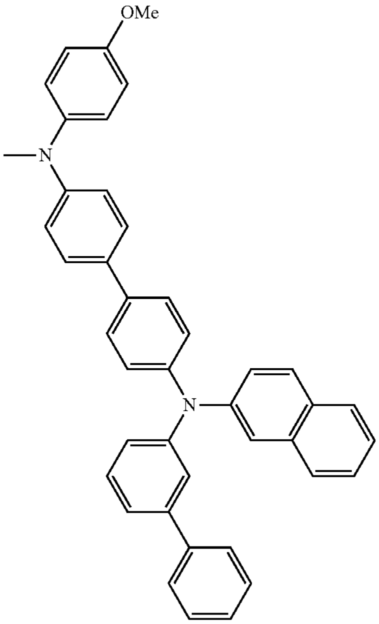
511
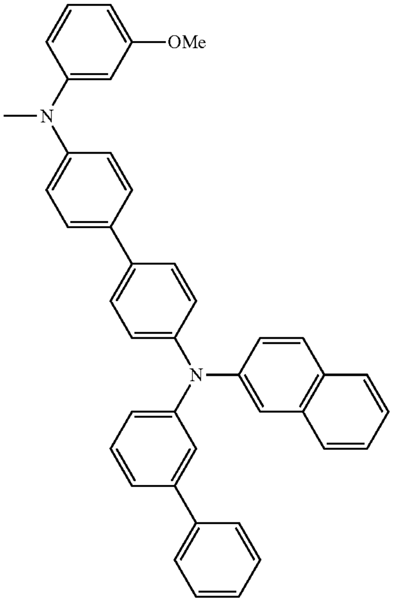

-continued
512
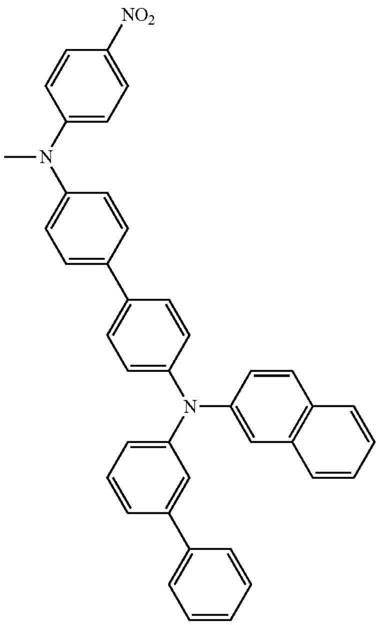
-continued
514
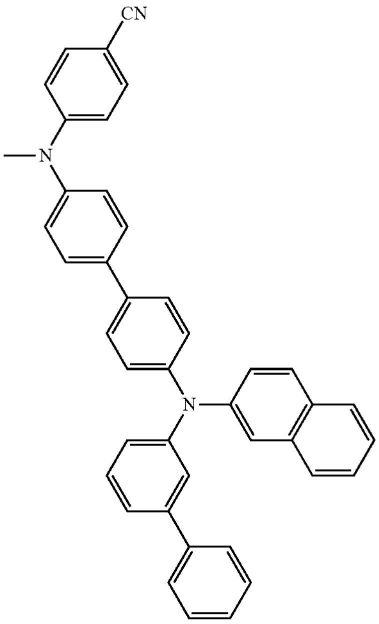
513
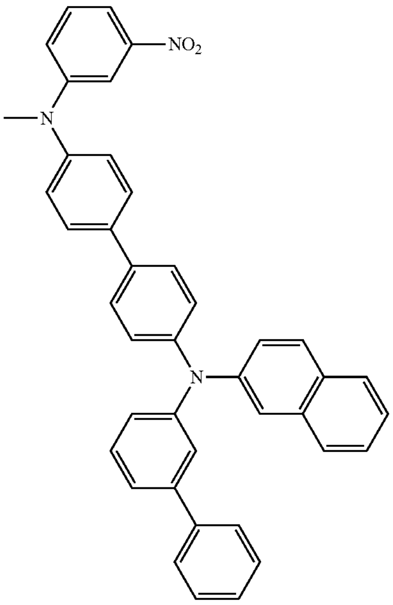
515
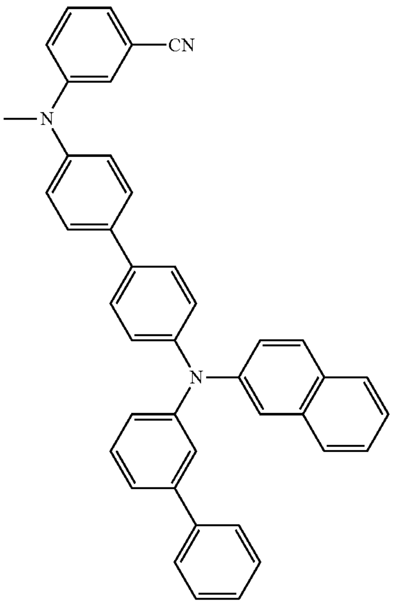

516
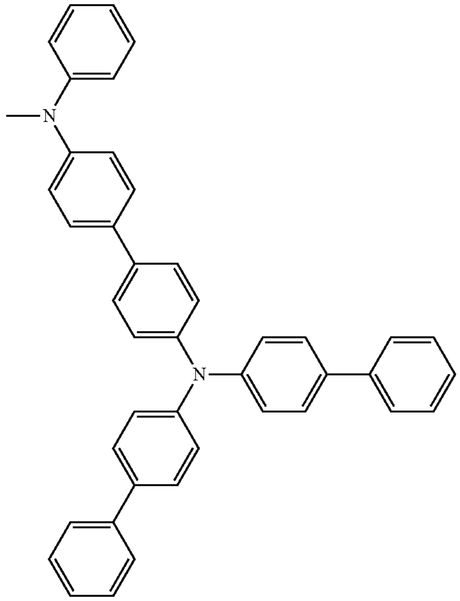
517
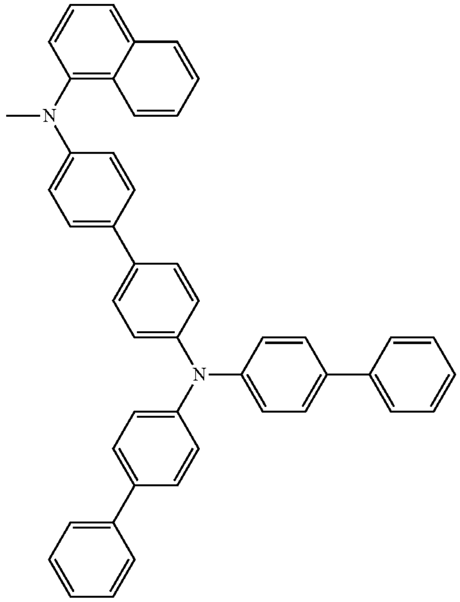
518
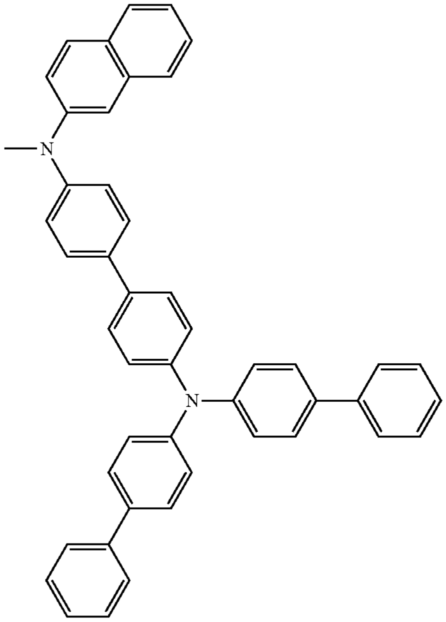
519
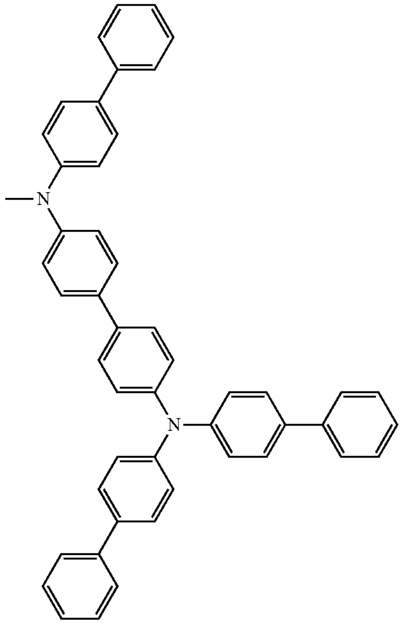

-continued
520
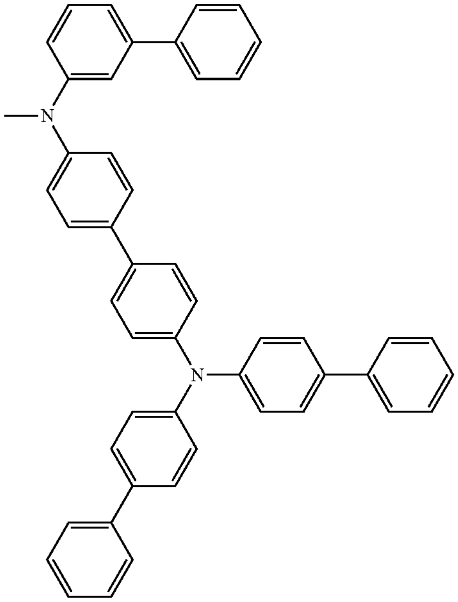
521
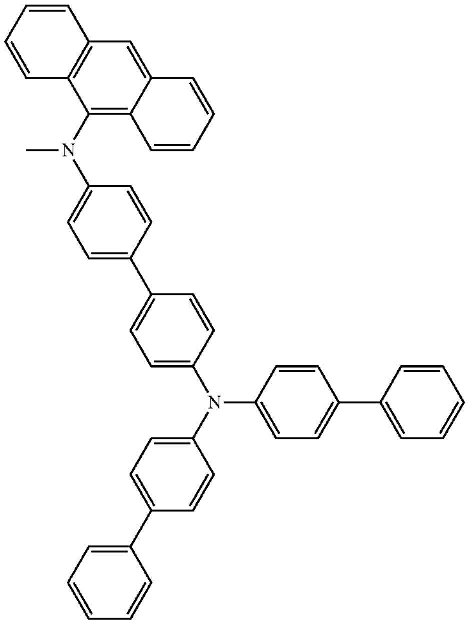
-continued
522
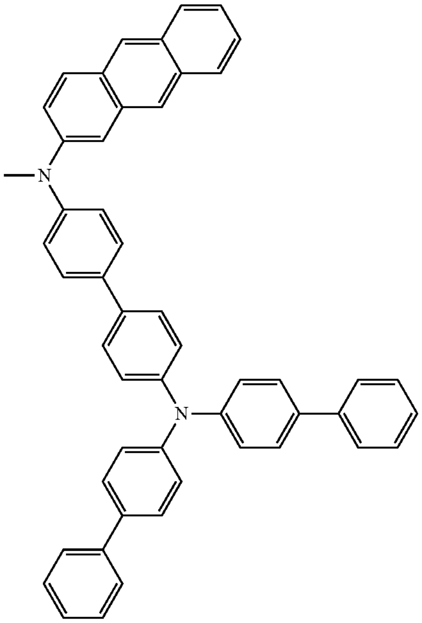
523
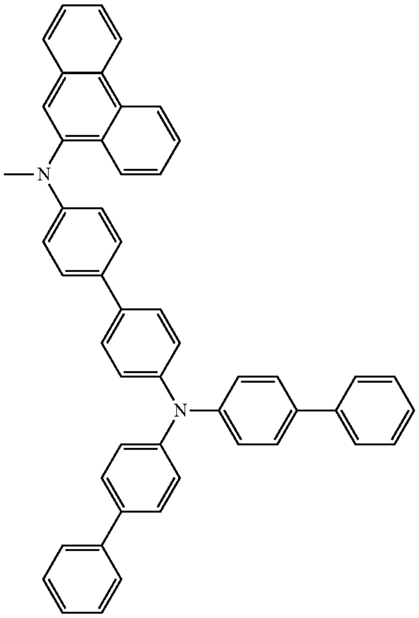

-continued
524
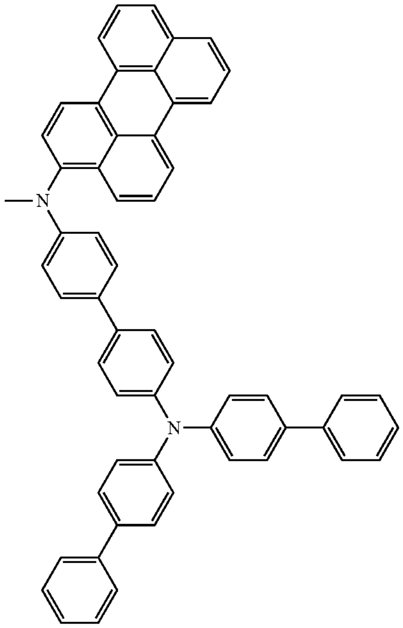
526
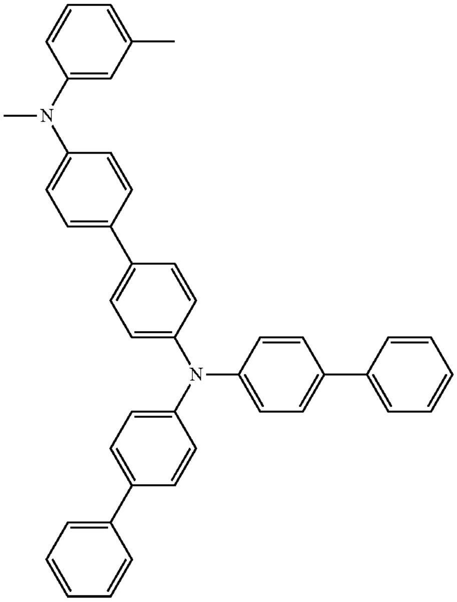
525
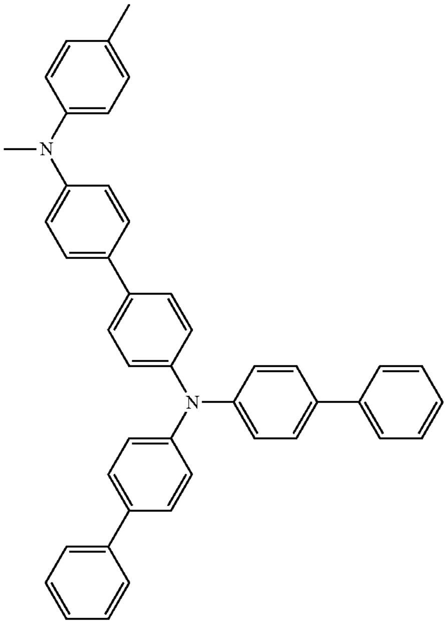
527
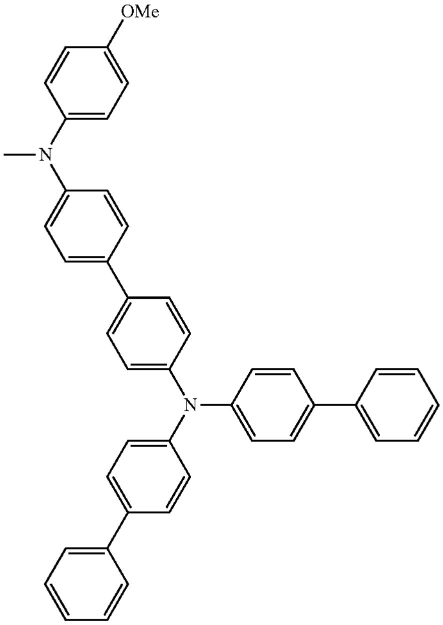

-continued
528
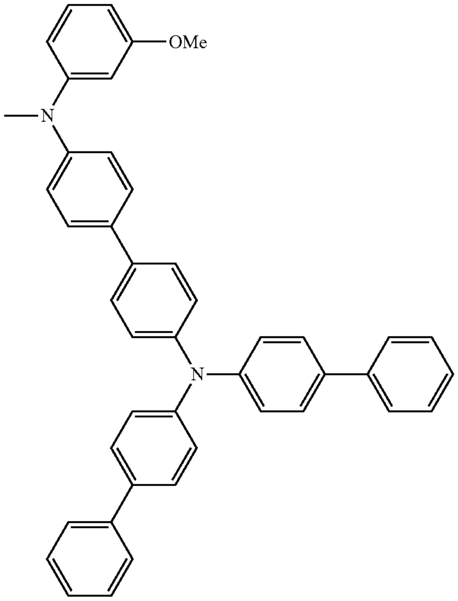
529
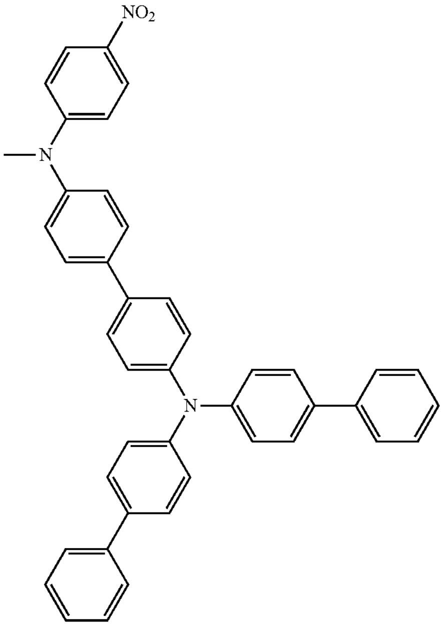
-continued
530
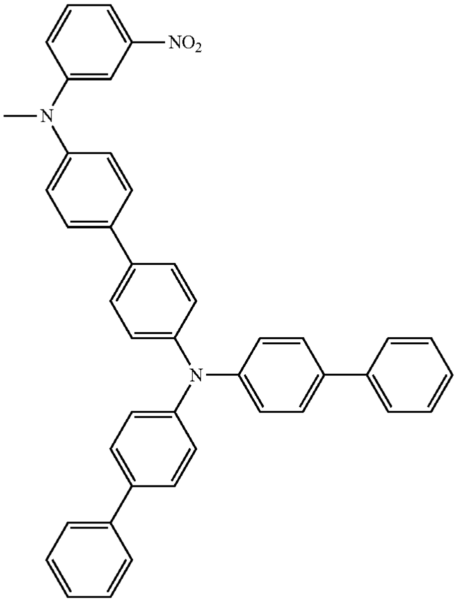
531
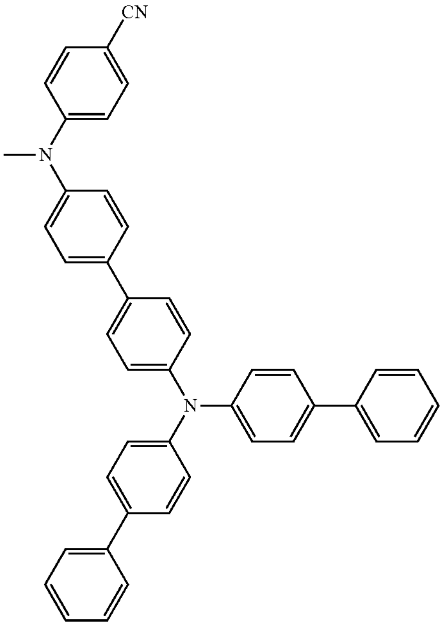

-continued
532
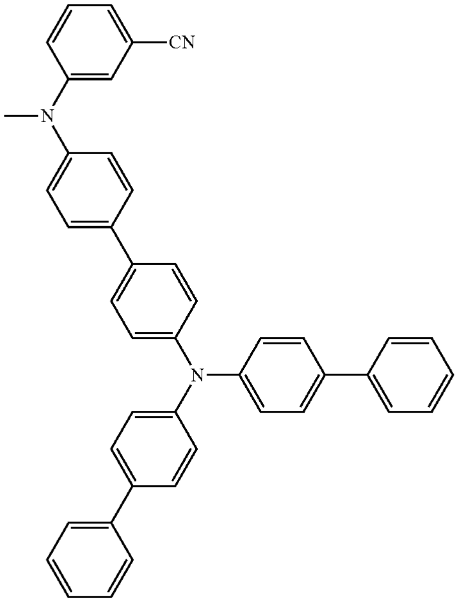
533
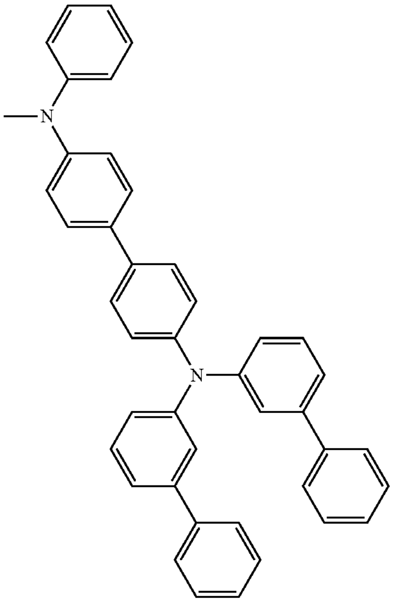
-continued
534
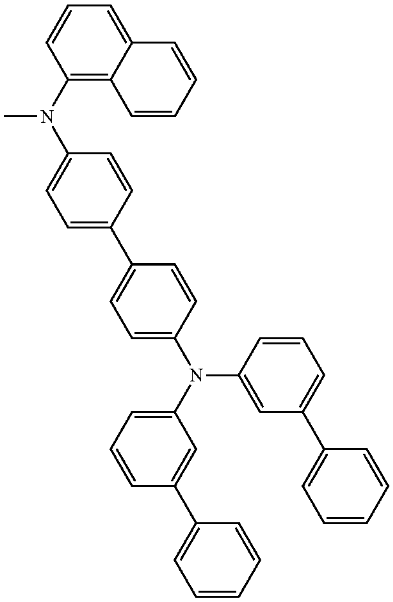
535
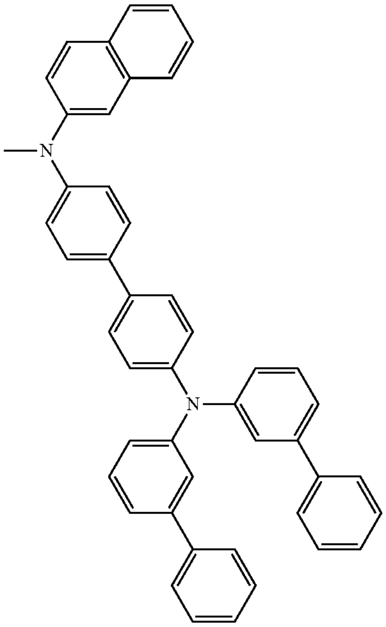

-continued
536
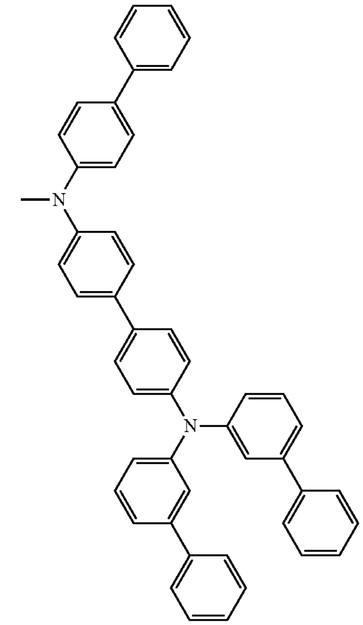
538
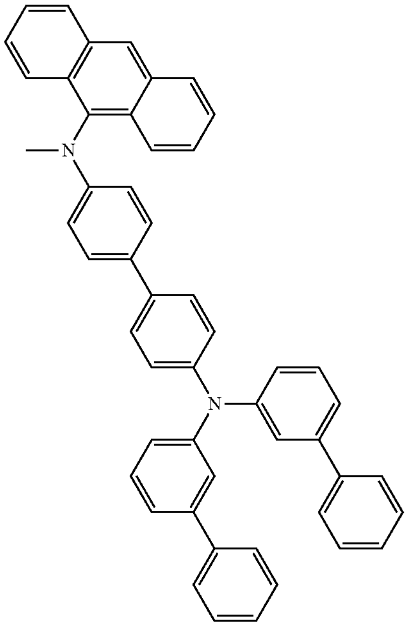
537
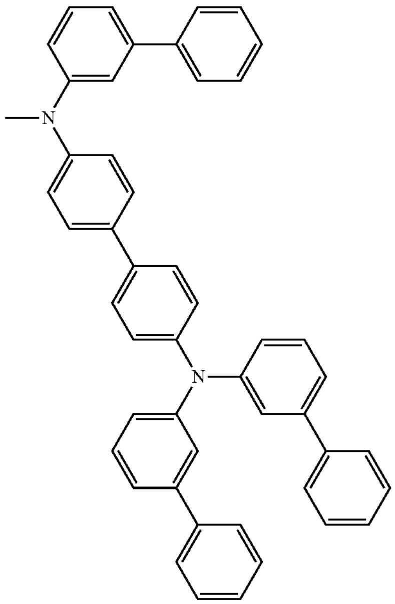
539
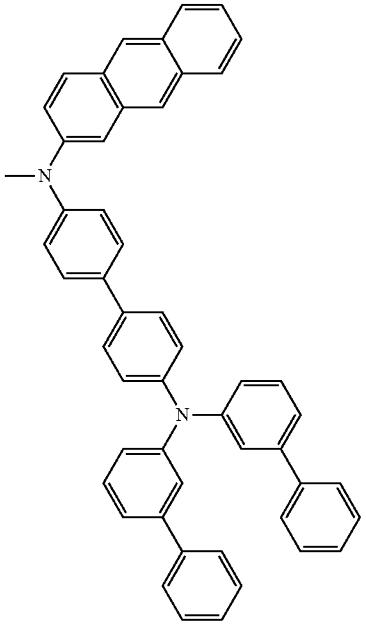
-continued -continued
540
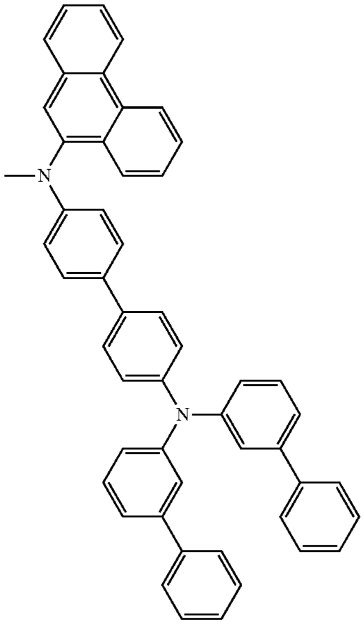
541
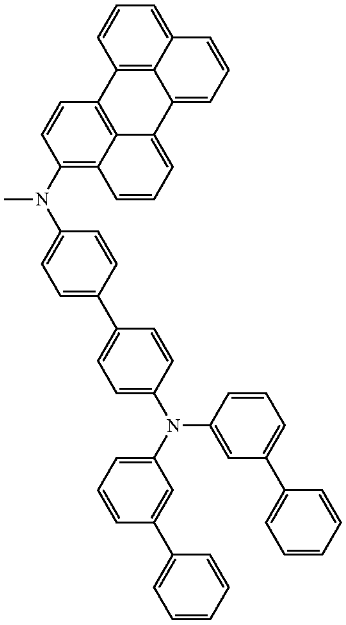
-continued
542
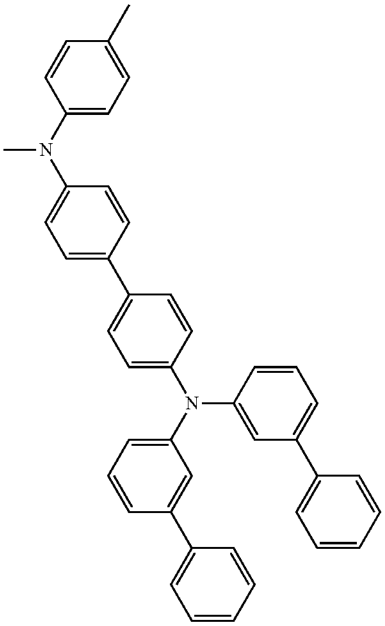
543
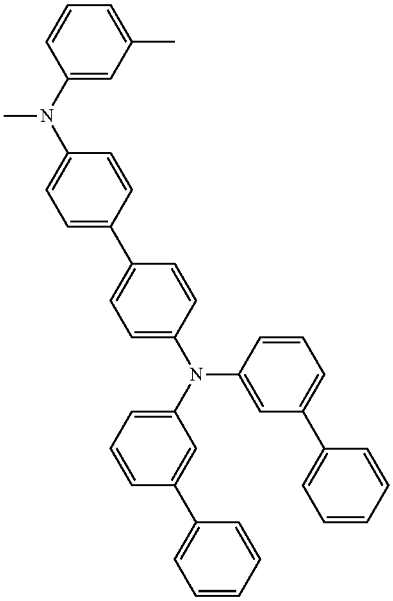

-continued
544
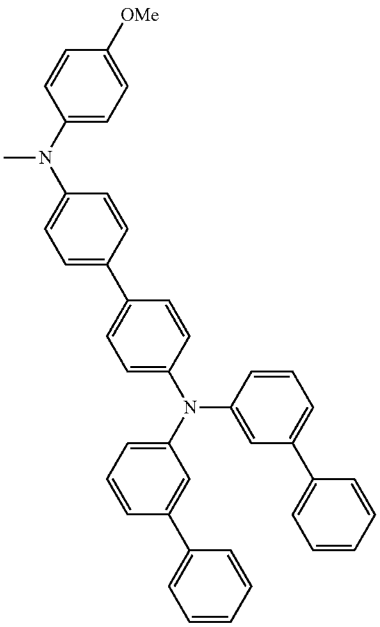
545
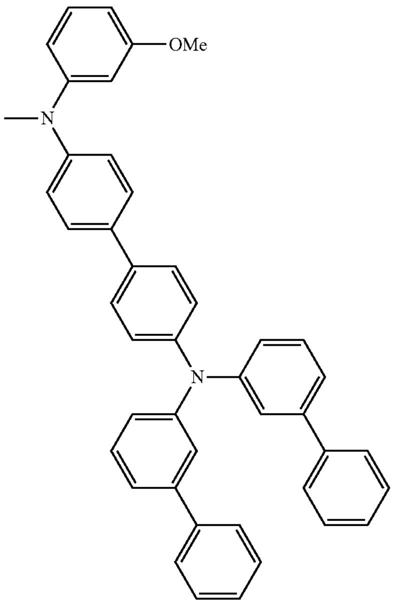
-continued
546
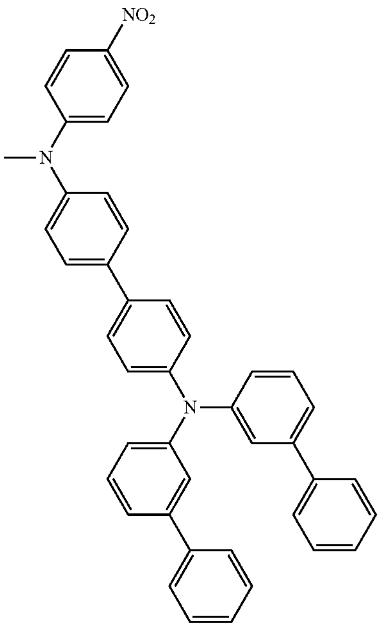
547
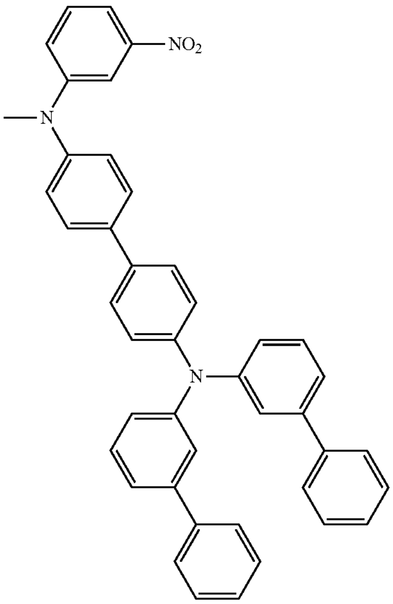

-continued
548
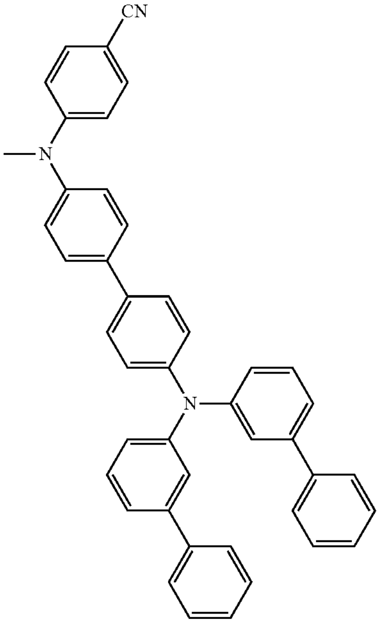
-continued
549
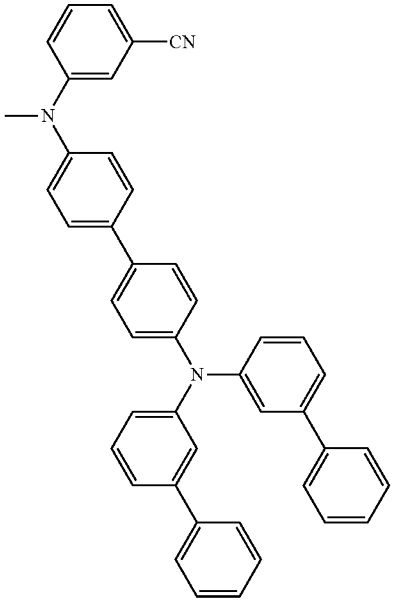
.
8. The compound of Formula 1 as set forth in claim 1, wherein Ar of Formula 1 is phenylene.
9. The compound of Formula 1 as set forth in claim 1, wherein the compound of Formula 1 is any one compound of the following Formula 4 to Formula 13:
[Formula 4]
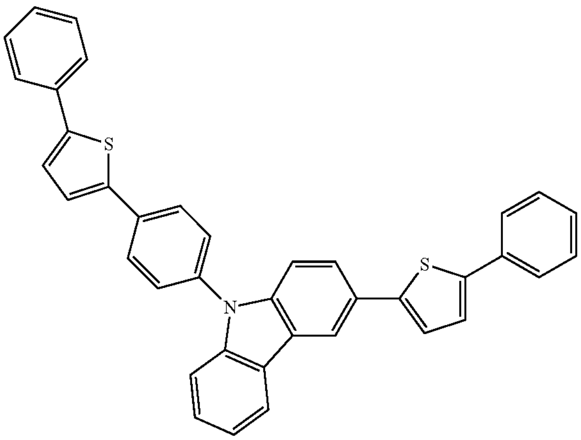

-continued
[Formula 5]
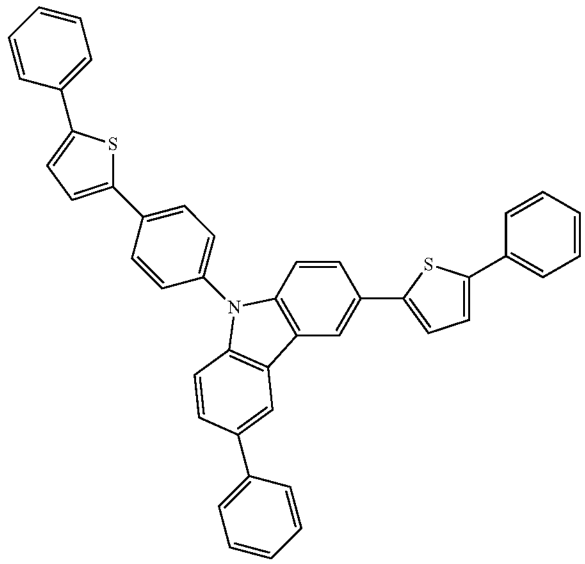
[Formula 6]
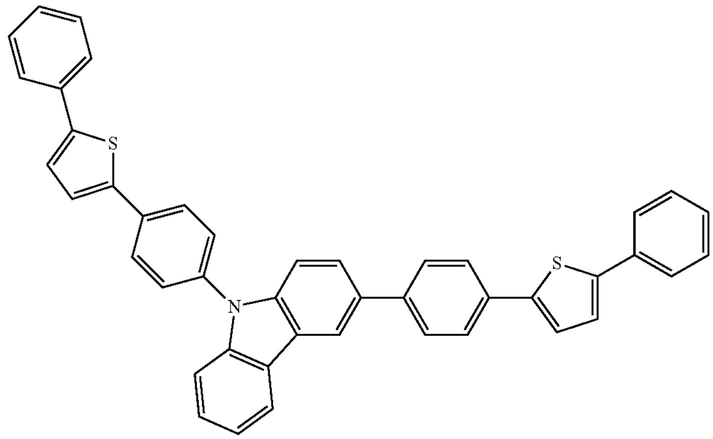
[Formula 7]
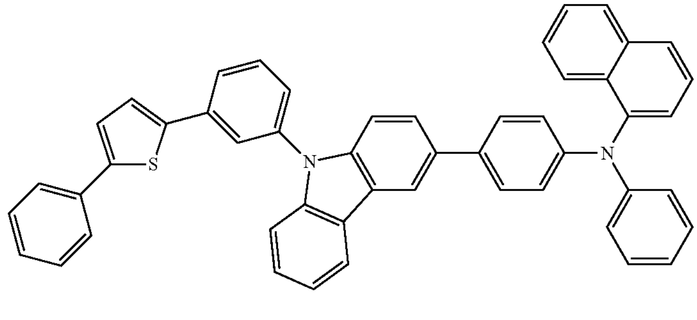

-continued
[Formula 8]
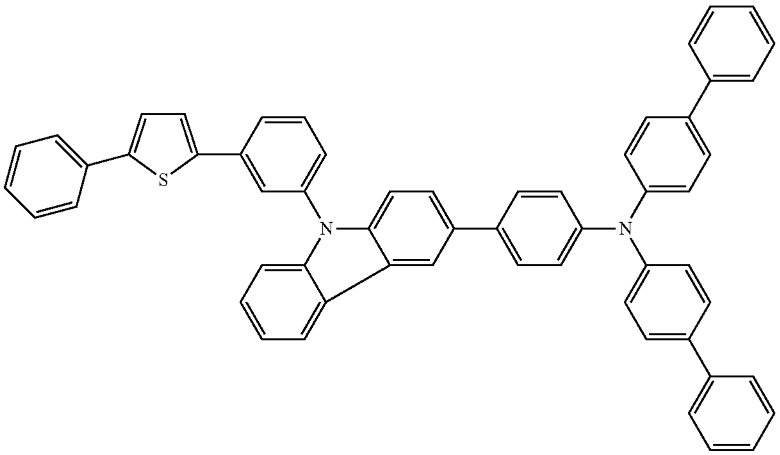
[Formula 9]
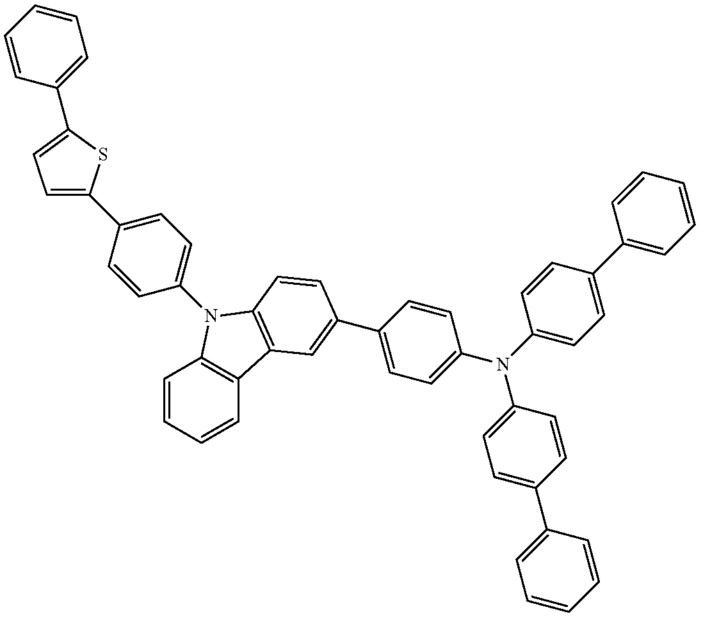
[Formula 10]
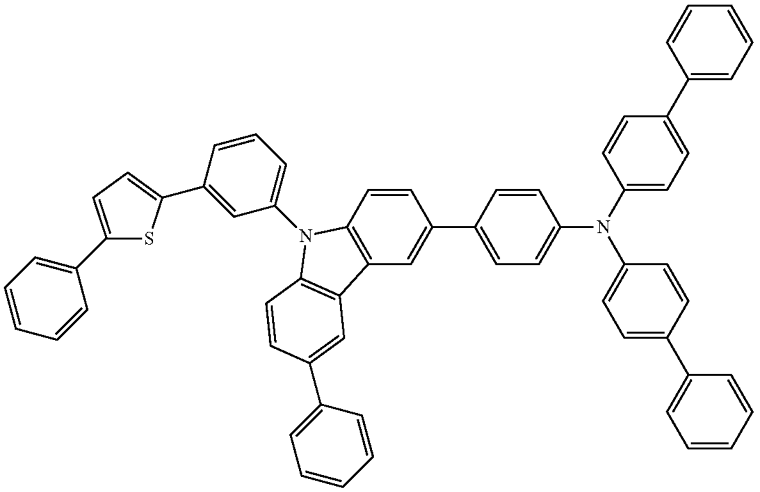

-continued
[Formula 11]
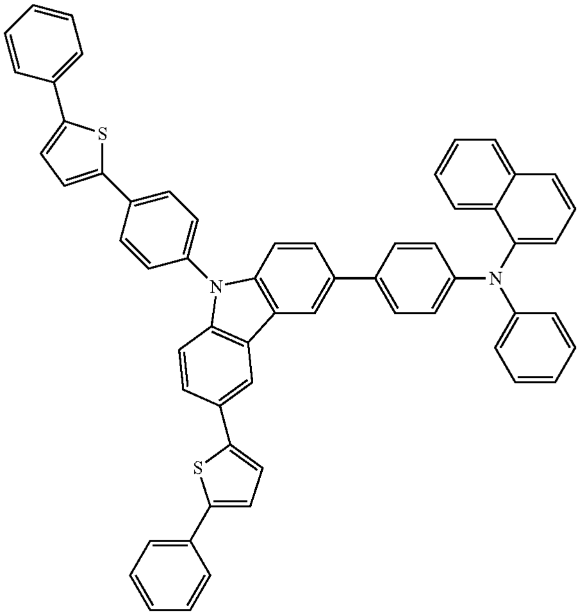
[Formula 12]
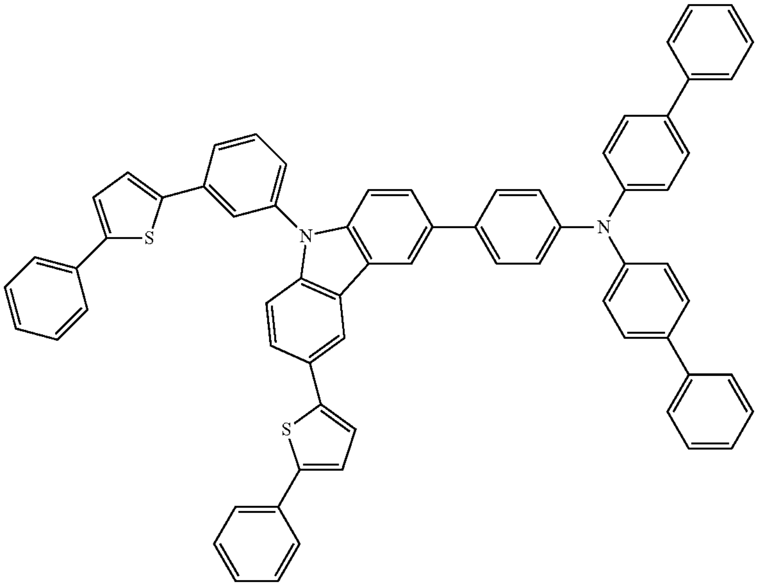
[Formula 13]
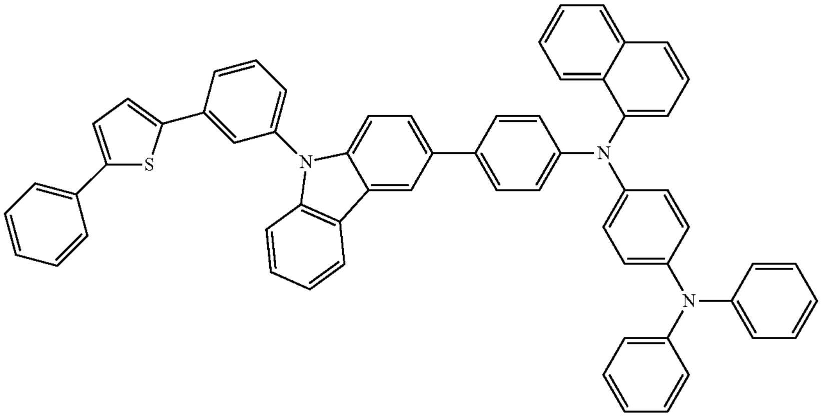
.

10. An organic light emitting device that includes a first electrode, an organic material layer that includes one or more layers having a light emitting layer, and a second electrode sequentially layered, wherein the organic light emitting device comprises one or more layers of the organic material layer that include the compound of Formula 1 of claim 1, or the compound of Formula 1 into which a thermosetting group or a photocurable functional group is introduced.

11. The organic light emitting device as set forth in claim 10, wherein the organic material layer includes a hole transport layer, and the hole transport layer includes the compound of Formula 1 or the compound of Formula 1 into which a thermosetting group or a photocurable functional group is introduced.

12. The organic light emitting device as set forth in claim 10, wherein the organic material layer includes a hole injection layer, and the hole injection layer includes the compound of Formula 1 or the compound of Formula 1 into which a thermosetting group or a photocurable functional group is introduced.

13. The organic light emitting device as set forth in claim 10, wherein the organic material layer includes a layer that collectively inject and transport a hole, and the layer includes the compound of Formula 1 or the compound of Formula 1 into which a thermosetting group or a photocurable functional group is introduced.

14. The organic light emitting device as set forth in claim 10, wherein the organic material layer includes an electron injection and transport layer, and the electron injection and transport layer includes the compound of Formula 1 or the compound of Formula 1 into which a thermosetting group or a photocurable functional group is introduced.

15. The organic light emitting device as set forth in claim 10, wherein the light emitting layer includes the compound of Formula 1 or the compound of Formula 1 into which a thermosetting group or a photocurable functional group is introduced.

* * * * *